(12) United States Patent
Bales, Jr. et al.

(10) Patent No.: US 9,107,690 B2
(45) Date of Patent: Aug. 18, 2015

(54) BATTERY-POWERED HAND-HELD ULTRASONIC SURGICAL CAUTERY CUTTING DEVICE

(75) Inventors: Thomas O. Bales, Jr., Coral Gables, FL (US); Derek Dee Deville, Coral Gables, FL (US); Kevin W. Smith, Miami, FL (US); Matthew A. Palmer, Coral Gables, FL (US)

(73) Assignee: Covidien AG, Neuhausen am Rheinfall (CH)

( * ) Notice: Subject to any disclaimer, the term of this patent is extended or adjusted under 35 U.S.C. 154(b) by 180 days.

(21) Appl. No.: 13/307,750

(22) Filed: Nov. 30, 2011

(65) Prior Publication Data

US 2012/0078278 A1    Mar. 29, 2012

Related U.S. Application Data

(63) Continuation-in-part of application No. 13/215,971, filed on Aug. 23, 2011, and a continuation-in-part of application No. 13/022,707, filed on Feb. 8, 2011, now Pat. No. 8,663,262, and a continuation-in-part of
(Continued)

(51) Int. Cl.
*H02J 7/00* (2006.01)
*A61B 17/32* (2006.01)
*A61B 17/00* (2006.01)

(52) U.S. Cl.
CPC .......... *A61B 17/320092* (2013.01); *A61B 2017/00734* (2013.01)

(58) Field of Classification Search
CPC .......... A61B 17/320068; A61B 17/320092; A61B 17/00734; H01M 10/4257; B25F 5/02

USPC .......... 606/169; 600/437, 461, 471; 601/2; 604/22; 429/96, 98, 121, 123; 320/106, 320/155–159, 112, 114

See application file for complete search history.

(56) References Cited

U.S. PATENT DOCUMENTS 1,813,902 A   7/1931  Bovie
2,874,470 A   2/1959  Richards
(Continued)

FOREIGN PATENT DOCUMENTS

EP   0 705 570   4/1996
EP   0 908 148   4/1999
(Continued)

OTHER PUBLICATIONS

Surgicon, Inc. SpringLock and SpringLock Remover Launch Presentation Materials, Revised Jan. 23, 2002.
(Continued)

*Primary Examiner* — Katherine M Shi

(57) ABSTRACT

A battery assembly for use with a surgical device having a battery terminal and operational parameters includes a housing having a shape formed to removably connect with the terminal. The housing contains a modular battery operable to supply power to the device at the terminal and has a control circuit with a microprocessor, a memory, and a real-time clock. The control circuit is communicatively coupled to the battery and is operable to detect an identity of the surgical device, to determine at least one piece of information pertaining to at least one of the operational parameters of the surgical device based upon the detected identity, to record the piece of information at least in the memory, and to selectively allow or prevent the battery from supplying power to the surgical device dependent upon the piece of information.

19 Claims, 78 Drawing Sheets

Related U.S. Application Data application No. 13/022,743, filed on Feb. 8, 2011, now Pat. No. 8,439,939, and a continuation-in-part of application No. 12/868,505, filed on Aug. 25, 2010, now Pat. No. 8,338,726, and a continuation-in-part of application No. 12/868,545, filed on Aug. 25, 2010, now Pat. No. 8,334,468, and a continuation-in-part of application No. 12/547,898, filed on Aug. 26, 2009, now Pat. No. 8,061,014, and a continuation-in-part of application No. 12/547,975, filed on Aug. 26, 2009, now Pat. No. 8,435,257, and a continuation-in-part of application No. 12/547,999, filed on Aug. 26, 2009, now Pat. No. 8,425,545, and a continuation-in-part of application No. 13/072,187, filed on Mar. 25, 2011, now Pat. No. 8,197,502, and a continuation-in-part of application No. 13/072,247, filed on Mar. 25, 2011, now Pat. No. 8,333,778, and a continuation-in-part of application No. 13/072,273, filed on Mar. 25, 2011, now Pat. No. 8,333,779, and a continuation-in-part of application No. 13/072,221, filed on Mar. 25, 2011, now Pat. No. 8,236,020, and a continuation-in-part of application No. 13/072,309, filed on Mar. 25, 2011, now Pat. No. 8,372,101, and a continuation-in-part of application No. 13/072,345, filed on Mar. 25, 2011, now Pat. No. 8,377,085, and a continuation-in-part of application No. 13/072,373, filed on Mar. 25, 2011, now Pat. No. 8,418,349, and a continuation-in-part of application No. 12/266,101, filed on Nov. 6, 2008, now Pat. No. 8,419,757, and a continuation-in-part of application No. 12/266,146, filed on Nov. 6, 2008, now Pat. No. 8,419,758, and a continuation-in-part of application No. 12/266,226, filed on Nov. 6, 2008, and a continuation-in-part of application No. 12/266,252, filed on Nov. 6, 2008, and a continuation-in-part of application No. 12/266,320, filed on Nov. 6, 2008, now Pat. No. 8,403,948, and a continuation-in-part of application No. 12/266,664, filed on Nov. 7, 2008, now Pat. No. 8,372,099, and a continuation-in-part of application No. 12/269,544, filed on Nov. 12, 2008, now Pat. No. 8,444,662, and a continuation-in-part of application No. 12/269,629, filed on Nov. 12, 2008, now Pat. No. 8,403,949, and a continuation-in-part of application No. 12/270,146, filed on Nov. 13, 2008, now Pat. No. 8,403,950.

(60) Provisional application No. 61/476,022, filed on Apr. 15, 2011, provisional application No. 61/376,983, filed on Aug. 25, 2010, provisional application No. 61/236,934, filed on Aug. 26, 2009, provisional application No. 61/081,885, filed on Jul. 18, 2008, provisional application No. 61/048,809, filed on Apr. 29, 2008, provisional application No. 61/045,475, filed on Apr. 16, 2008, provisional application No. 61/019,888, filed on Jan. 9, 2008, provisional application No. 60/992,498, filed on Dec. 5, 2007, provisional application No. 60/991,829, filed on Dec. 3, 2007.

(56) References Cited

U.S. PATENT DOCUMENTS

| | | | |
|---|---|---|---|
| 2,990,616 | A | 7/1961 | Arthur |
| 3,432,691 | A | 3/1969 | Shoh |
| 3,489,930 | A | 1/1970 | Shoh |
| 3,629,726 | A | 12/1971 | Popescu |
| 3,668,486 | A | 6/1972 | Silver |
| 3,809,977 | A | 5/1974 | Balamuth et al. |
| 3,875,945 | A | 4/1975 | Friedman et al. |
| 3,924,335 | A | 12/1975 | Balamuth et al. |
| 4,012,647 | A | 3/1977 | Balamuth et al. |
| 4,193,818 | A | 3/1980 | Young et al. |
| 4,227,110 | A | 10/1980 | Douglas |
| 4,300,083 | A | 11/1981 | Heiges |
| 4,302,728 | A | 11/1981 | Nakamura |
| 4,370,302 | A | 1/1983 | Suzuoka |
| 4,641,053 | A | 2/1987 | Takeda |
| 5,113,116 | A | 5/1992 | Wilson |
| 5,224,680 | A | 7/1993 | Greenstein |
| 5,264,925 | A | 11/1993 | Shipp |
| 5,275,166 | A | 1/1994 | Vaitekunas |
| 5,374,813 | A | 12/1994 | Shipp |
| 5,394,187 | A | 2/1995 | Shipp |
| 5,408,268 | A | 4/1995 | Shipp |
| 5,451,220 | A | 9/1995 | Ciervo |
| 5,490,860 | A | 2/1996 | Middle et al. |
| 5,565,520 | A | 10/1996 | Fock et al. |
| 5,593,414 | A | 1/1997 | Shipp et al. |
| 5,685,311 | A | 11/1997 | Hara |
| 5,717,306 | A | 2/1998 | Shipp |
| 5,728,130 | A | 3/1998 | Ishikawa et al. |
| 5,792,138 | A | 8/1998 | Shipp |
| 5,796,056 | A | 8/1998 | Bredow |
| 5,810,859 | A | 9/1998 | DiMatteo et al. |
| 5,858,018 | A | 1/1999 | Shipp et al. |
| 5,873,873 | A | 2/1999 | Smith |
| 5,897,569 | A | 4/1999 | Kellogg |
| 5,910,152 | A | 6/1999 | Bays |
| 5,938,633 | A | 8/1999 | Beaupre |
| 5,944,737 | A | 8/1999 | Tsonton |
| 5,947,984 | A | 9/1999 | Whipple |
| 5,954,736 | A | 9/1999 | Bishop et al. |
| 5,993,465 | A | 11/1999 | Shipp et al. |
| 5,994,855 | A | 11/1999 | Lundell et al. |
| 6,031,526 | A | 2/2000 | Shipp |
| 6,036,667 | A | 3/2000 | Manna et al. |
| 6,068,647 | A | 5/2000 | Witt et al. |
| 6,095,981 | A | 8/2000 | McGahan |
| 6,162,194 | A | 12/2000 | Shipp |
| 6,183,426 | B1 | 2/2001 | Saida et al. |
| 6,220,098 | B1 | 4/2001 | Johnson |
| 6,254,623 | B1 | 7/2001 | Haibel, Jr. et al. |
| 6,257,241 | B1 | 7/2001 | Wampler |
| 6,278,218 | B1 | 8/2001 | Madan et al. |
| 6,280,407 | B1 | 8/2001 | Manna et al. |
| 6,283,981 | B1 | 9/2001 | Beaupre |
| 6,284,185 | B1 | 9/2001 | Tokuda |
| 6,287,344 | B1 | 9/2001 | Wampler |
| 6,290,575 | B1 | 9/2001 | Shipp |
| 6,306,157 | B1 | 10/2001 | Shchervinsky |
| 6,309,400 | B2 | 10/2001 | Beaupre |
| 6,325,811 | B1 | 12/2001 | Messerly |
| 6,328,751 | B1 | 12/2001 | Beaupre |
| 6,350,269 | B1 | 2/2002 | Shipp et al. |
| 6,352,532 | B1 | 3/2002 | Kramer |
| 6,416,486 | B1 | 7/2002 | Wampler |
| 6,423,082 | B1 | 7/2002 | Houser et al. |
| 6,432,118 | B1 | 8/2002 | Messerly |
| 6,443,968 | B1 | 9/2002 | Holthaus et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,142 | B1 | 10/2002 | Faller et al. |
| 6,480,796 | B2 | 11/2002 | Wiener |
| 6,482,220 | B1 | 11/2002 | Mueller |
| 6,491,708 | B2 | 12/2002 | Madan |
| 6,500,188 | B2 | 12/2002 | Harper |
| 6,514,267 | B2 | 2/2003 | Jewett |
| 6,537,291 | B2 | 3/2003 | Friedman |
| 6,561,983 | B2 | 5/2003 | Cronin et al. |
| 6,565,520 | B1 | 5/2003 | Young |
| 6,588,277 | B2 | 7/2003 | Giordano |
| 6,589,200 | B1 | 7/2003 | Schwemberger et al. |
| 6,607,540 | B1 | 8/2003 | Shipp |
| 6,623,500 | B1 | 9/2003 | Cook et al. |
| 6,626,926 | B2 | 9/2003 | Friedman et al. |
| 6,633,234 | B2 | 10/2003 | Wiener et al. |

(56) References Cited

U.S. PATENT DOCUMENTS

| | | |
|---|---|---|
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener |
| 6,719,776 B2 | 4/2004 | Baxter |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger |
| 7,163,548 B2 | 1/2007 | Stulen et al. |
| 7,179,254 B2 | 2/2007 | Pendekanti |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang |
| 7,230,199 B2 | 6/2007 | Chou |
| 7,244,262 B2 | 7/2007 | Wiener |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal |
| 2002/0002379 A1 | 1/2002 | Bishop |
| 2002/0077645 A1* | 6/2002 | Wiener et al. ............... 606/169 |
| 2002/0091339 A1 | 7/2002 | Horzewski et al. |
| 2003/0144680 A1 | 7/2003 | Kellogg |
| 2003/0149424 A1 | 8/2003 | Barlev et al. |
| 2003/0199794 A1 | 10/2003 | Sakurai |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins, Jr. et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 | 4/2006 | Faller |
| 2006/0087286 A1 | 4/2006 | Phillips |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly |
| 2006/0206100 A1 | 9/2006 | Eskridge |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales |
| 2009/0143797 A1 | 6/2009 | Smith |
| 2009/0143805 A1 | 6/2009 | Palmer et al. |
| 2009/0223033 A1 | 9/2009 | Houser |
| 2010/0004669 A1* | 1/2010 | Smith et al. ............... 606/169 |

FOREIGN PATENT DOCUMENTS

| | | |
|---|---|---|
| EP | 1 594 209 | 11/2005 |
| EP | 1 707 131 | 10/2006 |
| EP | 2 200 145 | 6/2010 |
| JP | 2001-112768 | 4/2001 |
| JP | 2001-514541 | 9/2001 |
| JP | 2002-518067 | 6/2002 |
| JP | 2003-502102 | 1/2003 |
| JP | 2003-285008 | 10/2003 |
| JP | 2004-129871 | 4/2004 |
| JP | 2005-278932 | 10/2005 |
| JP | 2005-296411 | 10/2005 |
| WO | 2006/087885 | 8/2006 |
| WO | 2006/119376 | 11/2006 |
| WO | 2007/047380 | 4/2007 |
| WO | 2007-080723 | 7/2007 |

OTHER PUBLICATIONS

Examination Report of Australian Patent App. No. 2008334050 dated Apr. 10, 2013.

European Search Report of European Patent App. No. 11006960.6 dated Jul. 17, 2013.

Examination Report of Australian Patent App. No. 2011213852 dated May 9, 2013.

Notice of Rejection in Japanese Patent App. No. 2010-537005 dated May 7, 2013.

Office action in Japan Patent App. No. 2014077366 dated Sep. 9, 2014.

Office action in Japan Patent App. No. 2014077367 dated Sep. 9, 2014.

Office action in Japan Patent App. No. 2014077368 dated Sep. 9, 2014.

Office action in Japan Patent App. No. 2012093321 dated Aug. 26, 2014.

Office action in Canada Patent App. No. 2,774,751 dated Jul. 25, 2014.

European Search Report of European Patent App. No. 12164202.9, Aug. 7, 2012.

European Search Report of European App. No. 08858351.3, Jun. 15, 2012.

European Search Report of European App. No. 11010043.5, Jun. 11, 2012.

European Search Report of European App. No. 11010007.0, Jun. 13, 2012.

Office action in Japan Patent App. No. 2012-526970 dated Apr. 15, 2014.

Office action in Japan Patent App. No. 2012-526970 dated Nov. 18, 2014.

Office action in Canada Patent App. No. 2,707,837 dated Jul. 29, 2014.

Office action in Europe Patent App. No. 12 164 202.9 dated Jan. 5, 2015.

Canadian Office Action, Application No. 27747451 dated Apr. 23, 2015.

* cited by examiner

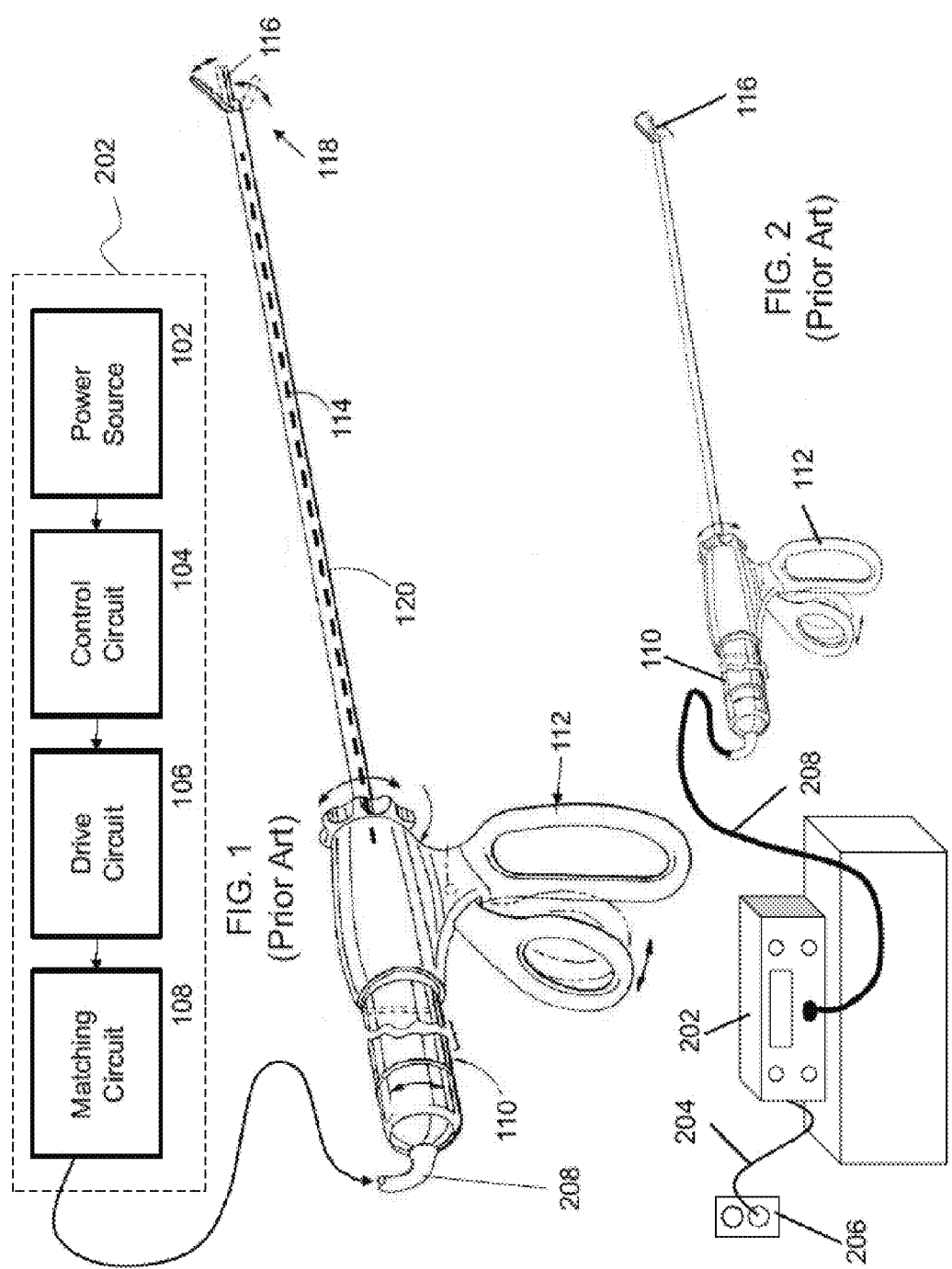

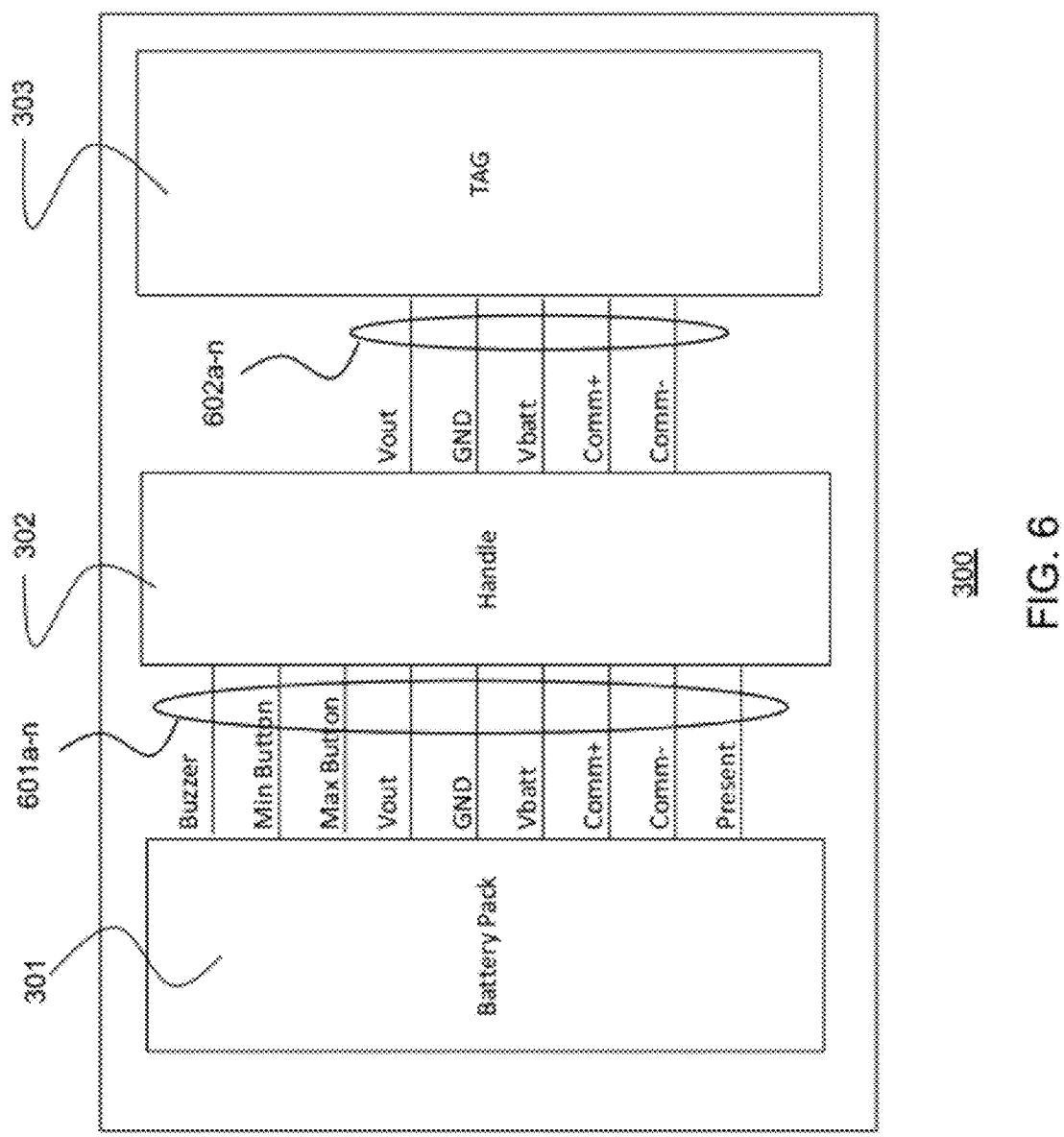

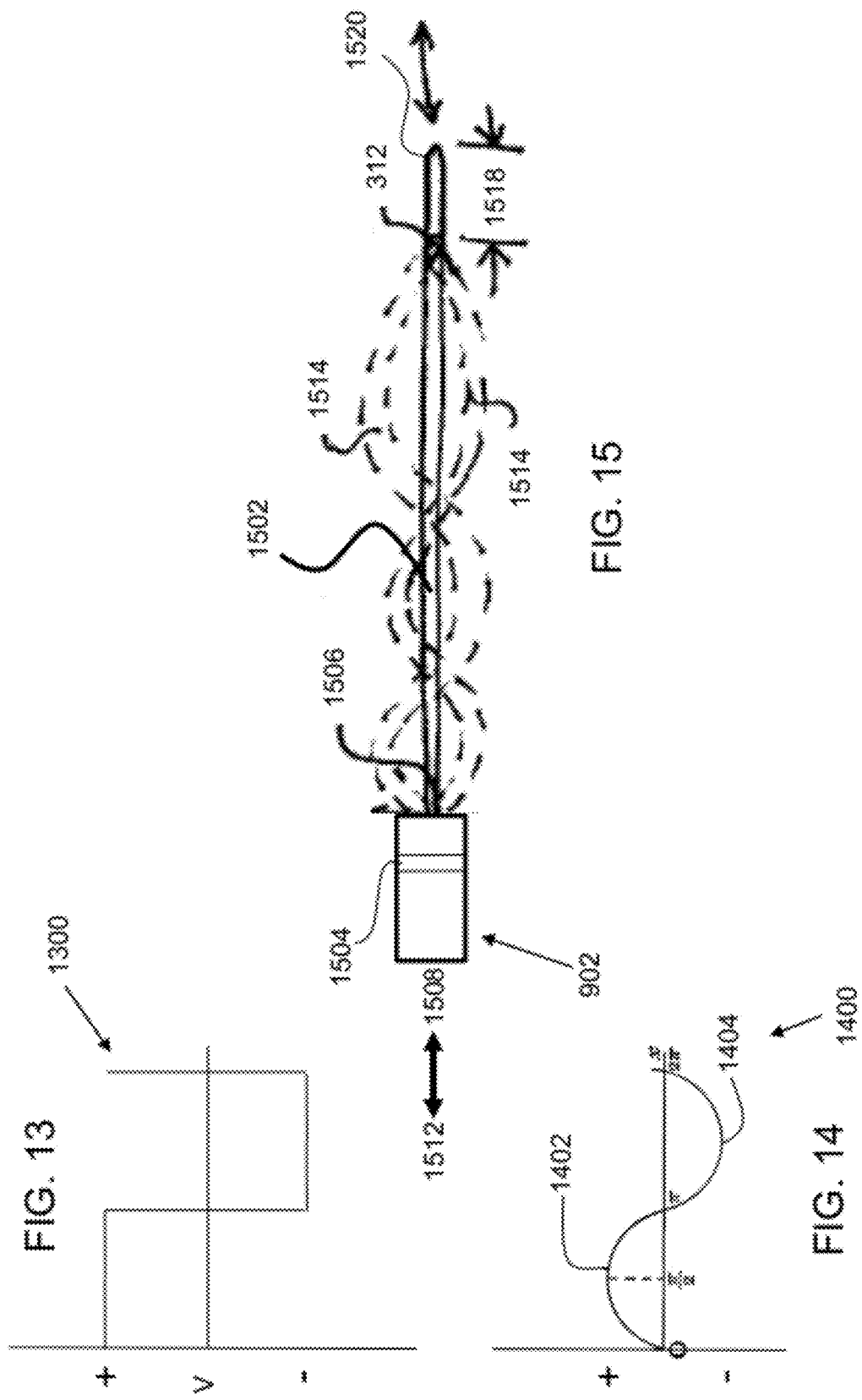

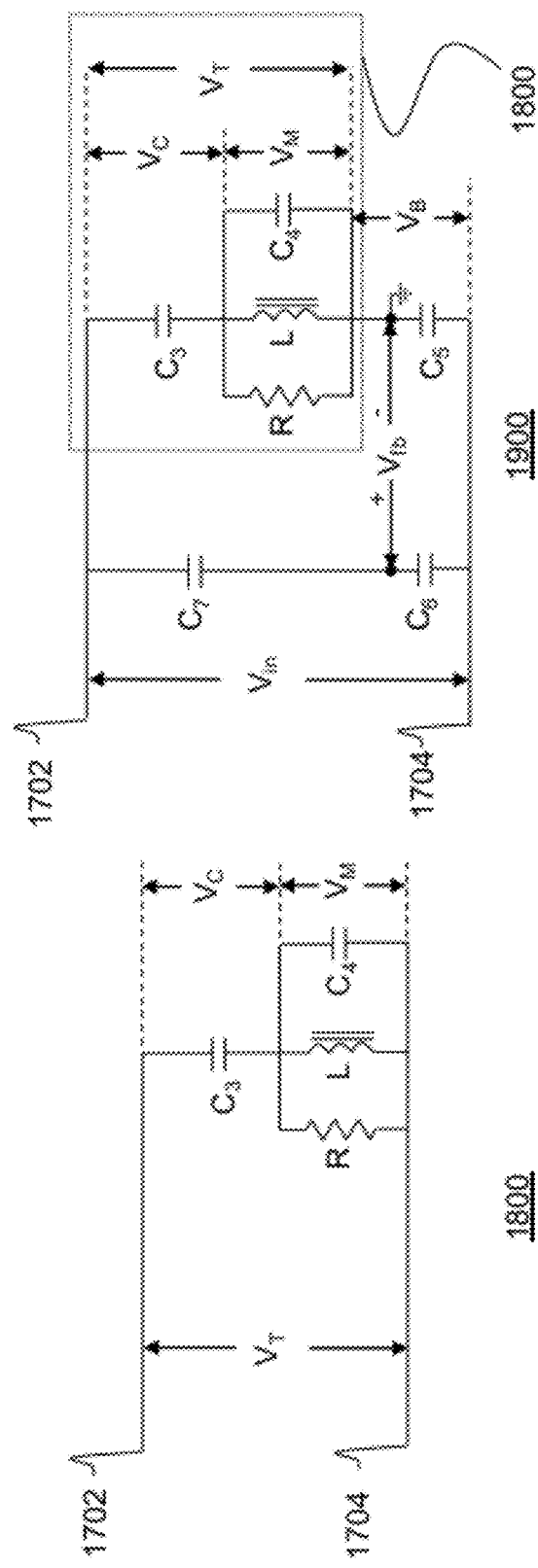

2300

2400

2500

Chart showing check valve opening event stages
X-axis is pressure
Y-axis is Flow

303

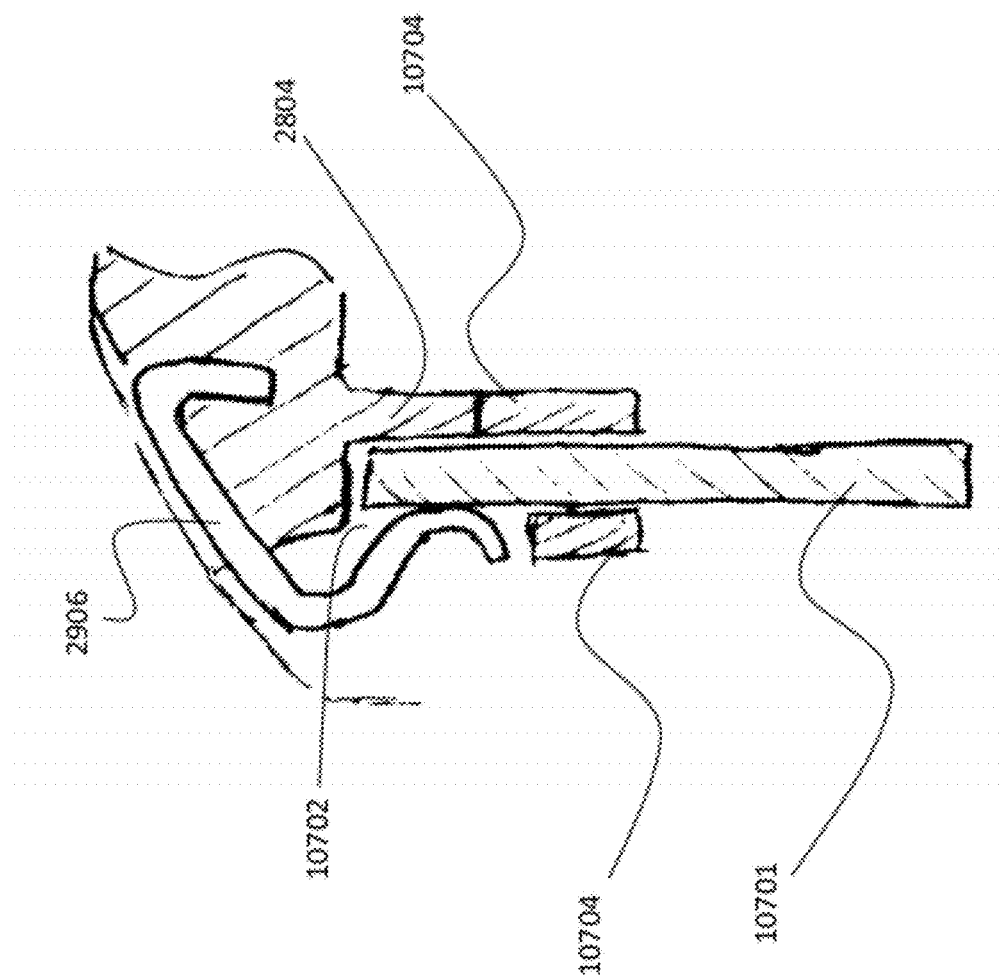

| Gain constant: | $G_0$ | $G_1$ | $G_2$ | $G_n$ | | $G_n$ | $G_1$ | $G_0$ |
|---|---|---|---|---|---|---|---|---|
| | |----------|----------|---...---|----------|----------|---...---|----------| |
| Percent away from $I_{ref}$: | 50% | 45% | 40% | ... 5% | $I_{ref}$ | -5% | -10% | -15% |

FIG. 111

| Gain constant: | $PID_0$ | $PID_1$ | $PID_2$ | $PID_3$..$PID_n$ | $PID_n$..$PID_3$ | $PID_2$ | $PID_1$ | $PID_0$ |
|---|---|---|---|---|---|---|---|---|
| Driving frequency: | $f_{min}$ | | | | $f_{res}$ | | | $f_{max}$ |
| Phase (sine func.; 90° shift): | +1 | +0.6 | +0.4 | +0.1 +.03 | 0 -0.2 -0.4 | -0.6 | -0.8 | -1 |

FIG. 112

BATTERY-POWERED HAND-HELD ULTRASONIC SURGICAL CAUTERY CUTTING DEVICE

CROSS-REFERENCE TO RELATED APPLICATIONS

This application:
claims the priority, under 35 U.S.C. §119, of U.S. Provisional Patent Application Ser. No. 61/476,022, filed Apr. 15, 2011;
is a continuation-in-part of U.S. patent application Ser. No. 13/215,971, filed on Aug. 23, 2011 (which application claims the priority, under 35 U.S.C. §119, of U.S. Provisional Patent Application Ser. No. 61/376,983, filed Aug. 25, 2010);
is a continuation-in-part of U.S. patent application Ser. Nos. 13/022,707 and 13/022,743, filed on Feb. 8, 2011;
is a continuation-in-part of U.S. patent application Ser. Nos. 12/868,505 and 12/868,545 filed Aug. 25, 2010 (which applications claim priority to U.S. Provisional Application Ser. No. 61/236,934, filed on Aug. 26, 2009);
is a continuation-in-part of U.S. patent application Ser. No. 12/547,898, now U.S. Pat. No. 8,061,014; Ser. Nos. 12/547,975; and 12/547,999, all filed on Aug. 26, 2009;
is a continuation-in-part of U.S. patent application Ser. Nos. 13/072,187; 13/072,247; 13/072,273; 13/072,221; 13/072,309; 13/072,345; and 13/072,373, all filed on Mar. 25, 2011;
is a continuation-in-part of:
   U.S. patent application Ser. Nos. 12/266,101; 12/266,146; 12/266,226; 12/266,252; and 12/266,320, all filed on Nov. 6, 2008;
   U.S. patent application Ser. No. 12/266,664, filed on Nov. 7, 2008;
   U.S. patent application Ser. Nos. 12/269,544 and 12/269,629, filed on Nov. 12, 2008; and
   U.S. patent application Ser. No. 12/270,146, filed on Nov. 13, 2008,
   (which applications each claim priority to U.S. Provisional Application Ser. Nos. 60/991,829, filed on Dec. 3, 2007; 60/992,498, filed on Dec. 5, 2007; 61/019,888, filed on Jan. 9, 2008; 61/045,475, filed on Apr. 16, 2008; 61/048,809, filed on Apr. 29, 2008; and 61/081,885, filed on Jul. 18, 2008),
the entire disclosures of which are all hereby incorporated by reference in their entireties.

BACKGROUND OF THE INVENTION

1. Field of the Invention

The present invention relates generally to an ultrasonic cutting device and, more particularly, relates to a battery-powered, hand-held, ultrasonic surgical cautery cutting device.

2. Description of the Related Art

Ultrasonic instruments are effectively used in the treatment of many medical conditions, such as removal of tissue and cauterization of vessels. Cutting instruments that utilize ultrasonic waves generate vibrations with an ultrasonic transducer along a longitudinal axis of a cutting blade. By placing a resonant wave along the length of the blade, high-speed longitudinal mechanical movement is produced at the end of the blade. These instruments are advantageous because the mechanical vibrations transmitted to the end of the blade are very effective at cutting organic tissue and, simultaneously, coagulating the tissue using the heat energy produced by the ultrasonic frequencies. Such instruments are particularly well suited for use in minimally invasive procedures, such as endoscopic or laparoscopic procedures, where the blade is passed through a trocar to reach the surgical site.

For each kind of cutting blade (e.g., length, material, size), there are one or more (periodic) driving signals that produce a resonance along the length of the blade. Resonance results in movement of the blade tip, which can be optimized for improved performance during surgical procedures. However, producing an effective cutting-blade driving signal is not a trivial task. For instance, the frequency, current, and voltage applied to the cutting tool must all be controlled dynamically, as these parameters change with the varying load placed on the blade and with temperature differentials that result from use of the tool.

FIG. 1 shows a block schematic diagram of a prior-art circuit used for applying ultrasonic mechanical movements to an end effector. The circuit includes a power source 102, a control circuit 104, a drive circuit 106, a matching circuit 108, a transducer 110, and also includes a handpiece 112, and a waveguide 114 secured to the handpiece 112 (diagrammatically illustrated by a dashed line) and supported by an outer, tubular cannula 120. The waveguide 114 terminates into a blade 116 at a distal end. A clamping mechanism 118, is part of the overall end effector and exposes and enables the blade portion 116 of the waveguide 114 to make contact with tissue and other substances. Commonly, the clamping mechanism 118 is a pivoting arm that acts to grasp or clamp onto tissue between the arm and the blade 116. However, in some devices, the clamping mechanism 118 is not present.

The drive circuit 106 produces a high-voltage self-oscillating signal. The high-voltage output of the drive circuit 106 is fed to the matching circuit 108, which contains signal-smoothing components that, in turn, produce a driving signal (wave) that is fed to the transducer 110. The oscillating input to the transducer 110 causes the mechanical portion of the transducer 110 to move back and forth at a magnitude and frequency that sets up a resonance along the waveguide 114. For optimal resonance and longevity of the resonating instrument and its components, the driving signal applied to the transducer 110 should be as smooth a sine wave as can practically be achieved. For this reason, the matching circuit 108, the transducer 110, and the waveguide 114 are selected to work in conjunction with one another and are all frequency sensitive with and to each other; this can be referred to as being matched or tuned.

Because a relatively high-voltage (e.g., 100 V or more) is required to drive a typical piezoelectric transducer 110, the power source that is available and is used in all prior-art ultrasonic cutting devices is an electric mains (e.g., a wall outlet) of, typically, up to 15 A, 120 VAC. Therefore, all known ultrasonic surgical cutting devices resemble that shown in FIGS. 1 and 2 and utilize a countertop box 202 with an electrical cord 204 to be plugged into the electrical mains 206 for supply of power. Resonance is maintained by a phase locked loop (PLL), which creates a closed loop between the output of the matching circuit 108 and the drive circuit 106. For this reason, in prior art devices, the countertop box 202 always has contained all of the drive and control electronics 104, 106 and the matching circuit(s) 108. A typical retail price for such boxes is in the thousands of dollars.

A supply cord 208 delivers a sinusoidal waveform from the box 202 to the transducer 110 within the handpiece 112 and, thereby, to the waveguide 114. The prior art devices present a great disadvantage because the cord 208 has a length, size, and weight that restricts the mobility of the operator/surgeon. The cord 208 creates a tether for the operator and presents an obstacle for the operator and those around him/her during any surgical procedure using the handpiece 112. In addition, the cord must be shielded and durable and, therefore, is very expensive. Finally, because the box 202 is not sterilized, both the box 202 and the supply cord 208 must be cleaned and maintained in a sterile condition for use in a surgical environment.

Another disadvantage exists in the prior art due to the frequency sensitivity of the matching circuit 108, the transducer 110, and the waveguide 114. By having a phase-locked-loop feedback circuit between the output of the matching circuit 108 and the drive circuit 104, the matching circuit 108 has always been located in the box 202, near the drive circuit 108, and separated from the transducer 110 by the length of the supply cord 208. This architecture introduces transmission losses and electrical parasitics, which are common products of ultrasonic-frequency transmissions.

In addition, prior-art devices attempt to maintain resonance at varying waveguide 114 load conditions by monitoring and maintaining a constant current applied to the transducer (when operating with series resonance). However, without knowing the specific load conditions, the only predictable relationship between current applied to the transducer 110 and amplitude is at resonance (in some instances herein, amplitude is sometimes referred to as displacement when the term relates to the mechanical output). Therefore, despite a constant current being applied, the amplitude of the wave along the waveguide 114 may not be constant across all frequencies. When prior art devices are under load, therefore, operation of the waveguide 114 is not guaranteed to be at resonance and, because only the current is being monitored and held constant, the amount of movement on the waveguide 114 can vary greatly. For this reason, maintaining constant current is not an effective way of maintaining a constant movement of the waveguide 114.

Furthermore, in the prior art, handpieces 112 and transducers 110 are replaced after a finite number of uses, but the box 202, which is vastly more expensive than the handpiece 112, is not replaced. As such, introduction of new, replacement handpieces 112 and transducers 110 frequently causes a mismatch between the frequency-sensitive components (108, 110, and 112), thereby disadvantageously altering the frequency introduced to the waveguide 114. The only way to avoid such mismatches is for the prior-art circuits to restrict themselves to precise frequencies. This precision brings with it a significant increase in cost.

Therefore, a need exists to overcome the problems associated with the prior art, for example, those discussed above.

SUMMARY OF THE INVENTION

Briefly, in accordance with exemplary embodiments, the present invention includes a battery-powered device that produces high frequency mechanical motion at the end of a waveguide for performing useful work, specifically, to cut and seal tissue during surgery. A piezoelectric transducer is used to convert electrical energy into the mechanical energy that produces the motion at the end of the waveguide. Particularly, when the transducer and waveguide are driven at their composite resonant frequency, a large amount of mechanical motion is produced. The circuit components of the present invention include, among others, a battery power supply, a control circuit, a drive circuit, and a matching circuit—all located within a handpiece of the ultrasonic cutting device and all operating and generating waveforms from battery voltages. The components are selected to convert electrical energy from the battery power supply into a high voltage AC waveform that drives the transducer. Ideally, the frequency of this waveform is substantially the same as the resonant frequency of the waveguide and transducer. The magnitude of the waveform is selected to be a value that produces the desired amount of mechanical motion.

Advantageously, the present invention, according to several embodiments, allows components of the device to be removed, replaced, serviced, and/or interchanged. Some components are "disposable," which, as used herein, means that the component is used for only one procedure and is then discarded. Still other components are "reusable," which, as used herein, means that the component can be sterilized according to standard medical procedures and then used for at least a second time. As will be explained, other components are provided with intelligence that allows them to recognize the device to which they are attached and to alter their function or performance depending on several factors.

The invention provides a cordless hand-held ultrasonic cautery cutting device that overcomes the hereinafore-mentioned disadvantages of the heretofore-known devices and methods of this general type and that allows disposal of inexpensive components but permits advantageous reuse of costlier components that are significantly cheaper than prior art reusable components.

Although the invention is illustrated and described herein as embodied in a cordless, battery-powered, hand-held, ultrasonic, surgical, cautery cutting device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

While the specification concludes with claims defining the features of the invention that are regarded as novel, it is believed that the invention will be better understood from a consideration of the following description in conjunction with the drawing figures, in which like reference numerals are carried forward. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. The figures of the drawings are not drawn to scale.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention.

DETAILED DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 is a diagrammatic illustration of components of a prior-art ultrasonic cutting device with separate power, control, drive and matching components in block-diagram form.

FIG. 2 is a diagram illustrating the prior-art ultrasonic cutting device of FIG. 1.

FIG. 6 is a schematic block diagram of a cordless, battery-powered, hand-held, ultrasonic, surgical, cautery cutting device in accordance with an exemplary embodiment of the present invention.

FIG. 13 is graph illustrating a square waveform input to a matching circuit in accordance with an exemplary embodiment of the present invention.

FIG. 14 is graph illustrating a sinusoidal waveform output from a matching circuit in accordance with an exemplary embodiment of the present invention.

FIG. 15 is a diagrammatic illustration of the affect that a resonant sine wave input to a transducer has on a waveguide of the ultrasonic cutting device in accordance with an exemplary embodiment of the present invention with the sinusoidal pattern shown representing the amplitude of axial motion along the length of the waveguide.

FIG. 18 is a fragmentary, schematic circuit diagram of an elemental parallel circuit model of a transducer in accordance with an exemplary embodiment of the present invention.

FIG. 19 is fragmentary, schematic circuit diagram of an inventive circuit with the circuit of FIG. 18 and is useful for monitoring the motional current of a transducer in accordance with an exemplary embodiment of the present invention.

FIG. 107 is a fragmentary, enlarged, cross-sectional view of a portion of the battery assembly of FIG. 4 exposing an underside of a multi-lead battery terminal and an interior of a shell half in accordance with an alternative exemplary embodiment of the present invention in which a card edge connector is used to connect the contacts of the multi-lead battery terminal to one or more circuit boards.

FIG. 111 is a table of an exemplary non-linear PID control loop or algorithm in accordance with the present disclosure.

FIG. 112 is a table of another exemplary non-linear, asymmetric PID loop or algorithm in accordance with the present disclosure.

DETAILED DESCRIPTION OF THE EMBODIMENTS

Figure 3:
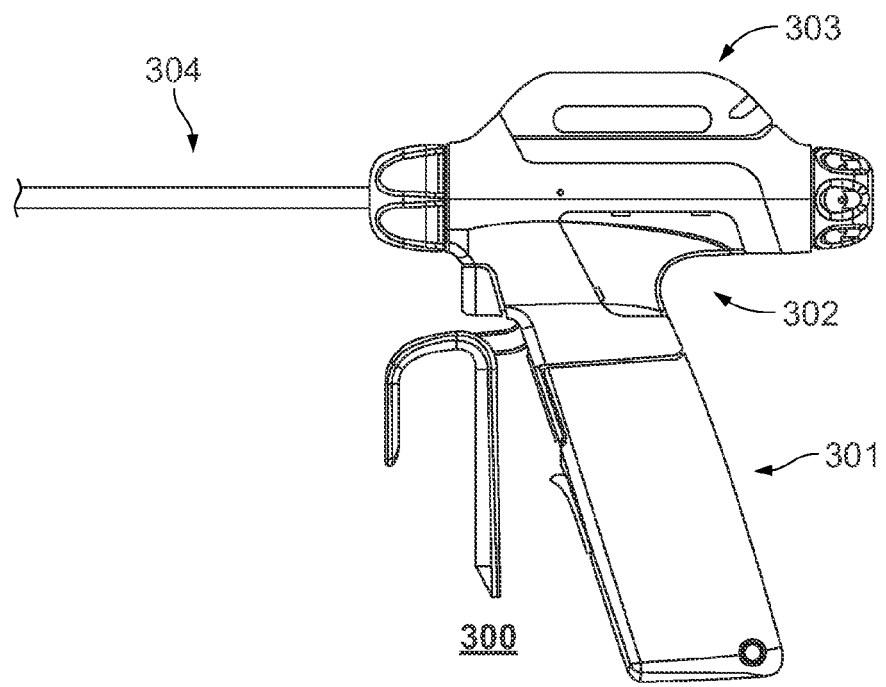
FIG. 3 is an elevational view of a left side of an ultrasonic surgical cautery assembly in accordance with an exemplary embodiment of the present invention.

It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

Before the present invention is disclosed and described, it is to be understood that the terminology used herein is for the purpose of describing particular embodiments only and is not intended to be limiting. In this document, the terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described.

It will be appreciated that embodiments of the invention described herein may be comprised of one or more conventional processors and unique stored program instructions that control the one or more processors to implement, in conjunction with certain non-processor circuits and other elements, some, most, or all of the functions of ultrasonic cutting devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

The present invention, according to one embodiment, overcomes problems with the prior art by providing a lightweight, hand-held, cordless, battery-powered, surgical cautery cutting device that is powered by and controlled with components that fit entirely within a handle of the device—the set-top box and the shielded cord are entirely eliminated. The hand-held device allows a surgeon to perform ultrasonic cutting and/or cauterizing in any surgical procedure without the need for external power and, particularly, without the presence of cords tethering the surgeon to a stationary object and constricting the range of movement of the surgeon while performing the surgical procedure.

Ultrasonic Surgical Device

Described now is an exemplary apparatus according to one embodiment of the present invention. Referring to FIG. 3, an exemplary cordless ultrasonic surgical cautery assembly 300 is shown. The inventive assembly 300 can be described as including three main component parts: (1) a battery assembly 301; (2) a handle assembly 302 with an ultrasonic-cutting-blade-and-waveguide assembly 304 (only a proximal portion of which is illustrated in FIG. 3; see FIG. 8); and (3) a transducer-and-generator ("TAG") assembly 303. The handle assembly 302 and the ultrasonic-cutting-blade-and-waveguide assembly 304 are pre-coupled but rotationally independent from one another. The battery assembly 301, according to one exemplary embodiment, is a rechargeable, reusable battery pack with regulated output. In some cases, as is explained below, the battery assembly 301 facilitates user-interface functions. The handle assembly 302 is a disposable unit that has bays or docks for attachment to the battery assembly 301, the TAG assembly 303, and the ultrasonic-cutting-blade-and-waveguide assembly 304. The handle assembly 302 also houses various indicators including, for example, a speaker/buzzer and activation switches.

The TAG assembly 303 is a reusable unit that produces high frequency mechanical motion at a distal output. The TAG assembly 303 is mechanically coupled to the ultrasonic-cutting-blade-and-waveguide assembly 304 and, during operation of the device, produces movement at the distal output of the ultrasonic-cutting-blade-and-waveguide assembly 304, i.e., the cutting blade. In one embodiment, the TAG assembly 303 also provides a visual user interface, such as, through a red/green/blue (RGB) LED or other display. As such, a visual indicator of the battery status is uniquely not located on the battery and is, therefore, remote from the battery.

The present invention's ability to provide all of the necessary components of an ultrasonic cutting tool in a hand-held package provides a great advantage over prior-art devices, which devices house substantially all of the device components within a very expensive and heavy desktop box 202, as shown in FIG. 2, and include an expensive tether 208 between the device's handpiece 112 and the desktop box 202, which, most significantly, is bulky and interferes with the surgeon's movements. Furthermore, the cord 208 must transit between the sterile field, where the device is present, and the non-sterile area where the generator rests. This sterile-to-non-sterile connection increases the risk of contamination of the sterile field and blurs the boundary between sterile and non-sterile.

Figure 4:
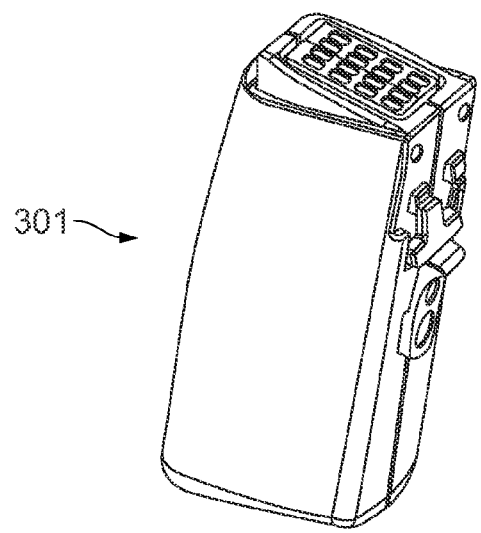
FIG. 4 is a perspective view from above a corner of a battery assembly in accordance with an exemplary embodiment of the present invention.
Figure 5:
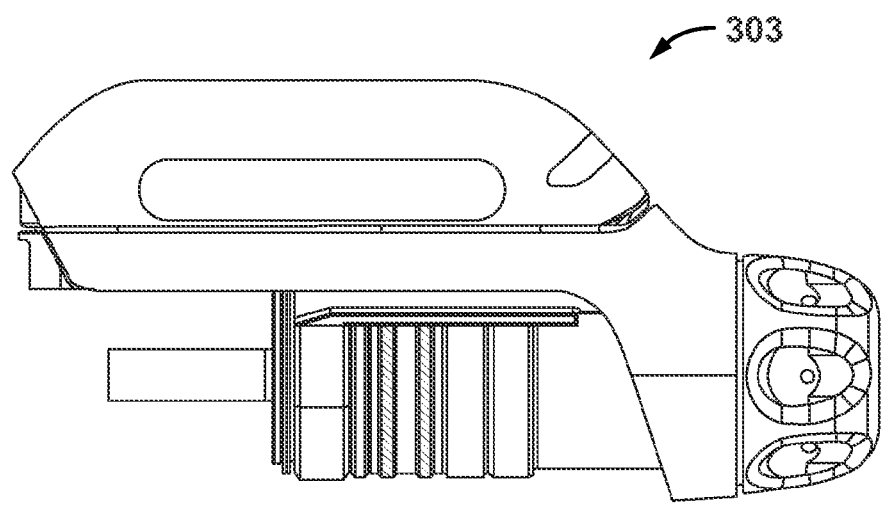
FIG. 5 is an elevational left side view of a transducer and generator ("TAG") assembly in accordance with an exemplary embodiment of the present invention.

In accordance with the present invention, the three components of the handheld ultrasonic surgical cautery assembly 300 are advantageously quickly disconnectable from one or more of the others. Each of the three components of the system is sterile and can be maintained wholly in a sterile field during use. Because each portion can be separated from one or more of the other components, the present invention can be composed of one or more portions that are single-use items (i.e., disposable) and others that are multi-use items (i.e., sterilizable for use in multiple surgical procedures). FIGS. 4 and 5 show the battery assembly 301 and TAG assembly 303 components, respectively, separate from the overall composite assembly shown in FIG. 3. The details of each of the components are shown and described throughout the remainder of the specification. These details include, inter alia, physical aspects of each component separate and as part of the handheld ultrasonic surgical cautery assembly 300, electronic functionality and capability of each component separate and as part of the overall assembly 300, and methods of use, assembly, sterilization, and others of each component separate and as part of the overall assembly 300. In accordance with an additional embodiment of the present invention, each of the components 301, 302/304, 303 is substantially equivalent in overall weight; each of these components 301, 302/304, 303 is balanced so that they weigh substantially the same. The handle 302 overhangs the operator's hand for support, allowing the user's hand to more freely operate the controls of the device without bearing the weight. This overhang is set to be very close to the center of gravity. This, combined with a triangular assembly configuration, makes the overall handheld ultrasonic surgical cautery assembly 300 advantageously provided with a center of balance that provides a very natural and comfortable feel to the user operating the device. That is, when held in the hand of the user, the overall assembly 300 does not have a tendency to tip forward or backward or side-to-side, but remains relatively and dynamically balanced so that the waveguide is held parallel to the ground with very little effort from the user. Of course, the instrument can be placed in non-parallel angles to the ground just as easily.

FIG. 6 provides a general block circuit diagram illustrating the communicative coupling between the battery assembly 301, the handle assembly 302, and the TAG assembly 303. FIG. 6 also shows various power and communication signal paths 601a-n between the battery assembly 301 and the handle assembly 302. The handle assembly 302 provides additional power and communication signal paths 602a-n that continue on to the TAG assembly 303. These power and communication signal paths 601a-n facilitate operation, to name a few, of:

1. a buzzer, e.g., audio frequency signal, which provides an audible user interface;
2. a minimum button, e.g., 0 to 3.3 V and 0 to 25 mA input signal, which is a user interface to activate ultrasound output at minimum displacement;
3. a maximum button, e.g., 0 to 3.3 V and 0 to 25 mA, which is a user interface to activate ultrasound output at maximum displacement;
4. a first output voltage (Vout), e.g., 0 to 10 Volt and 0 to 6 A output, from the battery assembly 301 to the TAG assembly 303 and provides power to the TAG assembly 303 to generate a transducer drive signal;
5. a ground or system common connection;
6. a second output voltage (Vbatt), which is a voltage output from battery for providing power for the system;
7. a first communication line (Comm+), which provides differential half duplex serial communications between the battery assembly 301 and the TAG assembly 303;
8. a second communication line (Comm−), which provides differential half duplex serial communications between the battery assembly 301 and the TAG assembly 303; and
9. a present line, which, when connected to the handle assembly 302, activates power in the battery assembly 301 and, thereby, to the entire system.

In accordance with an embodiment of the present invention, the above-described power and communication signal paths 601a-n are provided through a flex circuit that spans between a first multi-lead handle terminal assembly on the handle assembly 302 (where the battery assembly 301 electrically couples to the handle assembly 302) and a second multi-lead handle terminal assembly on the handle assembly 302 (where the TAG assembly 303 electrically couples to the handle assembly 302). Thus, the flex circuit electrically connects the battery assembly 301 to the TAG assembly 303.

I. Battery Assembly

Figure 7:
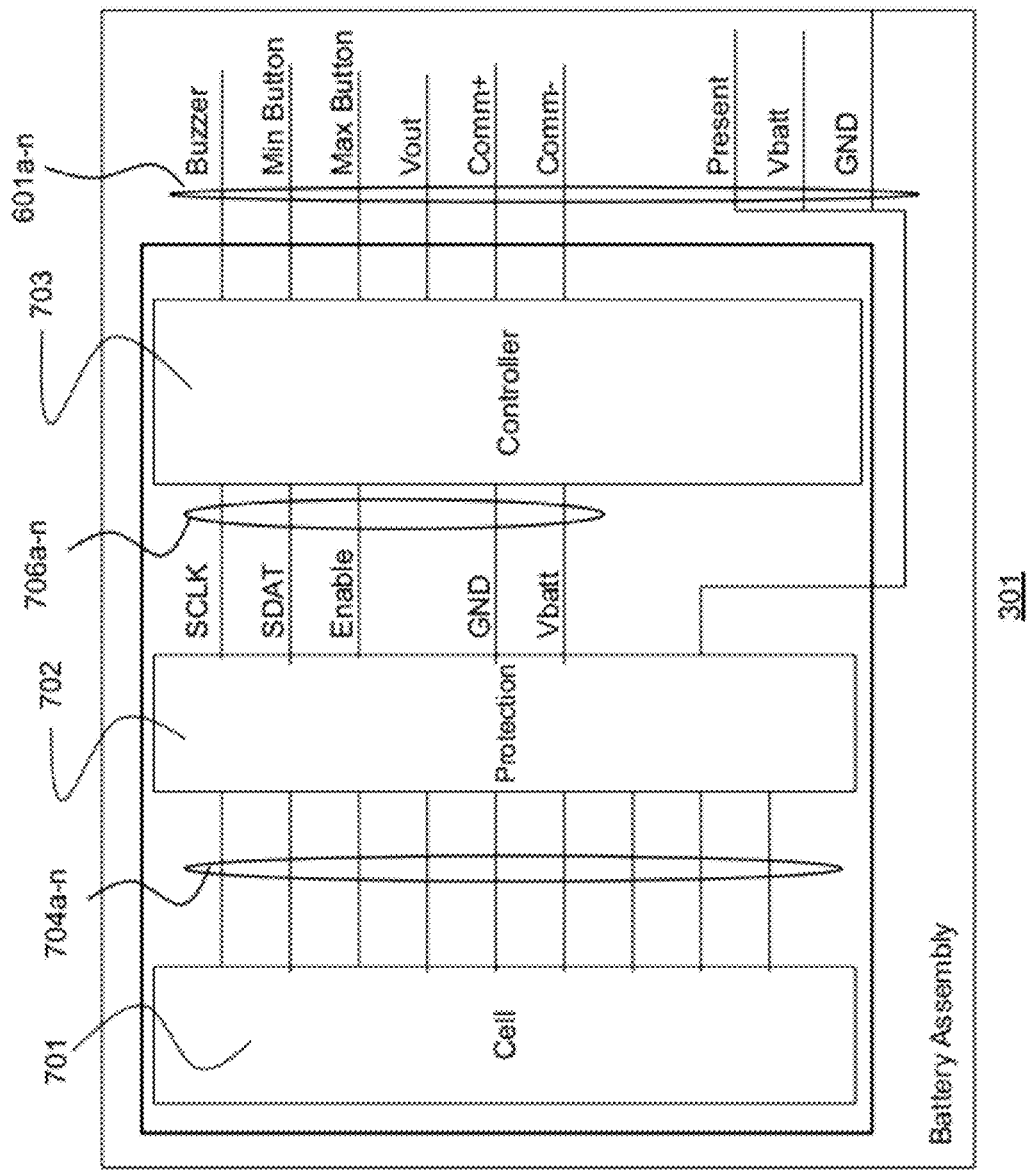
FIG. 7 is a schematic block diagram of a battery assembly of the device of FIGS. 3 and 4 in accordance with an exemplary embodiment of the present invention.

FIG. 7 provides a general block circuit diagram illustrating battery assembly 301 and internal components included therein. The battery assembly 301 generally includes one or more battery cells 701, a battery protection circuit 702, and a battery controller 703. Various power and signal paths 704a-n run between the battery cells 701 and the battery protection circuit 702. Power and communication signal paths 706a-n run between the battery protection circuit 702 and the battery controller 703. The power and signal paths 704a-n and 706a-n can be simple direct connections between components or can include other circuit elements not shown in the figures. The power and communication signal paths 706a-n include, among others:

1. a SMBus clock signal (SCLK), which is used for communications between the battery controller 703 and the battery fuel gauge/protection circuit 702;
2. a SMBus data signal (SDAT), which is used for communications between the battery controller 703 and the battery fuel gauge/protection circuit 702; and
3. an enable switch that turns off the battery controller 703 when the battery assembly 301 is in a charger by removing power to the switching power supply within the battery controller 703 once grounded.

a. Battery Cells

The battery cells 701 include, in one embodiment, a 4-cell lithium-ion polymer (LiPoly) battery. There is, of course, no limit to the number of cells that can be used and no requirement that the cells be of the LiPoly type. Advantageously, manufacturers can produce LiPoly batteries in almost any shape that is necessary. These types of batteries, however, must be carefully controlled during the charging process, as overcharging LiPoly batteries quickly causes damages to the cells. Therefore, these batteries must be charged carefully. For this reason, the present invention utilizes an inventive battery protection circuit 702.

b. Battery Protection

The battery protection circuit 702 controls charging and discharging of the battery cells 701 and provides battery protection and "fuel gauge" functions, i.e., battery power monitoring. More particularly, the battery protection circuit 702 provides over-voltage, under-voltage, over-temperature, and over-current monitoring and protection during both the charging and discharging stages. If overcharged, LiPoly batteries cannot only be damaged but can also ignite and/or vent. The battery protection circuit 702 provides multiple levels of protection. For example, the battery protection circuit could provide a triple level of protection for each of current, voltage and temperature. The protection is redundant and uses active components for the first and second levels of protection, and uses passive or redundant components for the higher third level of protection. In one example, the multiple levels of protection provided by the battery protection circuit may utilize components that join the battery cells together, such as PTC devices, thermal fuses, current fuses, and resettable elements.

The "fuel gauge" function of the battery protection circuit 702 limits the discharge of voltage and current, both continuous and transient, on the output of the battery assembly 301. During charging of the battery cells 701, the fuel gauge can limit the current level fed to the battery cells 701. Alternatively, a battery charging unit can perform this current-limiting function. The fuel gauge also monitors temperature and shuts down the battery assembly 301 when a temperature of the battery cells 701 exceeds a given temperature. The fuel gauge is further able to determine how much total energy is left in the battery cells 701, to determine how much previous charge has been received, to determine an internal impedance of the battery cells 701, to determine current and voltage being output, and more. By using this data, the present invention, through use of inventive algorithms, is able to determine the "State-of-Charge" (SOC) of the battery cells 701 based in part on the chemical attributes of the battery cells 701 and, in particular, to identify when there is not enough battery capacity to safely perform a surgical procedure as described in further detail below. The system has been programmed to include information regarding how much energy is needed to complete one cutting and cautery procedure safely. With that information stored, the fuel gauge compares that minimum amount of energy needed to the current state of charge of the battery when initially powered to begin a cut/cauterization or at a time during a procedure when a new cut/cauterization is to be performed. If the minimum threshold is not met (e.g., 1000 joules), then the device is not permitted to continue operating.

Furthermore, in order to ensure maximum energy delivery, efficiency and prevent overcharging of individual cells in the battery pack, it is important to verify that the State-of-Charge of all the cells is equal. A good indicator of the SOC is the cell voltage. Thus, during charging, cell voltage is monitored and the amount of current delivered to each cell is adjusted until the voltage of all cells is equalized. At this point, the cells are balanced.

In addition, a thermistor may be installed in the battery pack and located adjacent the battery cells (e.g., either in between two cells, in between all adjacent cells, or next to cells on any side) to provide an external device (e.g., a battery charger) with a measurement or way to monitor the cell temperature within the battery pack.

c. Battery Controller

Figure 11:
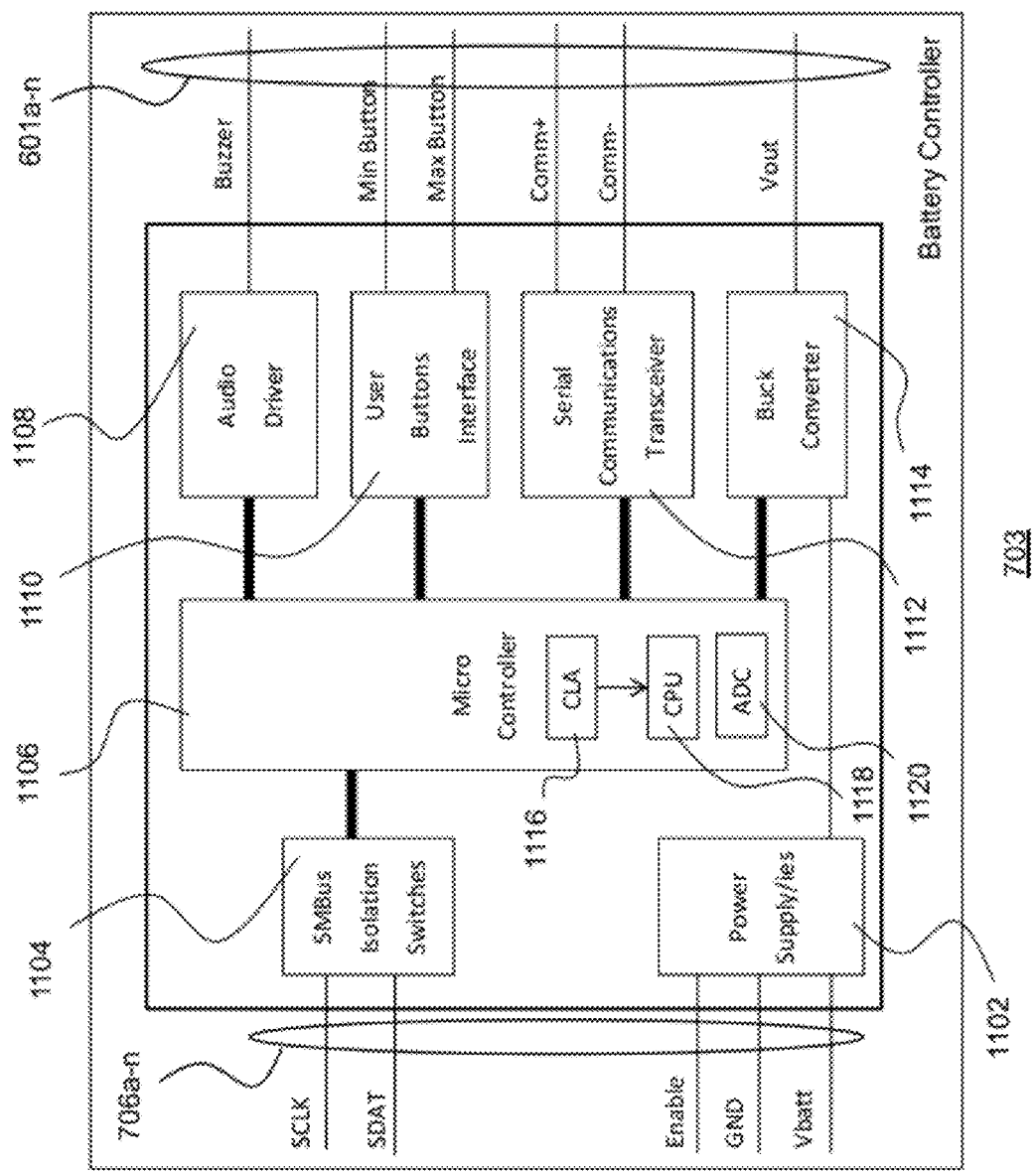
FIG. 11 is a schematic block diagram of the battery controller of the device of FIGS. 3 and 4 in accordance with an exemplary embodiment of the present invention.

FIG. 11 is a general block circuit diagram illustrating the internal components of the battery controller 703 of FIG. 7. As previously shown in FIG. 7, the battery controller 703 is fed signals and powered through power and communication signal paths 706*a-n*. Additionally, the battery controller 703 also provides output power and signals along power and communication signal paths 601*a-n*. The battery controller 703, according to one exemplary embodiment of the present invention, includes a power supply 1102, SMBus isolation switch(es) 1104, a microcontroller 1106, an audio driver 1108, a user buttons interface 1110, a serial communications transceiver 1112, and a buck converter 1114.

The power supply 1102 is composed of two subsystems: a buck switching power supply that first reduces the unregulated cell voltage to a substantially constant direct-current voltage, e.g., 4 VDC. A second linear power supply steps down and regulates the direct-current voltage to a level that is required by the low voltage components used in this device, e.g., 3.3 VDC. This two-step voltage reduction is implemented to ensure low battery consumption. Switching power supplies are inherently efficient, as compared to the traditional linear power supplies, but they tend to produce large output voltage ripple (noise), which could be problematic. Therefore, the voltage is first stepped down using an efficient switching regulator and is then fed to a linear regulator, which produces a better filtered and noise-free voltage to the digital components of the circuit. The output from the switching regulator is also used to feed the audio amplifier, which requires larger voltages and tends to generate additional noise—which is undesirable in the digital section of the circuit.

The SMBus isolation switches 1104 (also referred to as relays) are provided as a way to prevent voltages originating from the operation of the battery protection and charge control circuit, which is ON during the charge process, to be fed into the rest of the battery circuit, which is OFF during the charge process. In an exemplary embodiment, the switches used are optically driven and turned on by the PRESENT circuit in the device (see 601*a-n*).

Microcontroller 1106 is a highly-integrated processing unit that controls the functions of the battery controller 703. In an exemplary embodiment, the microcontroller 1106 stores and executes the software that allows operation of the device. Given the computational demand imposed by the operation of the device, the microcontroller 1106 is state of the art, for example, including two independent microcontroller cores in one package. In this embodiment, a main core runs a main program, which controls the device. When the device is activated, sampling of the various parameters required to ensure proper and efficient operation are monitored by a second core, for example, the Control Law Accelerator (CLA) 1116, shown in FIG. 11. The CLA also can be used to provide proportional-integral-derivative ("PID") control loop operation, which is very computationally demanding. This configuration, therefore, effectively allows one core of the device to run a state machine at very high speeds to maintain full and immediate control of the system while, at the same time, the second core handles the demanding computations of gathering data and handling the control loop. Preferably, the microcontroller 1106 lends itself to low power consumption applications and, therefore, a 3.3 volt unit can be used. Internal oscillators allow device startup without the need of external (and power consuming) components. The microcontroller 1106 can also be configured to have its own internal non-volatile memory section to store program and diagnostic information. The battery microcontroller 1106 monitors input voltage, output voltage, output current, and the battery and buck temperatures to provide total control of the voltage converter functions.

Audio driver 1108 produces a signal that ultimately drives the buzzer 802 that is located in the handle assembly 302. In an exemplary embodiment, the audio driver 1108 is a simple, but powerful, two-stage class A square wave amplifier. The amplifier is fed directly from the buck switching power supply (e.g., 4 VDC) to ensure maximum power capability. The amplifier is able to drive an audio speaker (no internal driver). Feeding the audio driver 1108 from the buck switching power supply also insures that noise generated by the audio amplifier is not fed to the supply rail of the digital and analog components of the device, which ensures noise-free operation. Capability to regulate volume by changing a single resistor is provided in case adjustment is necessary.

The user buttons interface 1110 conditions the signals received from the minimum 804 and maximum 806 activation switches housed within the handle assembly 302. In an exemplary embodiment, the user buttons interface 1110 is operable to continuously measure impedance of the activation switches to prevent false activation, for example, in the case of fluid ingress at the button. The battery controller 703 measures the impedance of the switch(es) and will not activate the system until the impedance detected falls below a predetermined threshold. This configuration eliminates accidental activations due to fluid ingress, which are generally detected as higher impedances in the switch(es) than that of a fully closed switch. The PRESENT line works on a similar principle, ensuring that the PRESENT line is closed through a low enough impedance before the battery is turned on. This is done so that exposure of the PRESENT pin to any conducting fluid will not accidentally turn on the battery pack. The user buttons interface 1110 operates in this exemplary embodiment by injecting a known current level through the switch lines. When the button is open (no activation) the current source will maximize its voltage output and this voltage is measured by the microcontroller 1106. When the switch is closed, the current source will adjust its voltage output to generate its target programmed current. If the button is working at optimally low impedance, the voltage output will be low. However, in the case where fluid enters the button, the impedance seen by the current source will be high, and a proportionally equivalent voltage, higher than that generated for a closed button, will indicate to the microcontroller 1106 that activation should not occur.

The exemplary embodiment of the circuitry is equipped with a calibrated current source, which can be used to calibrate the programmable current source during startup and to provide a tighter detection window. This calibration that occurs during the device startup narrows the window or impedance range in which a positive activation is detected. The calibration is performed by switching the circuitry of the impedance circuit to a precision current source and measuring the voltage to calibrate the circuit. During the device startup procedure, the battery controller can self-calibrate the activation button impedance detection circuitry to reduce the impedance range required to discern between a true button closure (activation) and an inadvertent activation signal that is erroneously caused by fluid contamination of the button(s).

Activation button impedance is measured by flowing a pre-determined current level through the button lines using a current source. By measuring the voltage across the contacts, Ohm's Law (i.e. R=V/I) can be used to determine the resistance in the line. During calibration, two analog switches are used. The first switch connects the microcontroller serial communication lines to the programmable current source to be able to control the current source. The second switch connects the output of the current source to a set of precision resistors. The current flow is adjusted by the microcontroller until a given voltage measurement (i.e. calibration value) is achieved. Once adjusted, the first switch is changed to connect the microcontroller to the SMBus lines and the second switch connects the current source to the activation button(s) to resume normal operation.

The microcontroller can switch the SMBus lines to be connected to the analog switch or to the main SMBus line. This allows the switch (non SMBus) to function and, at the same time, allows the microprocessor to connect to the SMBus lines.

In an exemplary embodiment, the serial communications transceiver 1112 allows the battery 301 to establish communication with the TAG 303 and external devices that can be used to obtain diagnostic or calibration information from the device. The serial communications transceiver 1112 provides transmission and reception of differential half-duplex communications between the battery controller 703 and the generator 904. The transceiver 1112 is capable of detecting loss of hardware connection for fault detection in addition to the explained software fault detection. An exemplary embodiment of the device used is configured to be compatible with USB communications for reliability and it can be used in a differential mode for common-mode noise rejection. Given the amount of data that the battery 301 exchanges with the TAG 303, a full-speed device is used (e.g., up to 12 Mbit/s).

Many possible fault conditions can be detected and responded to by the system, the responses sometimes taking the form of feedback to the user. For example, the system can issue a fault condition when a stuck switch condition exists. Such a condition can include when the high/low activation switch is improperly in the activated position at system start up, or where the high activation switch is activated but the low activation switch has not been activated, or where the high/low activation switch is in the activated position at the end of a use cycle. Other fault conditions exist when there is insufficient motional feedback or when the waveguide tip is in a stalled condition. Both low amplitude displacement and high amplitude displacement can cause a shutdown if detected. Various faults are associated with the TAG. For example, a fault condition exists where the output voltage is greater than a defined voltage limit. Another fault condition exists when the microprocessor temperature is greater than a given predefined range, for example, greater than approximately 100 degrees Celsius. Another fault occurs when the battery controller does not receive proper acknowledgement from the TAG either before, during ultrasonic start, or after ultrasonic start. Some fault conditions are associated with the battery. For example, if the battery charge is below any number of predefined thresholds or if a load requires more power than the system can deliver and the amplitude drops below the desired threshold, faults can be indicated. Other faults of the battery can include a failure of the battery's communications system, an over-temperature condition of the battery's microprocessor, fuel gauge, and/or regulator. Failure of the communications system can be through either or both of the TAG and battery. General faults of the system can be included as well. If the CLA ceases to function or functions inappropriately, a fault can be indicated. Failure to reset timers associated with the battery and the TAG can also indicate faults. Software failures also can trigger faults.

Lastly, in the exemplary embodiment, the buck converter 1114 provides step down voltage control to provide amplitude regulation. The buck converter 1114 steps down the battery voltage to produce a lower voltage for delivery to the TAG assembly 303 for generation of the ultrasound output signal to the transducer 902. The microcontroller 1106 controls the output of the buck regulator by varying or modulating the pulse widths of the input signals to the buck converter (i.e., pulse width modulation (PWM)). Off-phase PWM inputs are used for minimal output ripple. The device operates at 300 KHz for high efficiency using small inductors and capacitors. The buck converter 1114 is of a multi-phase synchronous design for maximum possible efficiency. The design utilizes high integrated components for small size and power consumption. The device includes internal current protection, output current sensing, output and input voltage sensing and over-temperature protection. The buck converter 1114 is capable of reacting at high speeds and step down voltages in the range of 2 VDC to 10.5 VDC.

The power supply 1102 produces various voltage levels at its output, which are used to power the various battery controller components shown in FIG. 11. The SMBus isolation switch(es) 1104 is/are used to disconnect the SMBus lines to the battery protection printed circuit board during charging and when the bus is used for other purposes within the battery controller.

As set forth in detail below, the battery controller 703 facilitates a user interface, e.g., a buzzer 802 and RGB LEDs 906, and converts the output voltage and current output of the buck converter 1114, which output powers the TAG assembly 303 through at least one voltage output path ($V_{out}$) 601a-n.

II. Handle Assembly

Figure 8:
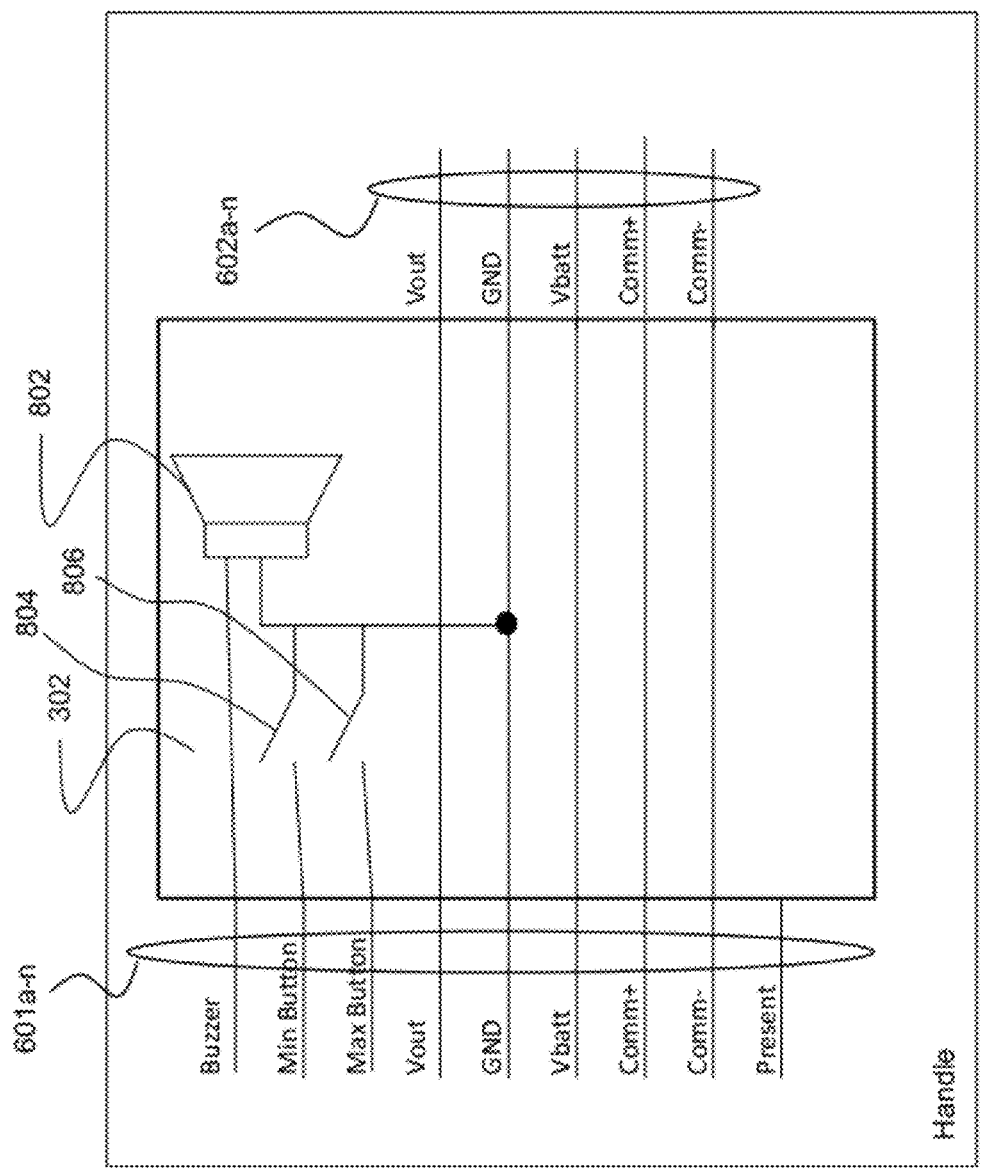
FIG. 8 is a schematic block diagram of a handle assembly of the device of FIGS. 3 and 4 in accordance with an exemplary embodiment of the present invention.

FIG. 8 is a general block and schematic circuit diagram illustrating the handle assembly 302 shown in FIG. 3. The handle assembly 302 receives control and power signals over attached power and communication signal paths 601a-n. A second set of power and communication signal paths 602a-n connect to the TAG assembly 303 when it is attached to the handheld ultrasonic surgical cautery assembly 300. As is explained in detail below, the handle assembly 302 houses the ultrasonic waveguide assembly 304 and provides a portion of the pistol grip that the operator uses to grasp and operate the entire handheld ultrasonic surgical cautery assembly 300 using, for example, a two-stage switch of button 4608 and trigger 4606 (as introduced in FIG. 46). The handle assembly 302, according to one exemplary embodiment, is provided with a speaker/buzzer 802 capable of receiving a buzzer output signal from the battery assembly 301 through a signal path 601a-n and of producing an audible output, e.g., 65 db, suitable for communicating specific device conditions to an operator. These conditions include, for example, successful coupling of assembly components (e.g., battery assembly 301 to handle assembly 302), high, low, or normal operation mode, fault conditions, low battery, device overload, mechanical failure, electrical failure, and others. The handle also includes a Min. Button switch 804 and a Max. Button switch 806 that, when activated, connects the respective button to ground (for example), which in an exemplary embodiment signals the battery controller to start the ultrasonic output in either low or high displacement mode. The handle assembly 302 also provides a pass-through interconnect for signals between the battery assembly 301 and the TAG assembly 303.

Figure 110:
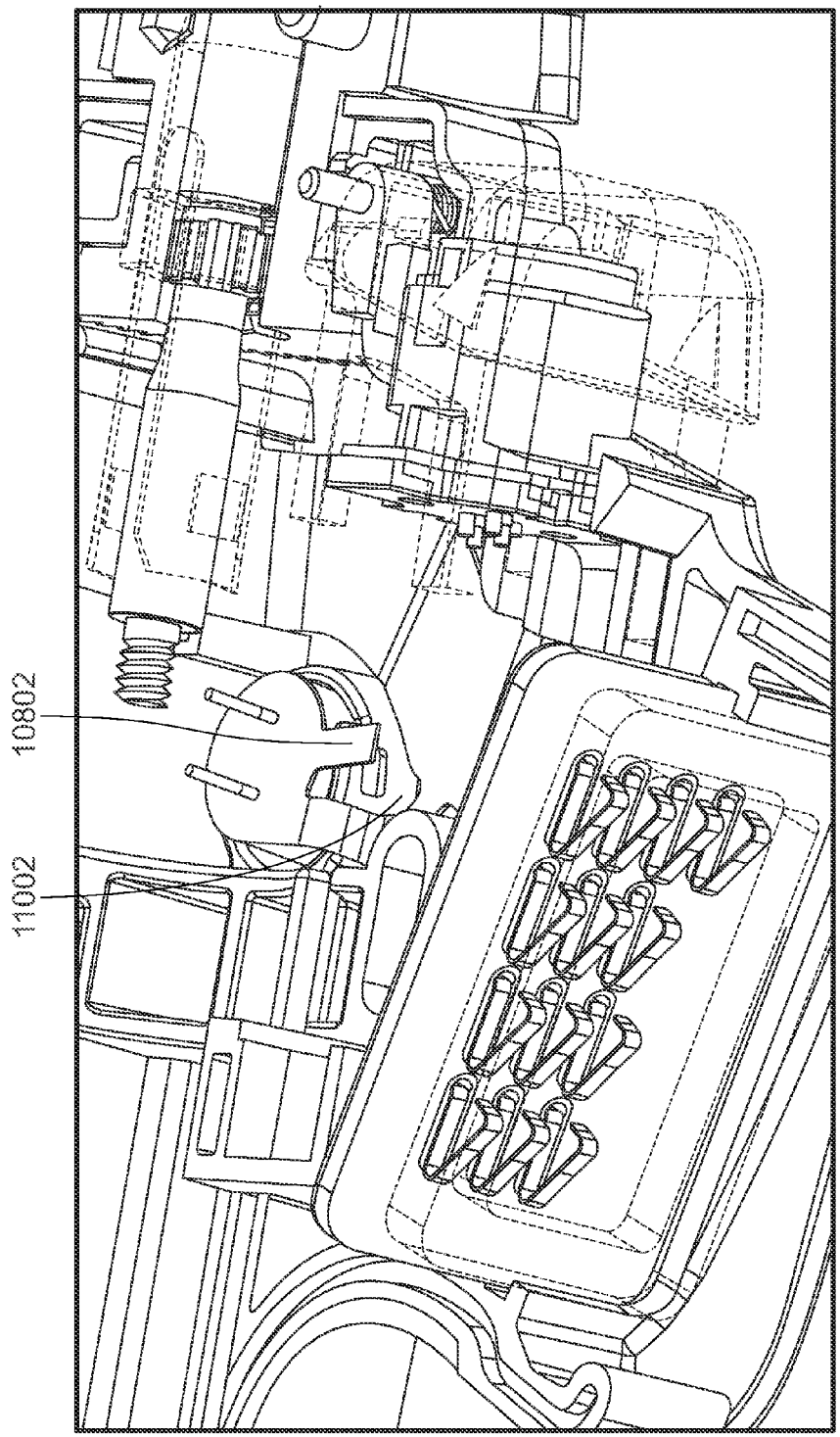
FIG. 110 is a fragmentary, bottom perspective view of an exemplary embodiment of a buzzer portion of the flex harness according to the invention.

The speaker/buzzer 802 and the Min. and Max Button switches 804, 806 are all part of the flex circuit of the handle assembly 302. According to an exemplary embodiment of the present invention, the buzzer 802 is held in place within the handle assembly 302 with the use of an extra tab of flex material that protrudes outward past the edge of the buzzer 802. This tab 10802 can be seen in FIGS. 108 and 110. The handle assembly 302 includes a slot 11002 configured to receive the flexible tab 10802 of material during assembly. The buzzer 802 is protected from fluid ingress by a buzzer seal, for example, an acoustically transparent mesh with adhesive on both sides that bonds the buzzer into the handle assembly 802 while still allowing sound to exit and prevent fluid from entering into the buzzer 802.

III. TAG

Figure 9:
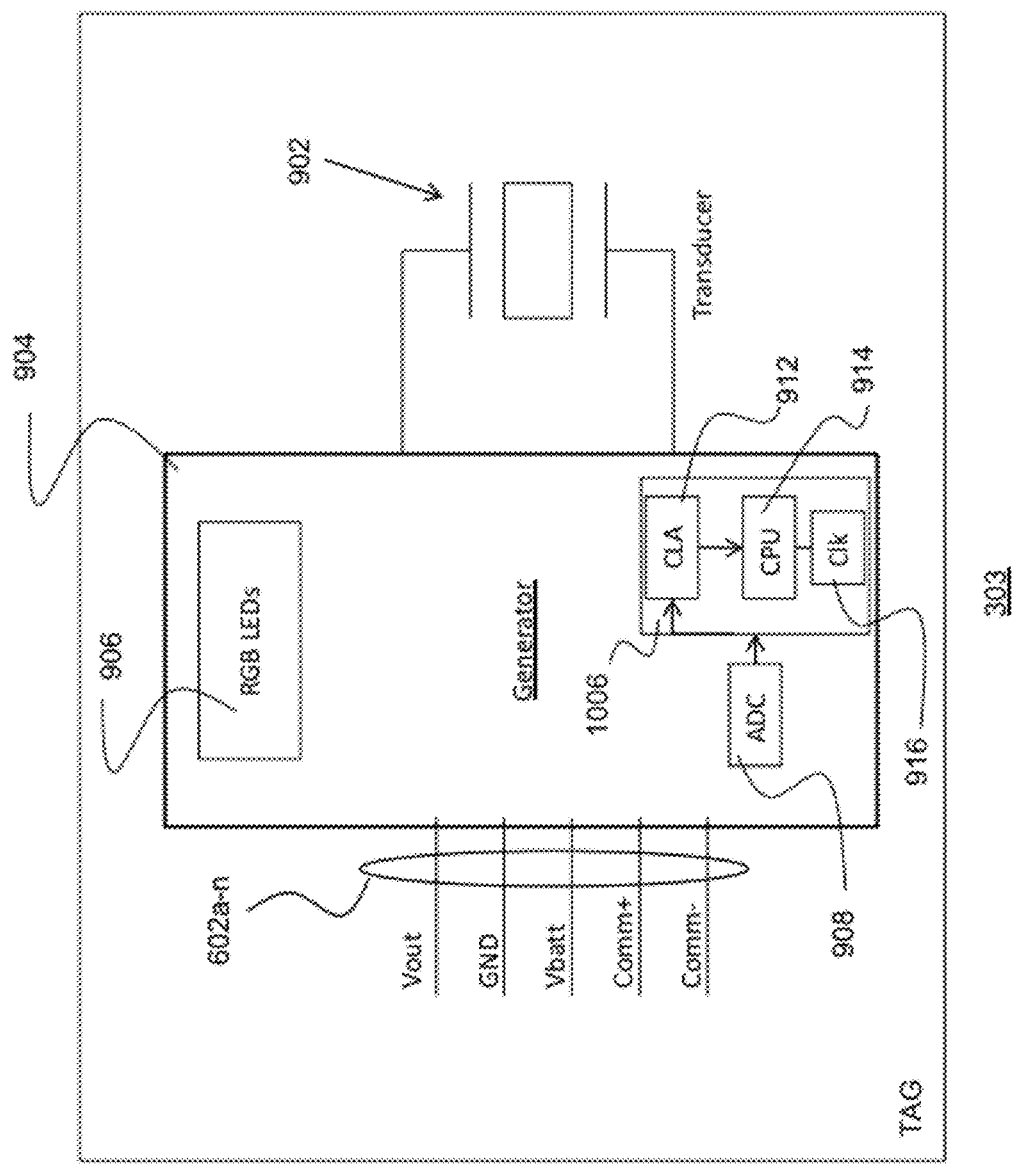
FIG. 9 is a schematic block diagram of the transducer and generator assembly of the device of FIGS. 3 to 5 in accordance with an exemplary embodiment of the present invention.

FIG. 9 is a block and schematic circuit diagram illustrating the TAG assembly 303 of FIGS. 3 and 5, which houses the transducer 902 and the generator 904. The generator 904 converts DC power from the battery controller 703 into a higher-voltage AC signal that drives the transducer 902, which converts the electrical signal into mechanical motion.

a. Generator

Figure 10:
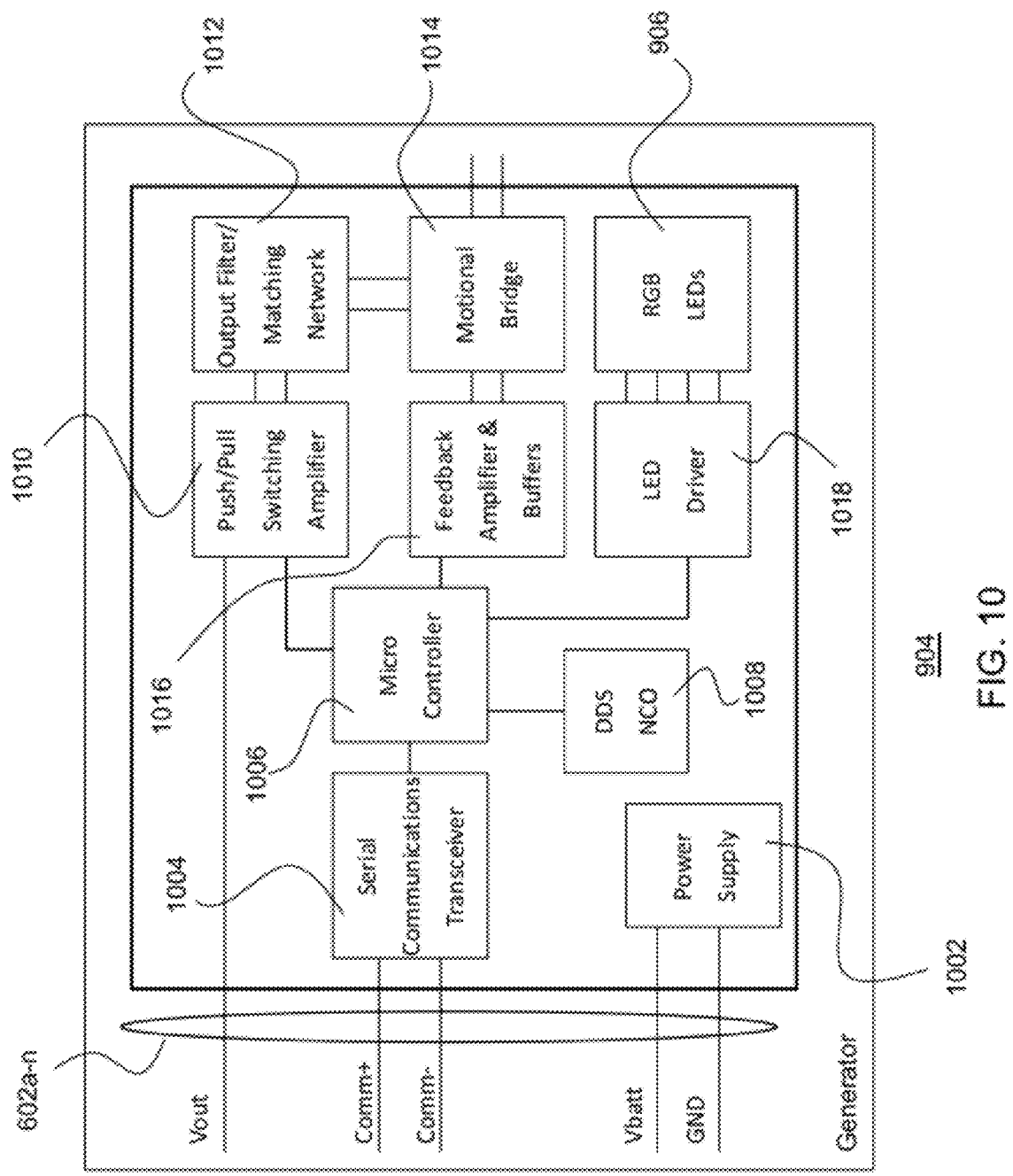
FIG. 10 is a schematic block diagram of the generator of FIG. 9 in accordance with an exemplary embodiment of the present invention.

FIG. 10 is a block circuit diagram illustrating the internal components of the generator 904. The generator 904, according to an exemplary embodiment of the present invention, includes a power supply 1002, a serial communications transceiver 1004, a microcontroller 1006, a numerically controlled oscillator ("NCO") 1008, a push/pull switching amplifier 1010, an output filter/matching network 1012, a motional bridge 1014, a feedback amplifier and buffer(s) 1016, an LED driver 1018, and indicators 906 (for example, RGB LEDs). The power supply 1002 receives power from the battery assembly 301 through lines Vbatt and GND of the power signal paths 602a-n and outputs various voltages that are used to power the generator 904. The serial communications transceiver 1004 provides transmission and reception communications between the battery controller 703 and the generator 904, here, through a serial data link Comm+/Comm− of the communication signal paths 602a-n, although this communication can occur through a single line or through a number of lines, in series or in parallel.

The microcontroller 1006 is a highly integrated processing unit that controls the functions of the generator 904 and is one of two microcontrollers in the system, the other being part of the battery controller 703. In the exemplary embodiment, a serial data link (Comm+, Comm−) exists between the two microcontrollers 1006, 1106 so they can communicate and coordinate their operation. The microcontroller 1006 in the TAG 303 controls generation of the high-voltage waveform driving the piezoelectric transducer 902. The microcontroller 1106 in the battery assembly 301 controls conversion of the DC voltage from the battery cells 701 to a lower DC voltage used by the TAG 303 when generating the high voltage AC to the transducer 902. The battery microcontroller 1106 regulates the DC output of the battery assembly 301 to control the amplitude of the mechanical motion, and the TAG microcontroller 1006 controls the frequency of the signal that drives the transducer 902. The battery microcontroller 1106 also handles the user interface, and the battery protection circuit 702 monitors the battery cells 701 during system operation. The microcontroller 1006 in the TAG 303 has a variable speed system clock that is adjusted constantly while the device is running in the high-power state in order to keep the microcontroller 1006 synchronized with the ultrasonic motion. The microcontroller 1106 in the battery assembly 301 runs at a fixed frequency while in the high-power state, regardless of the TAG clock. Because the system clock varies in frequency, a scale factor within the TAG microcontroller 1006 is changed along with the changing system clock to keep serial communication between the microcontrollers 1006, 1106 within the range of proper operation.

Direct digital synthesis ("DDS") is a technique used to generate a periodic waveform with a precise output frequency that can be changed digitally using a fixed frequency source. The numerically controlled oscillator ("NCO") 1008 is a signal source that uses the DDS technique, which can be performed through hardware or software. The fixed frequency input to the DDS is used to generate a clock for the NCO 1008. The output is a series of values that produce a time-varying periodic waveform. A new output value is generated during each clock cycle.

Figure 22:
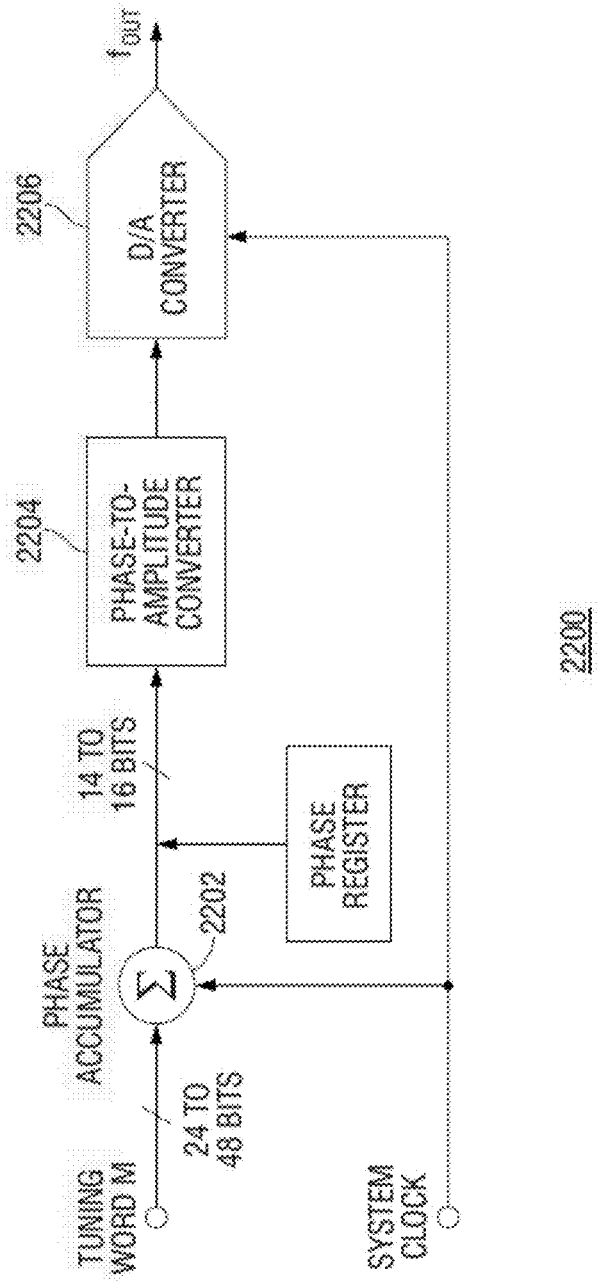
FIG. 22 is a schematic circuit diagram modeling a direct digital synthesis technique implemented in accordance with an exemplary embodiment of the present invention.

The DDS 2200, which is shown in schematic detail in FIG. 22, works by calculating the phase component of the output waveform that is then converted to amplitude, with a new phase value being generated each clock cycle. The phase value is stored in a variable register 2202, which register is referred to herein as the "phase accumulator." During each clock cycle, a fixed number is added to the number stored in the phase accumulator to produce a new phase value. This fixed number is often referred to as the frequency control word or frequency tuning word because it, along with the clock frequency, determines the output frequency. The value in the phase accumulator spans one cycle of the periodic output waveform from 0 to 360 degrees, with the value rolling over at 360 degrees.

The value in the phase accumulator is fed into a phase-to-amplitude converter 2204. For a sine wave, the amplitude can be computed using the arctangent of the phase value. For high speed applications, the converter usually uses a lookup table to generate the amplitude value from the phase value.

In a hardware implementation of DDS, the output of the amplitude converter is input to a digital-to-analog converter (DAC) 2206 to generate an analog output signal $f_{out}$. The analog signal is usually filtered by a band pass or low pass filter to reduce unwanted frequency components in the output waveform.

As a first example, the value in the phase accumulator 2202 can be set to an integer from 0 to 359. If the frequency tuning word is 1, the value in the phase accumulator 2202 will be incremented by 1 each clock cycle. When the value reaches 359, it rolls over to zero. If the clock frequency is 360 Hz, the frequency of the output waveform will be 1 Hz. The output will, therefore, be a series of 360 points during each 1 second period of the output waveform. If the frequency tuning word is changed to 10, the value in the phase accumulator is incremented by 10 each clock cycle, and the output frequency will be 10 Hz. The output will therefore be 36 points for each period of the output waveform. If the frequency tuning word is 100, the output frequency will be 100 Hz. In that case, there will be 3.6 points for each output period. Or, more accurately, some cycles of the output waveform will have 3 points and some will have 4 points, the ratio of cycles with 4 points versus 3 points being 0.6.

Figure 23:
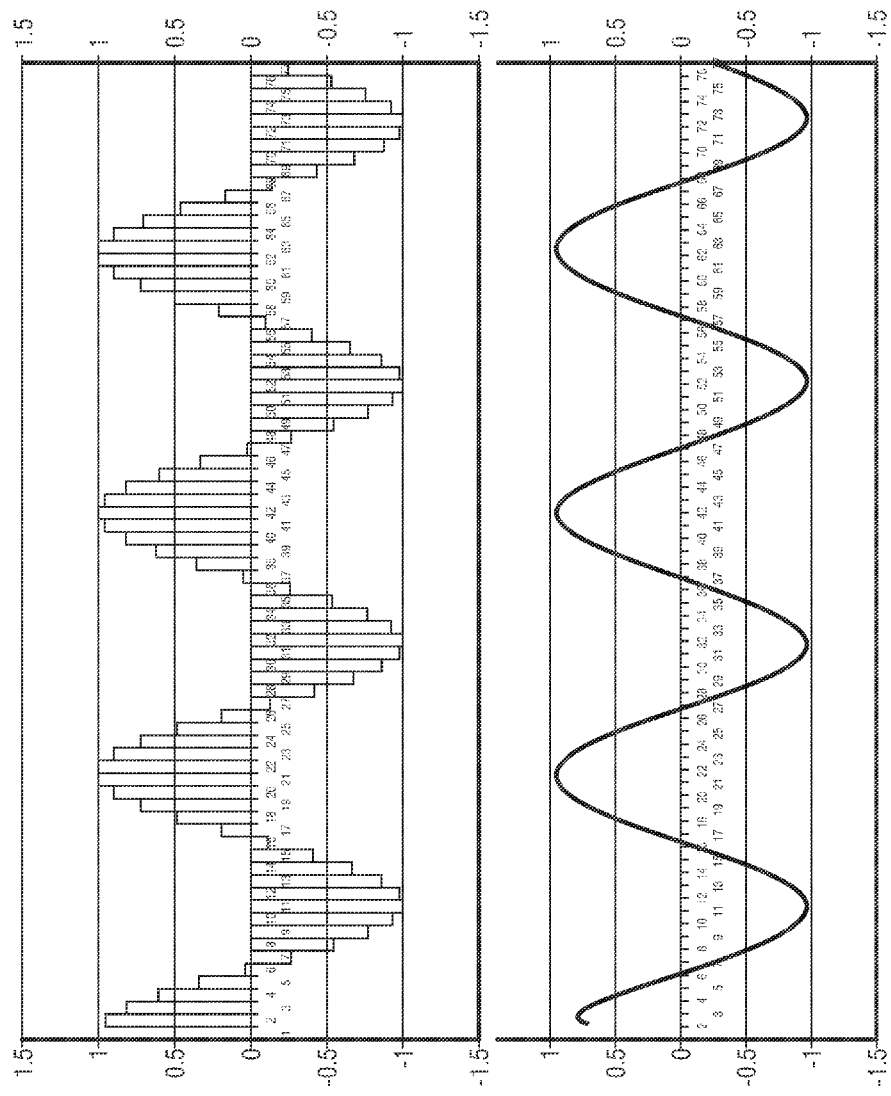
FIG. 23 is a graph illustrating an exemplary direct output of a digital-to-analog converter (DAC) positioned above a filtered output of the DAC in accordance with an exemplary embodiment of the present invention.

As a second example, the value in the phase accumulator 2202 can be a 10 bit number. The 10 bit number will have 1024 possible values. With a frequency tuning word of 50 and a clock frequency of 1 MHz, the output frequency will be 50*1 MHz/1024=48.828 kHz. FIG. 23 illustrates the output 2300 of the DAC 2206 and what the filtered DAC output might look like.

Figure 24:
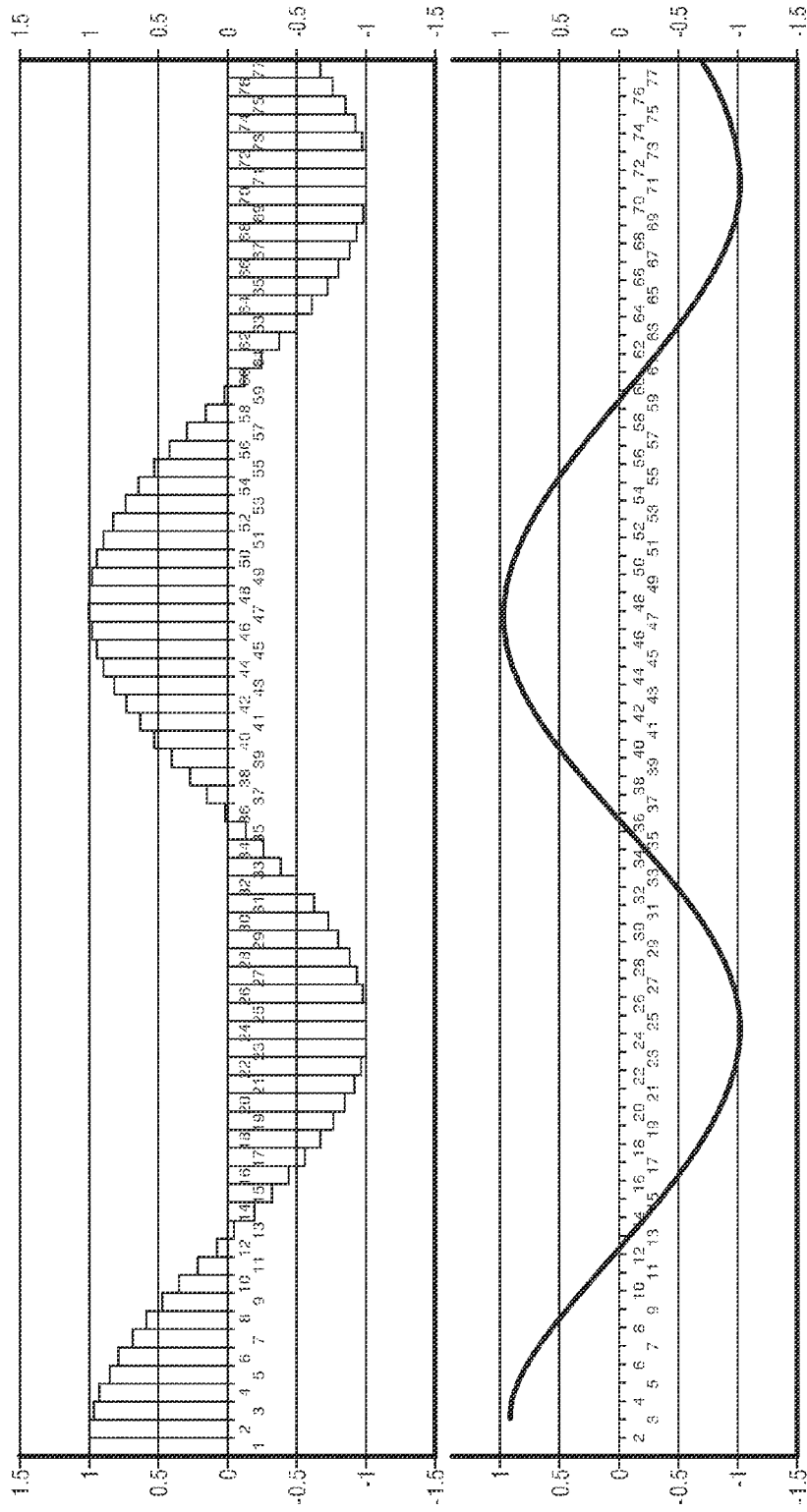
FIG. 24 is a graph illustrating an exemplary direct output of a digital-to-analog converter (DAC) with a tuning word shorter than the tuning word used to produce the graph of FIG. 23 positioned above a filtered output of the DAC using the same shortened tuning word in accordance with an exemplary embodiment of the present invention.

If the frequency tuning word is 22, the output frequency is 22*1 MHz/1024=21.484 kHz. In this case, FIG. 24 illustrates the output 2400 of the DAC 2206 and what the filtered DAC output might look like. When power is first applied to the generator, the state of the NCO 1008 may be undefined (or the output of the NCO 1008 may not be at a suitable frequency). This could lead to improper operation of the microcontroller. To ensure proper operation of the microcontroller, the NCO 1008 is not used to drive the clock frequency of the microcontroller when power is first applied. A separate oscillator is used. In one exemplary embodiment, the separate oscillator is integrated into the microcontroller 1006. Using this separate oscillator, the microcontroller initializes the various memory locations internal to the microcontroller and those in the NCO 1008. Once the NCO 1008 is operating at a suitable frequency, the microcontroller switches the source of its clock from the separate oscillator to the NCO 1008.

Figure 25:
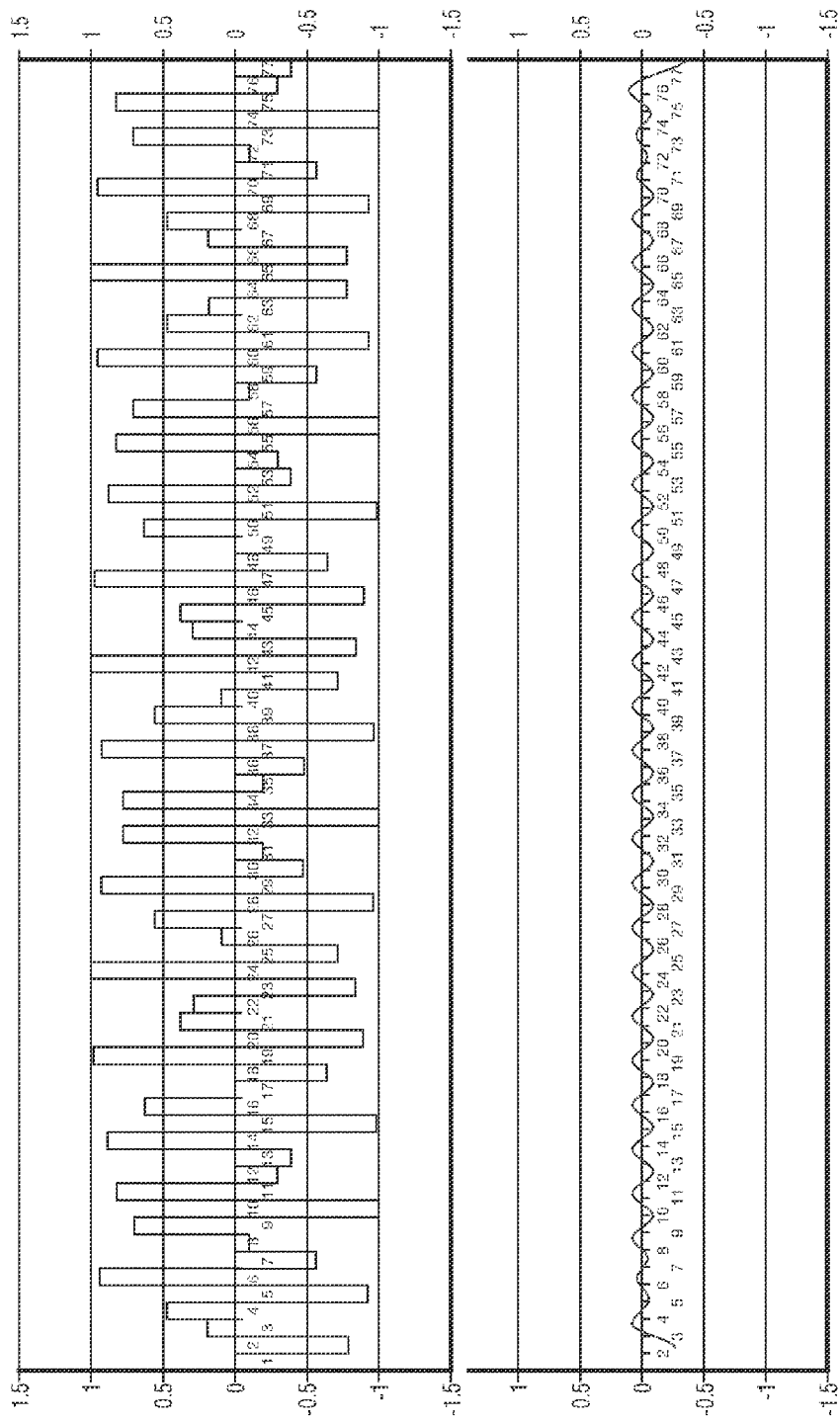
FIG. 25 is a graph illustrating an exemplary direct output of a digital-to-analog converter (DAC) with a tuning word longer than the tuning word used to produce the graph of FIG. 23 positioned above a filtered output of the DAC using the longer tuning word in accordance with an exemplary embodiment of the present invention.

If the frequency tuning word is 400, the output frequency is 400*1 MHz/1024=390.625 kHz. In this case, FIG. 25 illustrates the output 2500 of the DAC 2206 and what the filtered DAC output might look like. The output sometimes has 2 points per period and sometimes 3 points. The waveform in FIG. 25 clearly shows the need for a filter to obtain a clean sine wave.

Referring back to FIG. 10, the push/pull switching amplifier 1010 converts DC power from the battery controller 703 into a higher voltage square wave. The output filter/matching network is a passive filter that changes the square wave from switching amplifier 1010 into a smooth sinusoidal wave suitable for feeding to the transducer 902. The motional bridge 1014 is a circuit that produces a feedback signal in proportion to and in phase with the mechanical motion of the transducer 902 and waveguide assembly 304. The feedback amplifier and buffer(s) 1016 amplifies and buffers the motional feedback signal determined within the motional bridge 1014. As will be explained in greater detail below, the motional bridge 1014 allows the device to run with a constant displacement/amplitude mode and varies the voltage as the load varies. The motional bridge is used to provide amplitude feedback and, by virtue of using this type of feedback, i.e., motional feedback, the system is able to run with constant current.

In one embodiment, the TAG assembly 303 includes one or more red/green/blue (RGB) LEDs 906, which can be used for a variety of warning and communication purposes. For example, green can indicate the device is functioning normally whereas red indicates the device is not functioning normally. It is noted that the placement of the LEDs 906 at the generator 904 in FIG. 9 is only for illustrative purposes. The invention envisions placing the indicators anywhere at the TAG assembly 303.

Through communicative interaction between the handle assembly 302 and the TAG assembly 303, in particular, the speaker 802 and the LEDs 906, the inventive handheld ultrasonic surgical cautery assembly 300 provides full feedback to an operator during use to indicate a plurality of conditions associated with the ultrasonic surgical cautery assembly 300, whereby the feedback originates from the handle and not remotely. For instance, as mentioned above, the speaker/buzzer 802 can provide audible warnings and audible indicators of operational status of the ultrasonic surgical cautery assembly 300. A full class A or B amplifier (e.g., a full amplifier or an ON/OFF square-pulse amplifier) could be used to provide a broader frequency range to implement different sounds and/or audible messages. Similarly, the LEDs 906 can provide visual warnings and visual indicators of the operational status of the ultrasonic surgical cautery assembly 300. As an example, the LEDs 906 can provide an indication of an amount of power remaining within the battery cell(s) 701 or a lack of sufficient power to safely carry out a surgical procedure. For instance, a first color of the LEDs 906 indicates a fully charged battery cell(s) 701, while a second color indicates a partially charged battery cell(s) 701. Alternatively, various blinking patterns or constant on states of the LEDs 906 can provide condition indicators to the user. The LED driver 1018 that is shown in FIG. 10 is an exemplary configuration that provides a constant current when the LEDs 906 are illuminated. Importantly, all of the feedback indicators to the user are uniquely present on the handheld device and do not require the user to be within range of a remote feedback component that is away from the surgical field of vision or outside of the sterile field. This eliminates the requirement for the physician to shift his/her attention from the surgical field to a remote location to verify the nature of the feedback signal.

However, should it prove useful to relay or transmit any of the feedback indications to a device that is external to the handheld device, circuitry can be implemented in the generator or battery board(s) to provide a radio-frequency link (or other forms of communications links) for downloading, transferring or transmitting user interface, diagnostics, or other relevant data from the handheld device to the external device. In this way, the external device allows for the surgical staff or others overseeing the procedure, but who are not inside the surgical field or within the immediate vicinity of the handheld device, to receive the same relevant indications or pieces of information that are being received by the physician. The external device may also function as a valuable backup source or data log for storing information pertaining to the use and diagnostics of the handheld device. The external device may also be utilized to provide a range of more powerful data processing or software applications or tools than can reasonably be implemented in the handheld device. For example, the external device may be able to provide analytical or diagnostic results from the information being received from the handheld device. The handheld device and the external device may also be equipped with bi-directional communication such that the external device could re-program the internal software of the handheld device or issue commands or controls to the handheld device in an advantageous manner.

b. Transducer

A transducer 902 is an electro-mechanical device that converts electrical signals to physical movement. In a broader sense, a transducer 902 is sometimes defined as any device that converts a signal from one form to another. An analogous transducer device is an audio speaker, which converts electrical voltage variations representing music or speech to mechanical cone vibration. The speaker cone, in turn, vibrates air molecules to create acoustical energy. In the present invention, a driving wave 1400 (described below) is input to the transducer 902, which then converts that electrical input to a physical output that imparts movement to the waveguide 1502 (also described below). As will be shown with regard to FIG. 15, this movement sets up a standing wave on the waveguide 1502, resulting in motion at the end of the waveguide 1502. For purposes of the present invention, transducer 902 is a piezo-electric device that converts electrical energy into mechanical motion.

As is known, crystals in piezoelectric transducers expand when voltage is applied. In a transducer configuration according to the invention, as illustrated for example in FIG. 55, the crystals are clamped into a crystal stack 5502. See also FIGS. 54 and 56 to 58. A clamp bolt 5504 in this configuration acts as a spring if it is set to pre-compress the crystal stack 5502. As such, when the crystal stack 5502 is caused to expand by imparting a voltage across the stack 5502, the clamp bolt 5504 forces the stack 5502 back to its original, pre-compressed position (i.e., it retracts). Alternatively, the clamp bolt 5504 can be torqued so that there is no pre-compression on the stack 5502 and, in such a case, the bolt will still act as a spring to pull the mass back towards it original position. Exemplary configurations of the transducer can be a so-called Langevin transducer, a bolt-clamp Langevin transducer, or a bolt-clamped sandwich-type transducer.

When an ultrasonic transducer is caused to vibrate, a standing wave is established at the distal portion of the transducer. This standing wave extending along the transducer 902 and the waveguide 1502, exhibits nodes (points of minimal vibration) and anti-nodes (points of maximum vibration). Placement of the nodes and anti-nodes is important. For example, the blade portion 7304 is positioned at an anti-node because greatest vibratory characteristics are desired there. The same is true for the distal-most end, the ultrasonic waveguide couple 5004 of the transducer 902 as the greatest vibratory characteristics are desired to be coupled into the waveguide 1502. In the exemplary embodiment of the transducer illustrated in FIGS. 54 to 58, the node (the point at which vibration movement is lowest) exists where it is secured to the TAG assembly 303. This is beneficial because imparting vibration onto/into the TAG assembly 303 is not desirable.

In the transducer 902, a step-down in diameter is referred to as a gain-step because downstream vibratory characteristics increase as the circumferential diameter decreases. In the cross-sectional view of FIG. 54, for example, two gain-steps can be seen between the crystal stack 5502 and the ultrasonic waveguide couple 5004. Also present in this view is the flange 5450 of the transducer 902, which is the contact point of the transducer 902 to its housing. This contact point 5450 is located at a node of the transducer 902.

In an alternative exemplary embodiment to the transducer, 902, the crystal stack 5502 can be displaced and, in doing so, provides a more efficient system. More specifically, by moving the crystal stack 5502 more proximally, the gain step that is adjacent to the crystal stack 5502 is moved closer to the node, thereby increasing the overall gain of the system. The required displacement of the crystals is less with greater gain. The further the crystal is away from the node the less it contributes to the power handling capability. Therefore, it is desirous to have the node within the crystal stack but also as close to the gain step as possible. When more than one crystal is placed on one side of the node they work in series, thereby increasing the total displacement. As the crystals move further from the node, their contribution to the displacement is decreased because of their distance from the node. When crystals are placed on both sides of the node, they work in parallel to increase the power capacity of the system but do not increase the overall displacement. This configuration, therefore, reduces how hard the crystals need to be driven to get the same output. As losses go with the square of how hard the crystal are driven (current), lower current means it is more efficient. An amplitude versus power curve shows a typical squared relationship. From this, it can be seen that, in a space-limited system such as the TAG, such a configuration generates the most gain out of the system. In high drive conditions, there is an increased sensitivity to the losses in the crystals. But, by having the increased gain described here, the crystals do not have to be driven so close to the maximum power and, thereby, avoids this sensitivity. It is known that higher power through dielectric losses generates heat. Such heat leads to depolling and causes a frequency shift, which can result in a change in capacitance that move the nodes away from the normal supporting point(s), causing the output to decrease and to generate unwanted heat at other unforeseen places, which can further exacerbate this problem. Furthermore, with appropriate wiring, it is possible to selectively drive only a portion of the crystal stack, which increases efficiency when the load is low.

The transducer 902 of the invention is housed in a cylindrical casing 5430 that has an opening at the distal end to allow the horn 5002 to protrude. The transducer 902 also has two conductive rings 5406, 5408 that surround the transducer and carry the electrical signal from the generator 904 to the transducer 902. In an exemplary embodiment, the rings 5406, 5408 are single machined parts that are made as a flat part either by stamping or machining that, then, has a leg bent into the correct form. Alternatively, the leg can be a second part that is pressed or soldered into a flat ring. These ring/leg sets are overmolded to a distal housing portion 5434 of the transducer housing. The overmolding is not sufficient to create a gas-tight seal. Accordingly, a well is molded where the leg of the ring exits the plastic, which well can be filled with a potting material that creates the gas-tight seal. Alternatively, the leg can be a round pin. In such a case, an o-ring can be placed between the leg and the well to create the seal. The electrodes 5802, 5804 of the transducer crystal stack 5502 can be formed to have spade or pin style connector shapes that allow the electrical connection of the transducer to the leg to happen without solder. This simplifies manufacture and eliminates exposing the leg to heat from soldering, which could further compromise the seal. Portions of the connectors are illustrated in FIGS. 54 to 58 but are best seen in FIG. 58. The transducer 902 needs to be held by the flange 5450, which is at a node where no vibration occurs. The transducer 902 also needs to be rotationally locked to its housing, which can be accomplished with standard key-like features shown, for example, in FIG. 55, or can be done with four flats. By using flats, the wall thickness of the housing can be increased in the area of the contact rings, which increases the structure of this housing that will be exposed to repeated sterilization cycles. To create a seal between the transducer horn 5002 and the housing 5430, in an exemplary embodiment, the support flange is compressed against an o-ring 5452, which is supported by the distal housing portion 5434. To compress this seal sufficiently, the flange 5450 of the transducer 902 must be forcibly pushed against the o-ring 5452. To push on the interior face of the flange 5450, a pair of hermaphroditic pushers 5454 extend into the distal housing portion 5434 to allow the completion of the assembly to apply forward pressure through an elastomeric grommet. In an exemplary configuration, a pair of pusher parts is used to fit within a smaller diameter section of the horn because a single part would have to have clearance over the crystals and electrodes and, therefore, would force the overall housing diameter to be much larger. These pushers can also have crush pin features to join them together to facilitate easier installation. The pushers have geometries that lock them rotationally into the keying features of the housing. Further keying features on the proximal end of the pushers can key the proximal housing portion 5432 onto the assembly of the transducer 902 to align clearances within the proximal housing portion 5432 with the electrodes 5402, 5404 of the transducer 902. Mating of the proximal housing portion 5432 to the distal housing portion 5434 either with adhesive or welding or other bonding measures is done with sufficient pressure to drive the pushers forward into the grommet, which, in turn, pushes on the flange 5450 and compresses the o-ring 5452 between the flange 5450 and the distal housing portion 5434 to simultaneously create a seal and support the flange 5450 with elastomers on both sides, thereby reducing acoustical coupling between the transducer 902 and the housing 5430. Alternatively the proximal and distal housing portions 5432, 5434 can be joined with threads, the tightening of the threads creating compression of the above-described stack of parts. Alternative embodiments can accomplish the same result without the need to insert mold the contact rings by having other elastomeric seals between the rings 5406, 5408 and the housing 5434.

As described in further detail below, the transducer 902 is held in the TAG assembly 303 housing with a spiral ring or other retaining clip 5442 that is installed in a groove in a distal most portion of the distal housing portion 5434. Between the distal housing portion 5434 of the transducer 902, and the lower housing portion 5030 of the generator 904 is a ring of lubricious material, such as PTFE, that reduces rotational friction. Reduction of friction is important in this area because it is this force-bearing surface that holds the TAG assembly 303 into the handle 302 and compresses the seal around the electrical connection between the TAG assembly 303 and the handle 302.

IV. Signal Path

Figure 12:
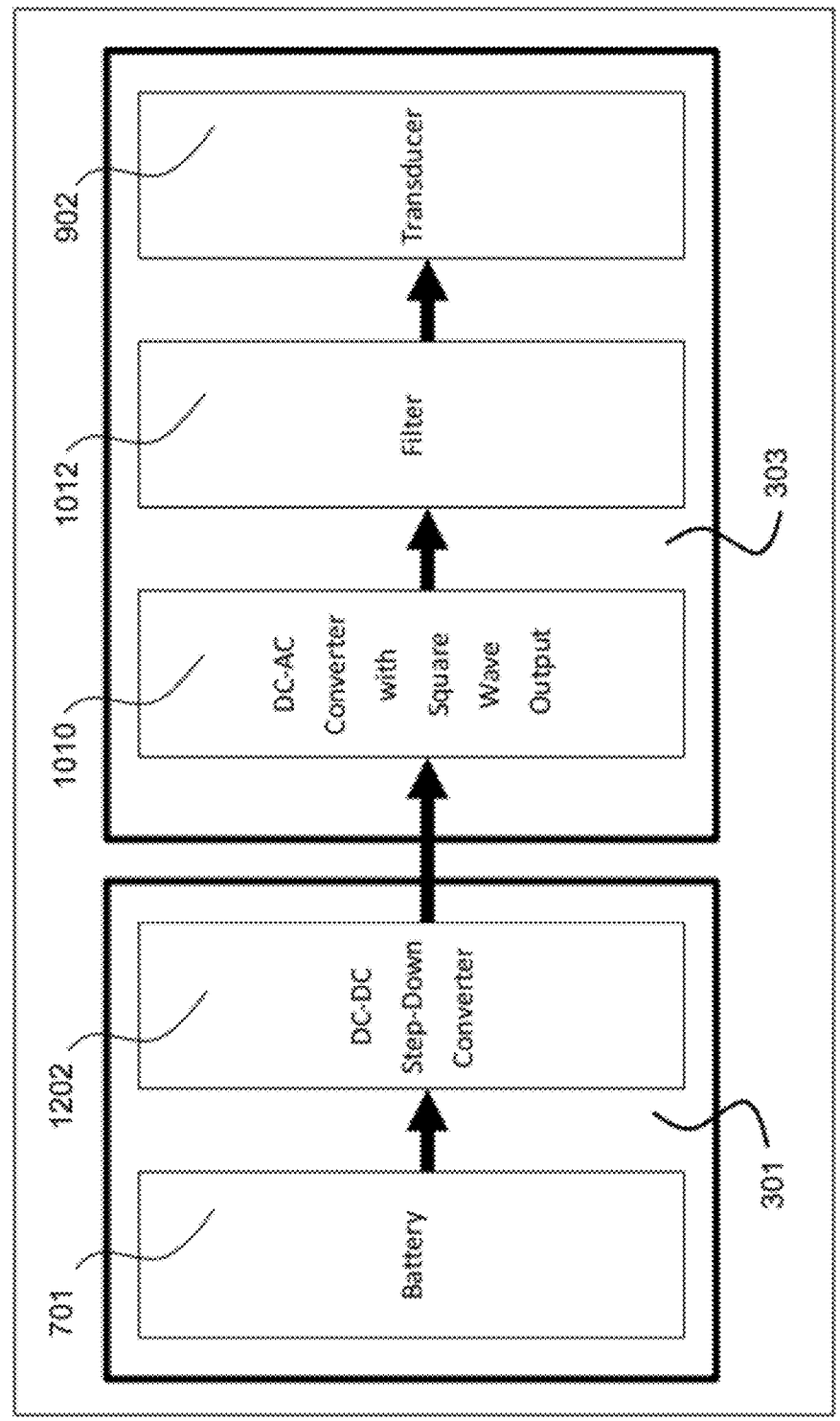
FIG. 12 is a schematic block diagram illustrating an electrical communicating relationship between the battery assembly and the transducer and generator assembly of the device of FIGS. 3 to 5 in accordance with an exemplary embodiment of the present invention.

FIG. 12 is a block diagram illustrating the signal path between the battery assembly 301 and the TAG assembly 303. As described further below, the design characteristics of the signal path and the interconnecting circuit components are determined, in part, by the acute objective to protect the signal integrity and efficiency of the components at this critical, and highly vulnerable, juncture between the power source and signal-generating circuitry.

First, a DC-DC step-down converter 1202 steps the voltage from the battery cells 701 down from a first voltage to a second, lower voltage. The DC-DC step-down converter 1202 includes the multi- or variable-phase (depending on the amount of power needed) buck converter 1114 and the battery microcontroller 1106, which are both shown in FIG. 11 within the battery assembly 301. The battery microcontroller 1106 controls the buck converter 1114 to regulate the DC voltage fed to the TAG assembly 303. Together, the buck converter 1114 and the microcontroller 1106 perform the DC-to-DC conversion function in the battery assembly 301. In an exemplary embodiment of the invention, a two-phase buck converter 1114 is used. Another exemplary embodiment can utilize a buck converter having additional phases. In such a case, phase shedding can be employed. The number of phases used can change dynamically to keep the converter operating at optimal efficiency, which is a consideration for a battery powered device. In other words, when less output power is required, the power losses internal to the converter can be reduced by reducing the number of active phases.

Uniquely, the generator printed circuit board is double-sided, in that the circuitry components are found on both sides of the board. In the exemplary embodiment, the power circuit components are installed on the top side of the PCB, the digital components are installed on the bottom of the board. A solid ground plane separates the two sides. Advantageously, by isolating the high-voltage power circuitry from the logic circuitry in this manner, the logic circuitry is effectively shielded from the injurious high-voltage noise that may be present in the power circuit.

The DC output voltage from the battery assembly 301 powers the push/pull switching amplifier 1010 in the TAG assembly 303, which assembly 303 converts the DC signal to a higher voltage AC signal. The TAG microcontroller 1006 controls the amplifier 1010. The output voltage of the push pull switching amplifier 1010 is, in general, a square wave, an example of which is shown in FIG. 13, which waveform 1300 is undesirable because it is injurious to certain components, in particular, to the transducer 902. Specifically, the abrupt rising and falling edges of a square wave cause corresponding abrupt starts and stops of the ultrasonic waveguide to produce a damaging "rattling" affect on the waveguide. The square wave 1300 also generates interference between components. For example, higher additional harmonic frequencies of a square wave can create unwanted electrical interference and undesired operation of the circuit(s). This is in contrast to a pure sine wave, which only has one frequency.

To eliminate the square wave, a wave shaping or matching circuit 1012 (sometimes referred to as a "tank circuit") is introduced. The tank circuit 1012 includes such components as, for example, an inductor, along with a capacitor in conjunction with the transducer capacitance, and filters the square wave into a smooth sine wave, which is used to drive the transducer 902 in a way that produces non-damaging ultrasonic motion at the waveguide. An exemplary sine wave 1400 suitable for driving the transducer 902 is shown in FIG. 14. The matching circuit 1012, in one exemplary embodiment of the present invention, is a series L-C circuit and is controlled by the well-known principles of Kirchhoff's circuit laws. However, any matching circuit can be used to produce a smooth sine wave 1400 suitable for driving the transducer 902. In addition, other driving signals can be output from the matching circuit 1012 that are not smooth sine waves but are useful for driving the transducer 902 in a way that is less injurious than a square wave.

Importantly, the design of the power filtering circuit is such that small variations in the inductance of the power inductor will not cause the system to operate outside its specifications. This configuration reduces sensitivity to variations in tuning of the LC filter and, thereby, eliminates the need to incorporate an adjusting screw.

In practice, the matching network 1012 is tuned to match a particular transducer to which it feeds. Therefore, transducers and matching networks are best matched if they remain as a pair and are not placed in combination with another device. In addition, if each transducer 902 had its own matching network, the smart battery 301 could feed different frequencies to the different transducers, the frequencies being respectively matched to a particular blade in a waveguide assembly 304. Two popular frequencies for ultrasonic surgery devices are 55 kHz and 40 kHz.

In addition, to prevent radio-frequency or electro-magnetic interference from entering the generator circuitry from the ultrasonic waveguide and transducer components, ferrite beads (or, coils) are installed in the generator output lines or traces to block the interference from reaching the circuitry.

Furthermore, the output traces of the generator are configured to be close to one another (e.g., in a triangular double trace) and in parallel to act as a common mode for filtering out any interference (i.e., to allow maximum common mode rejection).

V. Resonance

FIG. 15 is a diagrammatic illustration of the affect that a resonant sine wave input to the transducer 902 has on the waveguide 1502 of the ultrasonic cutting device. In accordance with an exemplary embodiment of the present invention, the sinusoidal pattern shown by the dotted lines in FIG. 15 represents the amplitude of axial motion along the length of the waveguide 1502, which is coupled to the transducer 902. Responding to a rising portion 1402 of the driving sine wave 1400 (shown in FIG. 14), the stack expands in a first direction 1508. During the negative portion 1404 of the driving wave 1400 (shown in FIG. 14), the pre-compression or the induced compression of the stack returns the stack to its steady-state, i.e., the portion 1504 of the transducer 902 is moved in a second direction 1512. As stated above, a smooth sine wave 1400, in contrast to the square wave 1300, allows the transducer 902 and waveguide 1502 to slow before changing directions. The smoother movement is less injurious to the device's components.

The alternating movement 1508, 1512 of the transducer portion 1504 places a sinusoidal wave 1514 along the length of the waveguide 1502. The wave 1514 alternatingly pulls the distal end 1520 of the waveguide 1502 toward the transducer 902 and pushes it away from the transducer 902, thereby longitudinally moving the distal end 1520 of the waveguide 1502 along a distance 1518. The tip of the waveguide 1502 is considered an "anti-node," as it is a moving point of the sine wave 1514. The resulting movement of the waveguide 1502 produces a "sawing" movement along distance 1518 at the distal end 1520 of the waveguide 1502. (The wave 1514 and linear movement along distance 1518 are greatly exaggerated in FIG. 15 for ease of discussion.) This high-speed movement along distance 1518, as is known in the art, provides a cutting instrument that is able to easily slice through many materials, in particular, tissue and bone. The rapidly moving distal end 1520 of the waveguide 1502 also generates a great deal of frictional heat when so stimulated, which heat is absorbed by the tissue that the waveguide 1502 is cutting. This heat is sufficient to cause rapid cauterization of the blood vessels within the tissue being cut.

If the driving wave 1514 traveling along the waveguide 1502 is not a resonant wave, there will be no standing wave, which means that are no nodes or antinodes. This means that there is very little motion. There also exists the possibility of operating the device at an incorrect resonant frequency. Operating at the wrong resonance can produce, for example, undesirable motion such as "slapping." In such a case, the distal end 1520 of the waveguide 1502 moves transverse to the longitudinal axis of the waveguide 1502. Any incorrect mode is not ideal and is unreliable for providing adequate cutting and surgical cautery. The invention, however, as is explained below, utilizes a phase locked loop (PLL) in the generator 904 to ensure that the movement 1508, 1512 of the waveguide 1502 remains resonant along the waveguide 1502 by monitoring the phase between the motional current and motional voltage waveforms fed to the transducer 902 and sending a correction signal back to the generator 904. The TAG microcontroller 1006 controls the frequency and ensures it is in the proper range so as not to excite an undesired resonant frequency. As an added feature, the present invention can be provided with piezo-electric crystal stacks 1504 that are cut in varying planes, thereby creating a torsional, or twisting motion of the blade rather than only a sawing motion. The present invention can easily be adapted to a full set of uses using requiring a drilling-type motion instead of or with the sawing motion just described.

As just explained, ideally, the transducer 902 and waveguide 1502 are driven at their resonant frequency. Resonance is achieved when current and voltage are substantially in phase at the input of the transducer 902. For this reason, the generator 904 uses the PLL and the signals derived from the current and voltage input to the transducer 902 to synchronize the current and voltage with one another. However, instead of simply matching the phase of the input current to the phase of the input voltage, the present invention matches the current phase with a phase of the "motional" voltage and/or matches the input voltage phase with a phase of the "motional" current. To accomplish this, a motional bridge circuit is used to measure the mechanical motion of the transducer and waveguide and to provide feedback as to the operation of the transducer and waveguide. The motional feedback signal from the bridge is proportional to and in phase with the motion of the transducer 902 and waveguide 1502.

VI. Motional Control a. Transducer Circuit Model

Figure 16:
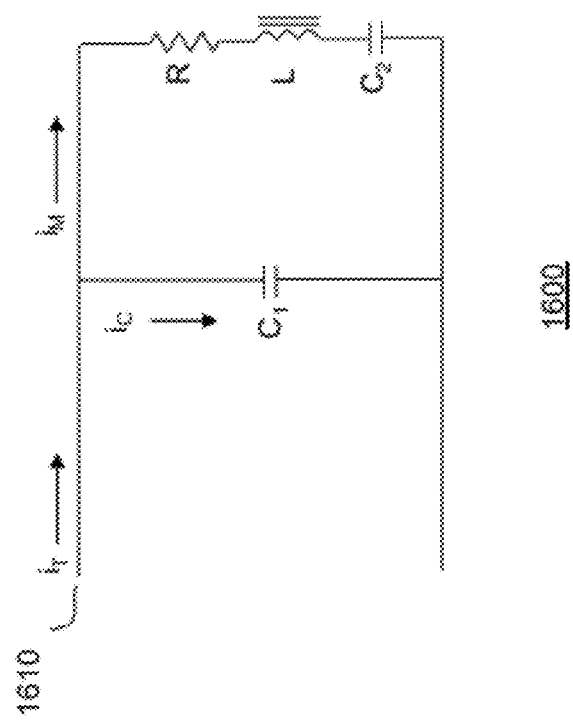
FIG. 16 is a fragmentary, schematic circuit diagram of an elemental series circuit model for a transducer in accordance with an exemplary embodiment of the present invention.

FIG. 16 is a schematic circuit diagram of a model transducer 1600, such as transducer 902, which contains piezoelectric material. Piezo-electric transducers are well known in the art. The mass and stiffness of the piezo-electric material creates a mechanically resonant structure within the transducer. Due to the piezo-electric effect, these mechanical properties manifest themselves as electrically equivalent properties. In other words, the electrical resonant frequency seen at the electrical terminals is equal to the mechanical resonant frequency. As shown in FIG. 16, the mechanical mass, stiffness, and damping of the transducer 902 may be represented by a series configuration of an inductor/coil L, a capacitor $C_2$, and a resistor R, all in parallel with another capacitor $C_1$. The electrical equivalent transducer model 1700 is quite similar to the well-known model for a crystal.

Flowing into an input 1610 of the electrical equivalent transducer model 1600 is a transducer current $i_T$. A portion $i_C$ of $i_T$ flows across the parallel capacitor $C_1$, which is of a type and value that, for the majority of the expected frequency range, retains a substantially static capacitive value. The remainder of $i_T$, which is defined as $i_M$, is simply $i_T - i_S$ and is the actual working current. This remainder current $i_M$ is referred to herein as the "motional" current. That is, the motional current is that current actually performing the work to move the waveguide 1502.

Known prior-art designs regulate and synchronize with the total current $i_T$, which includes $i_C$ and is not an indicator of the amount of current actually causing the motion of the waveguide 1502 by the transducer 902. For instance, when the blade of a prior-art device moves from soft tissue to denser material, such as other tissue or bone, the resistance R increases greatly. This increase in resistance R causes less current $i_M$ to flow through the series configuration R-L-$C_2$, and more current $i_C$ to flow across capacitive element $C_1$. In such a case, the waveguide 1502 slows down, degrading its performance. It may be understood by those skilled in the art that regulating the overall current is not an effective way to maintain a constant waveguide displacement. As such, one novel embodiment of the present invention advantageously monitors and regulates the motional current $i_M$ flowing through the transducer 902. By regulating the motional current $i_M$, the movement distance of the waveguide 1502 can be regulated easily.

b. Series Circuit Model

Figure 17:
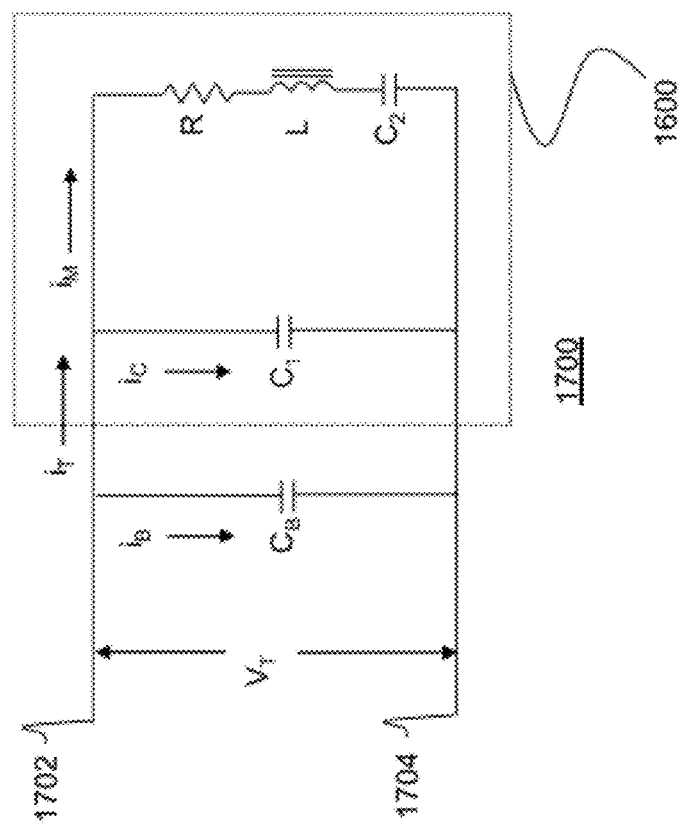
FIG. 17 is a fragmentary, schematic circuit diagram of an inventive circuit with the circuit of FIG. 16 and is useful for monitoring a motional current of a transducer in accordance with an exemplary embodiment of the present invention.

FIG. 17 is a schematic circuit diagram of an inventive circuit 1700 useful for understanding how to obtain the motional current $i_M$ of the transducer 902. The circuit 1700 has all of the circuit elements of the transducer model 1600 plus an additional bridging capacitive element $C_B$ in parallel with the transducer model 1600 of FIG. 16. However, the value of $C_B$ is selected so that $C_1/C_B$ is equal to a given ratio r. For efficiency, the chosen value for $C_B$ should be relatively low. This limits the current that is diverted from $i_M$. A variable power source $V_T$ is applied across the terminals 1702 and 1704 of the circuit 1700, creating a current $i_B$ through the capacitive element $C_B$, a current $i_T$ flowing into the model transducer 1600, a current $i_C$ flowing through capacitor $C_1$, and, finally, the motional current $i_M$. It then follows that $i_M = i_T - r \cdot i_B$. This is because:

$$i_B = C_B \cdot \frac{\Delta V_T}{\Delta_t} = \frac{C_1}{r} \cdot \frac{\Delta V_T}{\Delta_t} \text{ and } i_C = C_1 \cdot \frac{\Delta V_T}{\Delta_t}$$

Therefore, $i_C = r \cdot i_B$ and, substituting for $i_C$ in the equation $i_M = i_T - i_C$, leads to: $i_M = i_T - r \cdot i_B$.

Figure 27:
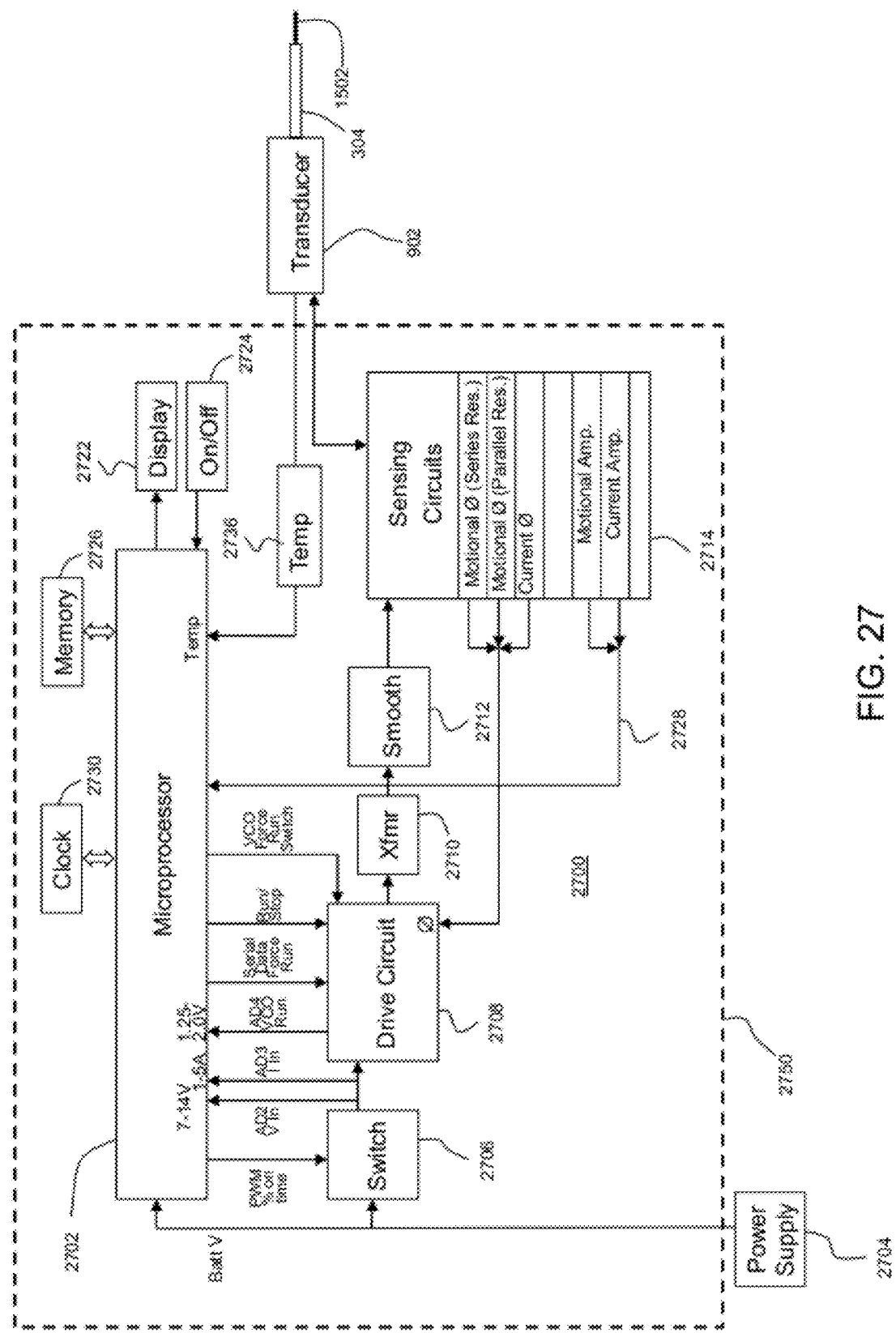
FIG. 27 is a block circuit diagram of the device of FIG. 3 in accordance with an exemplary embodiment of the present invention.

Now, by knowing only the total current and measuring the current through the bridge capacitor $i_B$, variations of the transducer's motional current $i_M$ can be identified and regulated. The driver circuit, represented by block 2708 and the transformer 2710 in FIG. 27, is included in the push-pull switching amplifier 1010 of FIG. 10. The driver circuit, then, acts as a current controller and regulates the motional current $i_M$ by varying an output of the driver circuit based on the product of the current flowing through the bridge capacitance $C_B$ multiplied by the ratio r subtracted from a total current $i_T$ flowing into the transducer 902. This regulation maintains a substantially constant rate of movement of the cutting blade portion of the waveguide 1502 across a variety of cutting loads—something that has not been possible to date. In one exemplary embodiment, sensing circuits 2714 measure the motional voltage and/or motional current. Current and voltage measuring devices and circuit configurations for creating voltage meters and current meters are known in the art. Values of current and voltage can be determined by the present invention in any way now known or later developed, without limitation.

Regulation of the motional current $i_M$ is a true way to maintain the integrity of the instrument and ensure that it will operate at its peak performance under substantially all conditions expected in an operating environment. In addition, such regulation provides these advantages within a package small enough and light enough to be easily held in one hand—a configuration that has never occurred in the field.

c. Transducer Circuit Model

FIG. 18 shows another embodiment of the present invention, where the transducer 902 is schematically represented as a parallel configuration of a resistive element R, an inductive element L, and a capacitive element $C_4$. An additional capacitive element $C_3$ is in a series configuration between an input 1702 and the parallel configuration of the resistive element R, the inductive element L, and the capacitive element $C_4$. This parallel representation models the action of the transducer in a so-called "antiresonant" mode of operation, which occurs at a slightly different frequency. A transducer voltage $V_T$ is applied between the input terminals 1702, 1704 of the transducer 902. The transducer voltage $V_T$ is split between a voltage $V_C$ across capacitive element $C_3$ and a motional voltage $V_M$ across the parallel configuration of the resistive element R, the inductive element L, and the capacitive element $C_4$. It is the motional voltage $V_M$ that performs the work and causes the waveguide 1502 to move. Therefore, in this exemplary embodiment, it is the motional voltage that is to be carefully regulated.

d. Parallel Circuit Model

FIG. 19 shows an exemplary embodiment of an inventive circuit configuration 1900 according to the present invention including the transducer model 1800 of FIG. 18. The circuit configuration 1900 adds to the transducer model 1800 three additional capacitive elements $C_5$, $C_6$, and $C_7$. Capacitive element $C_5$ is in series with the transducer model circuit 1800 of FIG. 18 while the capacitive elements $C_6$ and $C_7$ are in series with one another and, together, are in parallel with the series combination of the capacitive element $C_5$ and the transducer circuit model 1800.

This circuit is analogous to a Wheatstone bridge measuring instrument. Wheatstone bridge circuits are used to measure an unknown electrical resistance by balancing two legs of a bridge circuit, one leg of which includes the unknown component. In the exemplary circuit configuration shown in FIG. 19, a motional voltage $V_M$, which equals $V_T-V_C$, is the unknown. By determining and regulating the motional voltage $V_M$, the inventive configuration allows a consistent waveguide movement to be maintained as set forth below.

Advantageously, the capacitive element $C_7$ is selected so that its value is a ratio A of capacitive element $C_3$, with A being less than one. Likewise, the capacitive element $C_6$ is selected so that its value is the same ratio A of the capacitive element $C_5$. The ratio of $C_5/C_3$ is also the ratio A.

Because the ratio of $C_3/C_7$ is A and the ratio of $C_5/C_6$ is also A, the bridge is balanced. It then follows that the feedback voltage $V_{fb}$ divided by the motional voltage $V_m$ is also the ratio A. Therefore, $V_m$ can be represented as simply $A \cdot V_{fb}$.

If the voltage across the model transducer 1800 is still $V_T$, an input voltage $V_{in}$ equals $V_T$ plus the voltage $V_B$ across the capacitive element $C_5$. The feedback voltage $V_{FB}$ is measured from a first point located between capacitive elements $C_6$ and $C_7$ and a second point located between the transducer and the capacitive element $C_5$. Now, the upstream components of the TAG assembly 303 act as a voltage controller and vary the power $V_{in}$ to maintain a constant feedback voltage $V_{fb}$, resulting in a substantially constant motional voltage and maintaining a substantially constant rate of movement of the cutting blade portion of the waveguide 1502 across a variety of cutting loads. Again, unlike the prior art, the present invention is not simply regulating the input voltage $V_{in}$, it is varying the input voltage $V_{in}$ for the purpose of regulating the motional voltage $V_M$—which is novel in the art.

e. Transformer Series Monitoring

Figure 20:
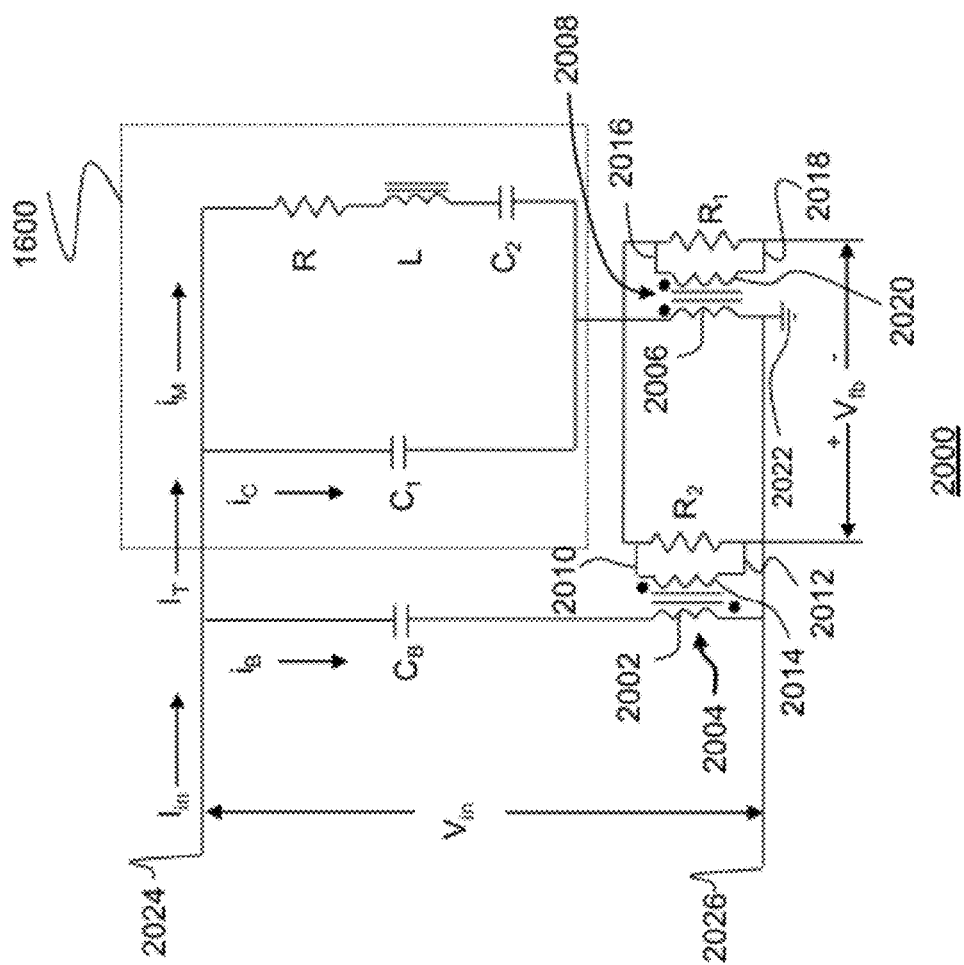
FIG. 20 is a fragmentary, schematic circuit diagram of an inventive circuit with the circuit of FIG. 16 and is useful for monitoring the motional current of a transducer in accordance with an exemplary embodiment of the present invention.

FIG. 20 shows another exemplary embodiment of the present invention where the transducer 902 is of the circuit configuration shown in FIG. 16. The configuration of FIG. 20 works similarly to that shown in FIG. 17 and as described above in connection with FIG. 17. However, in this circuit configuration 2000, a pair of transformers 2004 and 2008 is used to determine and monitor the motional current $I_M$. In this exemplary embodiment, a primary winding 2002 of the first transformer 2004 is in a series configuration with a bridge capacitor $C_B$. Similarly, a primary winding 2006 of the second transformer 2008 is in a series configuration with the model transducer 1600. The leads 2010, 2012 of the secondary winding 2014 of the first transformer 2004 are coupled through a resistor $R_2$. The leads 2016, 2018 of the secondary winding 2020 of the second transformer 2008 are coupled through a resistor $R_1$. In addition, the first lead 2010 of the secondary winding 2014 of the first transformer 2004 is directly connected to the first lead 2016 of the secondary winding 2020 of the second transformer 2008.

Current $i_B$ passing through the primary winding 2002 of the first transformer 2004 induces a current in the secondary winding 2014 of the first transformer 2004. Similarly, the currents including $i_C$ passing through the capacitive element $C_1$ of the transducer 1600 and the motional current $i_M$ of the transducer 1600 combine and go through the primary winding 2006 of the second transformer 2008 to find ground 2022. The current in the primary winding 2006 induces a current on the secondary winding 2020. As noted by the dots ("•") on the transformers 2004, 2008, the secondary windings 2014, 2020 are in opposite directions from one another, with reference to the primary windings 2002, 2006, respectively, and induce a voltage $V_{fb}$ across resistors $R_1$ and $R_2$. By selecting values for $R_1$ and $R_2$ so that a ratio of $R_1/R_2$ is equal to the ratio of the values $C_B/C_1$, the feedback voltage $V_{fb}$ will always be proportional to the motional current $i_M$. Now, the upstream components of the generator 904 act as a voltage controller and vary the input power ($V_{in}$ and $I_{in}$) to maintain a constant feedback voltage $V_{fb}$, resulting in a substantially constant motional current $i_M$ and maintaining a substantially constant rate of movement of the cutting blade portion of the waveguide 1502 across a variety of cutting loads. Again, unlike the prior art, the present invention is not simply regulating the input voltage $V_{in}$, it is varying the input current for the purpose of regulating the motional current $i_M$—which is novel in the art.

An alternative embodiment, which is not illustrated, substitutes use of the transformers 2004, 2008 with resistors. For example, with regard to FIG. 19, the capacitors $C_6$ and $C_5$ can be replaced with resistors, which are used to measure the currents $I_b$ and $I_t$.

f. Transformer Parallel Monitoring

Figure 21:
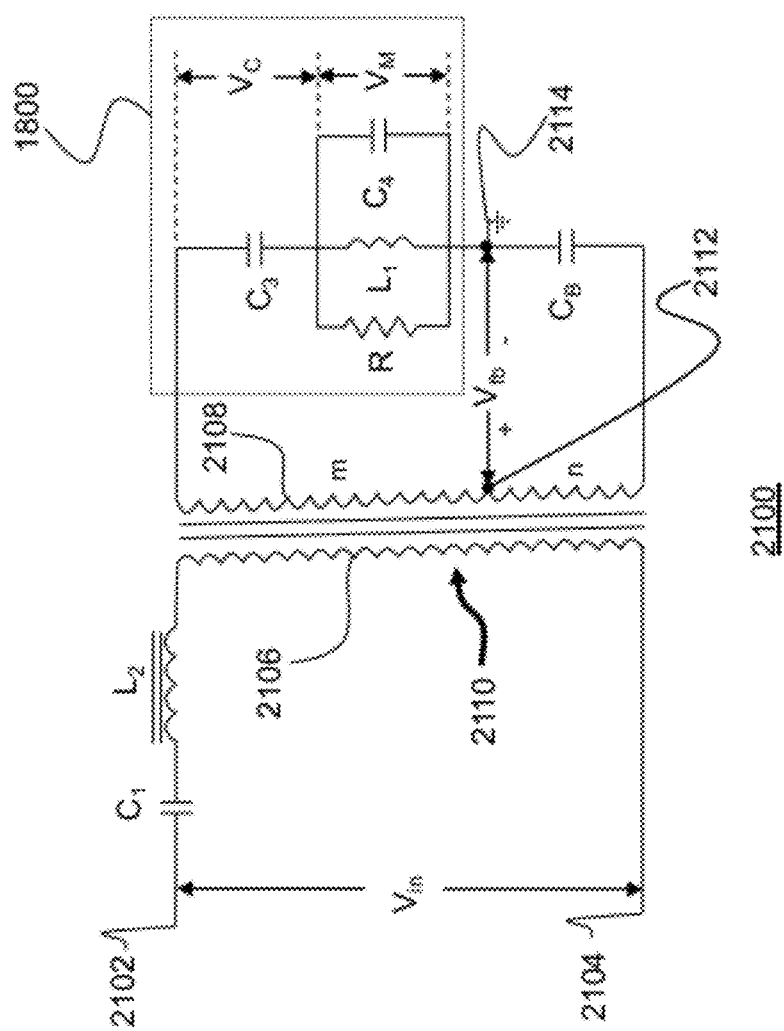
FIG. 21 is a fragmentary, schematic circuit diagram of an inventive circuit with the circuit of FIG. 18 and is useful for monitoring the motional voltage of a transducer in accordance with an exemplary embodiment of the present invention.

FIG. 21 shows another exemplary embodiment of the present invention where the model transducer 1800 is modeled by the circuit configuration shown in FIG. 18. The configuration of FIG. 21 works similarly to that shown in FIG. 19 and as described above in connection with FIG. 19. However, in this circuit configuration 2100, a transformer 2110 is used to determine and monitor the motional voltage $V_M$ of the transducer 1800. In this embodiment, a primary winding 2106 of the transformer 2110 is in a series circuit configuration with an inductive element $L_2$ and a capacitive element $C_1$. A voltage $V_{in}$ is applied across input leads 2102, 2104 of the circuit formed by the primary winding 2106 of the transformer 2110, the inductive element $L_2$, and the capacitive element $C_1$. A current through the primary winding 2106 induces a corresponding current in the secondary winding 2108 of the transformer 2110. The secondary winding 2108 of the transformer 2110 is in a parallel configuration with a combination of the transducer 1800 and a bridge capacitor $C_B$. The two components forming the combination are in a series configuration.

In this embodiment, the secondary winding 2108 is tapped at a point 2112. By tapping the secondary winding 2108 at a point where a first portion of the secondary winding 2108 has M turns and a second portion of the secondary winding 2108 has n turns (where n is less than M), a selectable percentage of the induced voltage on the secondary winding 2108 appears from point 2112 to ground 2114.

Again, this circuit is analogous to a Wheatstone bridge measuring instrument. One leg is the first secondary winding M, the second leg is the second secondary winding n, the third leg is the transducer model 1800, and the fourth leg is the capacitor $C_B$. In the instant circuit configuration shown in FIG. 21, the voltage $V_M$ is the unknown. By determining and regulating the motional voltage $V_M$, a consistent waveguide movement is maintained.

By selecting a value of the bridge capacitor $C_B$ to be less than the transducer capacitance $C_3$ by the same percentage that the number of turns n is less than the number of turns M (i.e., $m/n = C_3/C_B$), the value of a feedback voltage $V_{fb}$ will reflect the motional voltage $V_M$. The invention can determine whether the motional voltage $V_M$ is changing by monitoring the feedback voltage $V_{fb}$ for changes.

By using the equivalent-circuit transducer model 1800, which models a parallel-resonant (or "anti-resonant") transducer, the transducer may be driven in the parallel resonant mode of operation, where motion is proportional to voltage. The advantage of this mode of operation is that the required constant-voltage-mode power supply is simpler to design and safer to operate than a constant-current-mode power supply.

Also, because the transducer has a higher impedance when unloaded (rather than a lower impedance when unloaded in the series-resonant mode of operation), it naturally tends to draw less power when unloaded. The parallel-resonant mode of operation, however, is more difficult to maintain because the resonant bandwidth is narrower than that of the series-resonant mode and has a slightly different natural resonant frequency; hence, the mechanical components of the device must be specifically configured to operate at either the series resonant or parallel-resonant mode of operation.

The present invention controls the voltage and varies the power $V_{in}$ to maintain a constant feedback voltage $V_{fb}$, resulting in a substantially constant motional voltage $V_M$ and maintains a substantially constant rate of movement of the cutting blade portion of the waveguide 1502 across a variety of cutting loads. Again, unlike the prior art, the present invention is not simply regulating the input voltage $V_{in}$, it is varying the input voltage $V_{in}$ for the purpose of regulating the motional voltage $V_M$—which is novel in the art.

In accordance with the present invention, the microcontroller 1006 in the TAG 303 monitors the feedback signal through motional bridge 1014 to generate the signal that goes to the primary side of the transformer 1010. The TAG microcontroller 1006 calculates (in the CLA 912) the phase difference between these signals and adjusts the NCO 1008 output to make the phase difference equal to zero. When the motional feedback signal is in phase with the output of the push-pull switching amplifier 1010, the system is operating at series resonance. The phase and magnitude of the motional feedback signal is computed using a discrete Fourier transform (DFT). In one exemplary embodiment of the present invention, the phase reference for the DFT computation is the drive signal for the push-pull amplifier 1010. The frequency can be changed to cause the push-pull drive signal to be in phase with the motional feedback signal.

According to one exemplary embodiment of the present invention, if the phase of the motional feedback signal is positive, it is an indication the running frequency is below the resonant frequency and the running frequency should be increased; if the phase is negative, it is an indication the running frequency is above the resonant frequency and the running frequency should be decreased; if the phase is close to zero, the running frequency is close to the resonant frequency of the transducer 902 and waveguide 1502. In the generator 904, the NCO 1008 (utilizing DDS) is used to alter the frequency appropriately.

Significantly, the NCO 1008 outputs a clock to the CPU's external clock input at a frequency, for example, 6 times less that the operating frequency of the TAG microcontroller 1006. The external frequency input is fed into the processor's Phase Lock Loop (PLL) and multiplied by a factor of 6 to obtain the CPU's SYSCLK. The NCO 1008 is controlled by the processor through an SPI interface. The SPI interface is used to write a 32-bit divisor to the NCO 1008 that is used to divide the 25-MHz fixed frequency clock to obtain the desired output frequency. By controlling the DDS 2200, the TAG provides synchronized operation of hardware with the oscillation frequency. In other words, to the main processor 914, it appears as though the frequency is constant, thereby simplifying the sampling and calculation of the motion feedback phase.

VII. Startup Operation

Startup conditions are different than those during steady state operation, which is described in detail in the following section. At startup, the waveguide 1502 is initially at rest and, therefore, there is no waveguide motion. Accordingly, there is no immediate, ascertainable motional feedback signal that can be used to determine the composite resonant frequency of the transducer 902 and waveguide 1502. As a result, the inventive system has an ability to operate in a different mode during an initial startup period than during steady state.

Figure 72:
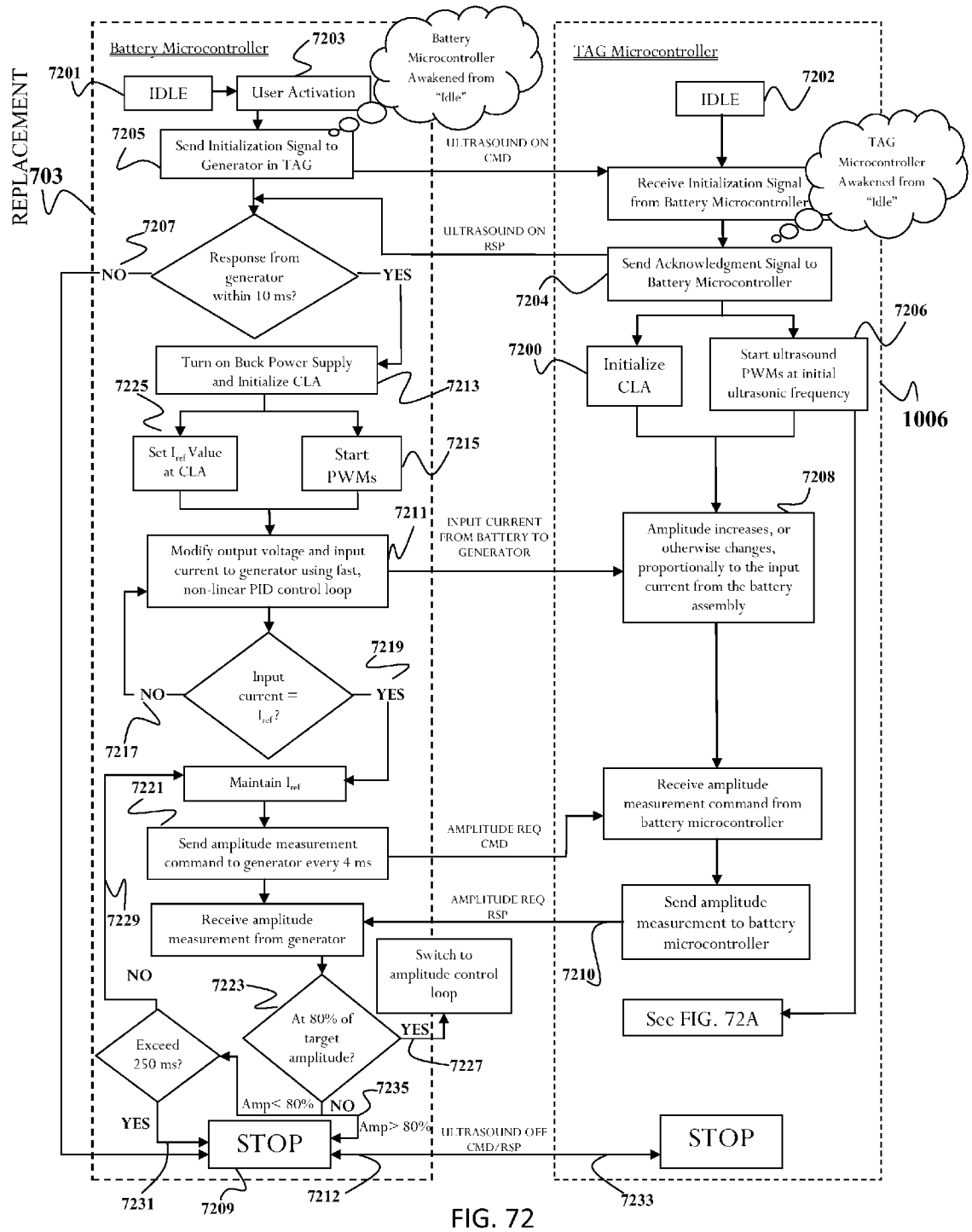
FIG. 72 is a process flow diagram illustrating a start-up procedure in accordance with an exemplary embodiment of the present invention.

A startup procedure according to an exemplary embodiment of the present invention is represented in the process flow diagram of FIG. 72, which illustrates an interchange between the battery controller 703 and the generator 904 of the TAG assembly 303. In this particular embodiment, as described in detail below, the relationship between the battery controller and generator can be described as a "master-and-slave" relationship, as the battery controller issues all commands to the generator 904 and the generator 904 receives all of its instructions from the battery controller 703. Alternatively, the generator 904 of the TAG assembly 303 could act as the "master" and issue all commands to the battery controller 703, or, the generator 904 of the TAG assembly 303 and the battery controller 703 may function as peers.

Prior to activation, both the battery controller 703 and the generator 904 are idle at steps 7201 and 7202, respectively. In step 7203, the battery controller 703 is awakened out of its idle condition, for example, by the user squeezing the button/trigger 4608. To begin the exchange between the battery controller 703 and the generator 904, the battery controller 703 relays a signal, such as an "ULTRASOUND ON" command 7205, to the generator 904 using the communication lines 602a-n (i.e., Comm+/Comm−). If operating properly, the generator acknowledges the command 7205 received from the battery controller 703 and, in return, signals a positive response 7204, such as an "ULTRASOUND ON" response, to the battery controller 703 using the communication lines 602a-n (i.e., Comm+/Comm−). However, if the generator 904 does not positively respond to the initial command 7205 from the battery controller 703 before a specific period of time has lapsed (e.g., 10 ms), the battery controller issues a fault condition at step 7207, such as a "FAILURE TO START" condition, and terminates the operation cycle at step 7209. At such time, appropriate indicators can be actuated.

a. Current and Amplitude Control

If there is a successful acknowledgment by the generator 904 of the "ULTRASOUND ON" command 7205 sent from the battery controller 703, the microcontroller 1106 in the battery controller 703 initiates a process for quickly and safely advancing the current rate in the TAG assembly 303 resulting in a resonant motion output from the TAG assembly 303 to the waveguide 1502. Advancement proceeds from an idle condition to a level predicted to be within a "ballpark window" for producing an ascertainable motional feedback signal and achieving a beginning resonant frequency condition. As shown in FIG. 11, the microcontroller 1106 in the battery controller 703 has two processing units. A first processing unit, the Control Law Accelerator ("CLA") 1116, handles a first, inner, current-control loop 2601 (see FIG. 26), and the second processing unit, a main processor 1118, handles a second, outer, amplitude-control loop 2602 (see FIG. 26). At the outset, in step 7213, microcontroller 1106 turns on the buck power supply 1114 and initializes the CLA 1116. The CLA 1116 uses a proportional-integral-derivative ("PID") control algorithm to compute a new duty cycle value for the Pulse Width Modulators ("PWMs") that are driving the two-phase buck converter 1114. At step 7215, the battery controller 703 starts the PWMs and begins, at step 7211, using a fast, non-linear PID control loop, to increase the output voltage of the DC-DC converter 1202. The increasing output voltage causes a corresponding increase in the input current to the push/pull amplifier 1010 of the generator 904. At step 7217, the output voltage increases, or is otherwise modified, until, at step 7219, the actual, measured input current reaches a predetermined reference current level, referred to herein as "$I_{ref}$." $I_{ref}$ is a calibrated value that is predicted to create a driving wave output from the transducer 902 that will achieve a displacement of the waveguide 1502 and place the resulting amplitude near a value sufficient to reach the target resonant frequency. $I_{ref}$ is initially set by the battery microcontroller 703 in step 7225. This calibrated value for $I_{ref}$ may be stored inside the TAG assembly 303 and read by the battery microcontroller 703 upon establishment of the communication link 7204. Simply put, $I_{ref}$ is a way to not overdrive the system during startup so that with low motion during startup, the system does not overreact and overshoot. $I_{ref}$ is the estimated current to drive the system at the target displacement. When the system gets close to target displacement, then the amplitude control takes over.

FIG. 111 illustrates an example of a non-linear PID control loop or algorithm in accordance with the present invention, whereby the output voltage level is modified until the actual, measured input current reaches the reference current, $I_{ref}$. In this example, the non-linear PID control loop divides the percent error of the actual, measured input current versus the reference current $I_{ref}$ into 5% bins, which are shown below as constants $G_o$ through $G_n$ (where "n" is some number of the last step prior to reaching Each bin has its own non-linear tuning coefficients (e.g., $K_p$, $K_i$, and $K_d$). The non-linear tuning coefficients allow for the output voltage and, in turn, the actual input current, to initially advance quickly towards the reference current point $I_{ref}$ when the input current is far away from the reference current point, and then slowly reach the reference current point $I_{ref}$ once the input current value is close to reaching the reference current point. As a result, the system is less prone to being disturbed by noise. In this particular example, the non-linear PID within the CLA 1116 shapes the overshoot to no more than 15% greater than $I_{ref}$. It is desirable to have the control loop maintain current but not to allow over current for any significant time; in other words, the loop must make the current retract from an overcurrent state quickly. Accordingly, the non-linear PID loop of the CLA 1116 shapes the increase of the output voltage and input current in such a way that the input current advances quickly and accurately to the desired reference current level $I_{ref}$, but does so in such a way that is stable and avoids a dangerous "overcurrent" condition.

In the meantime, while the input current is steadily increasing under the control of the battery microcontroller 1106, the initial signal, i.e., the "ULTRASOUND ON" command 7205 from the battery controller 703, received by the generator, causes the TAG microcontroller 1006 to begin its own initialization process in parallel with the operation of the battery controller 703. As set forth above with regard to FIG. 9, the microcontroller 1006 in the TAG assembly 303 has two independent processing units: the CLA 912 and the main processor 914. Referring back to FIG. 72, at steps 7200 and 7206, upon receiving the initial command 7205 from the battery controller 703, the TAG microcontroller 1006 initializes the CLA 912 and starts the ultrasound PWMs that drive the ultrasonic frequency at a frequency within the operating frequency range of the waveguide and transducer. At this initial start up stage, any motional feedback signal that is present is weak and, therefore, it is desirable to use a high gain amplifier to provide a higher signal level because the signal level is initially very small. At step 7208, as the input current from the battery assembly is increasing, the amplitude (i.e., the displacement of the mechanical motion) is incrementing proportionally until it reaches a set point or level within 20% of a "target amplitude," which should produce a motional feedback signal and place the TAG assembly 303 in a "ballpark window" for achieving the resonant frequency. The "target amplitude" is a pre-determined, safe, threshold level. It is undesirable to surpass this threshold level and, when surpassed (e.g., by 10-12%), indicates an "over-amplitude" condition that is undesirable and causes the device to initiate a fault condition and control shutdown.

The battery controller 703 closely monitors the amplitude to regulate the displacement level of the TAG assembly 303. The battery controller 703 issues a command 7221 at frequent intervals (e.g., every 4 ms), such as an "AMPLITUDE REQ" command, to the TAG assembly 303 using at least one of the communication lines 602a-n (e.g., Comm+/Comm−). In response, the battery controller 703 receives a signal 7210, through at least one of the communication lines 602a-n (e.g., Comm+/Comm−), such as an "AMPLITUDE REQ" response, from the TAG assembly 303, which provides the battery controller 703 with a measurement of the displacement level of the TAG assembly 303. At each interval that a measurement of the displacement level is determined by the battery controller 703, the battery microcontroller 1106, at step 7223, makes one of several possible determinations based upon the displacement measurement. If the amplitude level has reached the level of within 20% of the "target amplitude" or, effectively, 80% of the "target amplitude," in step 7227 the power control is switched from the inner, current-control loop 2601 to the outer, amplitude-control loop 2602, which is described in further detail below. If the amplitude level has not yet reached 80% of the "target amplitude," in step 7229, the current control loop will maintain the current at the reference current level $I_{ref}$ until the amplitude reaches the 80% point.

However, if the amplitude level still has not reached the 80% point within a set period of time (e.g., 250 ms), this indicates a "low amplitude" fault condition 7231 that may be due to, for example, a stalled blade of the waveguide 1502. In response, the battery microcontroller 1106 terminates the operation cycle at step 7209 and issues, for example, an "ULTRASOUND OFF" command 7233 to the generator 904. In return, the generator 904 relays a response 7212, such as an "ULTRASOUND OFF" response, indicating that it has ceased active operation. If the potentially dangerous condition occurs in which the amplitude level has actually surpassed the level of within 20% of the "target amplitude," the battery microcontroller 1106 immediately issues a fault condition 7235 and terminates the operation cycle at step 7209, as described above, due to this "over-amplitude" condition.

b. Frequency Lock

Figure 72A:
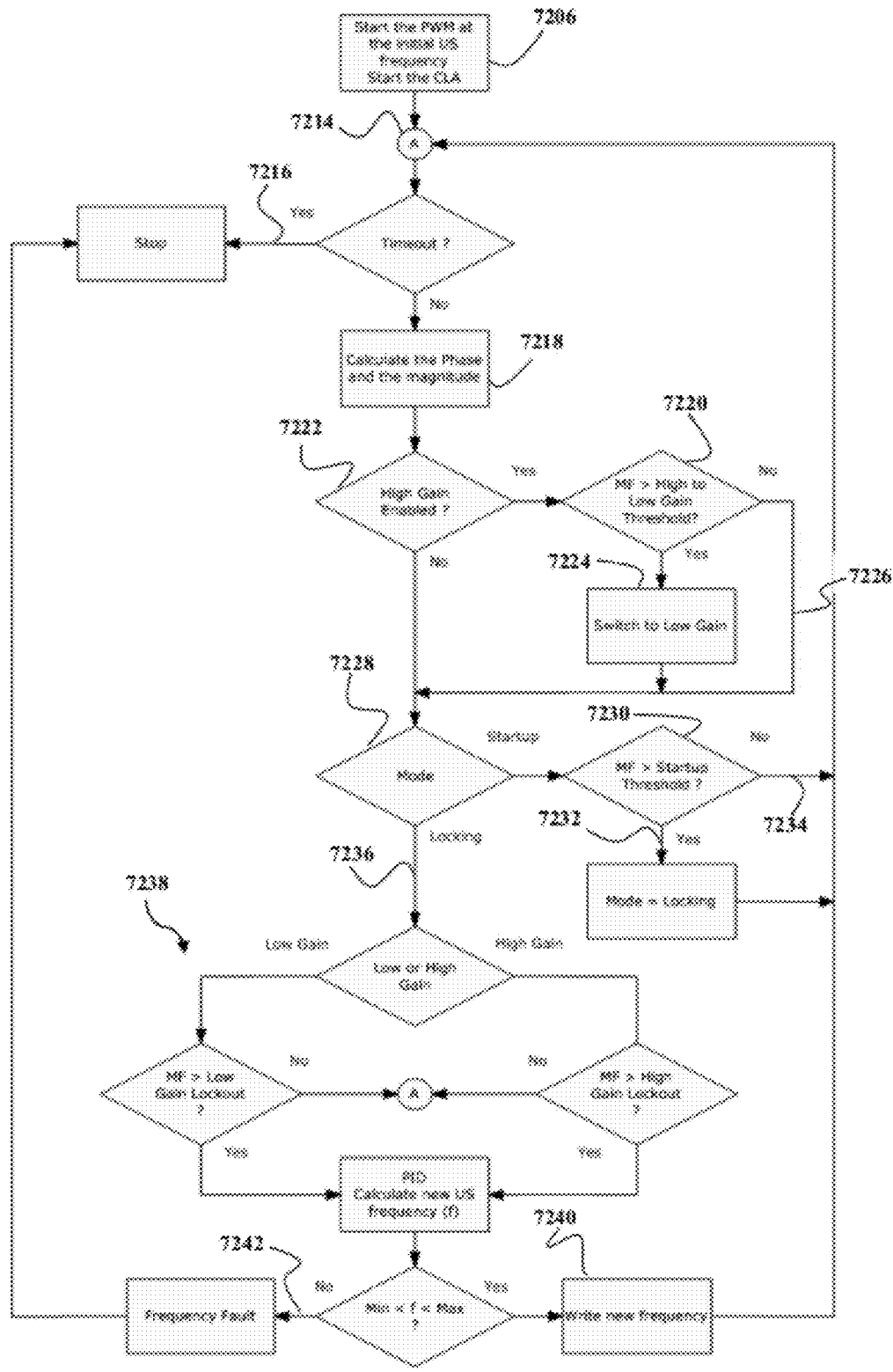
FIG. 72A is a process flow diagram illustrating a portion of the start-up procedure in accordance with an exemplary embodiment of the present invention.

Now, referring to FIG. 72A, as previously mentioned, upon initialization, the TAG microcontroller 1006 controls the frequency of the signal that drives the transducer 902 based upon its detection of the motional feedback signal. At the beginning of the startup process, in step 7206, the operating frequency is set at a fixed value that is within the operating frequency range of the transducer 902 and waveguide 1502 (e.g., 55.2 kHz). If present at that set frequency, a motional feedback signal from the bridge circuit is routed to a high and low gain buffer. Each of these signals is fed into the analog-to-digital converter ("ADC") 908 of the microcontroller 1006 in the TAG assembly 303. Initially, the high-gain, buffered-feedback signal is selected as the motional feedback signal will initially be small. A main function of the CLA 912 is to take the output from the ADC, perform the Discrete Fourier Transform ("DFT") calculations, and pass the results to the main processor 914. Shown as step 7218, the results from the DFT calculations are the phase and magnitude of the motional feedback ("MF") signal, as well as the real and imaginary terms for the signal.

A tuning loop is called once per ultrasound cycle. If, at step 7214, it is determined that a valid motional feedback signal does not exist at the set frequency, the system simply waits until there is a valid motional feedback signal. However, if a fixed period of time has been exceeded as determined by a cycle timeout timer, and there is still no valid motional feedback signal, a cycle activation limit "timeout" is triggered at step 7216 and the generator 904 turns off.

Initially, at step 7222, the system employs a high-gain-buffered A-to-D channel such that the high-gain-buffered feedback signal is selected. This allows the system to lock at a lower motional feedback signal level. A determination of whether or not the motional feedback signal has reached a defined "THRESHOLD" value is made at step 7220. If the motional feedback signal has reached the defined "THRESHOLD" value, the amplitude of the motional feedback signal has increased to the point that a valid motional feedback signal has emerged from any obstructive noise such that the DFT calculations in the CLA 912 are reliable. At this point, in step 7224, the system switches to the low-gain channel. However, should the system fall below this "THRESHOLD" value, the A-to-D channel can switch back to the high-gain channel as shown in step 7226. By having the ability to switch to the low-gain channel at this point, a higher resolution A/D converter is beneficially not required.

At step 7228, if the motional feedback signal is above a starting threshold value, the generator 904 enters a frequency-tuning mode for locking the set frequency onto the resonant frequency of the TAG assembly 303 in parallel with the current and amplitude controls described above. In accordance with an exemplary embodiment of the present invention, the process for achieving resonant frequency is not a process of sweeping for the optimum frequency, but rather is uniquely a tracking or tuning process for locking onto the optimum frequency. However, the present invention may also employ a frequency sweeping mode, whereby the initial operating or set frequency is chosen to be at a lower boundary of the "ballpark window" of the predicted resonant frequency and is steadily incremented until it reaches the resonant frequency or vice versa.

Once frequency tuning mode is entered, the main processor 914 of the TAG microcontroller 1006 uses the results of the DFT calculation (i.e., the phase and magnitude of the motional feedback signal) to control the running frequency of the generator. The tuning algorithm is divided into two states: STARTING and LOCKING. In the STARTING phase at step 7230, a determination is made of whether or not the motional feedback signal has reached a defined "STARTUP THRESHOLD" value. If the motional feedback signal has reached the defined "STARTUP THRESHOLD" value, the amplitude of the motional feedback signal has increased to the point that the system can actively begin moving towards resonance at step 7232. If the determination at step 7230 is that the motional feedback signal has not reached the defined "STARTUP THRESHOLD" value, the process moves to step 7234. At step 7234, the STARTING phase simply waits until the point is reached whereby there is a large enough motional feedback signal to allow locking.

In the LOCKING phase 7236, the sine of the phase offset between the motional feedback signal and the driving signal is used along with the differential of the sine to determine the size and direction of the frequency step to adjust the output frequency to move the system to resonance. Although the phase is naturally a tangent function, the sine of the phase is used to determine the frequency step because it is bounded by the value ±1 and closely approximates the phase value at small angles, whereas a tangent function has the undesirable, unbounded range of In step 7238, a PID loop is used to calculate the frequency step in either a plus or minus direction. The PID loop is non-linear, whereby the value of the sine is used to determine a bin number. That bin number is used as an index to access the tuning coefficients used by the PID. An index table contains the proportional gain, the integral gain, and the differential gain. In addition, the entry sine value to enter a bin differs from the value to exit a bin. This introduces hysteresis to prevent oscillations near the bin transitions.

As previously explained, a non-linear PID is used to achieve a rapid frequency lock. FIG. 112 illustrates an example of a non-linear, asymmetric PID loop or algorithm in accordance with the present invention whereby the size in frequency step is staggered until it reaches the target resonance frequency, $f_{res}$. In this example, the gain constants $PID0$ through $PID_n$ (whereby "n" is some number of the last frequency step prior to reaching $f_{res}$) are separated by non-linear increments. The gain values have been chosen to move the system toward resonance quickly when the system is far from resonance and slowly when the system is close to or at resonance. It is important to step slowly when close to or at resonance in order to avoid inducing frequency modulation, which would cause undesirable effects on the amplitude. During startup, the value for the maximum frequency step size is greater than during steady state operation; it is, for example, set to 8 Hz. If the phase is positive, it is an indication that the running frequency is below the resonant frequency of the transducer and needs to be increased. If the phase is negative, it is an indication the running frequency is above the resonant frequency and the running frequency should be decreased. If the phase is close to zero, the running frequency is close to the resonant frequency of the transducer 902 and waveguide 1502. The numerically controlled oscillator 1008 utilizing direct digital synthesis is used to change the frequency at step 7240.

The DDS 2200 (see FIG. 22) provides synchronized operation of hardware with the oscillation frequency. In other words, to the main processor 914, it appears as though the frequency is constant. Here, the clock frequency of the main processor 914 is a multiple of the oscillation frequency. The invention alters the PWM frequency in a unique and novel way. With the invention, PWM is performed inside the main processor 914. Because of this, the present invention actually increases/decreases the frequency of the main processor 914—which has not been done before. The A/D converter 908 adjustments are automatic as well because the A/D converter 908 exists inside the microcontroller 1006. This inventive technique can be analogized to a singer adjusting a speed of a metronome to match the singer's tempo rather than, as is conventionally done, the singer changing her/his tempo to match the metronome.

At anytime during operation of the device, if the frequency reaches a pre-set minimum or maximum frequency limit, $f_{min}$ and $f_{max}$, respectively, the generator 904 turns off and a fault condition is triggered, as shown in step 7242. Exemplary lower and upper frequency limits for the invention are 54 kHz and 58 kHz, respectively. A number of various conditions can cause the frequency to reach the minimum or maximum limit, including breakage of a component (such as the waveguide 1502) or a situation in which the waveguide 1502 is under such a heavy load that the device is not able to input the amount of power needed to find resonance.

Once frequency lock is achieved, the transition begins into steady state operation.

VIII. Steady State Operation

During steady state operation, the objective is to maintain the transducer and waveguide at resonant frequency and to control the displacement in response to any drifting that occurs as a result of a load on the waveguide 1502 during use of the device. When the transducer 902 and waveguide 1502 are driven at their composite resonant frequency, they produce a large amount of mechanical motion. The electrical energy from the battery is, in this state, converted into a high voltage AC waveform that drives the transducer 902. The frequency of this waveform should be the same as the resonant frequency of the waveguide 1502 and transducer 902, and the magnitude of the waveform should be the value that produces the proper amount of mechanical motion.

a. Amplitude Control

At resonance, the displacement is approximately proportional to the transducer current, and the transducer current is approximately proportional to the input current to the push/pull amplifier 1010. With constant current operation to maintain constant displacement, the output voltage will vary with a varying load. In other words, the voltage will increase if the output power requirement increases and vice versa.

Figure 26:
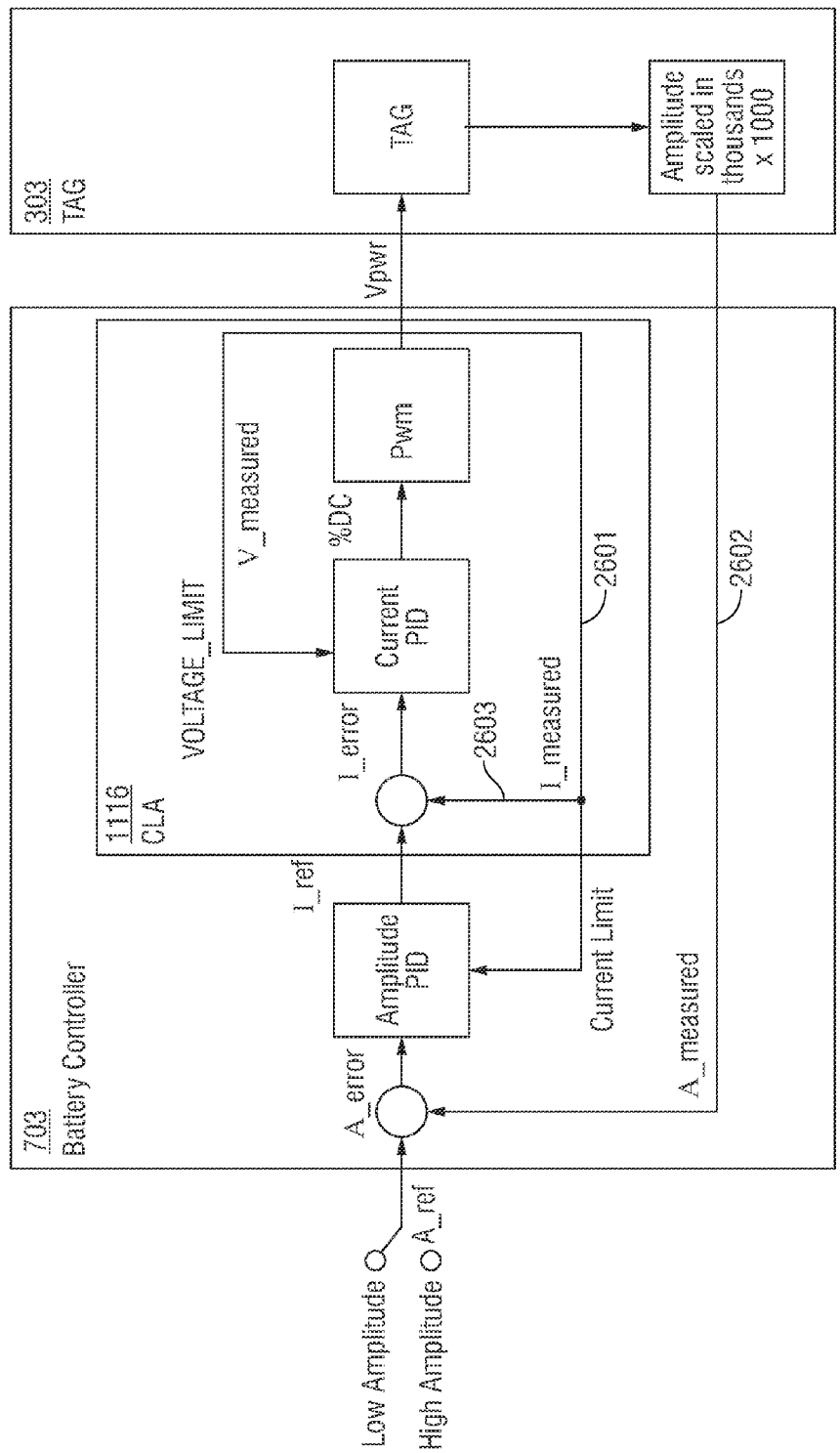
FIG. 26 is block circuit diagram of exemplary components comprising the current control loop in accordance with an exemplary embodiment of the present invention.

As described above in relation to the startup process, shown in FIG. 26 are two control loops, an inner, current control loop 2601 and an outer, amplitude control loop 2602 for uniquely regulating the amplitude of the driving wave input to the transducer 902. The current control loop 2601 regulates the current from the battery assembly 301 going into the push/pull amplifier 1010. The amplitude control loop 2602 compensates for load differences or any other changes that occur in the transducer and/or waveguide. To accomplish this goal, the amplitude control loop 2602 utilizes the motional feedback signal to generate the desired reference current level, "$I_{ref}$," that is used by the current control loop 2601 to alter the output voltage of the DC-DC converter as described above. To avoid interference-type interactions between the two loops, the current control loop 2601 operates at a higher frequency than the amplitude control loop 2602, e.g., approximately 300 KHz. The amplitude control loop 2602 typically operates, for example, at a frequency of 250 Hz.

To determine the desired reference current level, $I_{ref}$, the present amplitude value is subtracted from the desired "target amplitude" to generate an amplitude percent error signal. This amplitude percent error signal is the input into the PID control algorithm of the amplitude control loop 2601 for generating the new, desired reference current level "$I_{ref}$," based upon the operating conditions being experienced by the transducer 902 and waveguide 1502 at that particular time. In other words, the amplitude control loop 2602 changes the target or reference current value for the CLA 912 of the current control loop 2601 to reach the desired amplitude based on the percent error calculation. In this way, the output power is altered based on the variable need of the transducer 902 and waveguide 1502. The main processor 1118 of the battery controller 703 checks the new reference current value to make sure that it is not greater than the maximum output current value.

Based upon the new target or reference current value, $I_{ref}$, that is set by the amplitude control loop 2602, the current control loop 2601 proceeds to change the output voltage and input current to the push/pull amplifier 1010. A measurement of the actual current level 2603 of the battery pack output is fed into the ADC 1120 of the battery microcontroller 1106 (shown in FIG. 11). The CLA 1116 takes the value from the ADC 1120 and subtracts it from the target or reference input current level $I_{ref}$ to generate the current error signal. As described above, the CLA 1116 uses the PID control algorithm to compute a new duty cycle value for the PWMs that are driving the two-phase buck converter 1114. The CLA 1116 also computes a maximum PWM duty cycle to limit the output voltage. The algorithm to compute the maximum duty cycle uses the measured battery voltage and assumes the buck converter 1114 is operating in continuous conduction mode.

It is noted that, by utilizing amplitude control, rather than only looking at the current for steadying the amplitude, the present invention uniquely allows for finely adjusting the output of the transducer based on the motional feedback signal, achieving a more precise amplitude control. The use of a current control loop allows for faster initial response that would not be possible with amplitude control alone. Also, having the two loops provides for redundancy and individual calibration of the transducer and generator during manufacture. This "amplitude calibration factor" is critical for dialing out a variation in the electrical and mechanical variations in the transducer/piezoelectric crystals and for adjusting for variation in the electrical components of the generator magnitude feedback system. Within the generator, through the analog-to-digital converters, the feedback voltage is converted with this calibration factor to result in a magnitude value that is directly related to displacement. During the calibration process, this calibration value is adjusted while measuring the actual system output displacement. This adjustment pairs a given transducer and generator together so that, as a system, they will develop the proper displacement. Defaults for this value is intentionally set low as a safety mechanism should the adjusted values be lost, corrupted, or inadvertently not programmed. In this way, the default displacement will be lower than the target, resulting in slower but still effective tissue performance. This calibration scheme simplifies manufacturing and reduces the burden of controlling tolerances of the transducer and the generator. Furthermore, because this calibration is done entirely in software, no additional adjustment of physical parts is required either in the transducer or the generator. In effect, two control loops are being used to regulate the amplitude of the driving wave input to the transducer, which provides synchronized operation of the hardware with the oscillation frequency. Redundancy is useful to ensure the device is operating correctly. A malfunction in one loop will usually be detectable because the other loop will be unable to operate properly and the improper operation of either loop is usually detectable. Improper operation can be caused by a hardware fault. The proper operation of both loops requires measurement of both current and amplitude. Different hardware is used to measure amplitude and current. In one embodiment, the battery microcontroller 1106 measures current and the TAG microcontroller 1006 measures amplitude. As the transducer heats up, the capacitance of the transducer and the coupling coefficient will shift and the displacement of the system will decline slightly. This change in temperature also comes with a shift in frequency. By monitoring the frequency, it is possible to provide an offset to more tightly control the displacement through heavy use. This can be accomplished with a comparison to the frequency at startup or to an absolute frequency reference. Alternatively, other measurable characteristics of the transducer can be used to control this offset. Alternatively, the amount of energy put into the transducer can be used to estimate the change and adjust accordingly.

b. Frequency Control

In a similar operation to the initial frequency lock performed during the startup process, the main processor 914 of the generator 904 uses the results of the DFT calculation to adjust the running frequency of the generator 904 based on the phase of the motional feedback signal in order to maintain a resonant frequency during steady state operation. The motional feedback signal from the bridge circuit is proportional to and in phase with the motion of the transducer 902 and waveguide 1502. When the motional feedback signal is in phase with the output of the push/pull switching amplifier 1010, the system is operating at the series resonance. Again, the phase and magnitude of the motional feedback signal is computed using a Discrete Fourier Transform ("DFT"). The phase reference for the DFT computation is the drive signal for the push/pull amplifier 1010. The frequency is, then, simply changed to cause the push/pull drive signal to be in phase with the motional feedback signal.

The DFT calculation is simplified and made more accurate if the ADC sample time interval is exactly an integer multiple of the output frequency period. This technique is referred to herein as "coherent sampling." In one exemplary embodiment, the signals are sampled 12 times per output cycle such that the CLA 912 is sampling the motional feedback signal at 12 times the ultrasonic frequency. With coherent sampling, there are exactly 12 samples per cycle with each occurring at the same point in time relative to the phase of the drive signal. As shown in FIG. 9, the ADC sample clock is generated internally in the TAG microcontroller's 1006 system clock 916. Accordingly, for coherent sampling, the system clock 916 needs to be synchronized to the output. The PWM signal driving the metal-oxide field-effect transistors (MOSFETs) that, in turn, generate the output waveform, is also generated internally from the system clock 916. One exemplary embodiment of the present invention generates the system clock 916 from the DDS 1008. Advantageously, as the output frequency changes, the system clock 916 also changes.

It is also desirable not to sample shortly after the MOSFETs are switched on or off. This is when there is the largest amount of noise present in the system. Offsetting the sample time to avoid sampling shortly after the MOSFETs switch on or off minimizes the affect of transistor switching noise on the ADC sample. The two PWM outputs employ a deadband to ensure that both MOSFETs are never activated at the same time.

X. Simplified Circuit Block Diagram

FIG. 27 shows a simplified block circuit diagram illustrating another exemplary electrical embodiment of the present invention, which includes a microprocessor 2702, a clock 2730, a memory 2726, a power supply 2704 (e.g., a battery), a switch 2706 (e.g., a MOSFET power switch), a drive circuit 2708 (PLL), a transformer 2710, a signal smoothing circuit 2712 (also referred to as a matching circuit and can be, e.g., a tank circuit), a sensing circuit 2714, a transducer 902, and a waveguide assembly 304, which terminates at an ultrasonic cutting blade 1520, referred to herein simply as the waveguide 1502.

One feature of the present invention that severs dependency on high voltage (120 VAC) input power (a characteristic of all prior-art ultrasonic cutting devices) is the utilization of low-voltage switching throughout the wave-forming process and the amplification of the driving signal only directly before the transformer stage. For this reason, in one exemplary embodiment of the present invention, power is derived from only a battery, or a group of batteries, small enough to fit either within the handle assembly 302. State-of-the-art battery technology provides powerful batteries of a few centimeters in height and width and a few millimeters in depth. By combining the features of the present invention to provide an entirely self-contained and self-powered ultrasonic device, the capital outlay of the countertop box 202 is entirely eliminated—resulting in a significant reduction of manufacturing cost.

The output of the battery 2704 is fed to and powers the processor 2702. The processor 2702 receives and outputs signals and, as will be described below, functions according to custom logic or in accordance with computer programs that are executed by the processor 2702. The device 2700 can also include a main memory 2726, preferably, random access memory (RAM), that stores computer-readable instructions and data.

The output of the battery 2704 also is directed to a switch 2706 having a duty cycle controlled by the processor 2702. By controlling the on-time for the switch 2706, the processor 2702 is able to dictate the total amount of power that is ultimately delivered to the transducer 2716. In one exemplary embodiment, the switch 2706 is a MOSFET, although other switches and switching configurations are adaptable as well. The output of the switch 2706 is fed to a drive circuit 2708 that contains, for example, a phase detecting PLL and/or a low-pass filter and/or a voltage-controlled oscillator. The output of the switch 2706 is sampled by the processor 2702 to determine the voltage and current of the output signal (labeled in FIG. 27 as AD2 $V_{In}$, and AD3 $I_{In}$, respectively). These values are used in a feedback architecture to adjust the pulse width modulation of the switch 2706. For instance, the duty cycle of the switch 2706 can vary from about 20% to about 80%, depending on the desired and actual output from the switch 2706.

The drive circuit 2708, which receives the signal from the switch 2706, includes an oscillatory circuit that turns the output of the switch 2706 into an electrical signal having a single ultrasonic frequency, e.g., 55 kHz (referred to as VCO in FIG. 27). As explained above, a smoothed-out version of this ultrasonic waveform is ultimately fed to the transducer 902 to produce a resonant sine wave along the waveguide 1502.

At the output of the drive circuit 2708 is a transformer 2710 that is able to step up the low voltage signal(s) to a higher voltage. It is noted that all upstream switching, prior to the transformer 2710, is performed at low (i.e., battery driven) voltages, something that, to date, has not been possible for ultrasonic cutting and cautery devices. This is at least partially due to the fact that the device advantageously uses low on-resistance MOSFET switching devices. Low on-resistance MOSFET switches are advantageous, as they produce lower switching losses and less heat than a traditional MOSFET device and allow higher current to pass through. Therefore, the switching stage (pre-transformer) can be characterized as low voltage/high current. To ensure the lower on-resistance of the amplifier MOSFET(s), the MOSFET(s) are run, for example, at 10 V. In such a case, a separate 10 VDC power supply can be used to feed the MOSFET gate, which ensures that the MOSFET is fully on and a reasonably low on resistance is achieved. In one exemplary embodiment of the present invention, the transformer 2710 steps up the battery voltage to 120V RMS. Transformers are known in the art and are, therefore, not explained here in detail.

In each of the circuit configurations described and shown in FIGS. 3-12, 16-21, and 27, circuit component degradation can negatively impact the entire circuit's performance. One factor that directly affects component performance is heat. Known circuits generally monitor switching temperatures (e.g., MOSFET temperatures). However, because of the technological advancements in MOSFET designs, and the corresponding reduction in size, MOSFET temperatures are no longer a valid indicator of circuit loads and heat. For this reason, according to an exemplary embodiment, the present invention senses with a sensing circuit 2714 the temperature of the transformer 2710. This temperature sensing is advantageous as the transformer 2710 is run at or very close to its maximum temperature during use of the device. Additional temperature will cause the core material, e.g., the ferrite, to break down and permanent damage can occur. The present invention can respond to a maximum temperature of the transformer 2710 by, for example, reducing the driving power in the transformer 2710, signaling the user, turning the power off completely, pulsing the power, or other appropriate responses.

In one exemplary embodiment of the invention, the processor 2702 is communicatively coupled to the end effector 118, which is used to place material in physical contact with the blade portion 116 of the waveguide 114, e.g., the clamping mechanism shown in FIG. 1. Sensors are provided that measure, at the end effector, a clamping force value (existing within a known range) and, based upon the received clamping force value, the processor 2702 varies the motional voltage $V_M$. Because high force values combined with a set motional rate can result in high blade temperatures, a temperature sensor 2736 can be communicatively coupled to the processor 2702, where the processor 2702 is operable to receive and interpret a signal indicating a current temperature of the blade from the temperature sensor 2736 and to determine a target frequency of blade movement based upon the received temperature.

According to an exemplary embodiment of the present invention, the PLL 2708, which is coupled to the processor 2702, is able to determine a frequency of waveguide movement and communicate that frequency to the processor 2702. The processor 2702 stores this frequency value in the memory 2726 when the device is turned off. By reading the clock 2730, the processor 2702 is able to determine an elapsed time after the device is shut off and retrieve the last frequency of waveguide movement if the elapsed time is less than a predetermined value. The device can then start up at the last frequency, which, presumably, is the optimum frequency for the current load.

XI. Battery Assembly—Mechanical

Figure 28:
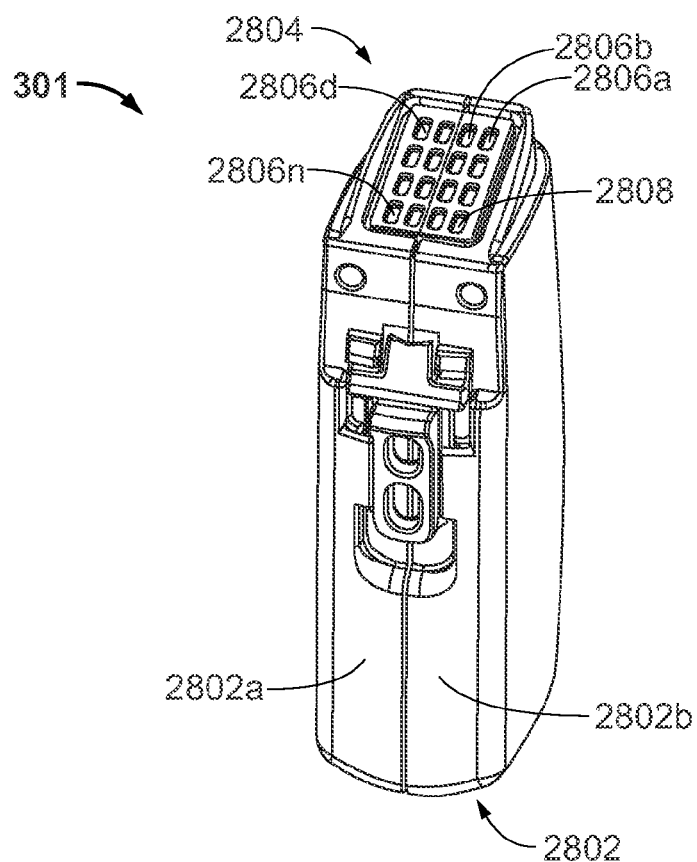
FIG. 28 is a perspective view from above the front of the battery assembly of FIG. 4 in accordance with an exemplary embodiment of the present invention.

FIG. 28 shows an exemplary embodiment of the battery assembly 301 separate from the handle assembly 302. The battery assembly 301 includes an outer shell 2802 that comprises a first half 2802*a* and a second half 2802*b*. There is, however, no requirement that the shell 2802 be provided in two halves. In accordance with an exemplary embodiment of the present invention, when the outer shell 2802 is provided in two halves, the first half 2802*a* can be ultrasonically welded to the second half 2802*b* in a clamshell configuration. Ultrasonically welding the two halves of the shell 2802 eliminates the need for gaskets while providing a "hermetic" seal between the components within the shell 2802 and the environment. A "hermetic" seal, as used herein, indicates a seal that sufficiently isolates a compartment (e.g., interior of the shell 2802) and components disposed therein from a sterile field of an operating environment into which the device has been introduced so that no contaminants from one side of the seal are able to transfer to the other side of the seal. This seal is at least gas-tight, thereby preventing intrusion of air, water, vapor phase $H_2O_2$, etc. Upon initial assembly, room air will be trapped in the enclosure with whatever moisture is present. This can easily be more moisture than is desirable in an electronics enclosure. Therefore, inclusion of a desiccant system inside the enclosure can serve two purposes. A primary purpose is to absorb any moisture that may ingress over the life of the device, but, if sized appropriately, the desiccant system will also serve to absorb any moisture that is trapped during assembly. Use of the desiccant system, therefore, simplifies assembly and eliminates the need to close the enclosure under any special environments.

FIG. 28 also shows a multi-lead battery terminal assembly 2804, which is an interface that electrically couples the components within the battery assembly 301 to an electrical interface of the handle assembly 302. It is through the handle assembly 302 that the battery assembly 301 is able to electrically (and mechanically) couple with the TAG assembly 303 of the present invention. As is explained above, the battery assembly 301, through the multi-lead battery terminal assembly 2804, provides power to the inventive ultrasonic surgical cautery assembly 300, as well as other functionality described herein. The multi-lead battery terminal assembly 2804 includes a plurality of contacts pads 2806*a-n*, each one capable of separately electrically connecting a terminal within the battery assembly 301 to another terminal provided by a docking bay (see FIG. 34) of the handle assembly 302. One example of such electrical connections coupled to the plurality of contact pads 2806*a-n* is shown in FIG. 6 as power and communication signal paths 601*a-n*. In the exemplary embodiment of the multi-lead battery terminal assembly 2804, sixteen different contact pads 2806*a-n* are shown. This number is merely illustrative. In an exemplary embodiment, an interior side of the battery terminal assembly 2804 has a well formed on the molded terminal holder that can be filled with potting materials to create a gas tight seal. The contact pads 2806*a-n* are overmolded in the lid and extend through the potting well into the interior of the battery 301. Here a flex circuit can be used to rearrange the array of pins and provide an electrical connection to the circuit boards. In the exemplary embodiment shown in FIG. 30, for example, a 4×4 array is converted to a 2×8 array.

Figure 29:
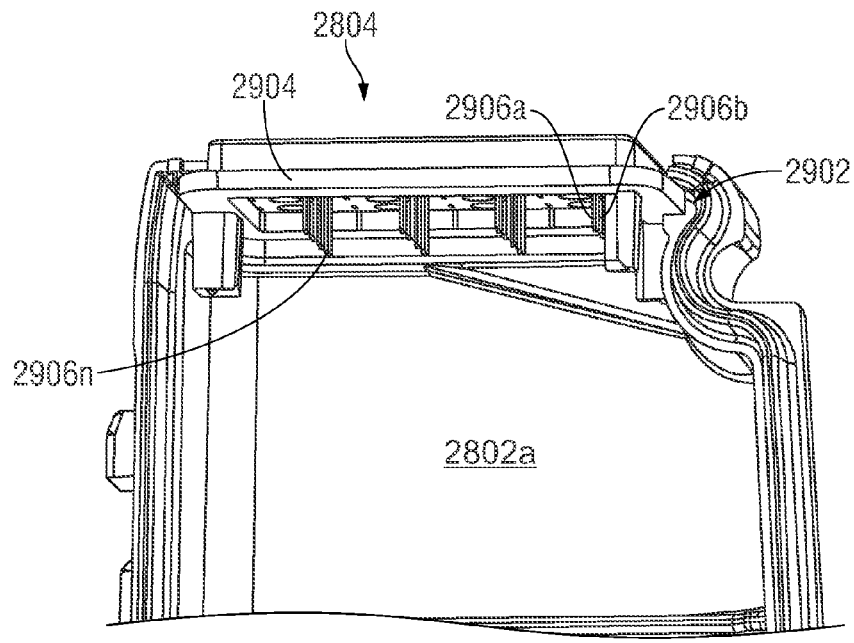
FIG. 29 is a fragmentary, perspective view from a left side of the battery assembly of FIG. 4 with one half of the shell removed exposing an underside of a multi-lead battery terminal and an interior of the remaining shell half in accordance with an exemplary embodiment of the present invention.
Figure 32:
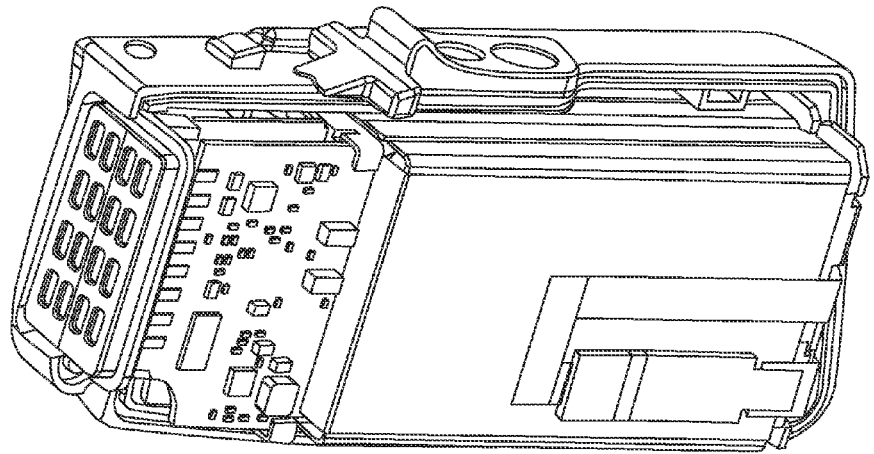
FIG. 32 is an elevated perspective view of the battery assembly shown in FIG. 31 with one half of the shell in place in accordance with an exemplary embodiment of the present invention.

FIG. 29 provides a view of the underside of an exemplary embodiment of the multi-lead battery terminal assembly 2804. In this view, it can be seen that the plurality of contact pads 2806*a-n* of the multi-lead battery terminal assembly 2804 include a corresponding plurality of interior contact pins 2906*a-n*. Each contact pin 2906 provides a direct electrical coupling to a corresponding one of the contact pads 2806. FIGS. 28 and 32 show two hemispherical depressions 2810 in the battery casing that, when combined with the hook feature 3302, a generally longitudinal void, can be used to retain the battery 301 into a charger. Such geometrical features are easy to fabricate and easy to clean and provide a simple way to capture the battery 301 in a charger in a way that does not require the releasing mechanism that normally is used to disconnect the battery 301 from the handle 302.

In the exemplary embodiment shown in FIGS. 28 to 33, the multi-lead battery terminal assembly 2804 is potted between the clam shell halves 2802*a* and 2802*b* of the shell 2802. More particularly, FIG. 29 provides a view of the multi-lead battery terminal assembly 2804 positioned inside an upper portion of the first shell half 2802*a* of the battery assembly 301. As is shown in the figure, an upper portion of the first shell half 2802*a* forms a mouth 2902 that accepts an outer peripheral edge 2904 of the multi-lead battery terminal assembly 2804.

Figure 30:
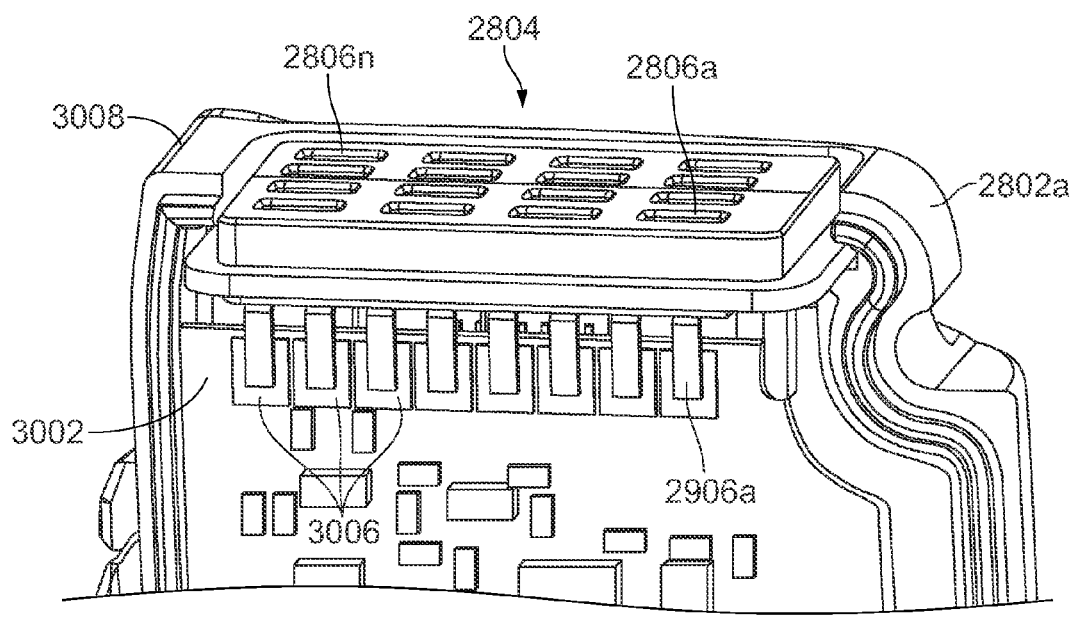
FIG. 30 is a fragmentary, perspective view from a right side of the battery assembly of FIG. 4 with one half of the shell removed exposing a circuit board connected to the multi-lead battery terminal in accordance with an exemplary embodiment of the present invention.
Figure 31:
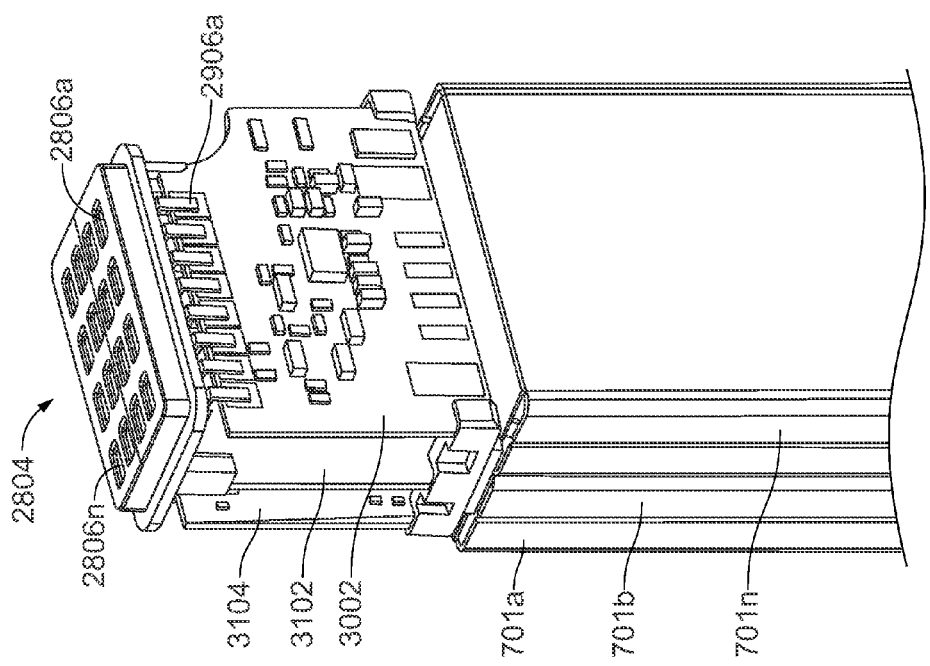
FIG. 31 is an elevated perspective view of the battery assembly of FIG. 4 with both halves of the shell removed exposing battery cells coupled to multiple circuit boards which are coupled to the multi-lead battery terminal in accordance with an exemplary embodiment of the present invention.

FIG. 30 provides an additional view of the interior of the first shell half 2802*a* with the multi-lead battery terminal assembly 2804 inserted within the mouth 2902 of the first shell half 2802*a* and an exemplary embodiment of a first circuit board 3002 having a plurality of contact pads 3006 coupled to the contact pins 2906 of the multi-lead battery terminal assembly 2804. In such an embodiment, each of the contact pins 2906 is soldered to its respective contact pad 3006 of the circuit board 3002. The battery assembly 301, according to exemplary embodiments of the present invention, includes, as is shown in FIG. 31, in addition to the first circuit board 3002, additional circuit boards 3102 and 3104.

In accordance with one exemplary embodiment of the present invention, the multi-lead battery terminal assembly 2804 comprises a flex circuit that converts the illustrated 4×4 array of contact pads 2006a-n to two 1×8 arrays of conductors that are coupled to one or more of the circuit boards 3002, 3102, 3104.

In an alternative exemplary embodiment, rather than using a flex connector and soldering to connect the one or more circuit boards 3002, 3102, and 3104, a card edge connector 10701 could provide connectivity between the boards and the multi-lead battery terminal assembly 2804 as shown in FIG. 107, which is a cross-sectional view of a shell half of the battery assembly 301 beneath a sloping curvature of the exterior surface of the multi-lead battery terminal assembly 2804. In this exemplary embodiment, the angle of the slope of the multi-lead terminal assembly 2804 is greater than that shown in FIG. 4. For purposes of illustration, only one of the plurality of interior contact pins 2906a-n is depicted. One end of the contact pin 2906 is embedded into the body of the multi-lead battery terminal assembly 2804. The other end of the contact pin 2906 is formed into an "S"-shaped curve that gives the contact pin a degree of flex and forms an interior groove or channel 10702 between the contact pin and the body of the multi-lead battery terminal assembly 2804. The inherent flex of the "S"-shaped portion of the contact pin 2906 allows for any of the one or more circuit boards 3002, 3102, 3104 to be easily inserted into the interior groove or channel 10702 to establish a direct electrical connection between the contact pin 2906 and one or more traces of the circuit board 3002, 3102, 3104. To maintain this direct connection, a card edge connector 10704 secures the circuit board in place, thereby eliminating any need for soldering the contact pin 2906 to the circuit board. As a result, the features of the card edge connector 10704 are integrated into the underside of the multi-lead battery terminal assembly 2804. Accordingly, it is easier to remove the boards for troubleshooting and simplifies manufacturing by eliminating solder joints.

Further, more than or less than three circuit boards is possible to provide expanded or limited functionality. As shown in FIG. 31, the multiple circuit boards 3002, 3012, 3104 may be positioned in a stacked architecture, which provides a number of advantages. For example, due to the smaller layout size, the circuit boards have a reduced footprint within the battery assembly 301, thereby allowing for a smaller battery. In addition, in this configuration, is possible to easily isolate power boards from digital boards to prevent any noise originating from the power boards to cause harm to the digital boards. Also, the stacked configuration allows for direct connect features between the boards, thereby reducing the presence of wires. Furthermore, the circuit boards can be configured as part of a single rigid-flex-rigid circuit to allow the rigid parts to be "fanned" into a smaller volumetric area. According to exemplary embodiments of the present invention, each circuit board 3002, 3102, and 3104 provides a specific function. For instance, circuit board 3002 can provide the components for carrying out the battery protection circuitry 702 shown in FIG. 7. Similarly, the circuit board 3102 can provide the components for carrying out the battery controller 703, also shown in FIG. 7. The circuit board 3104 can, for example, provide high power buck controller components. Finally, the battery protection circuitry 702 can provide connection paths for coupling the battery cells 701a-n shown in FIGS. 7 and 31. By placing the circuit boards in a stacked configuration and separating the boards by their respective functions, the boards may be strategically placed in a specific order that best handles their individual noise and heat generation. For example, the circuit board having the high-power buck controller components produces the most heat and, therefore, it can be isolated from the other boards and placed in the center of the stack. In this way, the heat can be kept away from the outer surface of the device in an effort to prevent the heat from being felt by the physician or operator of the device. In addition, the battery board grounds may be configured in a star topology with the center located at the buck controller board to reduce the noise created by ground loops.

The strategically stacked circuit boards, the low thermal conductivity path from the circuit boards to the multi-lead battery terminal assembly, and a flex circuit 3516 are all features that assist in preventing heat from reaching the exterior surface of the device. The battery cells and buck components are thermally connected to the flex circuit 3516 within the handle 302 (i.e., the disposable portion of the device) so that the heat generated by the cells and buck components enter a portion away from the physician's hand. The flex circuit 3516 presents a relatively high thermal mass, due to its broad area of exposure and the advantageous conduction characteristics of the copper, which redirects, absorbs, and/or dissipates heat across a broader area thereby slowing the concentration of heat and limiting high spot temperatures on the exterior surface of the device. Other techniques may be implemented as well, including, but not limited to, larger heat wells, sinks or insulators, a metal connector cap and heavier copper content in the flex circuit or the handle 302 of the device.

Another advantage of a removable battery assembly 301 is realized when lithium-ion (Li) batteries are used. As previously stated, lithium batteries should not be charged in a parallel configuration of multiple cells. This is because, as the voltage increases in a particular cell, it begins to accept additional charge faster than the other lower-voltage cells. Therefore, each cell must be monitored so that a charge to that cell can be controlled individually. When a lithium battery is formed from a group of cells 701a-n, a multitude of wires extending from the exterior of the device to the batteries 701a-n is needed (at least one additional wire for each battery cell beyond the first). By having a removable battery assembly 301, each battery cell 701a-n can, in one exemplary embodiment, have its own exposed set of contacts and, when the battery assembly 301 is not present inside the handle assembly 302, each set of contacts can be coupled to a corresponding set of contacts in an external, non-sterile, battery-charging device. In another exemplary embodiment, each battery cell 701a-n can be electrically connected to the battery protection circuitry 702 to allow the battery protection circuitry 702 to control and regulate recharging of each cell 701a-n. The battery assembly 301 of the present invention is provided with circuitry to prevent use of the battery assembly 301 past an expected term-of-life. This term is not only dictated by the cells but is also dictated by the outer surfaces, including the battery casing or shell and the upper contact assembly. Such circuitry will be explained in further detail below and includes, for example, a use count, a recharge count, and an absolute time from manufacture count.

Figure 33:
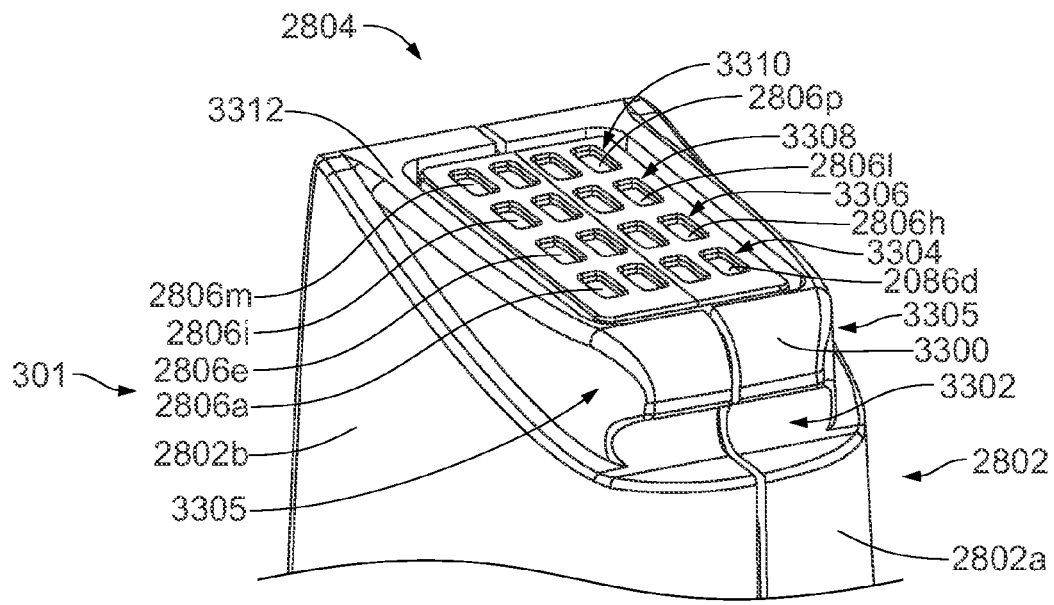
FIG. 33 is an elevated perspective view of the battery assembly of FIG. 4 showing a catch located on a rear side of the battery assembly in accordance with an exemplary embodiment of the present invention.
Figure 34:
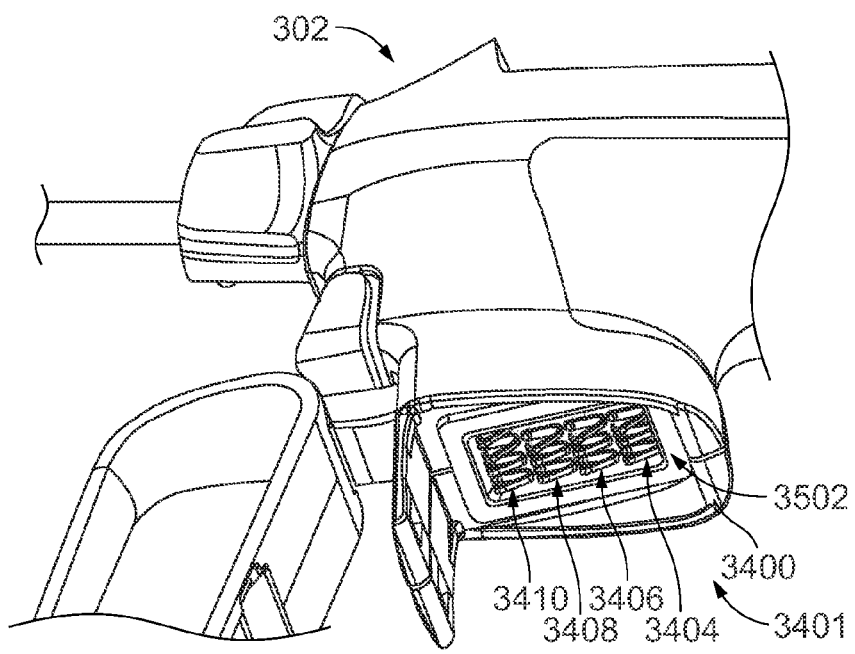
FIG. 34 is an underside perspective view of the handle assembly of FIG. 3 exposing a multi-lead handle terminal assembly and a receiver for mating with the battery assembly of FIG. 4 in accordance with an exemplary embodiment of the present invention.

Turning now to FIG. 33, at least one additional novel feature of the present invention is clearly illustrated. The battery assembly 301 shown in FIG. 33 shows a fully assembled battery assembly 301 that has been, for instance, ultrasonically welded so that the two shell halves 2802a and 2802b, as well as the potted multi-lead battery terminal assembly 2804, provide a hermetic seal between the environment and the interior of the battery assembly 301. The gap between the terminal assembly 2804 and the shell halves 2802a and 2802b is wide enough to allow for automated dispense of sealing materials such as light cure adhesives or epoxies. Although shown in several of the previous drawings, FIG. 33 illustrates an inventive catch 3300, which is formed by an extended portion of the shell 2802 that is shaped by a generally longitudinal void 3302 directly under the catch 3300, both being located at an upper portion of the exterior of the shell 2802. The catch 3300 is shaped to mate with a receiver 3400 in a lower battery dock 3401 of the handle assembly 302, which is shown in FIG. 34.

Figure 35:
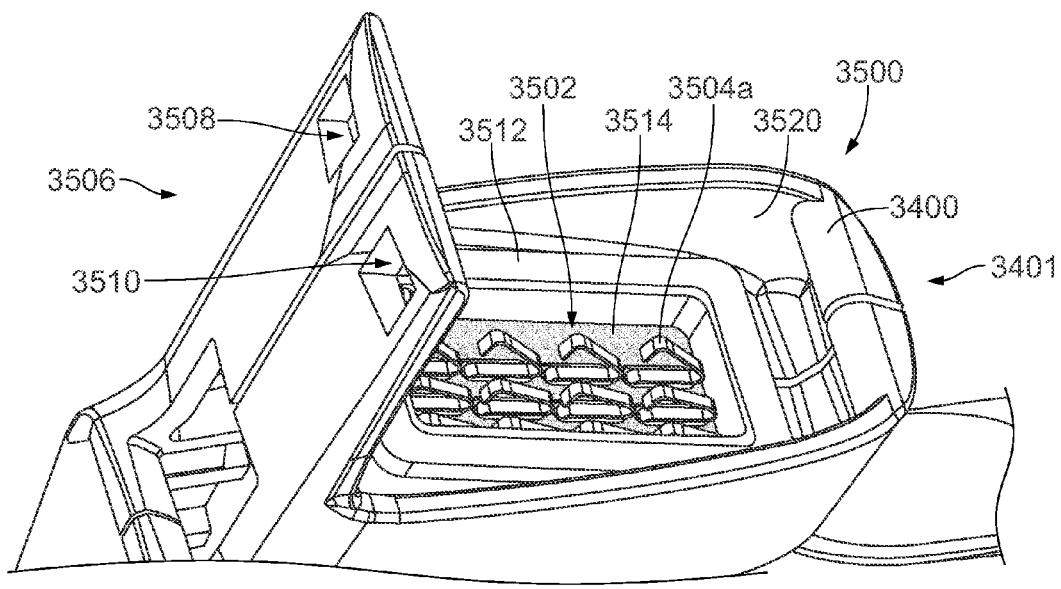
FIG. 35 is a close-up underside perspective view of the handle assembly of FIG. 3 exposing a multi-lead handle terminal assembly and a receiver for mating with the battery assembly of FIG. 4 in accordance with an exemplary embodiment of the present invention.

FIG. 35 illustrates an underside of the handle assembly 302 and provides an improved view of the receiver 3400 and the battery dock 3401. As is can be seen in FIG. 35, the receiver 3400 extends from the battery dock 3401 (formed by a handle shell 3500) and is shaped to mate with, i.e., fit within, the void 3302 of the battery assembly 301. In addition, the receiver 3400 is in close proximity to a multi-lead handle terminal assembly 3502, which includes a plurality of handle-connection pins 3504a-n. In the exemplary embodiment shown in FIG. 35, each handle contact pin in the multi-lead handle terminal assembly 3502 is a spring-type contact pin that is capable of being compressed while exerting an amount of force in a direction opposite the compression force and, thereby, maintaining a positive electrical connection between the handle-connection pin 3504a-n and the object applying the force. In addition, the handle-connection pins 3504a-n of the multi-lead handle terminal assembly 3502 are spaced so that each of the handle-connection pins 3504a-n physically aligns with a respective one of the contact pads 2806a-n of the multi-lead battery terminal assembly 2804.

Figure 36:
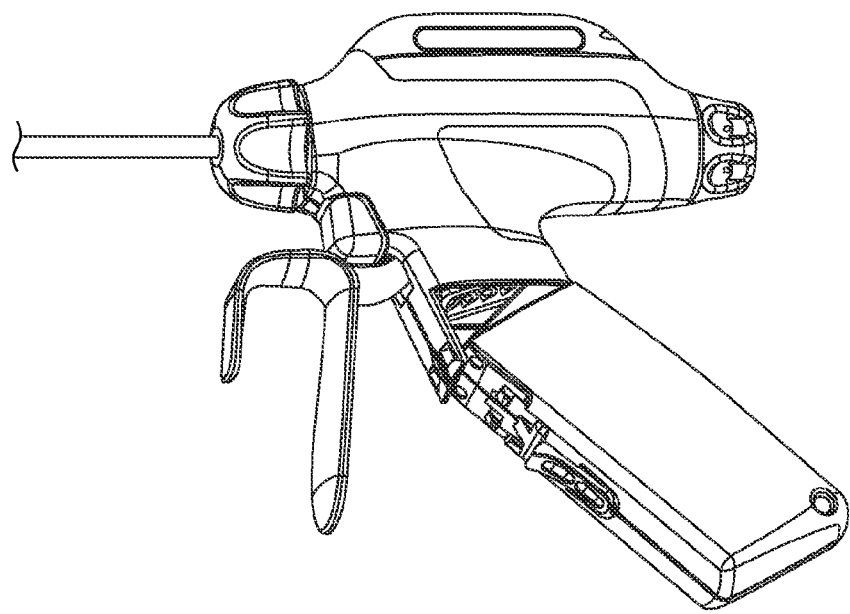
FIG. 36 is an underside perspective view illustrating an initial mating connection between the handle assembly and the battery assembly in accordance with an exemplary embodiment of the present invention.
Figure 37:
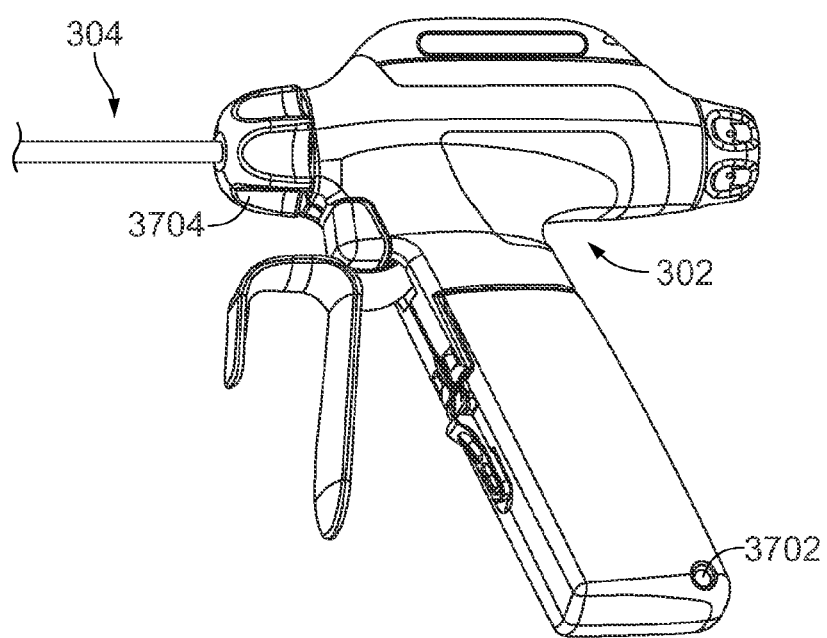
FIG. 37 is a perspective view of the battery assembly fully connected to the handle assembly in accordance with an exemplary embodiment of the present invention.

To couple the inventive battery assembly 301 to the inventive handle assembly 302, the catch 3300 is contacted with the receiver 3400, as is shown in FIG. 36, and the battery assembly 301 is rotated with respect to the handle assembly 302, as is shown in the progression from FIG. 36 to FIG. 37. Although not limited to the exemplary embodiments shown in the figures of the instant specification, the physical shapes of the catch 3300 and receiver 3400 shown in FIGS. 33-35 (particularly the rounded corners 3305 shown in FIG. 33) cause the battery assembly 301 to align itself with the handle assembly 302 virtually regardless of the angle to which the battery assembly 301 approaches the receiver 3400, as long as the catch 3300 and receiver 3400 are in physical contact with each other. With any rotation of the battery assembly 301 between the position shown in FIG. 36 and the position shown in FIG. 37, the catch 3300, or rather, the void 3302, automatically seats upon the receiver 3400. This means that a user in the sterile field can easily connect the battery assembly 301 to the handle assembly 302 and, especially, can do so without actually viewing the two parts during connection efforts.

Figure 59:
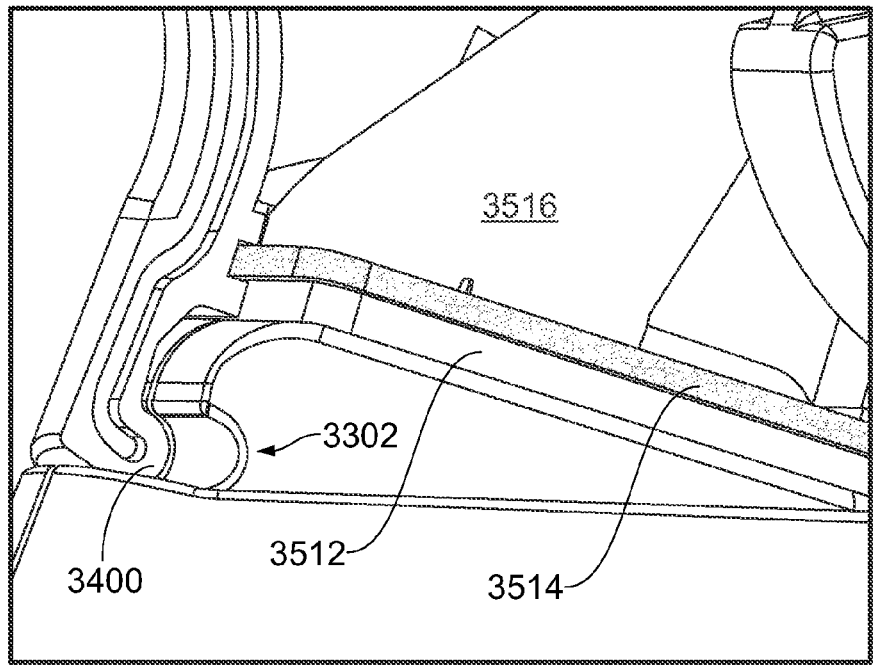
FIG. 59 is a perspective close-up view of the coupling relationship between the catch on the battery assembly and the receiver on the handle assembly as well as the sealing relationship between the multi-lead battery terminal assembly and the multi-lead handle terminal assembly in accordance with an exemplary embodiment of the present invention.
Figure 60:
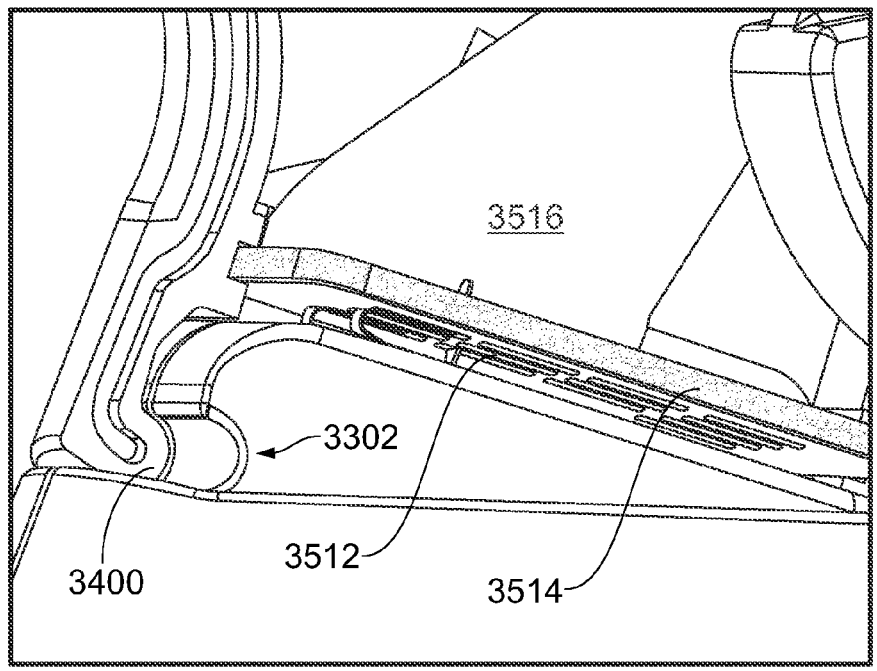
FIG. 60 is a perspective close-up transparent view of the sealing gasket of FIG. 59 in accordance with an exemplary embodiment of the present invention.

In accordance with one exemplary embodiment of the present invention, the multi-lead handle terminal assembly 3502, as shown in FIG. 35, includes a gasket 3512 that surrounds the handle-connection pins 3504a-n and is sealed to a flex circuit board 3514 that supports the handle-connection pins 3504a-n. In one exemplary embodiment, the gasket 3512 is part of a rigid-flex circuit that includes the flex circuit board 3514, a flex circuit or harness 3516 (to be connected to the TAG assembly 303), and the handle-connection pins 3504a-n. A portion of the flex circuit board 3514 is made relatively rigid or stiffer as compared to the rest of the flex harness 3516. When the gasket 3512 is compressed during connection of the battery assembly 301 to the handle assembly 302, rigid portions of the flex circuit board 3514 adjacent the gasket 3512 support the gasket 3512 and allow the gasket 3512 to be compressed without substantial movement when the battery assembly 301 is coupled to the handle assembly 302. When the multi-lead battery terminal assembly 2804 and the multi-lead handle terminal assembly 3502 are placed together, as shown in FIGS. 59 and 60, a seal exists between an outer periphery 3312 of the multi-lead battery terminal assembly 2804 and the gasket 3512 of the multi-lead handle terminal assembly 3502. The seal prevents moisture from penetrating the interior of the gasket 3512, i.e., reaching the handle-connection pins 3504a-n of the multi-lead handle terminal assembly 3502 or the contacts pads 2806a-n of the multi-lead battery terminal assembly 2804. This sealing method only requires that the portions of the contact pins that extend through the stiffener be insulated on the side opposite the gasket. Such a sealing method is also used on the TAG connector 5010 and on the handle 302 as described in further detail below. Such configuration allow for the production of a device where sealing all potential openings is not necessary, thereby resulting in a cost and complexity savings.

According to an exemplary embodiment of the present invention, the flex circuit board 3514 is made from two copper trace layers separated and insulated with polyimide. As provided above, portions of the flex circuit board 3514 can be made relatively stiffer. For example, certain portions of the flex circuit board 3514 may contain a stiffener, e.g., FR-4 stiffener, bonded to the flex circuit board 3514. The portions of the flex circuit board 3514 with the stiffener provide a mechanical way of rigidly holding components within the disposable handle assembly 302.

Figure 108:
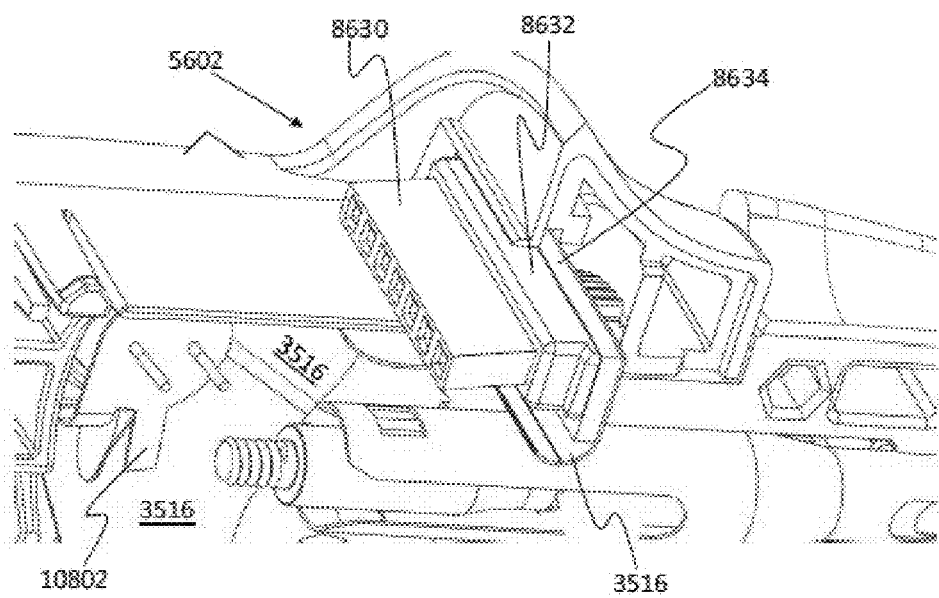
FIG. 108 is a fragmentary, perspective view of an exemplary embodiment of a TAG assembly connector according to the invention.

In accordance with another exemplary embodiment of the present invention, the two body halves 4503, 4603 of the handle assembly 302 hold the rigid sections therebetween within the handle assembly 302 under close tolerances. Where the flex circuit board 3514 has a stiffener 10902 in a horizontal orientation, and the flex circuit board 3514 transitions to a vertical orientation, as shown in FIG. 108, the flex circuit board 3514 can be damaged if not allowed to gradually transition. The rigid portions (e.g., 10902) of the flex circuit board 3514 are desired to be at or within a slot or track 10804 in the body material. Therefore, to hold the rigid portions firmly on all sides, a portion 10806 of the flex circuit board 3514 is designed to peel away from the rigid portion 10902 before reaching the end of the flex circuit board 3514. No adhesive is placed in this area. According to an exemplary embodiment of the present invention, on this battery side of the flex circuit board 3514, i.e., the stiffened board from which the battery contact pins 2906a-n protrude, has a custom connector made from, for example, FR-4 material or molded plastic. This can be seen, for example, in FIG. 60. The molded plastic can contain either insert molded metal contacts or the contacts can be inserted after molding and then potted for sealing purposes. The FR-4 or molded plastic is then bonded to the flex circuit board 3514 with an adhesive. In a molded configuration, the connector can be made to have rows of rigid material raised between the contacts or even a grid of material to protect the contact from mechanical damage.

Figure 56:
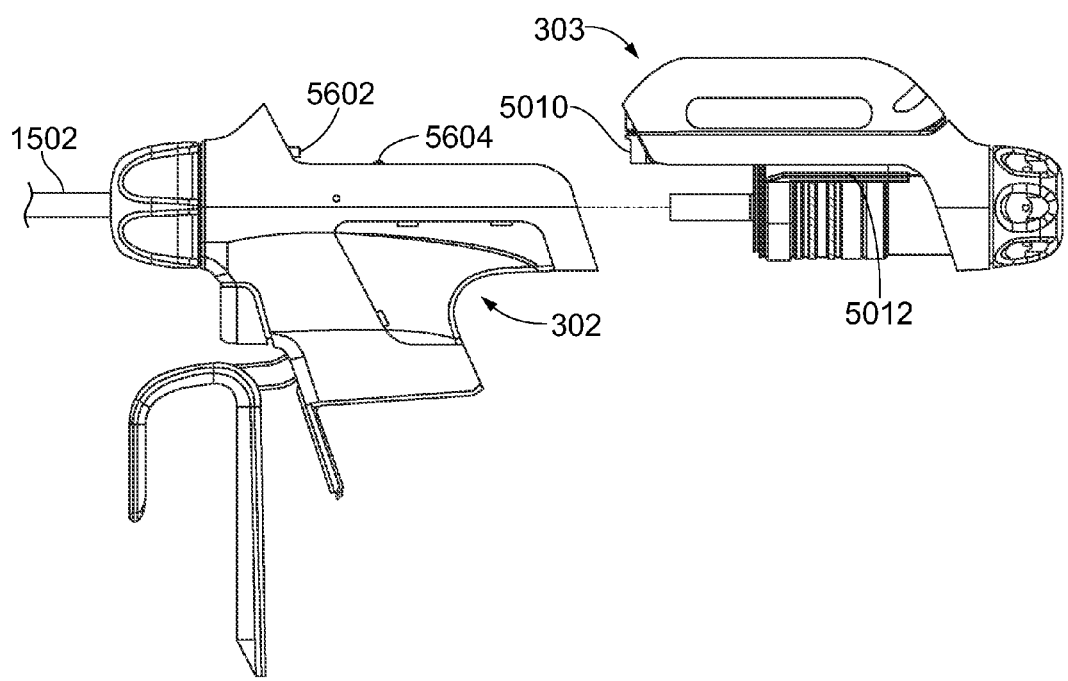
FIG. 56 is an elevational left side view of the handle assembly and the TAG, illustrating a coupling alignment between the handle assembly and the TAG in accordance with an exemplary embodiment of the present invention.

As shown in FIG. 56 and explained in detail below, the rigid-flex circuit of the handle assembly 302 electrically couples the handle-connection pins 3504a-n to the handle assembly's TAG electrical connector 5602.

Figure 38:
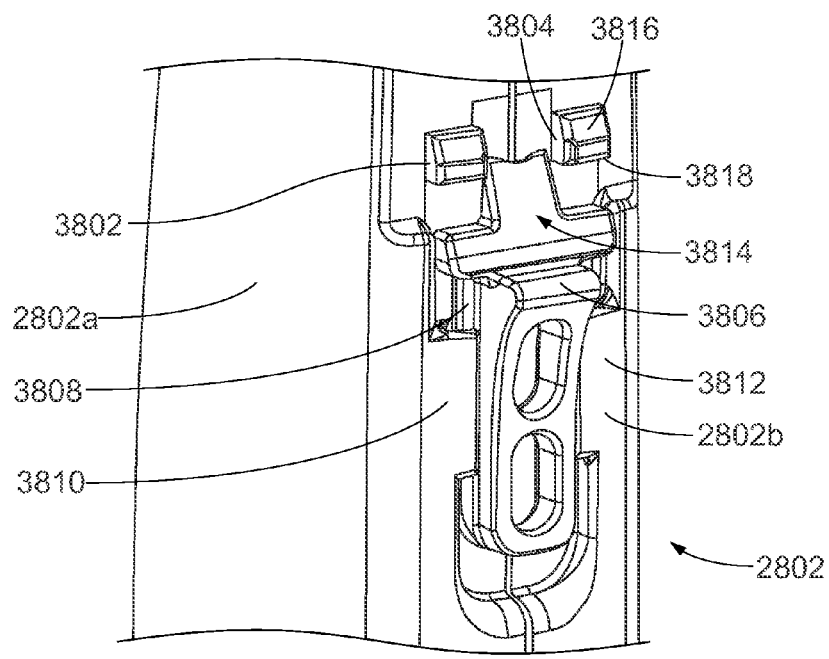
FIG. 38 is a close-up perspective view of the exterior surface of the battery assembly of FIG. 4 illustrating a release mechanism for coupling the battery assembly to the handle assembly in accordance with an exemplary embodiment of the present invention.

Referring briefly back to FIG. 35, the handle body 3500 of the handle assembly 302 is provided with an extended battery securing portion 3506. The extended battery securing portion 3506 is on a side of the multi-lead handle terminal assembly 3502 opposite the receiver 3400. It is noted that the particular exemplary embodiment of the handle-securing portion shown in FIG. 35 includes a pair of voids 3508 and 3510, which are not necessary to complete the battery-handle securing process. Referring now to FIG. 38, an additional feature of the battery assembly 301 is shown. In this view, a pair of bosses 3802, 3804 can be seen on an exterior side of the battery assembly shell 2802. The bosses 3802, 3804 are spaced and positioned to mate with the voids 3508, 3510 in the extended battery securing portion 3506 of the handle body 3500. This mating position is illustrated in FIG. 37. Referring still to FIG. 38, it can be seen that each of the bosses 3802, 3804 are provided with a sloped upper portion 3816 and an opposing sharp-edge bottom portion 3818. The sloped upper portion 3816 allows the bosses 3802, 3804 to easily slip into the voids 3508, 3510 in the extended battery securing portion 3506 of the handle assembly 302 when the battery assembly 301 is being secured to the handle assembly 302. The sharp-edge bottom portions 3818 secure and allow the bosses 3802, 3804 to remain seated within the extended battery securing portion 3506 of the handle assembly 302.

The combination of the mating between the catch 3300 and receiver 3400 at one side of the battery assembly 301 and the mating between the bosses 3802, 3804 and the voids 3508, 3510, respectively, at the other side of the battery assembly 301 provides a solid and secure attachment of the battery assembly 301 to the handle assembly 302 (see also FIGS. 3 and 37). In an exemplary embodiment, the two bosses 3802, 3804 are spaced as far apart from each other as is practical. This spacing improves the strength and stability of the attachment between the battery assembly 301 and the handle assembly 302. This stability is further improved by the overlap between the disposable and the battery at faces 3520 and 3305, seen in FIGS. 35 and 33, respectively.

FIG. 38 also illustrates a release mechanism 3806 coupled to the exterior of the battery assembly shell 2802. The release mechanism 3806 is provided with peripheral edges 3808 that are secured by and slide within a pair of corresponding channels 3810, 3812 formed within the same exterior side of the battery assembly shell 2802 as the bosses 3802, 3804. The fit between the release mechanism 3806 and the battery casing 2802a, 2802b is loose so that water is able to flow between the mating parts for cleaning before sterilization. To assist in the cleanability of the release mechanism 3806, holes can be added; in the exemplary embodiment, two oval holes are present. Additionally, all edges of release mechanism 3806 are curved to limit the contacted surface area. A face of the release mechanism 3806 facing the battery casing has a concave cut down the center of it to further reduce the mated surface area. The release mechanism 3806 has a sloped nose region 3814 that is operable for moving toward and away from the bosses 3802 and 3804 and, in the particular embodiment shown in FIG. 38, extends between the bosses 3802 and 3804 when the release mechanism 3806 is slid in an upwardly direction. This nose 3814 also forces the battery latch down and out of the way during connection of the battery assembly 301. The release mechanism 3806 is made of a lubricious yet tough material that can supply low friction but also withstand the extended use of the battery assembly 301—a reusable portion of the device. Materials such as graphite and/or carbon-fiber reinforced PTFE are suitable, for example.

When the battery assembly 301 is securely coupled to the handle assembly 302, as is shown in FIG. 37, the release mechanism 3806 remains in a position within the channels 3810, 3812 that is furthest away from the handle assembly 302. When a user desires to remove the battery assembly 301 from the handle assembly 302, the release mechanism 3806 is slid within the channels 3810, 3812 in a direction toward the handle assembly 302. This sliding action causes the sloped nose region 3814 to enter the area between the battery assembly 301 and the lowermost portion of the extended battery securing portion 3506. As the sloped nose region 3814 moves forward, it forces the extended battery securing portion 3506 to ride up on the sloped nose region 3814 and flex away from the battery assembly 301. Stated differently, the extended battery securing portion 3506 bends away from the multi-lead handle terminal assembly 3502 and receiver 3400. To eliminate risk of inadvertently releasing the battery assembly 301 from the handle assembly 302 while the jaw is closed, the trigger 4606 is configured to cover or protect the battery release mechanism 3806. Therefore, with the trigger 4606 fully depressed, the battery release mechanism 3806 is fully covered, thereby preventing user actuation of the release mechanism 3806 to release the battery assembly 301.

Once the extended battery securing portion 3506 flexes to a certain degree, the bottom edges 3818 of the bosses 3802 and 3804 no longer engage with the voids 3508 and 3510 and the battery assembly 301 can easily be rotated from the orientation shown in FIG. 37 to that shown in FIG. 36 and, ultimately, separated from the handle assembly 302. The release mechanism 3806 is, of course, only one example of a mechanism that secures the battery assembly 301 to and releases the battery assembly 301 from the handle assembly 302. The release mechanism 3806 is advantageous in that it renders unintended detachment very unlikely. To release the battery assembly 301, an operator needs to move the release mechanism 3806 toward the handle while, at the same time, rotating the battery assembly 301 away from the handle assembly 302. These two oppositely-directed forces/actions are very unlikely to occur simultaneously unless they are performed intentionally. Application of these different forces also requires the user's hands to be in a position different than an in-use position during surgery. Such a configuration virtually ensures that accidental separation of the battery assembly 301 and handle assembly 302 does not occur.

The present invention also provides a significant advantage over prior art devices in the way the electrical connection between the multi-lead handle terminal assembly 3502 and the multi-lead battery terminal assembly 2804 is formed. More specifically, looking again to FIG. 33, it can be seen that, in the illustrated exemplary embodiment of the multi-lead battery terminal assembly 2804, sixteen contact pads 2806 are present—the contact pads 2806a-d forming a first row 3304, contact pads 2806e-h forming a second row 3306, contact pads 2806i-1 forming a third row 3308, and contact pads 2806m-p forming a fourth row 3310.

Similarly, as is shown in FIGS. 34 and 35, the multi-lead handle terminal assembly 3502 includes a plurality of handle-connection pins 3504a-n (only twelve of the sixteen pins 3504a-n are shown in the view of FIG. 35). The handle contact pins are configured so that, when the battery assembly 301 is coupled to the handle assembly 302, each handle-connection pin 3504a-n is aligned with an individual one of the contact pads 2806. Therefore, the handle-connection pins 3504a-n are also disposed, in the particular embodiment shown in the drawings, in four rows 3404, 3406, 3408, and 3410.

When the battery assembly 301 is to be attached to the handle assembly 302, the catch 3300 is first placed in contact with the receiver 3400 and the battery assembly 301 is then rotated toward the extended battery securing portion 3506 until the bosses 3802, 3804, respectively, engage the voids 3508, 3510 in the extended battery securing portion 3506. One significant result of the rotation is that the physical/electrical connection between the multi-lead handle terminal assembly 3502 and the multi-lead battery terminal assembly 2804 occurs sequentially, one row at a time, starting with battery row 3304 and handle row 3404.

According to an exemplary embodiment of the present invention, the first battery row 3304 includes a grounding contact pad and the last battery row 3410 includes at least one power contact pad. Therefore, the first contact between the multi-lead battery terminal assembly 2804 and the multi-lead handle terminal assembly 3502 is a grounding connection and the last is a power connection. Installation of the battery assembly 301 will not cause a spark because the ground contact of the battery assembly 301 is a distance away from the last row 3410 of the multi-lead handle terminal assembly 3502 when the powered connection is made. As the battery assembly 301 is rotated into an attachment position (shown in FIG. 37), each battery row 3304, 3306, 3308, 3310 sequentially makes contact with each handle row 3404, 3406, 3408, 3410, respectively, but the power contact(s) is(are) only connected after a row having at least one grounding contact has been connected. In other words, as the battery assembly 301 is installed into the handle assembly 302, the battery assembly 301 is advantageously grounded before any power contacts are brought into contact with any portion of the handle assembly 302—a significant advantage over prior-art device power supply couples. In all known devices, the contacts supplying power (i.e., electric mains) are coupled simultaneous to other couplings, or randomly, depending on the approach orientation of the electric plug. This prior-art coupling leaves sparking or arcing as a persistent possibility. With the present invention, however, the possibility of sparking or arcing that is present in the prior art is entirely eliminated.

In addition, in accordance with one exemplary embodiment of the present invention, one or more pins in any of the first 3404, the second 3406, the third 3408, or the last row 3410 of the handle-connection pins 3504a-n are coupled to a battery presence detection circuit 3104. In particular, one of the contacts in the last row 3410 is used as a present pad. The battery presence detection circuit 3104, after detecting the proper connection of the grounding pin(s) and the present pin of the multi-lead handle terminal assembly 3502 to the multi-lead battery terminal assembly 2804, allows operation of the ultrasonic surgical assembly 300. In the embodiment where the battery present detection pad(s) is/are only in the last row, i.e., furthest away from the receiver 3400, the handle assembly 302 will not alter/change states until the battery assembly 301 is fully and securely installed, i.e., all contacts are properly connected. This advantageous feature prevents any improper operation of the overall assembly. Similarly, when disconnecting the battery assembly 301, the last row 3410 is the first row disconnected from the handle-connection pins 3504a-n. Therefore, the device immediately responds to the absence of the battery assembly 301 from the handle assembly 302.

In the exemplary embodiment, the battery protection circuit 702, i.e., the fuel gauge, monitors the present pad and waits for it to be grounded before powering the microprocessor 1006 within the TAG assembly 303. To do this, of course, the TAG assembly 303 must also be coupled to the handle assembly 302. More particularly, the TAG assembly 303 must be electrically coupled to the handle assembly's TAG electrical connector 5602. Once the TAG assembly 303 is coupled to the handle assembly's TAG electrical connector 5602 (see, e.g., FIGS. 36 and 37) and the battery assembly 301 is properly coupled to the multi-lead handle terminal assembly 3502 (see, e.g., the configuration shown in FIG. 37), communication between the battery assembly 301 and the TAG assembly 303 occurs. After such communication is established, the device is ready for use and the battery controller 703 can signal a "ready-for-use" state to the user, for example, by generating an indicative tone at the buzzer 802 within the handle assembly 302 and/or generating a visual indicator at the LEDs 906.

In one exemplary embodiment for establishing this communication, the battery protection circuit 702 senses the presence of a proper connection between the battery assembly 301 and the handle assembly 302 by periodically pulsing a low-voltage signal to the present pad. The battery protection circuit 702 monitors the present pad for a connection to ground, which ground is provided by the handle assembly 302 once the battery assembly 301 is properly connected thereto. However, because the battery assembly 301 may be exposed to bodily fluids or submerged in a solution, for example, water during cleaning, it is advantageous for the battery assembly 301 not to sense a false ground condition as if the battery assembly 301 has been properly connected to the handle assembly 301 when the ground condition is only due to the fluid or solution electrically coupling the present pad to ground. More specifically, when the device is being disinfected and cleaned, the contacts are exposed to electrolytes having a finite resistance. In such a case where protection circuitry is not provided, the circuit that turns on the battery pack will activate the boards in the presence of such electrolytes. Large currents are able to flow between the voltage-enabled pins to the battery ground. This current flow establishes a motion of metal ions that will cause pitting or electro-deposition in the contacts, which is undesirable because a brief exposure to electrolyte badly corrodes the contacts, rendering them unusable. Another undesirable situation could exist during battery installation. When a proper battery-handle contact closure is achieved, the resistance of the conductive lines sensed by the microcontroller is very low. But if fluid is present, a larger resistance exists. The microcontroller is so sensitive that such a large resistance could activate the device.

For these reasons, embodiments of the present invention provide a comparator, for example through software, that monitors the impedance between the present pad and ground (i.e., the GND line in the TAG assembly shown in FIG. 9). The comparator compares the impedance of a coupling between the present pad and ground to the reference impedance so that only when the impedance is less than a threshold impedance, i.e., less than that of a solution, will the battery assembly 301 operate. More specifically, the comparator circuit compares a reference voltage against the voltage generated both when the battery present contact is exposed to either a short-to-ground or to an electrolyte of finite resistance mentioned above. If the resistance is such that the voltage generated matches the reference voltage, then the battery will turn on. The reference voltage is adjusted so that fluids present during battery-handle contact will not allow the battery pack to turn on. The comparator circuit is configured with a strong hysteresis to prevent inadvertent self turn-off due to noise and the sensitive nature of this circuit.

Figure 39:
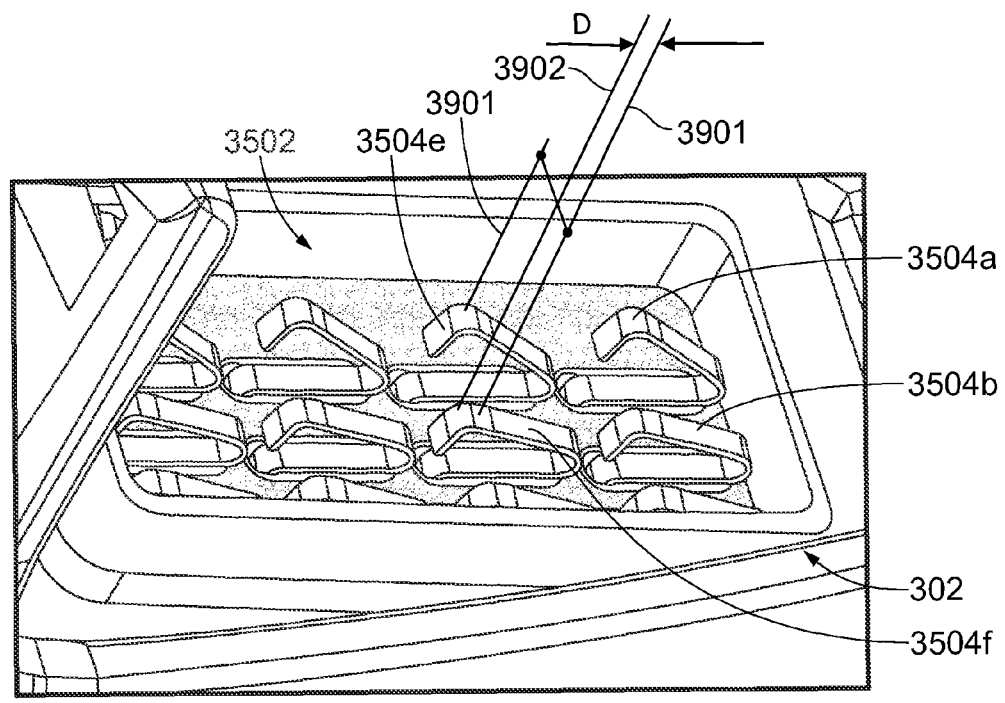
FIG. 39 is a close-up perspective view of the multi-lead handle terminal assembly in accordance with an exemplary embodiment of the present invention.

The illustrated design of the multi-lead handle terminal assembly 3502 provides even further advantages over the prior art. In particular, the inventive handle-connection pins 3504a-n, shown in the enlarged partial perspective view of FIG. 39, provide a physical connection along with a lateral displacement that ensures removal of any foreign substances from the contact region where the handle-connection pins 3504a-n of the multi-lead handle terminal assembly 3502 meet the contact pads 2806a-n of the multi-lead battery terminal assembly 2804. Specifically, FIG. 39 shows the first handle-connection pin 3504a in its at-rest, non-contact state.

That is, the handle-connection pin 3504*a* has a spring force that places and retains it in the natural resting shape shown in FIG. 39. However, when the multi-lead battery terminal assembly 2804 is fully mated with the multi-lead handle terminal assembly 3502, the handle-connection pins 3504*a*-*n* compress. This compressed state is shown, for example, by handle-connection pins 3504*b* and 3504*f* in FIG. 39.

Figure 40:
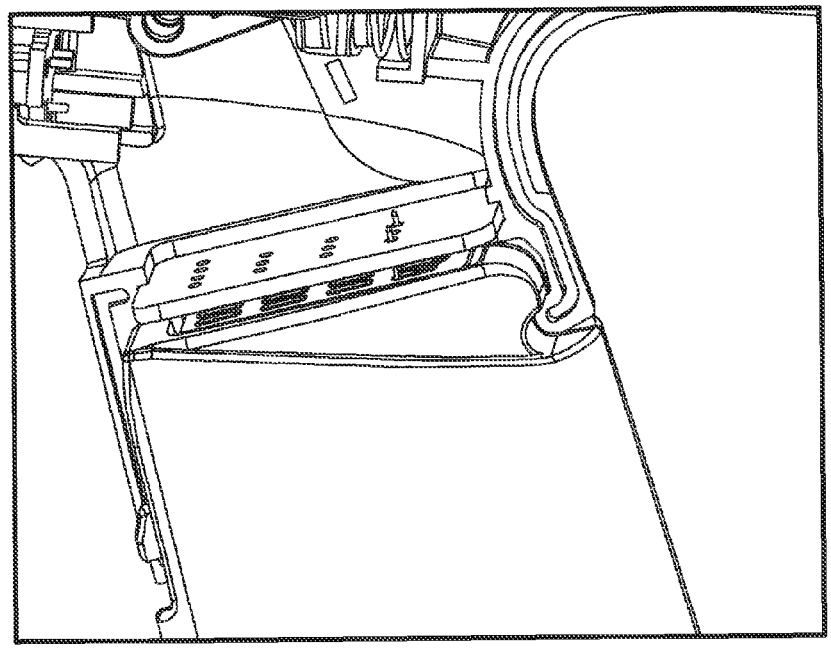
FIG. 40 is a close-up perspective view of the ultrasonic surgical cautery assembly of FIG. 1 with one half the shell of the handle assembly removed providing a detailed view of the mating position between the multi-lead handle terminal assembly and the multi-lead handle battery assembly in accordance with an exemplary embodiment of the present invention.

The compression placed on the handle-connection pin 3504*a*-*n* by the contact pad 2806 not only provides positive pressure to retain the electrical connection, but also causes the connecting surface of each handle-connection pin 3504*a*-*n* to move a distance D with respect to the longitudinal extent of the pin 3504. This distance D is illustrated in FIG. 39 by a first vertical line 3901 showing where an apex of a connecting surface of a first handle-connection pin 3504*e* exists when the pin 3504*e* is in its uncompressed state. A second vertical line 3902 shows where the apex of the connecting surface of the neighboring second handle-connection pin 3504*f* exists when the pin 3504*f* is compressed. The distance between the two lines defines a longitudinal distance D that the connecting surface of each pin 3504*a*-*n* translates when compressed. This movement is initiated when the handle-connection pin 3504*a*-*n* and the respective contact pad 2806 first make contact and continues until the battery assembly 301 is fully seated between the receiver 3400 and the extended battery securing portion 3506, as shown in the cutaway perspective view FIG. 40. The translation movement of the handle-connection pins 3504*a*-*n* produces a swiping motion that effectively wipes the contact pad 2806 clean, thus improving electrical connection therebetween. This wiping effect can prove highly advantageous when, for instance, a battery needs to be replaced in an operating environment and contaminant material, such as blood, comes into contact with the contact pads 2806 or when the pads are corroded from repeated use or due to exposure to cleaning agents.

The view of FIG. 35 shows yet another advantageous feature of the present invention. Therein, it can be seen that the multi-lead handle terminal assembly 3502 features flanged sides 3520 that protect the handle-connection pins 3504*a*-*n* of the handle assembly 302 from the left and right sides because they extend in a direction away from the plane of the pins 3504*a*-*n*. The receiver 3400 also extends in the direction away from the plane of the pins 3504*a*-*n* to protect the pins from the rear. Finally, the battery securing portion 3506 significantly extends in the direction away from the plane of the pins 3504*a*-*n* to protect the pins from the front. Users know from the ergonomic shape of the battery pack 301 and the handle 302 that the battery pack 301 is configured to attach to the handle 302 in a particular plane as illustrated clearly in FIGS. 36 and 37. Knowing this, the four extending sides of the lower battery dock 3401 are sized to prevent any injury to the pins 3504*a*-*n* when the user attempts to insert the battery 301 into the dock 3401. To illustrate this more specifically, two planes are defined, one for each of the battery 301 and the handle 302. These planes are parallel to the page including FIG. 3 and are coplanar when the battery 301 is installed in the handle 302. The plane relating to the handle 302 is referred to as a distal-to-proximal central handle plane and vertically bisects the handle like the page of the drawing of FIG. 3. Similarly, the plane relating to the battery 301 is referred to as the distal-to-proximal central battery plane and vertically bisects the handle like the page of the drawing of FIG. 3. With these planes defined, the pin safety feature is explained.

The receiver 3400 and the battery securing portion 3506 are shaped with a length that does not permit the front top corner 3008 of the battery from touching the pins 3504*a*-*n* when the distal-to-proximal central battery plane is within approximately 30 degrees of the distal-to-proximal central handle plane. Likewise, the receiver 3400 and the battery securing portion 3506 are shaped with a length that does not permit the rear top corner, i.e., the catch 3300, of the battery 301 from touching the pins 3504*a*-*n* when the distal-to-proximal central battery plane is within approximately 30 degrees of the distal-to-proximal central handle plane. This configuration ensures safe and easy connection of the battery 301 to the handle 302.

A further advantage of the present invention is that the entire battery assembly 301 can be sterilized. If there is a need for replacement during a medical procedure, the battery assembly 301 can be easily replaced with a new sterile battery assembly 301. The gas-tight construction of the battery assembly 301 allows it to be sterilized, for example, using low-temperature vapor phase Hydrogen Peroxide ($H_2O_2$) as performed by the sterilization devices manufactured by the Steris Corporation and referred to under the trade name V-PRO or manufactured by Advanced Sterilization Products (ASP), division of Ethicon, Inc., a Johnson & Johnson company, and referred to under the trade name STERRAD®. Because the Lithium cells of the battery assembly 301 are damaged when heated above 60° C., non-heating sterilization commonly used in hospitals today makes the battery assembly 301 easily re-used in surgical environments.

a. Battery Pressure Valve

Figure 41:
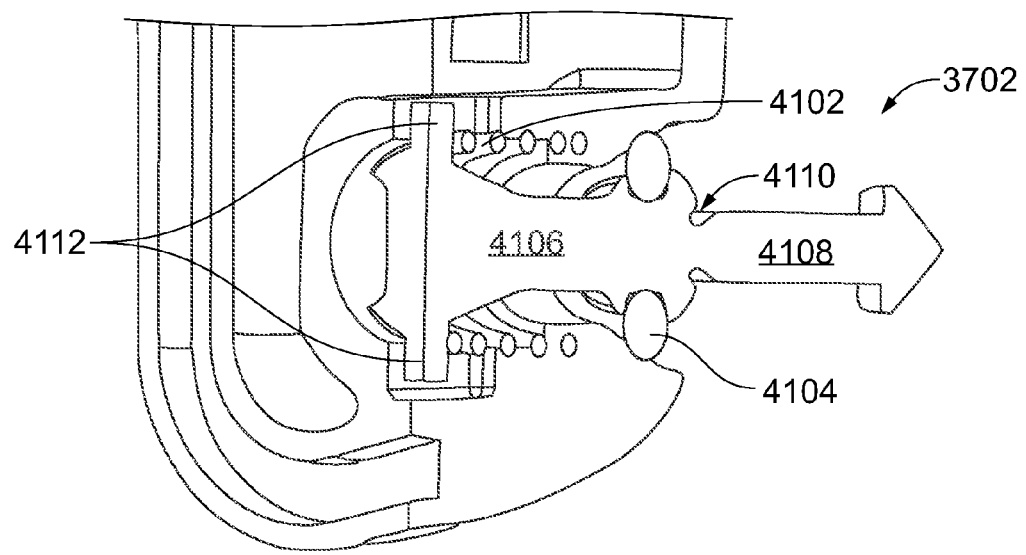
FIG. 41 is a fragmentary, cross-sectional and perspective view of a pressure valve of the battery assembly of FIG. 3 in accordance with an exemplary embodiment of the present invention viewed from a direction inside the battery assembly.
Figure 42:
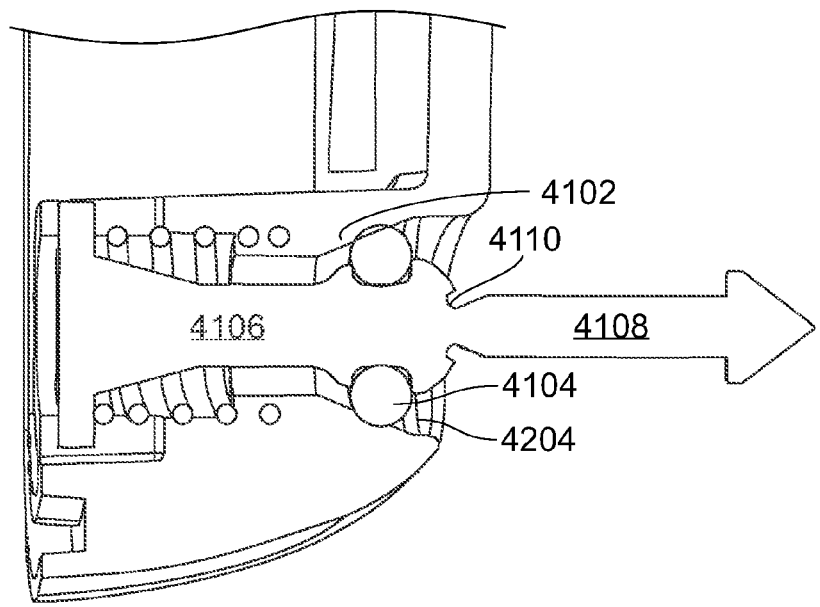
FIG. 42 is a fragmentary, cross-sectional view of the pressure valve of FIG. 41 viewed from a side of the valve.

The battery assembly 301 of the present invention features yet another inventive feature. As shown in FIG. 37, the battery assembly 301 includes an exemplary embodiment of a pressure valve 3702 that, as will be explained below, prevents the influence of external atmospheric pressure—both positive and negative—on the battery assembly's internal pressure, while providing for emergency pressure relief for excess internal pressure, e.g., >30 μsi. This valve 3702, advantageously, has a large enough opening to vent any internally accumulating gases quickly. Also advantageously, the inventive valve 3702 does not instantaneously open and close with small changes in pressure, as do some prior art venting devices. Instead, the opening and closing events of the valve 3702 have several defined stages. In an exemplary configuration of the valve 3702, during the first stage (<30 psi), the valve 3702 remains sealed, as shown in FIGS. 41 and 42, and does not allow gas flow into or out of the battery compartment. This exemplary embodiment can be referred to as a so-called poppet valve. In stage 2, once the battery assembly's internal pressure has increased just enough to counter the force of a spring 4102 holding an O-ring 4104 surrounding a poppet 4106 against a valve seat 4202, shown in the cutaway view of FIG. 42, fluid/gas will begin to escape between the O-ring 4104 and the seat 4202. In stage 3, the internal pressure has pushed the valve 3702 open enough to allow a significant amount of fluid/gas to pass the seal 4104, 4202. At this point, and up to stage 4, internal pressure has forced the valve completely open, i.e., the O-ring 4104 has moved completely off of the seat 4202. Additional pressure has diminished effect on the flow because the valve cannot open further.

Figure 44:
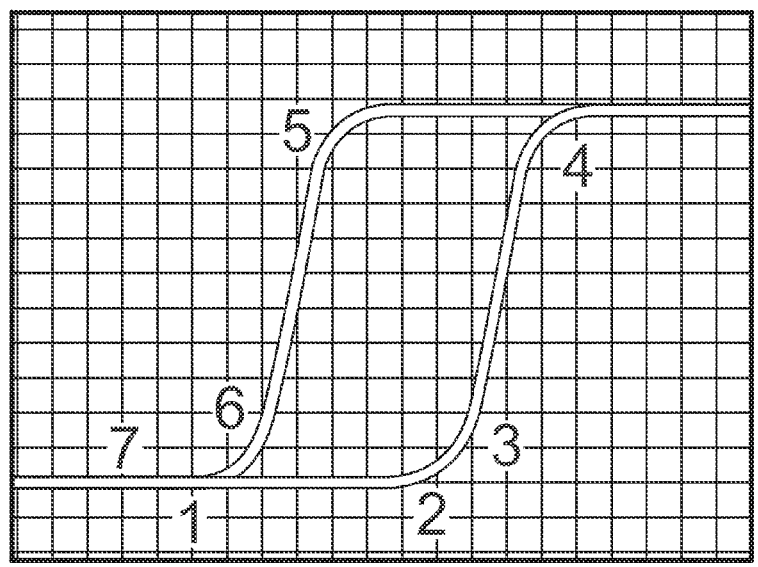
FIG. 44 is a graph illustrating pressure states of the pressure valve of FIG. 41 in accordance with an exemplary embodiment of the present invention.

In stage 5, pressure on the valve 3702 begins to decrease and the poppet 4106 starts to shut. As the poppet 4106 retracts, it follows the same sequence as occurred during opening through hysteresis (i.e., retardation of an effect when forces acting upon a body are changed, dictating that a lag in closing occurs). As a result, when the poppet 4106 begins its return, it lags in position relative to the curve of FIG. 44 traversed when the poppet 4106 was opening. At stage 6, the O-ring 4104 just touches the seat 4202. The valve 3702 does not seal at this point, as there is no force pressing the O-ring 4104 into the seat 4202. In step 7, the force of the spring 4102 compresses the O-ring 4104 with sufficient force to seal the valve shut. The valve 3702 can now return to stage 1, shown in FIGS. 41 and 42. The valve 3702 is re-sealable multiple times as the sealing surface is tapered to minimize stiction.

For ease of testing the valve 3702, the poppet 4106 is formed with a tear-off handle 4108. The handle 4108 is operable to move the poppet 4106 (manually or automatically) to provide access within the battery assembly 301 for the purpose of testing the ultrasonic weld or the bonded shell halves 2802a, 2802b for leaks. For example, a user or leak-testing fixture can grasp the handle 4108 and move the poppet 4106 out and back within the valve dock 4204, which is shown in FIGS. 41 and 42 as located in one half of the outer shell 2802a or 2802b of the battery assembly 301. Alternatively, the handle 4108 may be used to provide access to the interior of the battery assembly 301 to back fill the battery compartment with inert gas or trace gas, e.g., helium, or even to pull a vacuum within the interior of the battery assembly 301. When testing is finished, the user, for example, the manufacturer, can tear off or otherwise remove the handle 4108 to prevent further user-controlled poppet 4106 movement. Removal of the handle 4108 is made easier with a narrowing 4110 formed at the base of the handle 4108. For example, the narrowing 4110, shown in FIGS. 41 to 43, includes sharp corners to provide a consistent and smooth breaking point.

Figure 43:
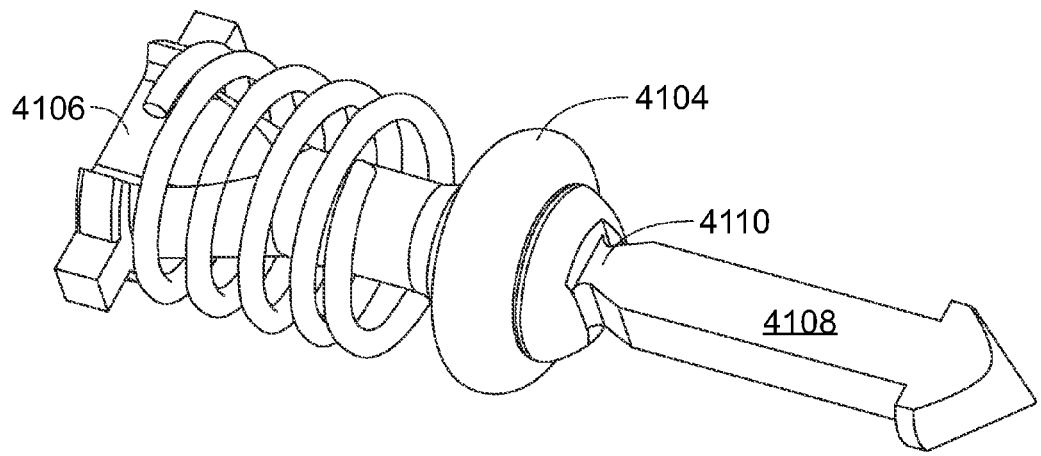
FIG. 43 is a perspective view of the pressure valve of FIG. 41 separated from the battery assembly.

In this exemplary embodiment, the handle 4108 has an arrowhead and tab configuration. As shown in FIGS. 41 to 43, the poppet 4106 includes clocking tabs 4112 on at least one side of the poppet 4106 to maintain the arrowhead in a desired orientation, e.g., horizontal to the ground when the ultrasonic surgical assembly 300 is in use, to facilitate machine or automated access to the inside of the battery assembly 301 for leak-testing operations. The arrowhead includes a gentle taper, which assists in the installation of the O-ring 4104—the O-ring 4104 is able to slide easily over the tapered arrowhead without breaking off the arrowhead tab.

In an exemplary embodiment, the O-ring 4104 is made of a STERRAD® compatible material having a durometer of between approximately 40 and approximately 60 (e.g., VITON®) as such materials seal more reliably on molded parts having irregular surface finishes.

In another exemplary embodiment, the poppet 4106 is formed from a different material than the battery shell 2802 to prevent sympathetic welding during ultrasonic welding of the battery shell halves 2802a, 2802b.

As shown in FIG. 37, the valve 3702 is advantageously disposed at the very bottom of the battery assembly 301. In this exemplary configuration, the valve 3702 remains outside the working area of the hand grip, i.e., the battery outer shell 2802, to prevent interference with the user's handling of the ultrasonic surgical assembly 300. Further, this positioning of the valve 3702 increases safety by preventing injury to the user's hand should venting occur through the valve 3702. At the same time, the user's hand does not block the valve 3702 from venting.

Also advantageously, the valve 3702 is easy to clean. The smooth outer surface of the poppet 4106 allows direct access to the O-ring 4104 seal area. Likewise, the blended smooth features of the poppet 4106 create no hidden areas in which dirt or grime could become trapped.

The battery assembly 301 of the present invention may include inventive features alternative to the valve 3702 described above. In one exemplary embodiment, the battery assembly 301 may include a non-illustrated burst plug installed within a battery access hole or relief port in the bottom side of one of the shell halves 2802a, 2802b. In this exemplary configuration, the burst plug is formed from a molded flexible material and is able to be press fit into the access hole. Alternatively, the burst plug may be molded to the inside of the battery access hole. As installed, the burst plug is flush with the outer surface of the battery shell 2802 to prevent dirt or grime collection or interference with the user's hand. The burst plug provides emergency pressure relief for excess internal pressure, e.g., >30 psi. Such excess internal pressure forces the burst plug to exit the battery relief port and vent any internally accumulating gases quickly. In this exemplary embodiment, a T-tail on the inside end of the molded burst plug prevents the burst plug from detaching from the battery assembly 301 and becoming lost or potentially falling into a patient during a surgical procedure. Further, where the burst plug is retained to the battery with the T-tail, the dangling burst plug becomes an advantageous visual indicator to a user that adverse conditions in the battery assembly 301 have occurred.

In another exemplary embodiment, the battery assembly 301 may include a burst disk installed over the battery access hole or relief port in the bottom side of one of the shell halves 2802a, 2802b. In this exemplary embodiment, the burst disk may comprise a foil tape disk placed over the battery relief port, or a disk of material with known shear characteristics. The disk can be ultrasonically welded, bonded, or otherwise sealed in place over the battery relief port to serve as a blow-off relief valve. Advantageously, the relief port may include an array or grid of many small openings. Such a configuration prevents inadvertent rupture of the disk from external mechanical measures.

In yet another exemplary embodiment, one of the shell halves 2802a or 2802b of the battery assembly outer shell 2802 may include a molded blow-out or relief area where the molded material of the outer shell half 2802a or 2802b is particularly thinner than the rest of the outer shell 2802. The relief area of the outer shell 2801 is thus designed to fail when a pre-defined, undesirable pressure is reached within the interior of the battery assembly 301. Further, a pattern, e.g., a flower-petal pattern, may be scored onto the molded surface of one of the shell halves 2802a or 2802b to provide additional stress concentrators as well as serve as a hinge to prevent petal loss after pressure relief occurs, and thus prevent pieces of the ruptured molded material of the shell 2802 from detaching from the battery assembly 301 and possibly becoming lost or falling into a patient.

In again another exemplary embodiment, the battery assembly 301 may include a pressure relief configuration akin to a turkey popper valve. Rather than having a self-reseating valve, as described above with respect to the poppet valve 3702, the turkey popper valve is retained in an actuated position after relief of excess internal pressure within the battery assembly 301. This provides a visual indicator to the user that adverse conditions existed within the battery. In this configuration, the turkey popper valve may be selectively reseated to allow for further use of the battery assembly 301.

b. Intelligent Battery

In additional exemplary embodiments of the present invention, an intelligent or smart battery is used to power the surgical ultrasonic surgical cautery assembly 300. However, the smart battery is not limited to the ultrasonic surgical cautery assembly 300 and, as will be explained, can be used in a variety of devices, which may or may not have power requirements (i.e., current and voltage) that vary from one another. The smart battery, in accordance with an exemplary embodiment of the present invention, is advantageously able to identify the particular device to which it is electrically coupled. It does this through encrypted or unencrypted identification methods. For instance, a battery assembly 301 shown in FIG. 57 can have a connection portion, such as portion 5702. The handle assembly 302 can also be provided with a device identifier 5704 communicatively coupled to the multi-lead handle terminal assembly 3502 and operable to communicate at least one piece of information about the handle assembly 302. This information can pertain to the number of times the handle assembly 302 has been used, the number of times a TAG assembly 303 (presently connected to the handle assembly 302) has been used, the number of times a waveguide assembly 304 (presently connected to the handle assembly 302) has been used, the type of waveguide assembly 304 that is presently connected to the handle assembly 302, the type or identity of the TAG assembly 303 that is presently connected to the handle assembly 302, and/or many other characteristics. When the smart battery assembly 301 is inserted in the handle assembly 302, the connection portion 5702 within the smart battery assembly 301 makes communicating contact with the device identifier 5704 of the handle assembly 302. The handle assembly 302, through hardware, software, or a combination thereof, is able to transmit information to the smart battery assembly 301 (whether by self-initiation or in response to a request from the battery assembly 301). This communicated identifier is received by the connection portion 5702 of the smart battery assembly 301. In one exemplary embodiment, once the smart battery assembly 301 receives the information, the communication portion 5702 is operable to control the output of the battery assembly 301 to comply with the device's specific power requirements.

In an exemplary embodiment, the communication portion 5702 includes a processor, such as processor 1118, and a memory, which may be separate or a single component. The processor 1118, in combination with the memory, is able to provide intelligent power management for the handheld ultrasonic surgical cautery assembly 300. This embodiment is particularly advantageous because an ultrasonic device, such as handheld ultrasonic surgical cautery assembly 300, has a power requirement (frequency, current, and voltage) that may be unique to the handheld ultrasonic surgical cautery assembly 300. In fact, handheld ultrasonic surgical cautery assembly 300 may have a particular power requirement or limitation for one dimension or type of waveguide 1502 and a second different power requirement for a second type of waveguide having a different dimension, shape, and/or configuration.

A smart battery 301 according to the invention, therefore, allows a single battery assembly to be used amongst several surgical devices. Because the smart battery 301 is able to identify to which device it is attached and is able to alter its output accordingly, the operators of various different surgical devices utilizing the smart battery 301 no longer need be concerned about which power source they are attempting to install within the electronic device being used. This is particularly advantageous in an operating environment where a battery assembly needs to be replaced or interchanged with another surgical device in the middle of a complex surgical procedure.

In a further exemplary embodiment, the smart battery 301 stores in a memory 5706 a record of each time a particular device is used. This record can be useful for assessing the end of a device's useful or permitted life. For instance, once a device is used 20 times, all such batteries 301 connected to the device will refuse to supply power thereto—because the device is defined as a "no longer reliable" surgical instrument. Reliability is determined based on a number of factors. One factor can be wear, which can be estimated in a number of ways including the number of times the device has been used or activated. After a certain number of uses, the parts of the device can become worn and tolerances between parts exceeded. For instance, the smart battery 301 can sense the number of button pushes received by the handle assembly 302 and can determine when a maximum number of button pushes has been met or exceeded. The smart battery 301 can also monitor an impedance of the button mechanism which can change, for instance, if the handle gets contaminated, for example, with saline.

This wear can lead to an unacceptable failure during a procedure. In some exemplary embodiments, the smart battery 301 can recognize which parts are combined together in a device and even how many uses each part has experienced. For instance, looking at FIG. 57, if the battery assembly 301 is a smart battery according to the invention, it can identify both the handle assembly 302, the ultrasonic-cutting-blade-and-waveguide assembly 304, as well as the particular TAG assembly 303, well before the user attempts use of the composite device. The memory 5706 within the smart battery 301 can, for example, record each time the TAG assembly 303 is operated, and how, when, and for how long it is operated. If each TAG assembly 303 has an individual identifier, the smart battery 301 can keep track of each TAG assembly's use and refuse to supply power to that TAG assembly 303 once the handle assembly 302 or the TAG assembly 303 exceeds its maximum number of uses. The TAG assembly 303, the handle assembly 302, the ultrasonic-cutting-blade-and-waveguide assembly 304, or other components can include a memory chip that records this information as well. In this way, any number of smart batteries 301 can be used with any number of TAG assemblies, staplers, vessel sealers, etc. and still be able to determine the total number of uses, or the total time of use (through use of the clock 330), or the total number of actuations, etc. of each TAG assembly, each stapler, each vessel sealer, etc. or charge or discharge cycles.

When counting uses of the TAG assembly 303, in order to intelligently terminate the life of the TAG assembly 303, it becomes important to be able to accurately distinguish between completion of an actual use of the TAG assembly 303 in a surgical procedure and a momentary lapse in actuation of the TAG assembly 303 due to, for example, a battery change or a temporary delay in the surgical procedure. Therefore, as an alternative to simply counting the number of activations of the TAG assembly 303, a real-time clock (RTC) circuit can be implemented to keep track of the amount of time the TAG assembly 303 actually is shut down. From the length of time measured, it can be determined through appropriate logic if the shutdown was significant enough to be considered the end of one actual use or if the shutdown was too short in time to be considered the end of one use. Thus, in some applications, this method may be a more accurate determination of the useful life of the TAG assembly 303 than a simple "activations-based" algorithm, which for example, may provide that ten "activations" occur in a single surgical procedure and, therefore, ten activations should indicate that the counter is incremented by one. Generally, this type and system of internal clocking will prevent misuse of the device that is designed to deceive a simple "activations-based" algorithm and will prevent incorrect logging of a complete use in instances when there was only a simple de-mating of the TAG assembly 303 or the battery 301 that was required for legitimate reasons.

Although the battery and TAG assemblies of the device are reusable, it is desirable to set a finite number of uses of the device. This could be necessary since the device is subjected to harsh conditions during cleaning and sterilization. More specifically, the battery pack is configured to be sterilized.

Regardless of the material employed for the outer surfaces, there is a limited expected life for the actual materials used. This life is determined by various characteristics which could include, for example, the amount of times the pack has actually been sterilized, the time from which the pack was manufactured, and the number of times the pack has been recharged, to name a few. Also, the life of the battery cells themselves is limited. Software of the invention incorporates inventive algorithms that verify the number of uses in both the TAG and battery assemblies and disables the device when this number of uses has been reached or exceeded. Analysis of the battery pack exterior in each of the possible sterilizing methods can be performed. Based on the harshest sterilization procedure, a maximum number of permitted sterilizations can be defined and that number can be stored in a memory of the battery assembly 301. If it is assumed that a charger is non-sterile and that the battery pack 301 is to be used after it is charged, then the charge count can be defined as being equal to the number of sterilizations encountered by that particular pack.

It is also desirable to permanently disable the hardware in the battery pack to minimize or eliminate safety concerns due to continuous drain in from the battery cells after the pack has been disabled by software. A situation can exist where the battery's internal hardware is incapable of disabling the battery under certain low voltage conditions. In such a situation, in an exemplary embodiment, the charger can be used to "kill" the battery. Due to the fact that the battery microcontroller is OFF while the battery is in its charger, a non-volatile, SMBus-based EEPROM can be used to exchange information between the battery microcontroller and the charger. Thus, a serial EEPROM can be used to store information that can be written and read even when the battery microcontroller is OFF, which is very beneficial when trying to exchange information with the charger or other peripheral devices. This exemplary EEPROM can be configured to contain enough memory registers to store at least (a) a use-count limit at which point the battery should be disabled (Battery Use Count), (b) the number of procedures the battery has undergone (Battery Procedure Count), and/or (c) a number of charges the battery has undergone (Charge Count), to name a few. Some of the information stored in the EEPROM, such as the Use Count Register and Charge Count Register are stored in write-protected sections of the EEPROM to prevent users from altering the information. In an exemplary embodiment, the use and counters are stored with corresponding bit-inverted minor registers to detect data corruption.

Any residual voltage in the SMBus lines could damage the microcontroller and corrupt the SMBus signal. Therefore, to ensure that the SMBus lines of the battery controller 703 do not carry a voltage while the microcontroller is OFF, relays are provided between the external SMBus lines and the battery microcontroller board.

During charging of the battery 301, an "end-of-charge" condition of the battery 301 is determined when, for example, the current flowing into the battery falls below a given threshold in a tapering manner when employing a constant-current/constant-voltage charging scheme. To accurately detect this "end-of-charge" condition, the battery microcontroller and buck boards are powered down and turned OFF during charging of the battery to reduce any current drain that may be caused by the boards and that may interfere with the tapering current detection. Additionally, the microcontroller and buck boards are powered down during charging to prevent any resulting corruption of the SMBus signal.

With regard to the charger, it is desirable to prevent insertion of the smart battery 301 into the charger in any way other than the correct insertion position. Accordingly, as shown in FIG. 28, for example, the exterior of the battery 301 is provided with charger-holding features 2810. A cup for holding the battery 301 securely in the charger is configured with a contour-matching taper geometry to prevent the accidental insertion of the battery pack 301 in any way other than the correct (intended) way. It is further contemplated that the presence of the battery assembly 301 may be detectable by the charger itself. For example, the charger may be configured to detect the presence of the SMBus transmission from the battery protection circuit, as well as resistors that are located in the protection board. In such case, the charger would be enabled to control the voltage that is exposed at the charger's pins until the battery assembly 301 is correctly seated or in place at the charger. This is because an exposed voltage at the charger's pins would present a hazard and a risk that an electrical short could occur across the pins and cause the charger to inadvertently begin charging.

In some exemplary embodiments, the smart battery 301 can communicate to the user through audio and/or visual feedback. For example, the smart battery 301 can cause the LEDs 906 to light in a pre-set way. In such a case, even though the microcontroller 1006 in the generator 904 controls the LEDs 906, the microcontroller 1006 receives instructions to be carried out directly from the smart battery 301.

In yet a further exemplary embodiment, the microcontroller 1006 in the generator 904, when not in use for a predetermined period of time, goes into a sleep mode. Advantageously, when in the sleep mode, the clock speed of the microcontroller 1006 is reduced, cutting the current drain significantly. Some current continues to be consumed because the processor continues pinging waiting to sense an input. Advantageously, when the microcontroller 1006 is in this power-saving sleep mode, the microcontroller 1106 and the battery controller 703 can directly control the LEDs 906. For example, a decoder circuit could be built into the generator board 5460 and connected to the communication lines such that the LEDs 906 can be controlled independently by the battery microcontroller 1106 while the TAG microcontroller is "OFF" or in a "sleep mode." This is a power-saving feature that eliminates the need for waking up the microcontroller 1006. Power is conserved by allowing the generator to be turned off while still being able to actively control the user-interface indicators.

Another exemplary embodiment slows down one or more of the microcontrollers to conserve power when not in use. For example, the clock frequencies of both microcontrollers can be reduced to save power. To maintain synchronized operation, the microcontrollers coordinate the changing of their respective clock frequencies to occur at about the same time, both the reduction and, then, the subsequent increase in frequency when full speed operation is required. For example, when entering the idle mode, the clock frequencies are decreased and, when exiting the idle mode, the frequencies are increased.

In an additional exemplary embodiment, the smart battery 301 is able to determine the amount of usable power left within its cells 701 and is programmed to only operate the surgical device to which it is attached if it determines there is enough battery power remaining to predictably operate the device throughout the anticipated procedure. For example, the smart battery 301 is able to remain in a non-operational state if there is not enough power within the cells 701 to operate the surgical device for 20 seconds. According to one exemplary embodiment, the smart battery 301 determines the amount of power remaining within the cells 701 at the end of its most recent preceding function, e.g., a surgical cutting. In this embodiment, therefore, the battery assembly 301 would not allow a subsequent function to be carried out if, for example, during that procedure, it determines that the cells 701 have insufficient power. Alternatively, if the smart battery 301 determines that there is sufficient power for a subsequent procedure and goes below that threshold during the procedure, it would not interrupt the ongoing procedure and, instead, will allow it to finish and thereafter prevent additional procedures from occurring.

The following explains an advantage of the invention with regard to maximizing use of the device with the smart battery 301 of the invention. In this example, a set of different devices have different ultrasonic waveguides. By definition, each of the waveguides could have a respective maximum allowable power limit where exceeding that power limit overstresses the waveguide and eventually causes it to fracture. One waveguide from the set of waveguides will naturally have the smallest maximum power tolerance. Because prior-art batteries lack intelligent battery power management, the output of prior-art batteries must be limited by a value of the smallest maximum allowable power input for the smallest/thinnest/most-frail waveguide in the set that is envisioned to be used with the device/battery. This would be true even though larger, thicker waveguides could later be attached to that handle and, by definition, allow a greater force to be applied. This limitation is also true for maximum battery power. For example, if one battery is designed to be used in multiple devices, its maximum output power will be limited to the lowest maximum power rating of any of the devices in which it is to be used. With such a configuration, one or more devices or device configurations would not be able to maximize use of the battery because the battery does not know the particular device's specific limits.

In contrast thereto, exemplary embodiments of the present invention utilizing the smart battery 301 are able to intelligently circumvent the above-mentioned prior art ultrasonic device limitations. The smart battery 301 can produce one output for one device or a particular device configuration and the same battery assembly 301 can later produce a different output for a second device or device configuration. This universal smart battery surgical system lends itself well to the modern operating room where space and time are at a premium. By having a single smart battery pack operate many different devices, the nurses can easily manage the storage, retrieval, and inventory of these packs. Advantageously, the smart battery system according to the invention requires only one type of charging station, thus increasing ease and efficiency of use and decreasing cost of surgical room charging equipment.

In addition, other surgical devices, such as an electric stapler, may have a completely different power requirement than that of the ultrasonic surgical cautery assembly 300. With the present invention, a single smart battery 301 can be used with any one of an entire series of surgical devices and can be made to tailor its own power output to the particular device in which it is installed. In one exemplary embodiment, this power tailoring is performed by controlling the duty cycle of a switched mode power supply, such as buck, buck-boost, boost, or other configuration, integral with or otherwise coupled to and controlled by the smart battery 301. In other exemplary embodiments, the smart battery 301 can dynamically change its power output during device operation. For instance, in vessel sealing devices, power management is very important. In these devices, large constant current values are needed. The total power output needs to be adjusted dynamically because, as the tissue is sealed, its impedance changes. Embodiments of the present invention provide the smart battery 301 with a variable maximum current limit. The current limit can vary from one application (or device) to another, based on the requirements of the application or device.

XII. Handle Assembly—Mechanical

Figure 45:
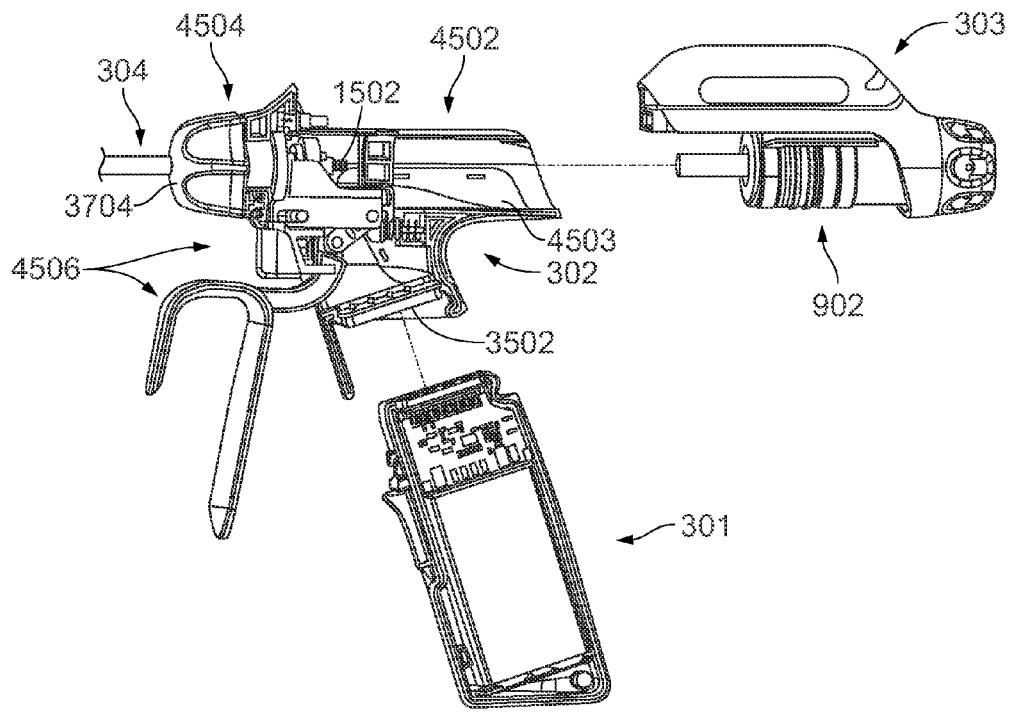
FIG. 45 is an elevational exploded view of the left side of the ultrasonic surgical cautery assembly of FIG. 3 showing the left shell half removed from the battery assembly and the left shell half removed from the handle assembly in accordance with an exemplary embodiment of the present invention.

FIG. 45 illustrates an exemplary embodiment of a left-hand side of the handle portion 302 with the left shell half removed. The handle assembly 302 has four basic functions: (1) couple the battery assembly 301 to the multi-lead handle terminal assembly 3502; (2) couple the TAG assembly 303 to a TAG attachment dock 4502; (3) couple the ultrasonic-cutting-blade-and-waveguide assembly 304 to a waveguide attachment dock 4504; and (4) provide the triggering mechanics 4506 to operate the three components (battery assembly 301, TAG assembly 303, and ultrasonic-cutting-blade-and-waveguide assembly 304).

a. TAG Attachment Dock

The TAG attachment dock 4502 is exposed to the environment and shaped to interchangeably secure the TAG assembly 303 to the handle assembly 302. The waveguide attachment dock 4504 is shaped to align a proximal end of the waveguide 1502 to the transducer 902. When the transducer 902 is docked in the TAG attachment dock 4502 and the waveguide assembly 304 is docked in the waveguide attachment dock 4504, and the transducer 902 and waveguide 1502 are attached together, the waveguide 1502 and the transducer 902 are held at the handle assembly 302 in a freely rotatable manner.

Figure 46:
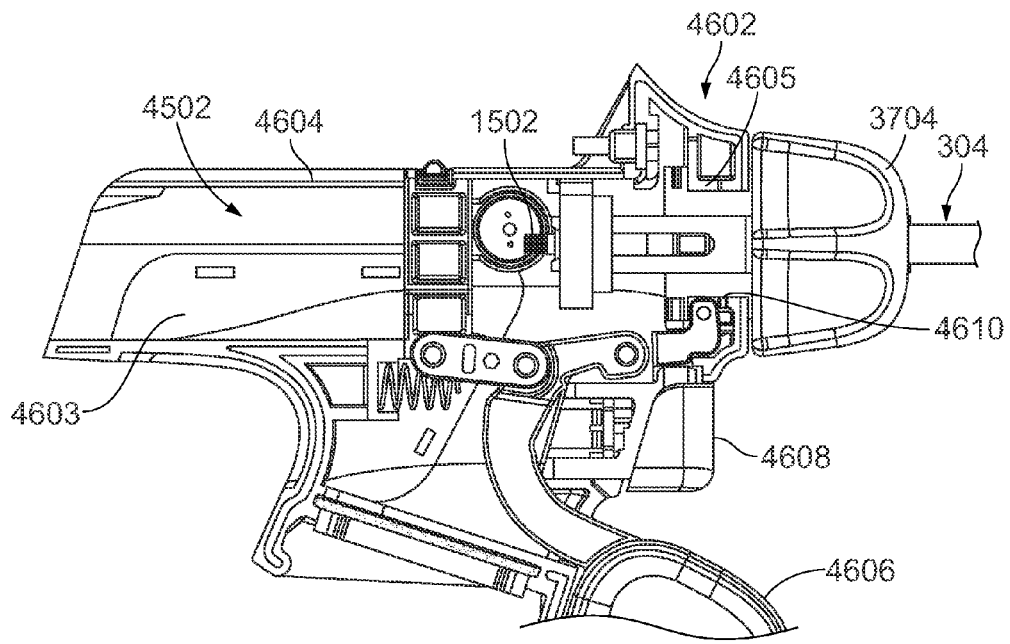
FIG. 46 is an elevational right-hand view of the handle assembly of FIG. 3 with the right shell half removed showing controls in accordance with an exemplary embodiment of the present invention.

As can be seen in FIGS. 45 and 46, the handle assembly 302 includes two clamshell-connecting body halves, the right half 4503 being shown in FIG. 45 and the left half being shown in FIG. 46. The two halves 4503, 4603 form at least a portion of the waveguide attachment dock 4504, which can be considered as being exposed to the environment when a waveguide rotation spindle 3704 is not present. A first couple 4602 is operable to selectively removably secure the ultrasonic waveguide assembly 304 to the handle assembly 302. In the exemplary embodiment shown, the waveguide rotation spindle 3704 has an intermediate annular groove 4610 shaped to receive an annular boss 4605. When the two halves 4503, 4603 are connected, the groove 4610 and boss 4605 form a longitudinal connection of the waveguide assembly 304 that is free to rotate. In an exemplary embodiment, the ultrasonic-cutting-blade-and-waveguide assembly 304 is not user-removable from the handle assembly 302.

The TAG attachment dock 4502 sits opposite the waveguide attachment dock 4504. The TAG attachment dock 4502 is exposed to the environment and has a second couple 4604 operable to removably secure the ultrasonic transducer 902 to the ultrasonic waveguide 1502 when the ultrasonic waveguide assembly 304 is coupled to the waveguide attachment dock 4504. The couples 4602 and 4604 can simply be aligned passageways or any other structure that place the waveguide 1502 into axial alignment with the transducer 902. Of course, the couples 4602 and 4604 can provide more structure, such as threads, that actually hold the waveguide 1502 and/or transducer 902 to the handle or to one another. Some examples of the couple 4604 include a rail, a dovetail, a T-slot, at least one pin, more than one pin, and an undercut slot.

b. Controls

Looking now to FIG. 46, a trigger 4606 and a button 4608 are shown as components of the handle assembly 302. The trigger 4606 activates the end effector 118, which has a cooperative association with the blade portion 116 of the waveguide 114 to enable various kinds of contact between the end effector 118 and blade portion 116 with tissue and/or other substances. As shown in FIG. 1, the end effector 118 is usually a pivoting jaw (see also, e.g., FIG. 73 et seq.) that acts to grasp or clamp onto tissue disposed between the jaw and the blade 116. In an exemplary embodiment, an audible feedback is provided in the trigger that clicks when the trigger is fully depressed. The noise can be generated by a thin metal part that the trigger snaps over while closing. This feature adds an audible component to user feedback that informs the user that the jaw is fully compressed against the waveguide and that sufficient clamping pressure is being applied to accomplish vessel sealing.

The button 4608, when depressed, places the ultrasonic surgical assembly 300 into an ultrasonic operating mode, which causes ultrasonic motion at the waveguide 1502. In a first exemplary embodiment, depression of the button 4608 causes electrical contacts within a switch 4702, shown in FIG. 47, to close, thereby completing a circuit between the battery assembly 301 and the TAG assembly 303 so that electrical power is applied to the transducer 902. In another exemplary embodiment, depression of the button 4608 closes electrical contacts to the battery assembly 301. Of course, the description of closing electrical contacts in a circuit is, here, merely an exemplary general description of switch operation. There are many alternative embodiments that can include opening contacts or processor-controlled power delivery that receives information from the switch 4702 and directs a corresponding circuit reaction based on the information.

Figure 47:
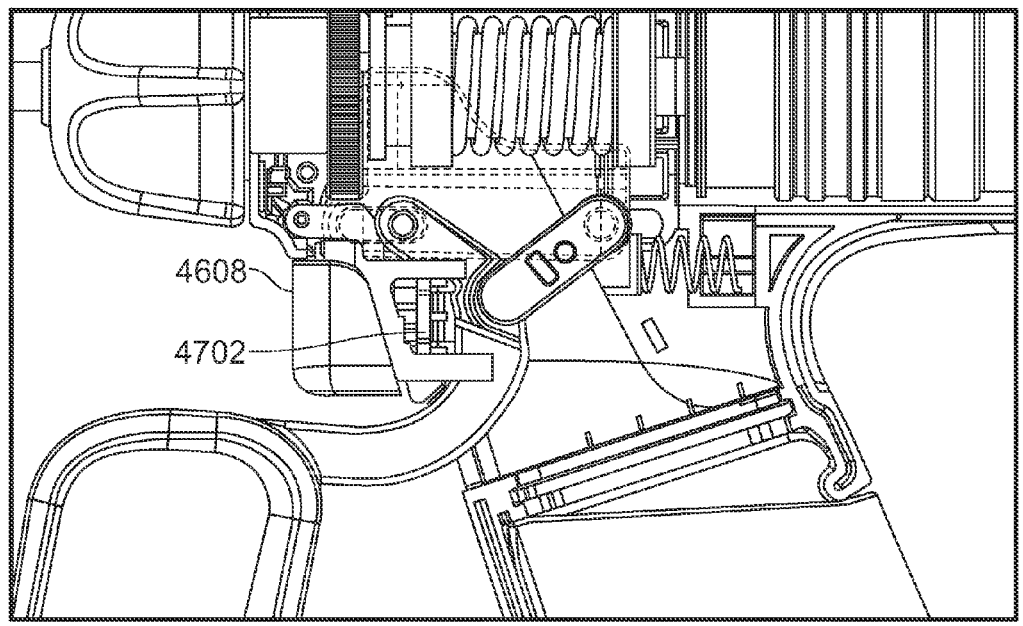
FIG. 47 is elevational close-up view of the handle assembly of FIG. 3 with the left shell half removed showing the trigger mechanism of FIG. 46 in accordance with an exemplary embodiment of the present invention.
Figure 48:
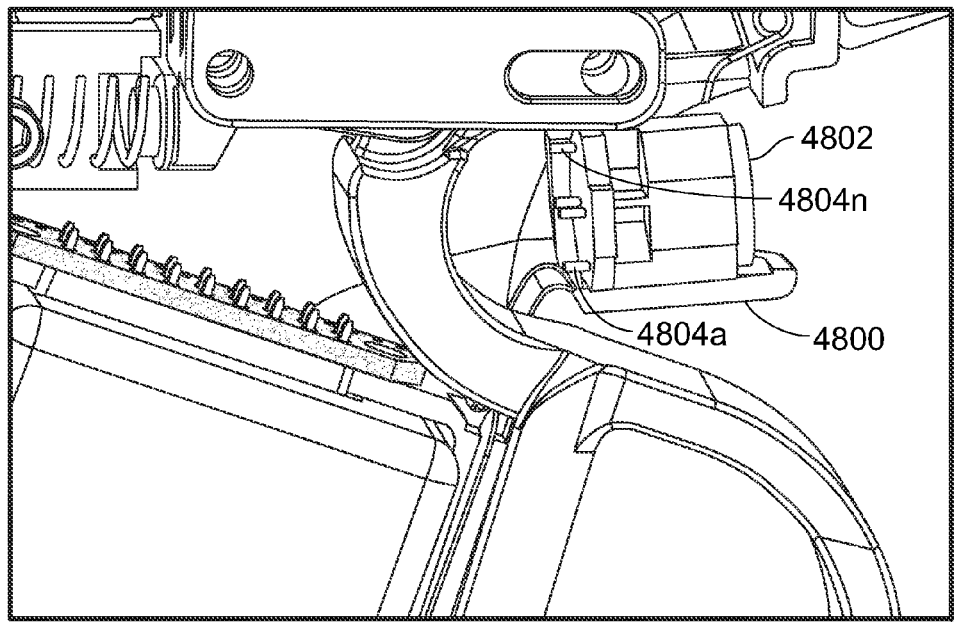
FIG. 48 is an elevational close-up view of a two-stage switch in the handle assembly activated by the button of FIG. 46 in accordance with an exemplary embodiment of the present invention.

FIG. 47 shows the switch 4702 from a left-side elevational view and FIG. 48 provides a cutaway perspective view of the interior of the right side of the handle body, revealing different detail of the switch 4800. In a first exemplary embodiment, the switch 4800 is provided with a plurality of contacts 4804a-n. Depression of a plunger 4802 of the switch 4702 activates the switch and initiates a switch state change and a corresponding change of position or contact between two or more of the plurality of contacts 4804a-n. If a circuit is connected through the switch 4702, i.e., the switch 4702 controls power delivery to the transducer 902, the state change will either complete or break the circuit, depending on the operation mode of the switch 4702.

Figure 49:
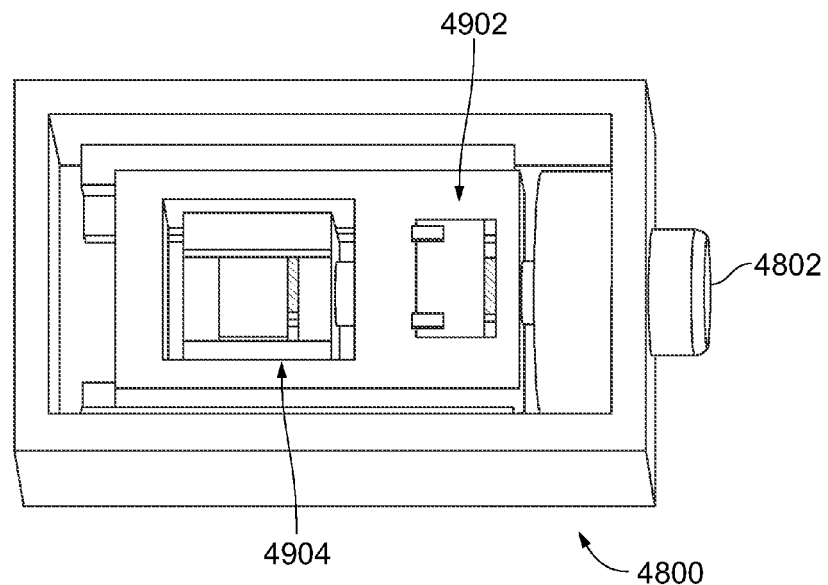
FIG. 49 is an elevational view of an example of a two-stage switch of FIG. 48 in accordance with an exemplary embodiment of the present invention.

FIG. 49 shows an exemplary embodiment of the switch 4702 that provides two switching stages. The switch 4702 includes two sub-switches 4902 and 4904. The sub-switches 4902 and 4904 advantageously provide two levels of switching within a single button 4802. When the user depresses the plunger 4802 inward to a first extent, the first sub-switch 4902 is activated, thereby providing a first switch output on the contacts 4804a-n (not shown in this view). When the plunger 4802 is depressed further inward to a second extent, the second sub-switch 4904 is activated, resulting in a different output on the contacts 4804a-n. An example of this two-stage switch 4702 in actual use would be for the generator 904 to have two possible output power levels available, each resulting in a different motion displacement value of the waveguide 1502. Activation of the first sub-switch 4902 can, for example, initiate the first output power level from the generator 904 and activation of the second sub-switch 4904 could result in a second power level to be output from the generator 904. An exemplary embodiment of this two stage switch 4702 provides a low-power level for the first displacement and a high-power level for the second displacement. Configuring the sub-switches 4902 and 4904 in a stack, shown in FIG. 49, advantageously makes it easy and intuitive for an operator to move from the first switch mode, i.e., first power level, to the second switch mode, i.e., second power level, by simply squeezing the plunger 4802 of the button 4702 with increased force.

In one embodiment of the sub-switches 4902 and 4904, spring force could be utilized, with each spring having a different spring-force rating. When the plunger 4802 is initially depressed, the first spring in the first sub-switch 4902 begins to compress. Because a second spring located in the second sub-switch 4904 is stiffer than the first spring, only the first sub-switch 4902 is caused to change switching states. Once the first sub-switch 4902 is depressed a sufficient distance to change switching states, further (greater) force applied to the plunger 4802 causes the second stiffer spring to depress and the second sub-switch 4904 to change states.

In practice, ultrasonic cutting devices, such as ones employing the present invention, encounter a variety of tissue types and sizes and are used in a variety of surgical procedure types, varying from precise movements that must be tightly controlled to non-delicate cutting material that requires less control. It is therefore advantageous to provide at least two ultrasonic cutting power levels that allow an operator to select between a low-power cutting mode and a higher-power cutting mode. For example, in the low-power cutting mode, i.e., only the first sub-switch 4902 is depressed, the tip of the waveguide 1502 moves at about 0.002 inches of displacement. In the higher-power cutting mode, i.e., both the first and second sub-switches 4902 and 4904 are depressed, the tip of the waveguide 1502 moves at about 0.003 inches of displacement, providing a more robust cutting tool that can move through tissue at a quicker rate or cut though tougher, denser matter quicker than the lower-power setting. For example, cutting through mesentery is generally performed at a more rapid rate at higher power, whereas vessel sealing can be performed at lower power and over a longer period of time.

The present invention, however, is in no way limited to stacked switches and can also include switches that are independent of one another. For instance, the shape of the button 4608 may have a first portion that makes contact with a first low-power switch and a second portion that, upon further movement of the button, makes contact with a second high-power switch. The present invention is to be considered as including any multiple-stage switch that engages different stages by movement of a single button.

In one exemplary embodiment of the present invention, the switch 4702, 4800 provides a physical resistance analogous to a compound bow. Compound bows, which are well known for shooting arrows at a high rate of speed, have a draw-force curve which rises to a peak force and then lets off to a lower holding force. By recreating this physical affect with the second sub-switch 4904, the user of the device will find moving into and engaging the first sub-switch 4902 to be rather easy, while moving into the higher-power mode, initiated by depression of the second sub-switch 4904 requiring a higher depression force, to be an occurrence that takes place only by the operator consciously applying an increased force. Once the higher depression force is overcome, however, the force required to maintain the second sub-switch 4904 in the depressed position decreases, allowing the operator to remain in the higher-power mode, i.e., keeping the button depressed, without fatiguing the operator's finger. This compound-bow-type effect can be accomplished in a variety of ways. Examples include an offset cam, overcoming a pin force or other blocking object, software control, dome switches, and many others.

In one exemplary embodiment of the present invention, the switch 4702 produces an audible sound when the switch 4702 moves from the first mode to the second higher-power mode. For example, the audible sound can be emanated from button, itself, or from the buzzer 802. The sound notifies the operator of entry into the higher-power mode. The notification can advantageously prevent unintended operation of the inventive ultrasonic device.

c. Waveguide Node Bumps

Figure 57:
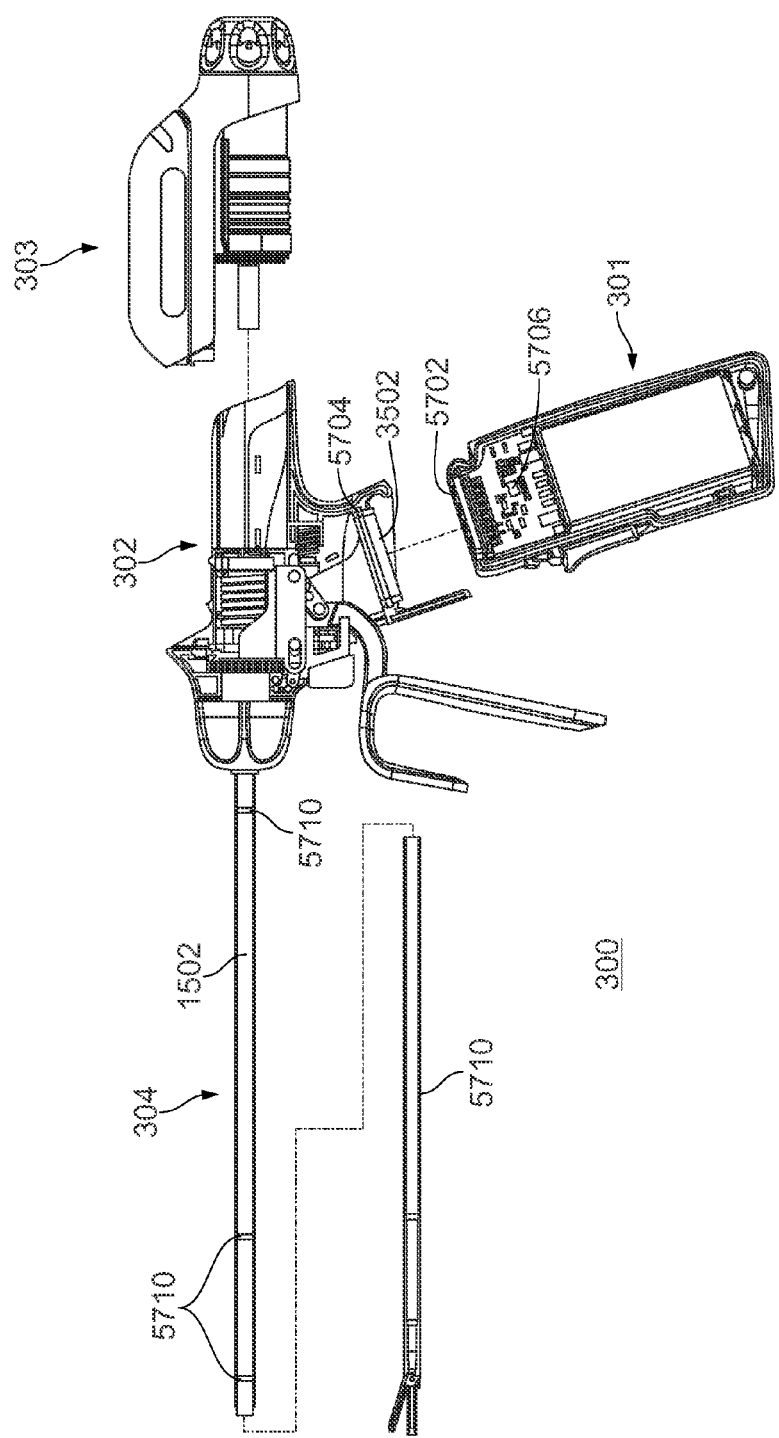
FIG. 57 is an elevational exploded view of the left side of the ultrasonic surgical cautery assembly of FIG. 3 showing the left shell half removed from handle assembly exposing a device identifier communicatively coupled to the multi-lead handle terminal assembly in accordance with an exemplary embodiment of the present invention.
Figure 58:
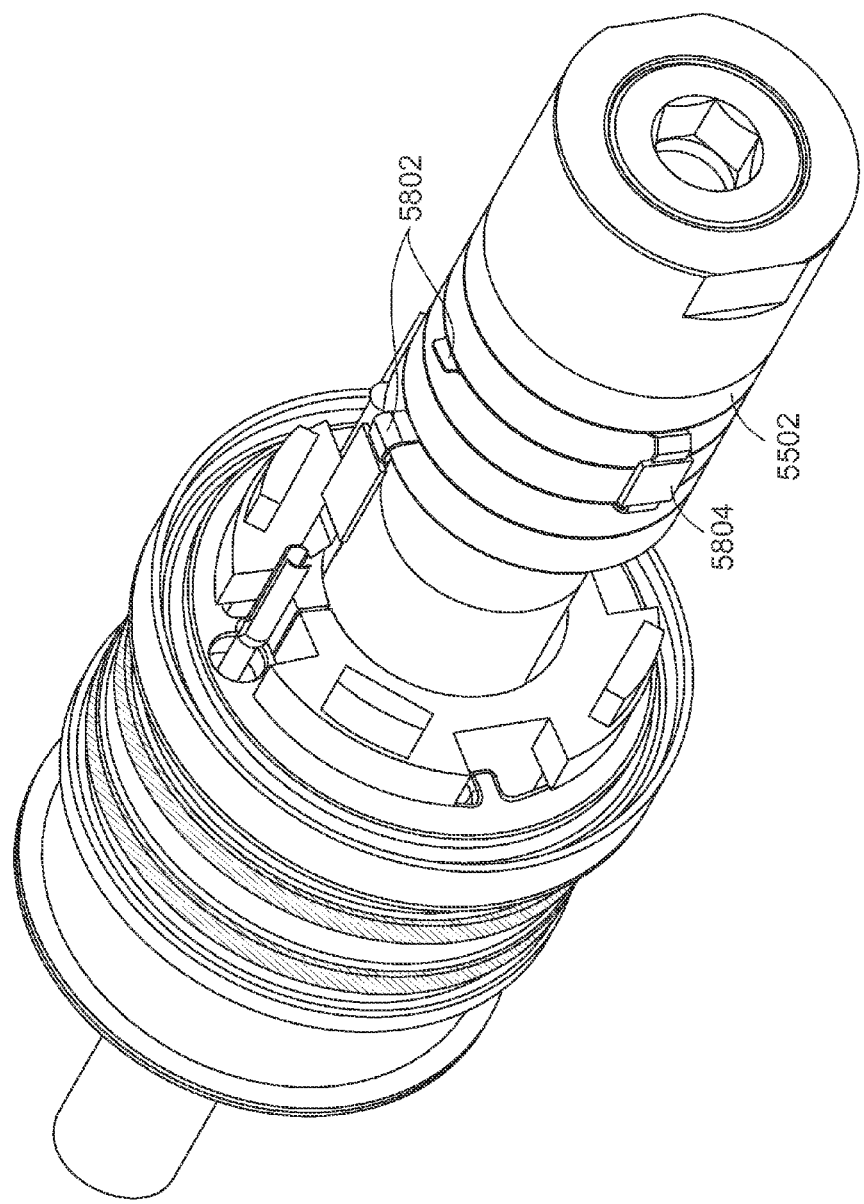
FIG. 58 is a perspective enlarged view of a transducer with the outer shell removed in accordance with an exemplary embodiment of the present invention.
Figure 76:
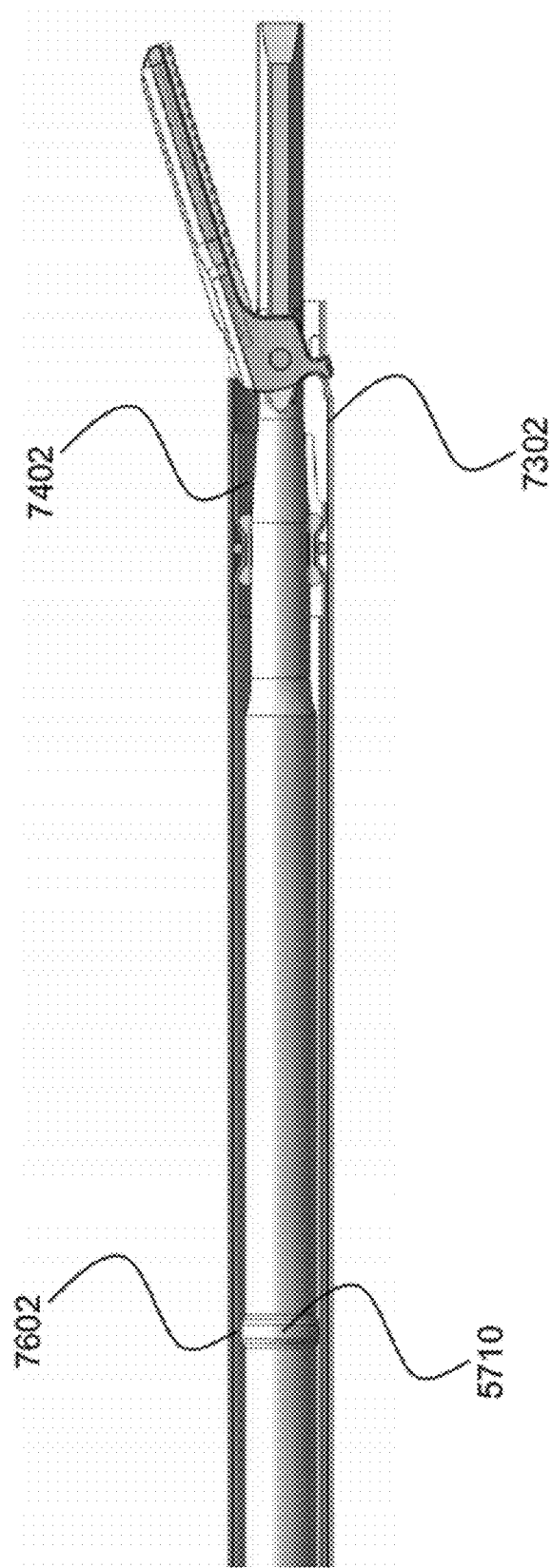
FIG. 76 is a fragmentary, enlarged side cross-sectional view of the end effector of FIG. 73 with the jaw in a partially closed position.

In accordance with an exemplary embodiment of the present invention, as shown in FIG. 57, at least one bump 5710 is/are provided at a node(s) of the ultrasonic waveguide 1502. In other words, the bumps 5710 are located at points along the waveguide 1502 where the waveguide 1502 does not exhibit ultrasonic motion at resonant frequency. The bumps 5710 are radially and longitudinally symmetrical and, therefore, the change in diameter of each bump 5710 and its physical waveguide characteristics of decreasing (radially larger) and then increasing (radially smaller) transmitted vibration does not adversely affect the waveguide's ability to resonate at an ultrasonic frequency or to transmit the desired vibration at the distal blade tip. The bumps are discussed in further detail with regards to FIG. 76.

d. Near-Over-Center Trigger

Referring now to FIGS. 61 to 64, an exemplary embodiment of a variable-pressure trigger will be shown and described. The components of the variable pressure trigger can be seen in the perspective partial view of the right hand side of the handle assembly 302 illustrated in each of FIGS. 61 to 64. In this view, several of the internal components are exposed and viewable because much of the shell of the handle assembly 302 is not present. In practice, many of the components shown in FIGS. 61 to 64 are covered by the shell, protected, and not viewable.

Figure 61:
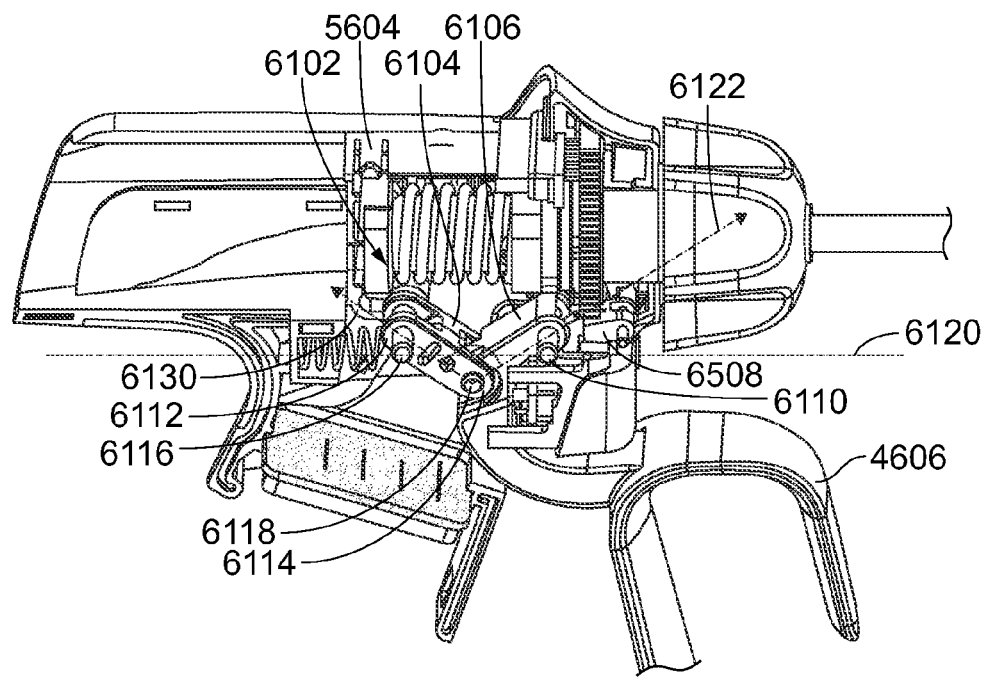
FIG. 61 is a perspective partial view of the handle assembly with the right-hand cover half removed, exposing a near-over-centering trigger mechanism in accordance with an exemplary embodiment of the present invention.

Looking first to FIG. 61, at least a portion of a trigger pivot assembly 6102 is shown. The assembly 6102 includes a first pivoting member 6104 and a second pivoting member 6106. In the following discussion, a comparison between FIG. 61 and each of FIGS. 62 to 64 will be described that illustrates the interaction between the first pivoting member 6104 and the second pivoting member 6106 as the trigger 4606 is progressively squeezed by an operator.

The first pivoting member 6104 is an elongated structure and has a first end 6112 and a second end 6114. The first end 6112 of the first pivoting member 6104 is rotationally coupled to a first pivot pin 6116 while the second end 6114 is rotationally coupled to a second pivot pin 6118. In the perspective view of FIG. 61, the exemplary embodiment of the first pivoting member 6104 can be seen as including two separate halves, each half coupled to the first pivot pin 6116 and the second pivot pin 6118 and being connected together at a center section. In this embodiment, the center pivot is comprised of a round boss on the trigger that is captured by two links. The two links are hermaphroditic parts and are pressed together so that the boss is constrained by two holes, one on each link. This configuration creates the third pivoting section. There is, however, no requirement that this pivoting member comprise this configuration. The pivoting member can be any structure that couples the two pivot pins 6116 and 6118 and provides the proximally directed force at the first pivot pin 6116 to translate the actuator for the end effector 118, which end effector 118 will be described in further detail below. As can be seen in FIGS. 61 to 64, the first pivot pin 6116 rides within a longitudinally extending guide track 6130 shown on the left body half 4603 of the handle assembly 302, a mirror image of which is similarly present on the opposing right body half 4503. As the trigger 4606 is depressed, shown in the progression of FIG. 61 to FIG. 62 to FIG. 63 to FIG. 64, the first pivot pin 6116 translates in the proximal direction a sufficient distance to actuate the end effector 118 from an at-rest position (shown by the first pivot pin position in FIG. 61) to a fully actuated position (shown by the first pivot pin position in FIG. 64).

In accordance with the exemplary embodiment shown, the second pivot pin 6118 is coupled to and is part of the trigger 4606. In particular, the entire second pivoting member 6106, including the pivot pin 6118, actually comprises a furthest extent of the trigger 4606. This furthest extent of the trigger 4606 (the second pivoting member 6106) is, itself, rotationally coupled to a third (fixed) pivot pin 6110 within the handle assembly 302. This third pivot pin 6110 defines the axis about which the trigger 4606 rotates with respect to the handle assembly 302. The third pivot pin 6110 is shared by a sliding rotational-lockout member 6508, which works in conjunction with a rotational lockout blade. The purpose and details of the rotational lockout blade will be explained in the following section.

Because the position of the third pivot pin 6110 is fixed with respect to the handle assembly 302, when the trigger 4606 is squeezed by the operator, the first pivot pin 6116 moves away from the third pivot pin 6110. In addition, as the first pivot pin 6116 is moving away from the third pivot pin 6110, the second pivot pin 6118 traverses an arc starting at the position shown in FIG. 61, where the second pivot pin 6118 is well below an imaginary line 6120 connecting the first pivot pin 6116 to the third pivot pin 6110, to the position shown in FIG. 64, where the second pivot pin 6118 is much closer to that imaginary line 6120 still connecting the first pivot pin 6116 to the third pivot pin 6110.

Figure 62:
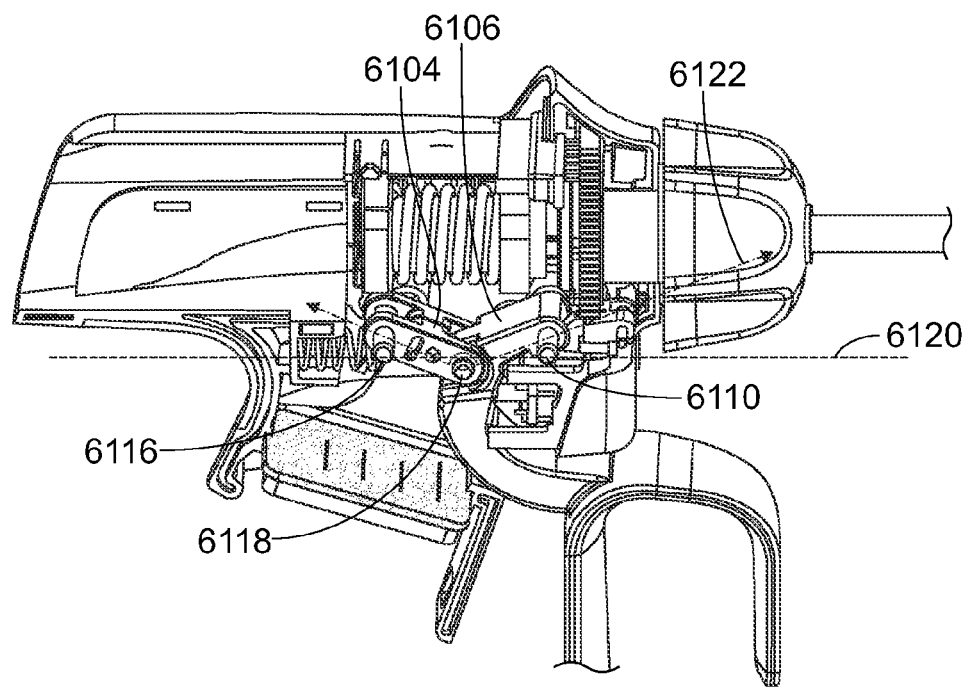
FIG. 62 is a perspective partial view of the near-over-centering trigger mechanism of FIG. 61, with the trigger slightly depressed, in accordance with an exemplary embodiment of the present invention.
Figure 63:
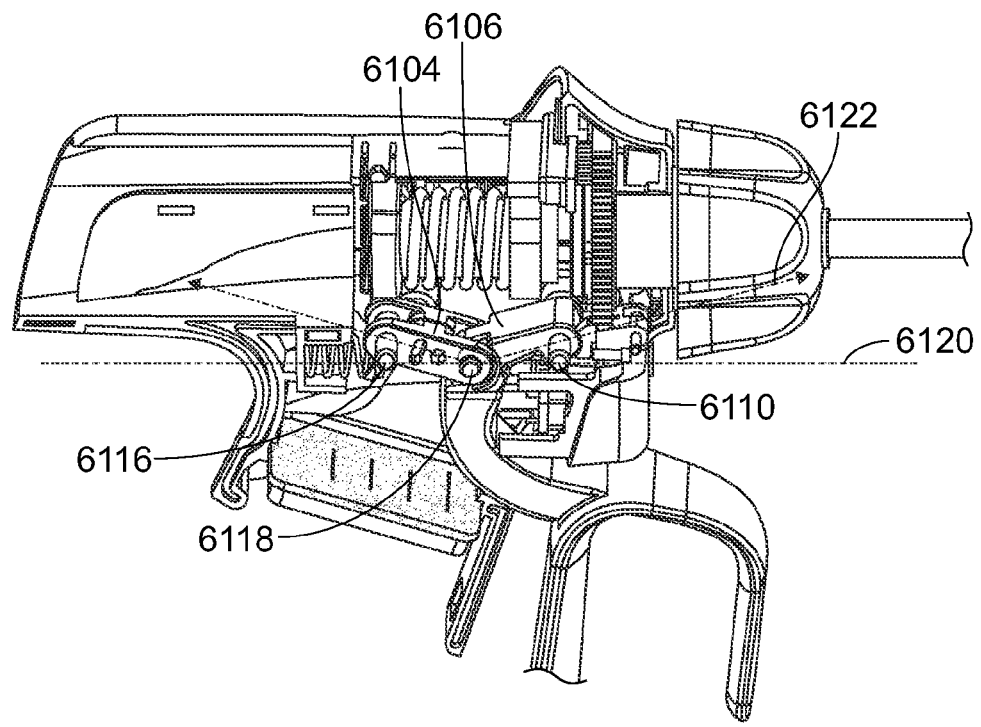
FIG. 63 is a perspective partial view of the near-over-centering trigger mechanism of FIG. 61, with the trigger further depressed, in accordance with an exemplary embodiment of the present invention.
Figure 64:
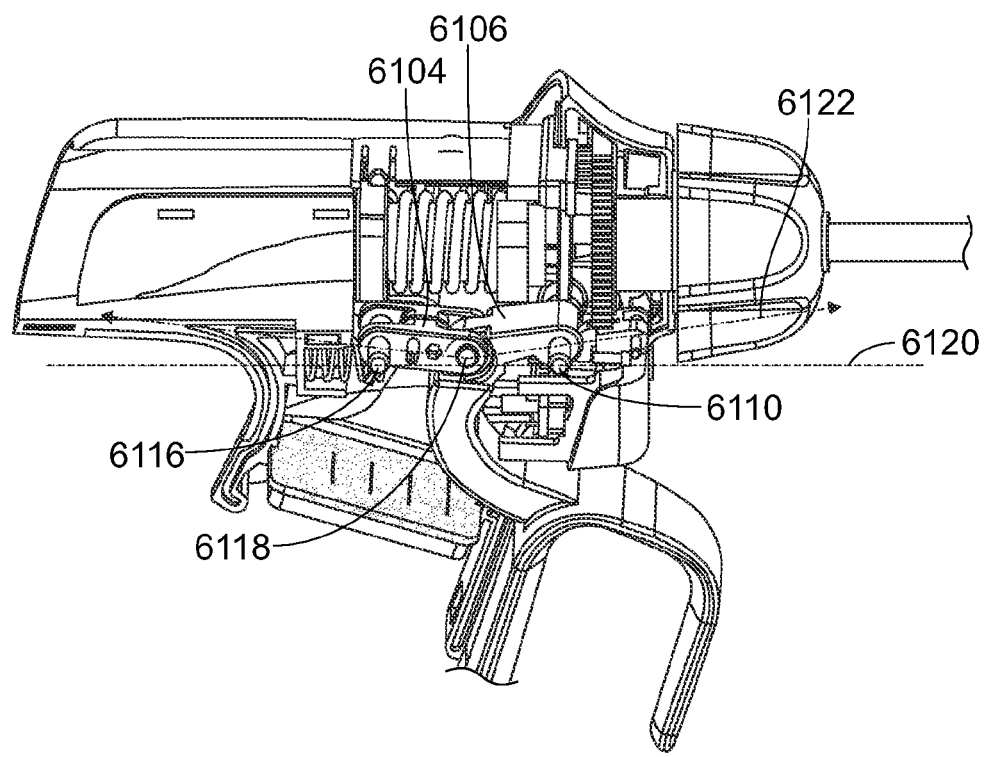
FIG. 64 is a perspective partial view of the near-over-centering trigger mechanism of FIG. 61, with the trigger fully depressed, in accordance with an exemplary embodiment of the present invention.

The movement of the trigger 4606 from the position shown in FIG. 61, through the positions shown in FIGS. 62 through 64 results in a clamping movement of the end effector 118 in a direction towards the waveguide 1502. In other words, squeezing the trigger 4606 causes the end effector 118 to move from an open position to a closed position (via movement of the outer tube 7302 as described below). Advantageously, interaction between the first pivoting member 6104 and the second pivoting member 6106, illustrated in a comparison of FIGS. 61 through 64, provides a trigger motion with varying requisite pressures to maintain trigger depression. This variable pressure linkage (6110, 6106, 6118, 6104, 6116) advantageously reduces fatigue on the operator's hand because, once fully depressed, it requires much less pressure to keep the trigger 4606 in the depressed position as compared to the pressure required to partially depress the trigger 4606 as shown, for example, in FIG. 62.

More specifically, when an operator first applies pressure to the trigger 4606, a first force is required to move the second pivot pin 6118 (with reference to the orientation shown in FIG. 61) upwards. The force required to actuate the end effector 118 is actually longitudinal because the first pivot pin 6116 must move proximally. This force moves the second pivot pin 6118 along an arc that, consequently, moves the first pivot pin 6116 away from the third pivot pin 6110 and defines two force vectors along the pivoting members 6104, 6106. The two force vectors, in the position shown in FIG. 61, are at an angle 6122 of approximately 100° and are indicated with a left-pointing black vector and a right-pointing white vector for clarity.

Turning now to FIG. 62, it can be seen that the trigger 4606 has been moved from the resting position shown in FIG. 61. This partial movement occurs when the trigger is squeezed during a typical medical procedure at first tissue contact. As the trigger 4606 is squeezed, i.e., moved toward the handle assembly 302, the first pivot pin 6116, the first pivoting member 6104, the second pivoting member 6106, and the second pivot pin 6118 all change positions. More specifically, the second pivoting member 6106 rotates about the third pivot pin 6110, which is fixed in its position. Because the third pivot pin 6110 is fixed, the second pivot pin 6118 begins to swing upward, i.e., toward the imaginary line 6120. As the second pivot pin 6118 swings upward, a force is applied to the first pivot member 6104, which translates along the first pivot member 6104 and is applied to the first pivot pin 6116. In response, the first pivot pin 6116 slides proximally in a direction away from the waveguide assembly 304. In this first stage of translation, shown in FIG. 62, the angle of the force vectors 6122 can be seen as having increased from that shown in FIG. 61.

In FIG. 63, the trigger 4606 is closed even further. As a result, further movement of the first pivoting member 6104, the second pivoting member 6106, the first pivot pin 6116, and the second pivot pin 6118 occurs. As this movement takes place, the second pivot pin 6118 moves even closer to the imaginary line 6120, i.e., closer to being collinear with the first 6116 and third 6110 pivot pins. As indicated by the force vectors 6122, the forces applied to the pivoting member's 6104, 6106 begin to significantly oppose each other. The exemplary angle between the vectors 6122 is, in this position, approximately 150°.

Finally, in FIG. 64 the trigger 4606 has been squeezed until it makes contact with the battery assembly holding portion of the handle assembly 302. This is the point of maximum translation of the first pivoting member 6104, second pivoting member 6106, and the first pivoting pin 6116. Here, the force vectors substantially opposite one another, thereby reducing the amount of force felt at the trigger 4606. That is, as is known in the field of mechanics, maximum force is required when two vector forces are additive, i.e., point in the same direction, and minimum force is required when two vector forces are subtractive, i.e., point in opposite directions. Because, in the orientation shown in FIG. 64, the vectors become more subtractive than additive, it becomes very easy for the user to keep the trigger 4606 depressed as compared to the position shown in FIG. 61. The ultimate closed position shown in FIG. 64 is referred to herein as a "near-over-centered" position or as "near over centering." When the trigger 4606 is in the near-over-centered position, the force required to keep the trigger depressed is approximately 45% or less than the force required to initially squeeze the trigger away from the position shown in FIG. 61.

e. Rotational Lock-Out

The present invention provides yet another inventive feature that prevents rotation of the waveguide assembly 304 whenever ultrasonic motion is applied to the waveguide 1502. This rotational lockout feature provides enhanced safety by preventing the cutting blade from unintentional rotational movement during a surgical procedure. In addition, prevention of rotation ensures that a solid electrical connection is maintained throughout operation of the device 300. More specifically, the electrical contacts 5402, 5404 (e.g., pogo pins) between the generator and the transducer do not have to slide along the transducer's contact rings 5406, 5408 in order to maintain electrical contact because a fixed electrical connection at one location along the contact rings 5406, 5408 is maintained during operation by virtue of the rotational lockout. The rotational lockout, according to one exemplary embodiment of the present invention, is accomplished through use of a rotational lockout member 6508 shown in FIGS. 65 and 66.

Figure 65:
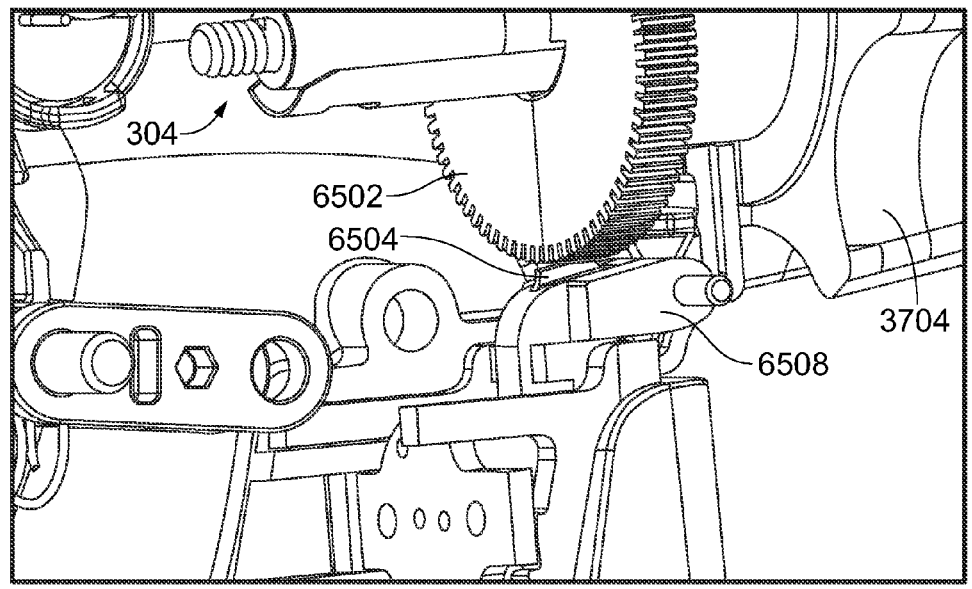
FIG. 65 is a perspective fragmentary view of a rotational lockout member and blade adjacent, but not engaging with, a waveguide assembly rotation-prevention wheel, in accordance with an exemplary embodiment of the present invention.

Referring first to FIG. 65, a perspective close-up view of the right hand side of handle assembly 302 is shown with the right-side cover removed. In this view, a rotational lockout member 6508 can be seen positioned adjacent a rotation-prevention wheel 6502 (which is rotationally fixed to the waveguide rotation spindle 3704 and, thereby, to the waveguide assembly 304). The waveguide assembly 304 is, therefore, able to rotate along its longitudinal axis only if the rotation-prevention wheel 6502 is unencumbered and also able to rotate upon that longitudinal axis.

To prevent revolution of the rotation-prevention wheel 6502, the rotational lockout member 6508 includes a wheel-engagement blade 6504 that extends therefrom in a direction toward the rotation-prevention wheel 6502. In the position shown in FIG. 65, the rotational lockout member 6508 does not interfere with the rotation prevention wheel 6502 because the wheel-engagement blade 6504 is at a distance from the outer circumference thereof. In such an orientation of the blade 6504, the rotation-prevention wheel 6502, as well as the waveguide assembly 304, can freely spin upon the longitudinal axis of the waveguide assembly 304.

Figure 66:
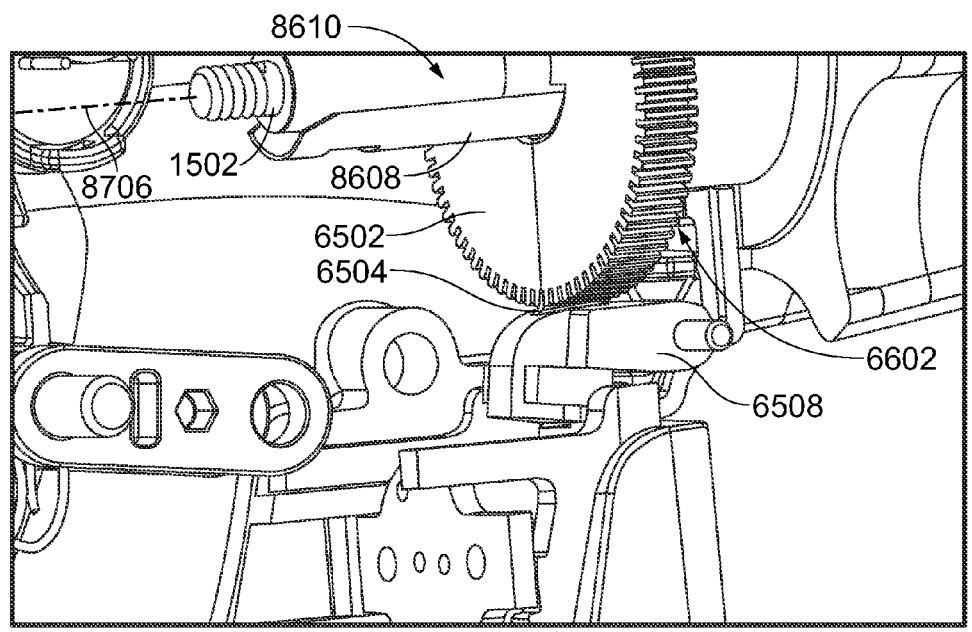
FIG. 66 is a perspective fragmentary view of the rotational lockout member and blade of FIG. 65 engaging the waveguide assembly rotation-prevention wheel in accordance with an exemplary embodiment of the present invention.
Figure 67:
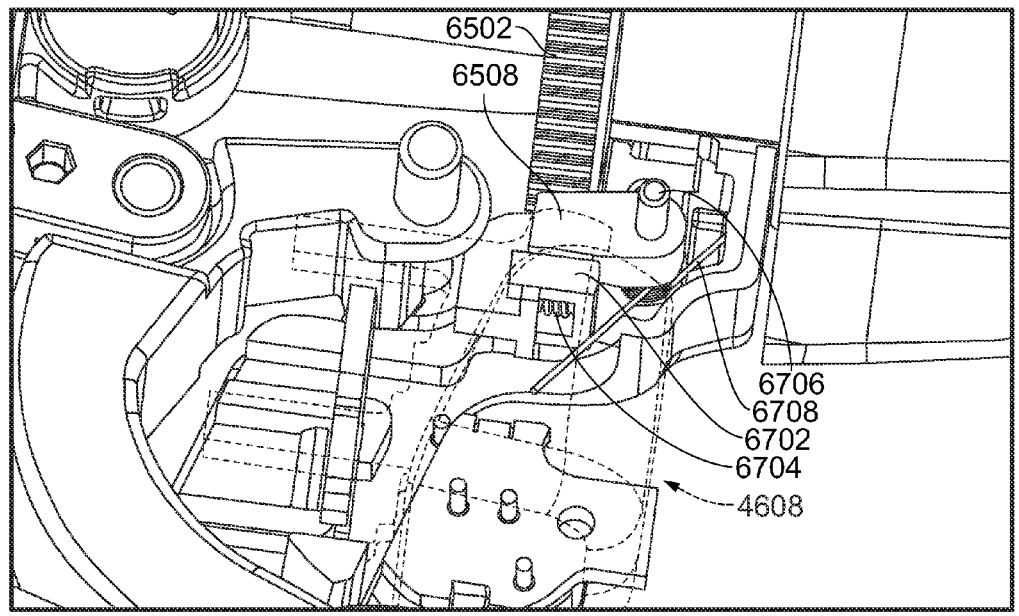
FIG. 67 is a perspective fragmentary view of a two-stage button in an undepressed state and in physical communication with the rotational lockout member of FIG. 65 in accordance with an exemplary embodiment of the present invention.
Figure 68:
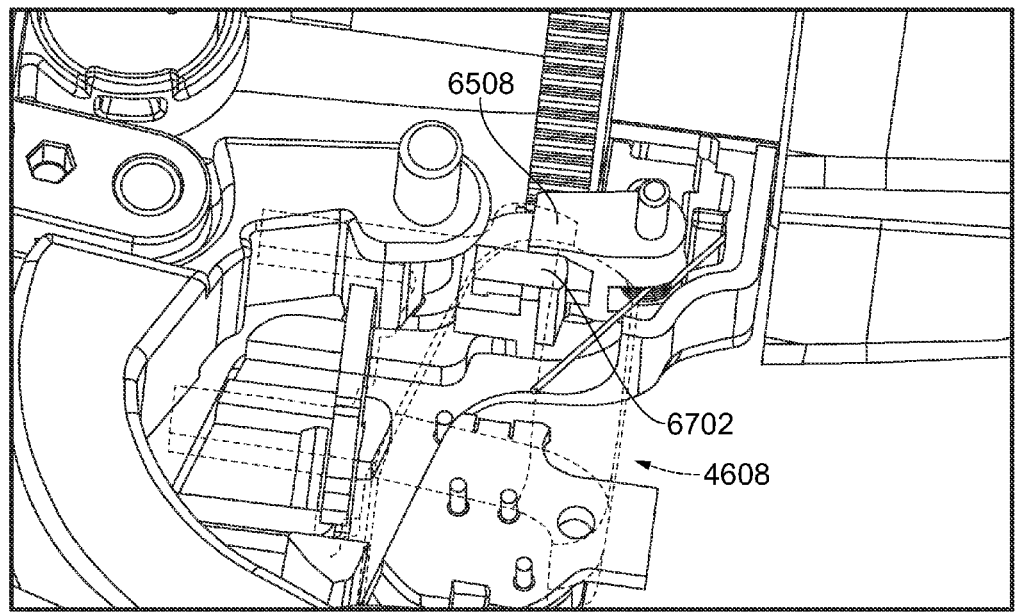
FIG. 68 is a perspective fragmentary view of the two-stage button in a first depressed state and physically engaging the rotational lockout member of FIG. 65 in accordance with an exemplary embodiment of the present invention.
Figure 69:
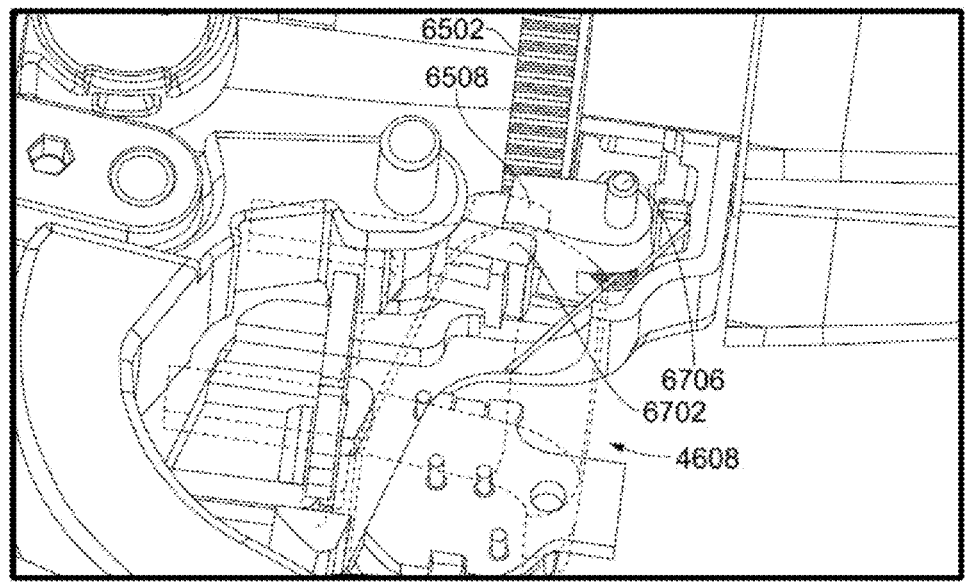
FIG. 69 is a perspective fragmentary view of the two-stage button of FIG. 68 in a second depressed state and fully engaging the rotational lockout member of FIG. 65, which, in turn, is engaging the waveguide assembly rotation-prevention wheel in accordance with an exemplary embodiment of the present invention.

Referring now to FIG. 66, the rotational lockout member 6508 has been displaced into a rotation blocking position. In this position, the wheel-engagement blade 6504 enters the space between two adjacent castellations 6602 on the outer circumference of the rotation-prevention wheel 6502 and engages the side surfaces of the castellations 6602 if the rotation-prevention wheel 6502 rotates. The rotational lockout member 6508 is fixed in its position within the handle assembly 302 and, because of this connection, the engagement between the wheel-engagement blade 6504 and the rotation-prevention wheel 6502 entirely prevent the rotation-prevention wheel 6502 from rotating about the longitudinal axis of the waveguide assembly 304. For example, with seventy-two castellations 6602 on the outer circumference, the rotation-prevention wheel 6502 has substantially no rotational play when rotationally locked. FIGS. 67 through 69 show that the wheel-engagement blade 6504 engages the rotation-prevention wheel 6502 only when the button 4608 is depressed, thereby preventing substantially all rotational movement of the waveguide assembly 304 when ultrasonic movement of the waveguide 1502 occurs.

FIG. 67 shows a perspective underside view of the rotational lockout member 6508 within the handle assembly 302. Once again, the right-hand cover of the handle assembly 302 is removed, thereby exposing several of the internal mechanical components of the handle assembly 302. These components include the button 4608, shown here in a transparent view, a U-shaped member 6702 that slidably engages with the rotational lockout member 6508, and a spring 6704 that biases the U-shaped member 6702 away from a bottom portion of the rotational lockout member 6508. FIG. 67 shows the rotational lockout member 6508, the U-shaped member 6702, and the spring 6704. In the position shown in FIG. 67, the spring 6704 is preloaded by pressure that is asserted by the U-shaped member 6702. The rotational lockout member 6508 is rotationally coupled to and pivots about a pivot pin 6706, which is fixedly coupled to the handle assembly 302.

In addition, FIG. 67 shows a torsional spring 6708 that biases the rotational lockout member 6508 away from the castellations 6602 of the rotation-prevention wheel 6502. The torsional spring 6708 ensures that the natural resting position of the rotational lockout member 6508 is disengaged from the rotation-prevention wheel 6502. A spring force of the torsional spring 6708 is selected so that it is less than a spring force of the spring 6704. Therefore, movement of the rotational lockout member 6508 can occur prior to the spring 6704 being fully compressed.

In operation of the rotation prevention system, when the button 4608 is depressed after a short distance, a rear side of the button 4608 physically contacts the U-shaped member 6702 and moves the U-shaped member 6702 as further proximal button movement occurs. In other words, when depressed, the button 4608 imparts a proximal force on the U-shaped member 6702 in a direction against the biasing force of the spring 6704. This proximal force causes the spring 6704 to compress and allows the U-shaped member 6702 to move in a direction toward the rotational lockout member 6508. This movement is shown in FIG. 68, where the U-shaped member 6702 is closer to the rotational lockout member 6508 than the position shown in FIG. 67. In the view of FIG. 68, the spring 6704 is no longer visible because the U-shaped member 6702 has moved proximate to the rotational lockout member 6508 to a point that the lockout member 6508 completely obscures the spring 6704 in this view. Such contact without a rigid connection ensures that the lockout mechanism does not impede release of the activation button 4608, which is critical to safe operation of the device. Additionally, the connection helps to minimize force that the switch will have to release and reduces operator fatigue.

When the button 4608 is further depressed, as shown in FIG. 69, the rotational lockout member 6508 pivots around the pivot pin 6706 and swings upwardly toward the rotation-prevention wheel 6502. As this upward swing occurs, the wheel-engagement blade 6504 engages the castellations 6602 of the rotation-prevention wheel 6502. In other words, the position of the rotational lockout member 6508 shown in FIG. 69 corresponds to the position of the rotational lockout member 6508 shown in FIG. 66. Similarly, the position of the rotational lockout member 6508 shown in FIG. 67 corresponds to the position of the rotational lockout member 6508 shown in FIG. 65.

In some circumstances, when the button 4608 is depressed, the wheel-engagement blade 6504 lands on one of the castellations 6602 and does not fall between two of the castellations 6602. To account for this occurrence, a stroke distance, i.e., the distance the U-shaped member 6702 is able to move towards the rotational lockout member 6508 allows an electrical activation of the device without requiring actual physical movement of the rotational lockout member 6508. That is, the rotational lockout member 6508 may move slightly, but does not need to fit between two of the castellations 6602 for ultrasonic operation to occur. Of course, rotation is still prevented, as any rotational movement in either direction will cause the rotational lockout member 6508 to move up and into the castellations 6602.

Figure 70:
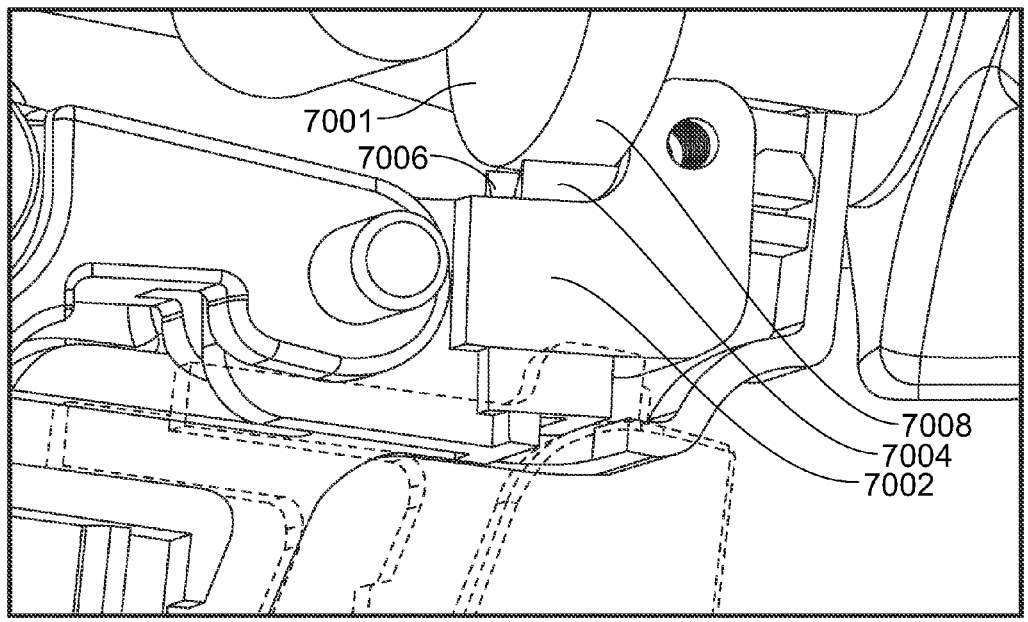
FIG. 70 is a perspective fragmentary view of a rotational lockout member and dual blades adjacent, but not engaging with, a waveguide assembly rotation-prevention wheel, in accordance with an exemplary embodiment of the present invention.
Figure 71:
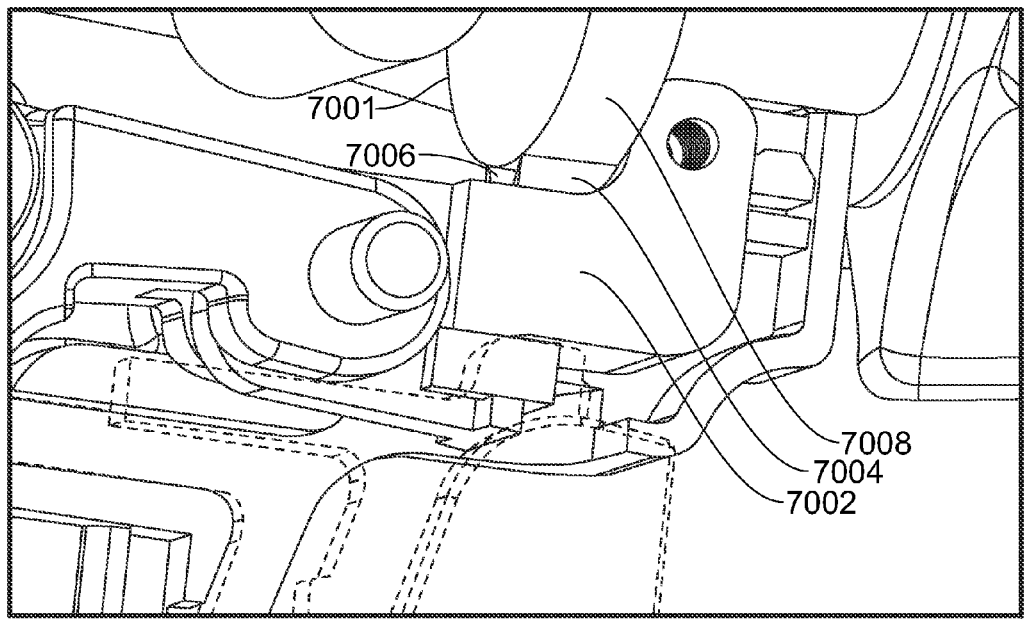
FIG. 71 is a perspective fragmentary view of the rotational lockout member and dual blades of FIG. 70 engaging the waveguide assembly rotation-prevention wheel in accordance with an exemplary embodiment of the present invention.
Figure 105:
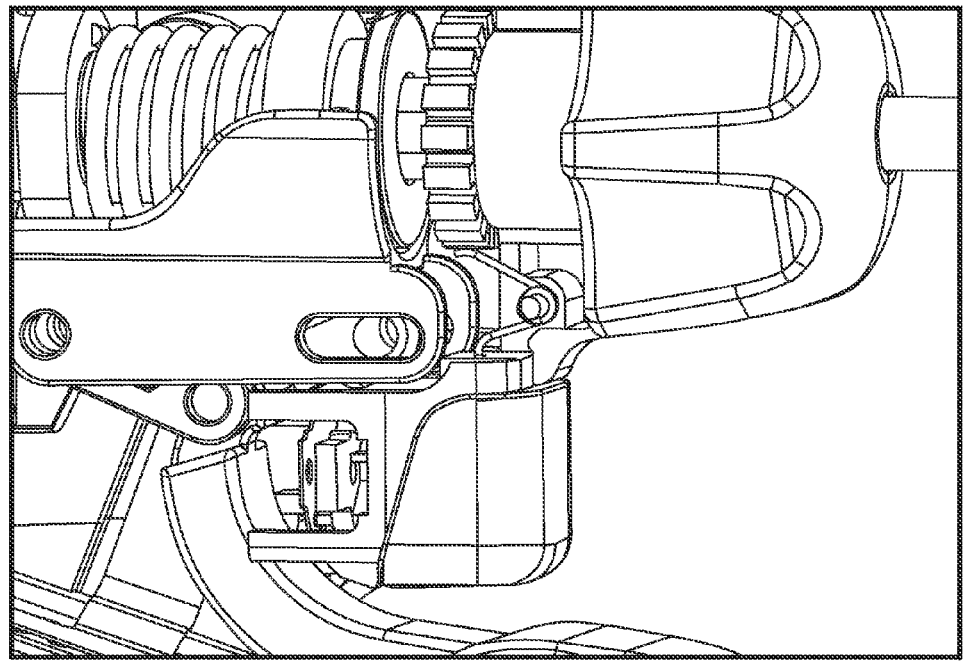
FIG. 105 is a fragmentary, side perspective view of an alternative exemplary embodiment of a spindle rotation prevention assembly of the handle according to the invention.
Figure 106:
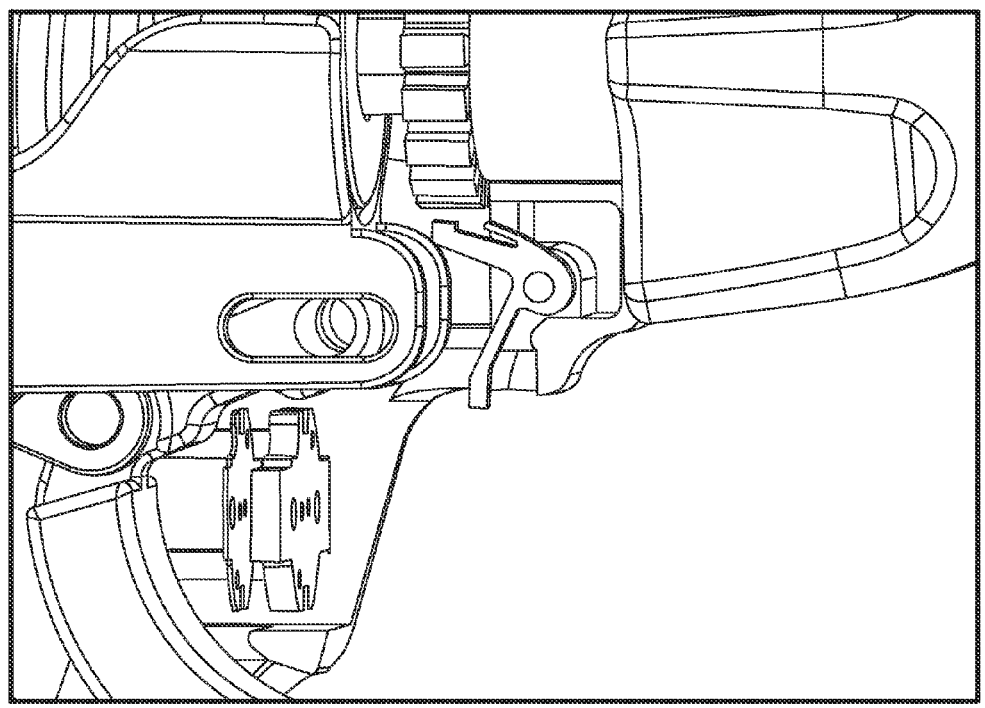
FIG. 106 is a fragmentary, side perspective view of another alternative exemplary embodiment of a spindle rotation prevention assembly of the handle according to the invention.
Figure 109:
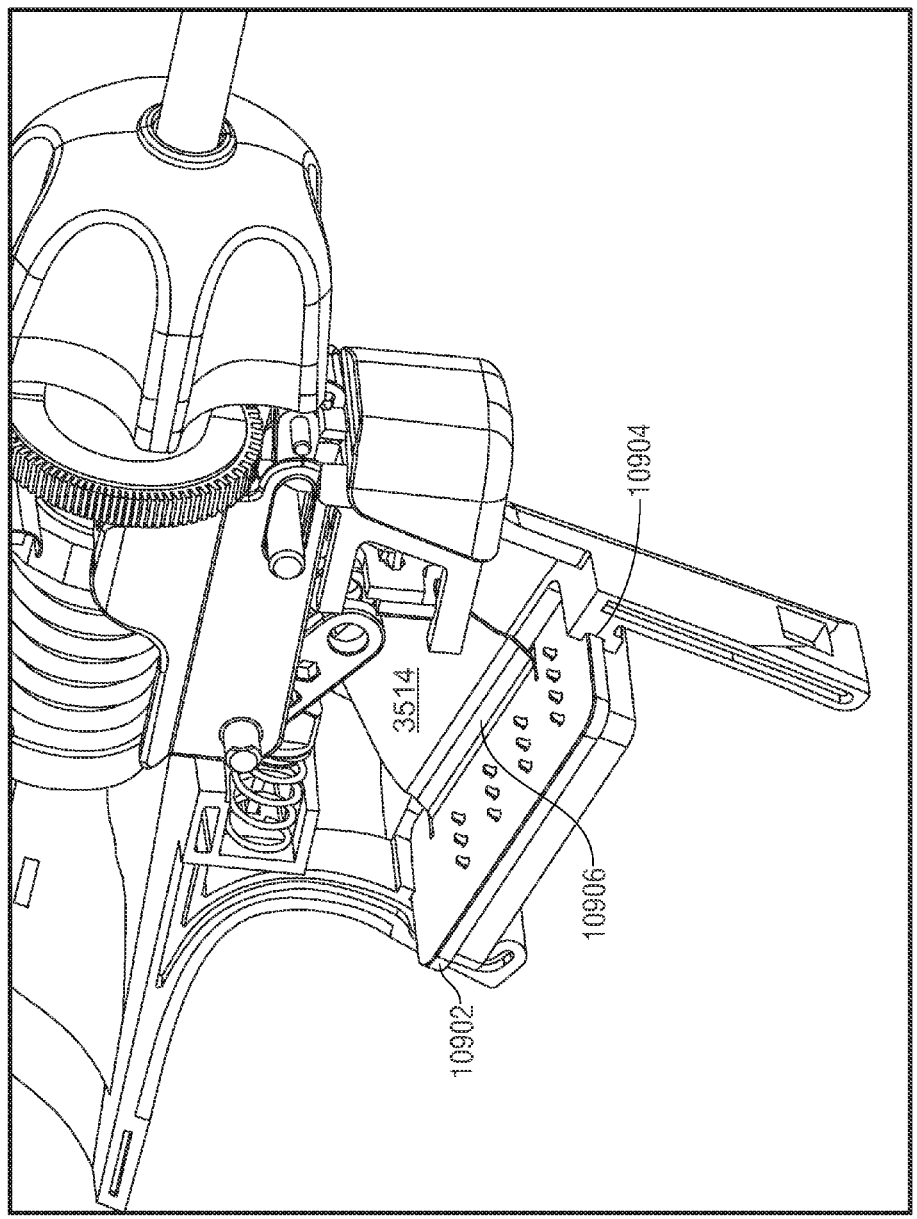
FIG. 109 is a fragmentary, side perspective view of an exemplary embodiment of a battery connection portion of the flex harness according to the invention.

In a further exemplary embodiment of the present invention, a rotational lockout member 7002, as shown in FIGS. 70 and 71, can be provided with one or more blades 7004, 7006 that engage with an outer surface 7008 of a rotation-prevention wheel 7001. In this particular embodiment, the rotation-prevention wheel 7001 does not have teeth on its outer circumference, as the embodiment of the rotation-prevention wheel 6502 of FIGS. 65 to 69. In the embodiment of FIGS. 70 and 71, the outer surface 7008 of the rotation-prevention wheel 7001 is sufficiently malleable to allow the blades 7004, 7006 to engage the outer surface 7008, for example, to actually cut into the outer circumference of the rotation prevention wheel 7001. However, in certain embodiments, where razor-type blades 7004, 7006 are utilized, the rotation-prevention wheel 7001 is sufficiently hard to prevent the blades 7004, 7006 from penetrating more than a predefined depth when an expected amount of force is applied. Furthermore, the lockout member 6508 and U-shaped member 6702 can be, instead, replaced with a single stamped/etched or wireformed lockout member that, within its geometry, replaces at least one of the springs with a flexing feature. FIGS. 105 and 106 show two exemplary embodiments of this alternative configuration.

Once the blades 7004, 7006 are driven into the outer surface 7008 of the rotation-prevention wheel 7001, as is shown in FIG. 71, the rotation-prevention wheel 7001 is rendered unable to rotate about the longitudinal axis of the waveguide assembly 304. Of course, a single blade or three or more blades can be used to prevent the rotation-prevention wheel 7001 from rotating. By separating and angling the blades 7004 and 7006 from one another, rotation prevention is enhanced in either rotational direction. In other words, when the blades 7004 and 7006 are angled away from one another, rotation of the rotation-prevention wheel 7001, in either direction, causes one of the blades 7004 or 7006 to dig deeper into the rotation-prevention wheel 7001. The lockout member 7002 disengages from the rotation-prevention wheel 7001 when pressure is removed from the button, for example, due to a button-return spring. In addition, in this particular embodiment of the rotational-lockout member 7002, a portion of the rotation-lockout member 7002 may capture the third pivot pin 6110. Additional ways of preventing the application of energy while rotating are present using electromechanical and electro-optical technologies. Any combination of sensors, such as magnetic position encoders or optical position sensors, could be used to stop application of energy to the waveguide 1502 if rotation is detected or can be used as a trigger to engage a mechanical lockout such as a solenoid or knife switch. These mechanical measures can also be used without the sensors and can lockout rotation during any energy application. Optical encoders could be placed within the generator housing and directed outward through windows to watch for motion of the transducer housing. Magnetic encoders can be completely buried within the enclosures to further reduce leak path risk.

XIII. TAG—Mechanical

Figure 50:
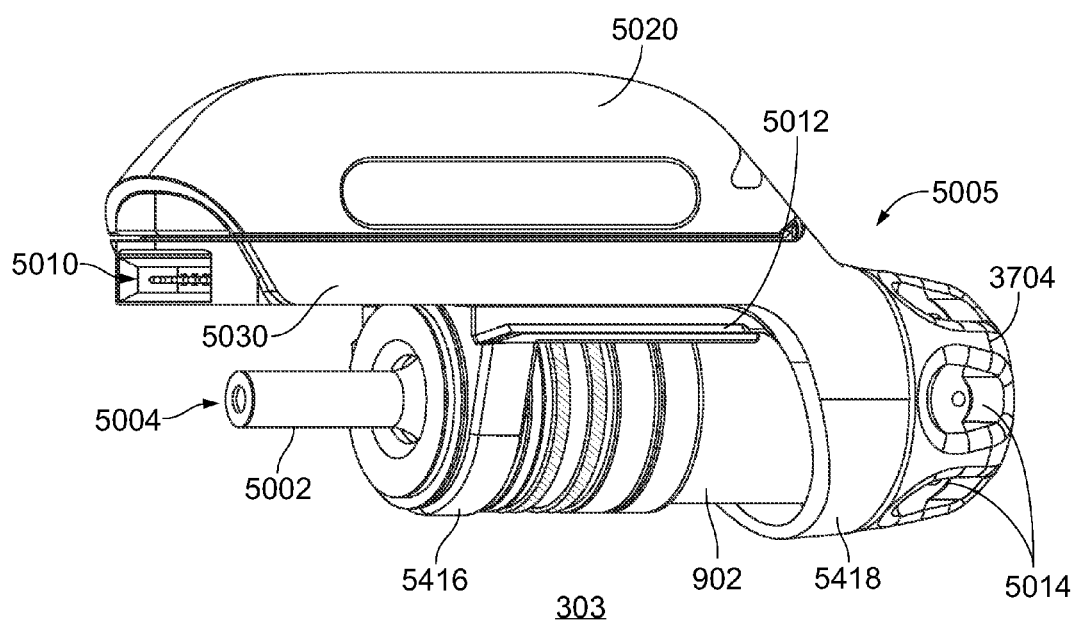
FIG. 50 is an elevational side view of the TAG of FIG. 3 in accordance with an exemplary embodiment of the present invention.

Referring to FIG. 50, the reusable TAG assembly 303 is shown separate from the handle assembly 302. The inventive TAG assembly 303 includes a transducer horn 5002 with an ultrasonic waveguide couple 5004 that is configured to attach a waveguide securely thereto and, upon activation of the transducer horn 5002, to excite the attached waveguide, i.e., impart ultrasonic waves along the length of the waveguide.

In this exemplary embodiment, the waveguide couple 5004 is female and includes interior threads, which are used to secure the TAG assembly 303 to the waveguide 1502 (see, e.g., FIG. 45) by screwing an end of the waveguide 1502 onto the threads of the waveguide couple 5004 with a predefined amount of torque. The torque should be sufficient so that a mechanical connection created by the torque is not broken during normal operation of the device. At the same time, the torque applied to couple the threads should not exceed a force that will cause the threads to become stripped or otherwise damaged. During initial coupling of the transducer 902 and waveguide 1502, all that is needed is that one of the transducer 902 and waveguide 1502 remains relatively stationary with respect to the other. The waveguide rotation spindle 3704 is rotationally fixedly coupled to the transducer 902, which, together, are rotationally freely connected to the body 5005 of the TAG assembly 303. As such, the waveguide rotation spindle 3704 and the transducer 902 are both able to freely rotate with respect to the body 5005. To make the waveguide-transducer connection, therefore, the waveguide 1502 can be held stationary as the waveguide rotation spindle 3704 is rotated to couple the interior threads of the transducer horn 5002 with the corresponding male threads at the proximal end of the waveguide 1502. Preferably, the waveguide 1502 is coupled, i.e., screwed onto the threads of the waveguide couple 5004 to a point where the mechanical connection is sufficient to transfer the mechanical ultrasonic movement from the TAG assembly 303 to the waveguide 1502.

In one exemplary embodiment of the present invention, a torque wrench 8800 (see FIG. 88) couples to the waveguide rotation spindle 3704 and allows the user to rotate the spindle 3704 to a predetermined amount of torque. Once the rotational coupling pressure between the waveguide couple 5004 and the waveguide 1502 exceeds a predetermined amount of torque, the outer portion of the torque wrench 8810 slips about an inner portion 8820 and, thereby, the spindle 3704, and no further rotation of the spindle 3704 takes place. Through use of the inventive torque wrench 8800, an operator is able to apply precisely the proper amount of tension to the junction between the TAG assembly 303 in the waveguide 1502 and is also prevented from damaging the threads on either the waveguide couple 5004 or on the waveguide 1502.

This exemplary embodiment of the torque wrench also clips onto the spindle 3704 to prevent any possibility of the wrench slipping off of the TAG assembly 303 without outside force acting upon it. More specifically with regard to FIG. 50, the spindle 3704 is provided with wrench-gripping surfaces 5014 disposed circumferentially about the proximal end of the spindle 3704. In this exemplary embodiment, the wrench-gripping surfaces 5014 are indentations. The inner portion 8820 of the torque wrench 8800 is, conversely, provided with flexible tines 8822, each having an inner distal surface defining a spindle-gripping surface 8824. In this exemplary embodiment, the spindle-gripping surfaces 8824 have somewhat convexly hemispherical-shaped protrusions that have a corresponding shape to concavely hemispherical-shaped indentations of the wrench-gripping surfaces 5014. In this way, as the inner portion 8820 is coupled to the proximal end of the spindle 3704, each tine 8822 of the inner portion 8820 flexes outwardly and, then, snap back to place the corresponding protrusions 8824 of the tines 8822 within the respective indentations 5014. The user can, then, release the outer portion 8820 completely and the wrench 8800 remains on the spindle 3704 for as long as needed until removal is desired.

To enable coupling of the inner and outer portions 8810, 8820 of the torque wrench 8800 to remain rotationally coupled to one another until a predetermined amount of torque exists, the outer portion 8810 is provided with a ratchet gear 8812 and the inner portion 8820 is provided with a ratchet 8826. The slope and inward-extent of the gear 8812 and the outer circumference and tooth size of the ratchet 8826 are selected to slip at a predetermined amount of torque. With use of sufficiently resilient materials, the torque value at which the two portions 8810, 8820 slip with respect to one another, can be set with great accuracy. Through use of the inventive torque wrench 8800, an operator is able to apply precisely the proper amount of tension to the junction between the TAG assembly 303 in the waveguide 1502 and is also prevented from damaging the threads on either the waveguide couple 5004 or on the waveguide 1502. To counter the torque of the torque wrench the operator must hold the rotation wheel while rotating the torque wrench. For this operation, in an exemplary embodiment, a lockout button can be integrated into the handle halves. This lockout button is depressed by the operator and, when depressed, engages the rotation prevention wheel, stopping the free rotation of the shaft assembly with minimal applied force.

The TAG assembly 303 also has a housing comprised of an upper housing portion 5020 and a lower housing portion 5030 that protects and seals the internal working components from the environment. See FIGS. 50 and 53. Because the TAG assembly 303 will be in the sterile field of the operating environment, it is sterilizable, advantageously, by vapor phase hydrogen peroxide, for example. As such, the seal between the upper housing portion 5020 and the lower housing portion 5030 is aseptic and/or hermetic.

Figure 87:
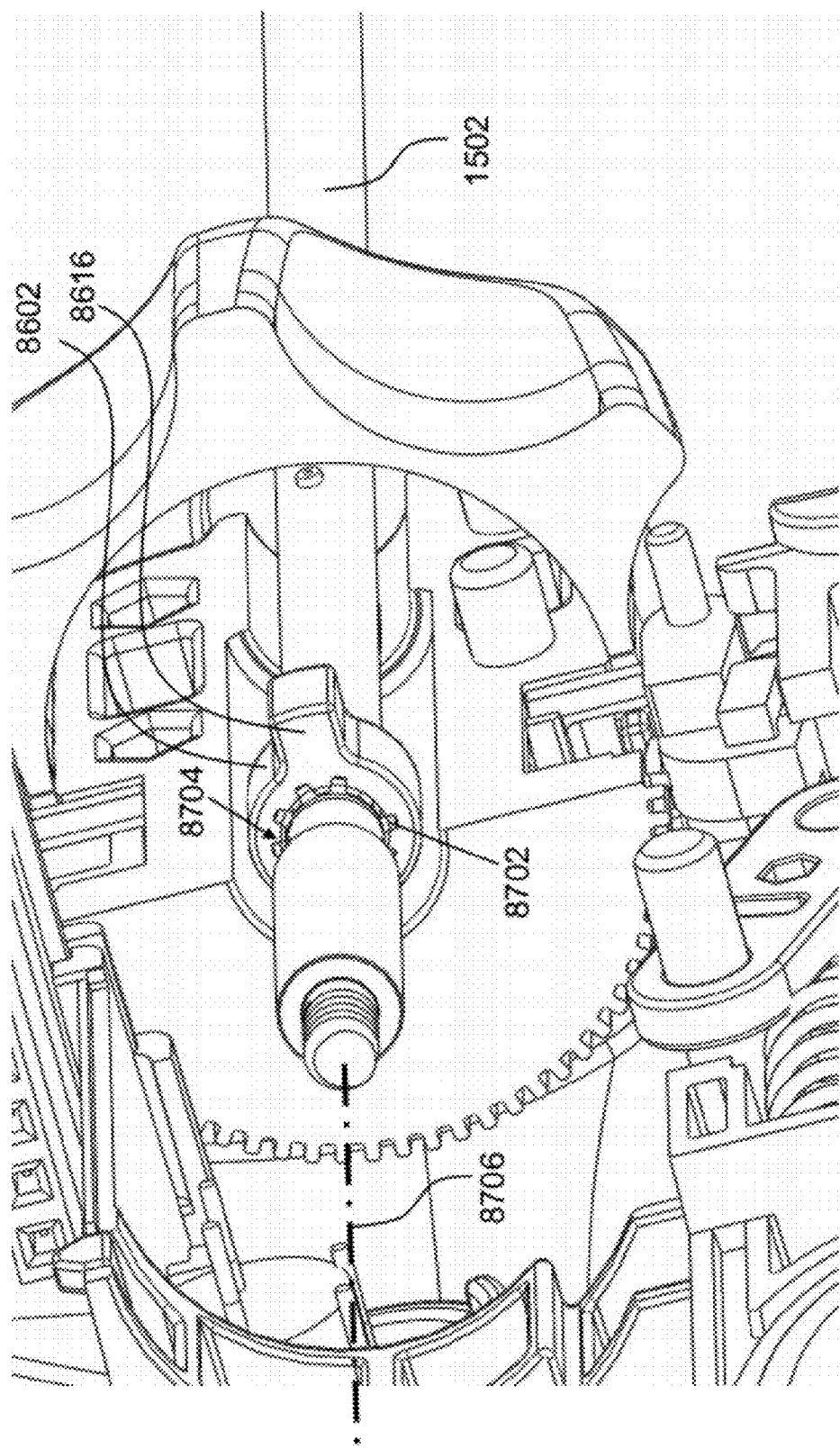
FIG. 87 is a fragmentary, enlarged, perspective view of the handle assembly of FIG. 86 with an outer tube removed and only a right half of the rotation-prevention wheel removed.
Figure 88:
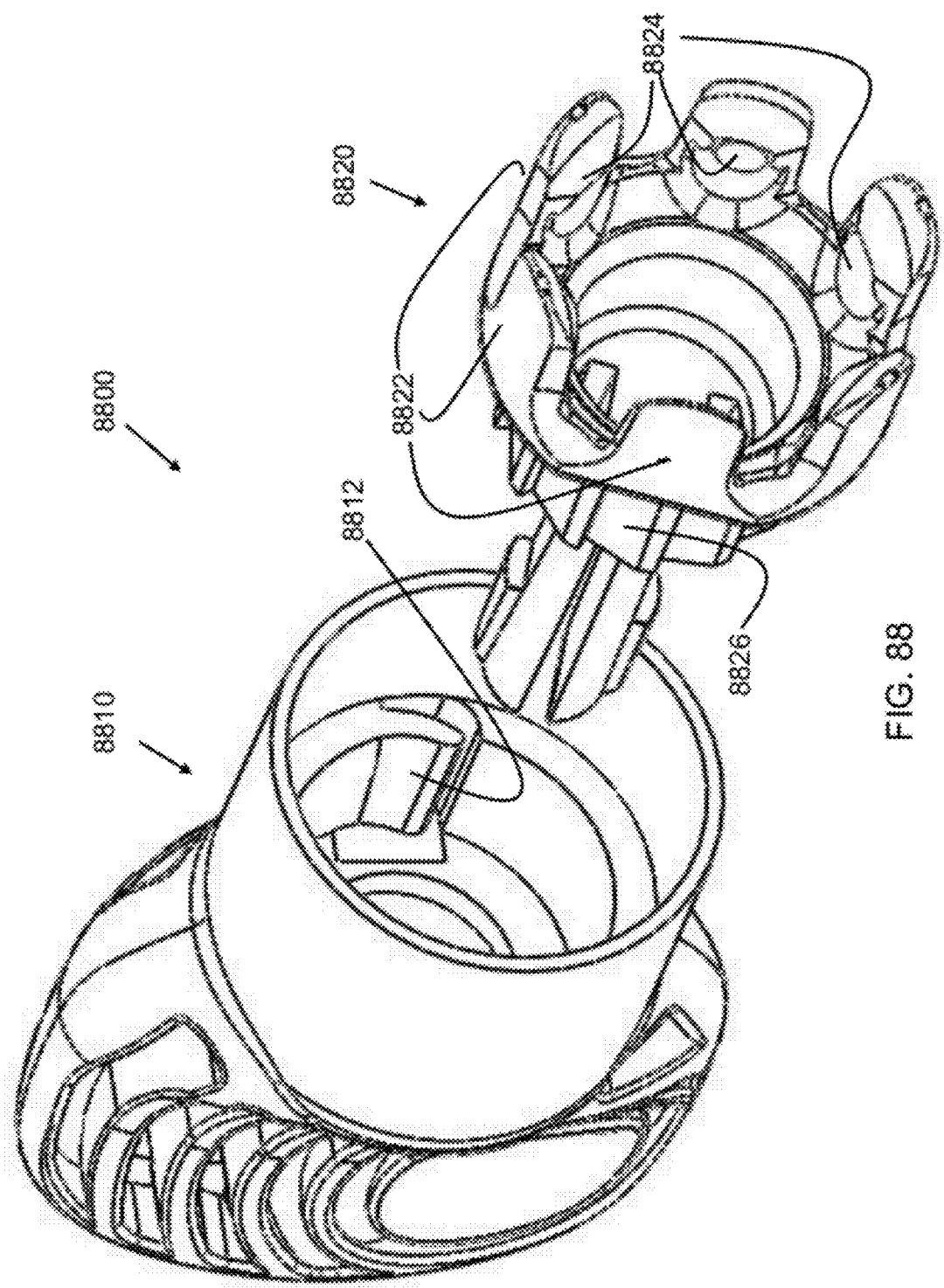
FIG. 88 is a perspective view of a torque wrench according to an exemplary embodiment of the invention.

According to one exemplary, non-illustrated embodiment of the present invention, the transducer 902 is located entirely inside the housing 5005—where it cannot be readily secured by the operator, for example, by holding it steady by hand when the waveguide assembly 304 is being secured. In such an embodiment, the TAG assembly 303 is provided with a transducer rotation lock. For example, the transducer rotation lock can be a button that slides into a recess in the housing 5005 or, alternatively, by fixing the rotation of the transducer 902 at a maximum rotational angle so that, once the maximum rotation is reached, for example, 360 degrees of rotation, no additional rotation is possible and the waveguide assembly 304 can be screwed thereon. Of course, a maximum rotation in the opposite direction will allow the waveguide assembly 304 to be removed as well. In another exemplary embodiment, the torque wrench is incorporated into the handle itself. This exemplary embodiment is not illustrated but can be understood from looking at FIGS. 87 and 88. As can be seen in FIG. 88, one possible torque-limiting device is configured with an inner ratchet portion 8826 and a ratchet gear 8812. This ratcheting assembly can be built into the rotation prevention wheel 6502, a portion of which is shown in FIG. 87. If this rotation prevention wheel 6502 is made of an inner radial part and an outer radial part, the two parts being able to rotate with respect to one another, then either can be formed with one of the inner ratchet portion 8826 with the other one being formed with the ratchet gear 8812. In this way, a user could hold the proximal knob of the transducer still and use rotation of the spindle 3704 to connect the waveguide and the transducer together. When the desired torque is reached, the inner ratchet portion 8826 and the ratchet gear 8812 would slip to prevent over torque. After the waveguide is connected to the transducer with the correct amount of torque, use of spindle rotation during a procedure will not be affected as the number of pounds needed to rotate the spindle 3704 is far less than the number of pounds that is required to overcome torque ratcheting feature.

The housing 5005 has a securing connection 5012 shaped to selectively removably secure to a corresponding connector part of the handle assembly 302. See, e.g., FIG. 56. The connection 5012 can be any coupling connection that allows the TAG assembly 303 to be removably attached and secured to the handle assembly 302, such as the exemplary "dove-tail" design shown in FIGS. 50 to 53 and 56. In FIG. 56, a TAG-retention device 5604 is provided. The TAG-retention device 5604 is a mechanical feature that stops the TAG assembly 303 from sliding off of the handle assembly 302 under its own weight. The retention device 5604 imparts friction to the securing connection 5012 that makes it hard to pull the TAG assembly away from the disposable without overcoming at least a force greater than the weight of the TAG assembly 303. The TAG-retention device 5604 can be in the form of a finger, as shown in FIGS. 61 to 64 and 86, or one or more bumps that interfere with the slide rail. The force that is required to separate the two parts prevents accidental dropping of the TAG assembly 303 during exchange or removal. The area of contact between the handle assembly 302 and the TAG assembly 303 can be sealed so that, in the event of surgical fluids contacting the TAG assembly 303, they will not introduce themselves into the interior of the TAG attachment dock 4502.

It is advantageous for the TAG assembly 303 to be selectively removable from the handle assembly 302. As a separate component, the TAG assembly 303 can be medically disinfected or sterilized (e.g., STERRAD®, V-PRO®, autoclave) and reused for multiple surgeries, while the less-expensive handle assembly 302 itself may be disposable. In addition, the TAG assembly 303 can be used in multiple handles or in the same handle up to a desired maximum number of times before it is required to be disposed. In a further embodiment, the transducer 902 of the TAG assembly 303 can be selectively removable from the generator 904 allowing for better access for cleaning. In such an embodiment, the benefits provided by the invention to matching a transducer to a generator can be maintained by configuring the transducer with a communication system that sends to the generator the transducer's calibration coefficients.

Figure 51:
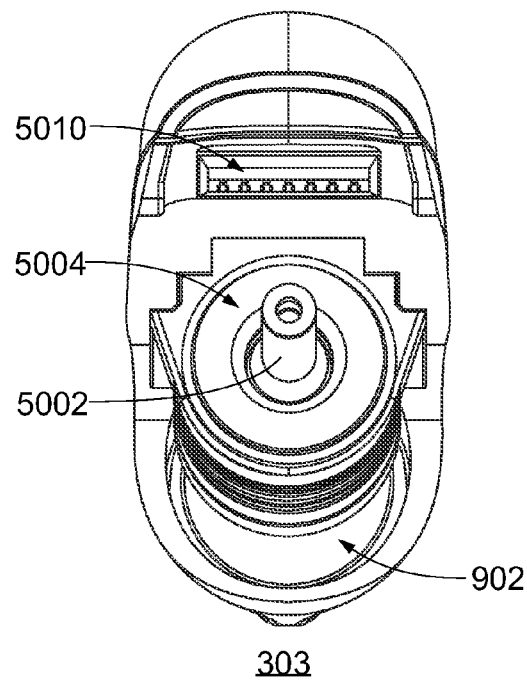
FIG. 51 is an elevational underside view of the TAG of FIG. 50 in accordance with an exemplary embodiment of the present invention.
Figure 52:
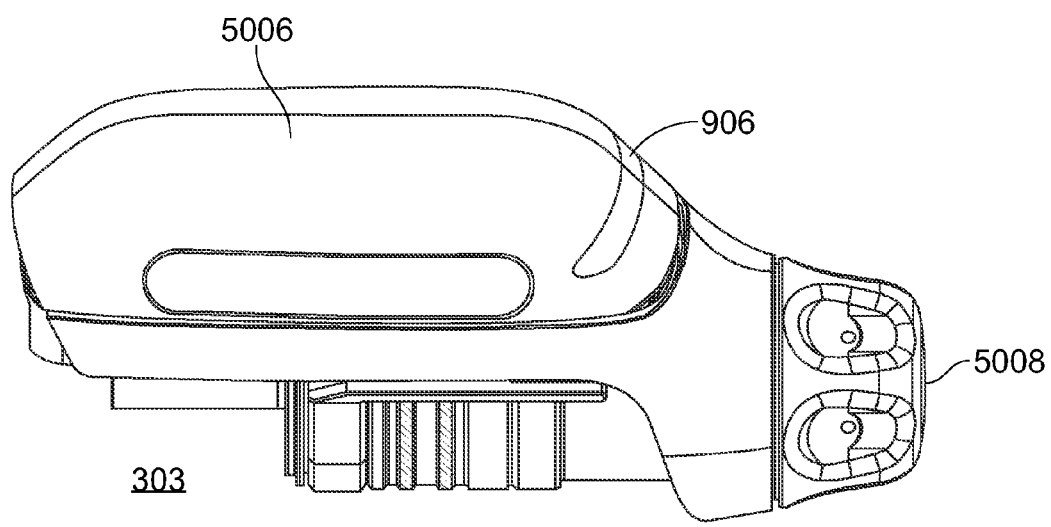
FIG. 52 is an elevational upper view of the TAG of FIG. 50 in accordance with an exemplary embodiment of the present invention.

FIGS. 51 and 52 provide two additional perspective views of the TAG assembly 303. FIG. 52 depicts an exemplary display window for a user display system (for example, RGB LED(s) 906) on the external surface of the housing 5005 of the TAG assembly 303. As explained above, the RGB LED 906 provides various signaling to the user indicating conditions and modes of the surgical assembly 300. Various conditions and modes displayed to the user can also include an indication that the battery level on installation is inadequate—it does not have enough energy to perform the start-up check and initiate software—or that the battery itself is bad. Positive displays can include proper start-up—that, upon connection of the battery to the TAG, there is proper power, verified by battery/TAG communications and, possibly, the amount of available TAG life—or that the system is ready and idling for use. Activation of both the low and high modes can be displayed. With regard to the TAG, expiration of life or other TAG-related faults can be displayed. With regard to the battery, a low condition can be indicated after the battery is connected or during its use. The display can indicate, for example, if the battery only has approximately 20% of charge remaining when first attached. An end of battery charge or other battery faults can be indicated. Finally, various system faults including general faults, battery or TAG software being non-functional, can be displayed.

Figure 53:
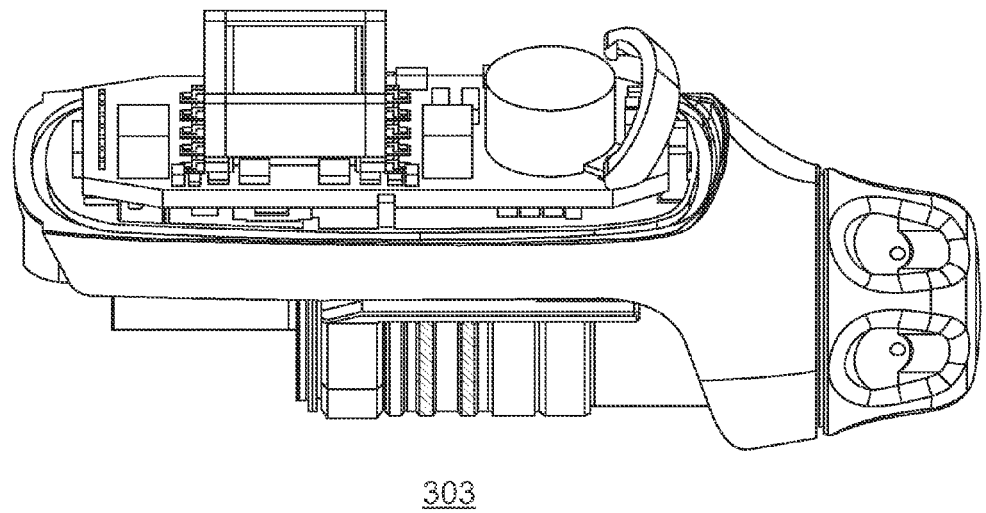
FIG. 53 is an elevational view of the TAG of FIG. 50 with an upper cover removed revealing generator circuitry in accordance with an exemplary embodiment of the present invention.

FIG. 53 provides a top view of the TAG assembly 303 with the upper housing portion 5020 removed, thereby exposing the generator circuitry of the TAG assembly 303, see, e.g., FIG. 9. In a further exemplary embodiment, the generator circuitry includes a memory electrically connected at least to the processor of the TAG assembly 303 or to the processor in the battery assembly 301 (or integrated in any circuit thereof). The memory can be used, for instance, to store a record of each time the TAG assembly 303 is used. Other data relevant to the TAG assembly 303 and/or the waveguide assembly 304 and/or the housing assembly 302 and/or the battery assembly 301 can be stored as well for later access and analysis. This record can be useful for assessing the end of any part of the device's useful or permitted life, in particular, the TAG assembly 303 itself. For instance, once the TAG assembly is used twenty (20) times, the TAG assembly 303 or the battery assembly 301 can be programmed to not allow a particular handle or battery to function with that "old" TAG assembly (e.g., because the TAG assembly 303 is, then, a "no longer reliable" surgical instrument). The memory can also store a number of uses any of the device's peripherals. For an illustrative example only, after a certain number of uses, it is possible that one of the parts of the device can be considered worn, as tolerances between parts could be considered as exceeded. This wear could lead to an unacceptable failure during a procedure. In some exemplary embodiments, the memory stores a record of the parts that have been combined with the device and how many uses each part has experienced.

At times, it may be desirable to provide feedback to the user even when the TAG assembly 303 is disconnected from the battery assembly 301, such as the "end of life" or "no longer reliable" indications of the TAG assembly 303, which indications require that the TAG assembly 303 be taken out of circulation because it has exceeded its useful life and can no longer be used. As is often the case, the physician may not be the same person who is responsible for the proper assembly of the device or for removing the TAG assembly 303 from the device. Accordingly, the TAG assembly 303 can be beneficially configured to have a persistent indicator having its own power source separate from the battery assembly 301. This indicator provides an "end of life" termination warning following the most recent (or last) mating between the TAG assembly 303 and a battery assembly 301 to prompt an immediate disposal of the TAG assembly 303 before any wasteful energy is used in subsequently mating the spent TAG assembly 303 to the same or a different battery assembly 301 for use. Or, alternatively, the indicator could provide the warning immediately upon being subsequently mated to another battery assembly 301 so that it may be disposed of before starting up the device. In either implementation, the warning will be preserved for the party responsible for assembling the device. Multiple schemes can be devised to provide the end-of-life indication to the user, such as primary cells, super capacitors or displays that do not require or draw power. For example, a super capacitor and an ultra-low-power LED drive can be used to provide a strobing indicator. These circuits consume current in the micro-amp range and, therefore, can provide a reliable indication for a number of hours or even days.

In some exemplary embodiments, a memory exists at the battery assembly 301, and the handle assembly 302 is provided with a device identifier that is communicatively coupled at least to the battery assembly 301 and is operable to communicate to the smart battery 301 at least one piece of information about the ultrasonic surgical assembly 300, such as the use history discussed in the preceding paragraph, a surgical handle identifier, a history of previous use, and/or a waveguide identifier. In this way, a single smart battery assembly 301 can record use information on a number of different handle and TAG assemblies 302, 303. When the battery assembly 301 is placed into a charging unit, such a memory can be accessed and the data about each part of the system 301, 302/304, 303 can be downloaded into the charger and, if desired, transmitted to a central facility that is communicatively coupled (e.g., through the Web) to the charging station.

Figure 54:
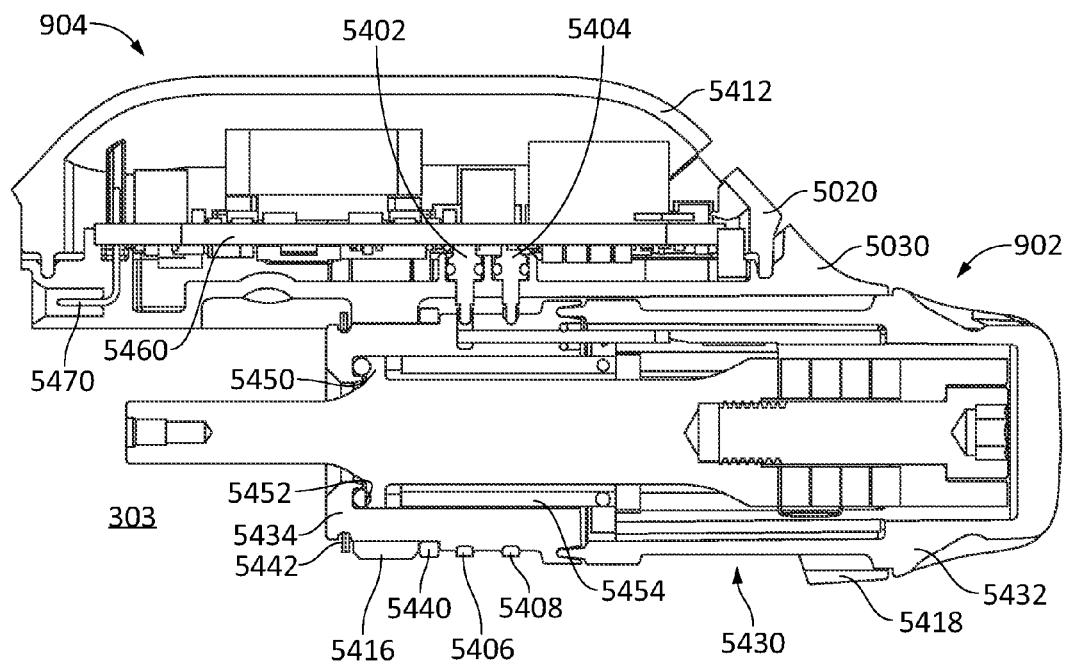
FIG. 54 is an elevational underside view of the TAG of FIG. 50 with an underside cover removed revealing electrical coupling between the generator and the transducer in accordance with an exemplary embodiment of the present invention.

FIG. 54 shows one example of how the generator 904 and the transducer 902 are electrically and physically coupled so that a physical rotation of the transducer 902 with respect to the generator 904 is possible. In this example, the generator 904 has a pair of contacts 5402, 5404 protruding from its underside, adjacent the transducer 902. The contacts 5402, 5404 can be connected to the TAG housing in any way. The illustrated exemplary embodiment captures the contacts 5402, 5404 in place between the generator board and a portion of the TAG housing. As can be seen, the TAG housing is defined by an upper generator housing 5410 and a lower transducer housing 5430. The generator housing has an upper housing portion 5020 and a lower housing portion 5030. To install the contacts 5402, 5404, therefore, the contacts 5402, 5404 are placed into the lower housing portion 5030 and are sealed in place by o-rings (shown) or adhesive. The generator board 5460 is then set on top of the contacts 5402, 5404 and mated for electrical contact. As the upper housing portion 5020 placed on the TAG assembly, it has features that hold the generator board 5460 in place, thereby trapping the contacts 5402, 5404 from moving. These features on the upper housing portion 5020 can be, for example, fingers that push against the board 5460 itself or push on larger components on the generator board 5460. Additionally compressive materials can be used to take up tolerances therebetween and reduce the ability of the board to move around and potentially cause intermittent contact with the connections.

Proximity of the transducer 902 to the generator 904 places one of the pair of contacts 5402, 5404 in physical communication with a corresponding pair of contact rings 5406, 5408 on the body of the transducer 902 so that a driving signal can be steadily and reliably applied to the transducer 902 when needed. Advantageously, the pair of contacts 5402, 5404 maintains electrical contact regardless of the angle of rotation of the transducer 902. Therefore, in this exemplary embodiment, the transducer 902 can rotate without any limitation as to the maximum angle or number of rotations. Additionally, the rings 5406, 5408 and contacts 5402, 5404 ensure that the transducer 902 remains in electrical contact with the generator circuitry regardless of the point of rotation at which the torque wrench stops the tightening the transducer 902 to the waveguide 1502. In an exemplary embodiment that helps alleviate wear between the contact rings and the contacts, the rings are provided with a highly polished surface finish. Also since the contacts are spring-loaded, the contacting spring force is minimized to reduce contact forces and, ultimately, friction. With a smooth surface and a low pin-pushing force, the friction is kept to a minimum, thereby minimizing wear between the two rotating parts. This, along with the plating process, ensures that electrical connection between the mating parts is not interrupted.

The transducer housing 5430 is also made of two parts, a proximal housing portion 5432 and a distal housing portion 5434. As can be seen well in FIG. 50, the lower housing portion 5030 has two housing rings 5416, 5418 that rotatably secure the transducer housing 5430 to the generator housing 5410. The proximal housing ring 5418 merely radially captures the circular outer-diameter proximal transducer portion 5432. It is the distal housing ring 5416 that both radially and longitudinally captures the transducer 902. More specifically, a proximal o-ring 5440 on the proximal side of the distal housing ring 5416 provides one part of the longitudinal capture and a fastener 5442 on the distal side of the distal housing ring 5416 provides the other part of the longitudinal capture. The fastener 5442 can be, for example, one or more snap rings. With this secure longitudinal capture, the two transducer contact rings 5406, 5408 become longitudinally aligned with the two contacts 5402, 5404 for a secure electrical connection between the generator 904 and the transducer 902.

As shown in FIG. 37, the surgical handle assembly 302 has a spindle 3704 attached to the waveguide assembly 304. The spindle 3704 has indentions that allow a surgeon to easily rotate the spindle 3704 with one or more fingers and, therefore, to correspondingly rotate the attached waveguide assembly 304 and the transducer 902 connected to the waveguide 1502. Such a configuration is useful for obtaining a desired cutting-blade angle during surgery.

Figure 55:
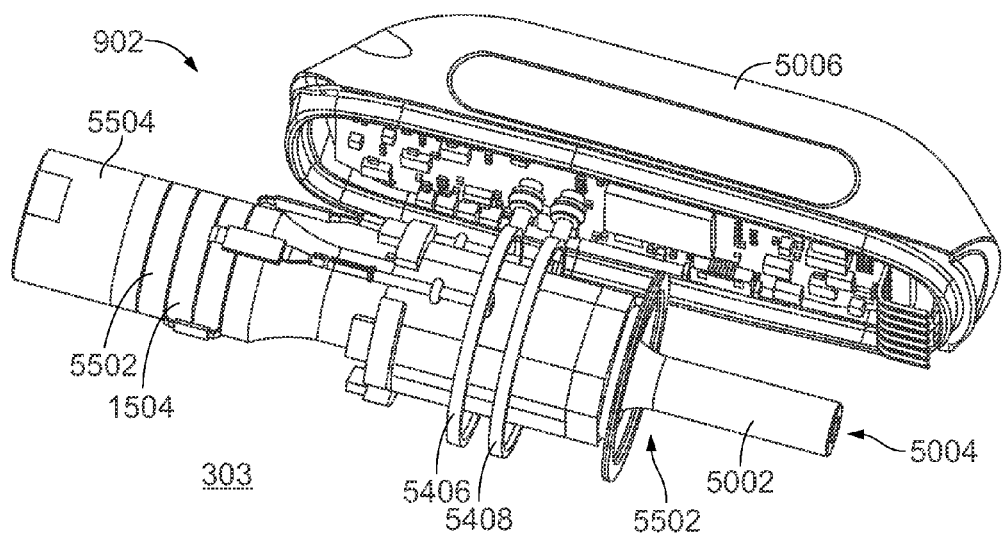
FIG. 55 is a perspective underside view of the TAG of FIG. 50 with an underside cover of the TAG removed and the transducer cover removed revealing components of the transducer in accordance with an exemplary embodiment of the present invention.

FIG. 55 shows one exemplary embodiment of the TAG assembly 303 where the body 5005 and the transducer's shell have been removed. When a voltage is applied to the piezoelectric crystal stack 1504, the horn 5002 moves longitudinally within and relative to the housing 5020, 5030. In this embodiment, the waveguide coupler 5004 is female and includes internal threads (not visible in this view), which are used to secure the TAG assembly 303 to the waveguide 1502 (not illustrated here) by screwing the waveguide 1502 into the threads with an appropriate amount of torque.

A novel feature of the TAG assembly 303 is its ability to mechanically and electrically connect at the same time. FIG. 56 shows an exemplary embodiment of the TAG assembly 303 in the process of docking with the handle assembly 302. At the same time the transducer 902 is being coupled to a waveguide 1502 (attached to the handle assembly 302), the TAG assembly's electrical connector 5010 is brought into contact with the handle assembly's electrical connector 5602. The coupling of the TAG's electrical connector 5010 with the handle's electrical connector 5602 places the piezoelectric crystal stack 1504 in electrical communication (direct or indirect) with the battery assembly 301 docked with the handle assembly 302, as shown in FIG. 37 for example. This substantially simultaneous coupling can be configured to occur in all embodiments of the present invention. The pins of this connection are unique and are shown well in the left side of FIG. 54. Here, a single right angle pin is overmolded into the plastic generator housing 5030 to thereby create pins for the connector 5010. Likewise, these pins each extend upwards into the interior of the generator enclosure to make connection to the generator circuit board 5460. The circuit board connection can be accomplished with solder or, in a simpler form, through sockets mounted to the generator board 5460. In this way, the assembly process is simplified when combined with the sockets that make the connection to the electrodes (pogo pins) 5402, 5404 of the transducer 902. The assembly of the generator housing 5410, therefore, becomes a matter of merely placing the generator board 5460 over the arrays of vertical pins and sealing the housing 5410. Protrusions extending upward from the lower housing portion 5030 support the circuit board 5460 laterally and providing the upper housing portion 5020 with similar protrusions completely trap the generator board 5460 therebetween. Visual outputs from the generator 904 are made through translucent windows 5410 in the upper housing potion 5410. LEDs are strategically placed on the generator 904 to allow illumination of the windows. The space between the LEDs and the windows allows for the light to spread over a larger area and addition of diffusing materials at the windows makes the illumination even. In an exemplary embodiment, the windows wrap around the upper curved surface of the upper housing portion 5020 to be visible over a wide range of viewing and operating angles.

In accordance with further exemplary embodiments of the present invention, the TAG assembly 303 provides a mechanical connection prior to establishing an electrical connection. That is, when attaching the TAG assembly 303 to the handle 302, a mechanical connection is established between the waveguide 1502 and the ultrasonic waveguide couple 5004 prior to an electrical connection being made between the TAG assembly's electrical connector 5010 and the handle assembly's TAG electrical connector 5602. Advantageously, because an electrical connection is not made until after the mechanical connection is established, electrical "bouncing" is avoided in this embodiment. More specifically, as the threads 8604 of the waveguide 1502 couple to the ultrasonic waveguide couple 5004, the electrical connection being made after a solid mechanical connection insures that the TAG assembly's electrical connector 5010 and the handle assembly's electrical connector 5602 to the TAG are in a fixed positional relationship, at least momentarily, and instantaneous removal and reestablishment of the electrical connection will not take place. Similarly, when the assembly 300 is being disassembled, the electrical connection is broken prior to a full separation of the mechanical connection.

Figure 86:
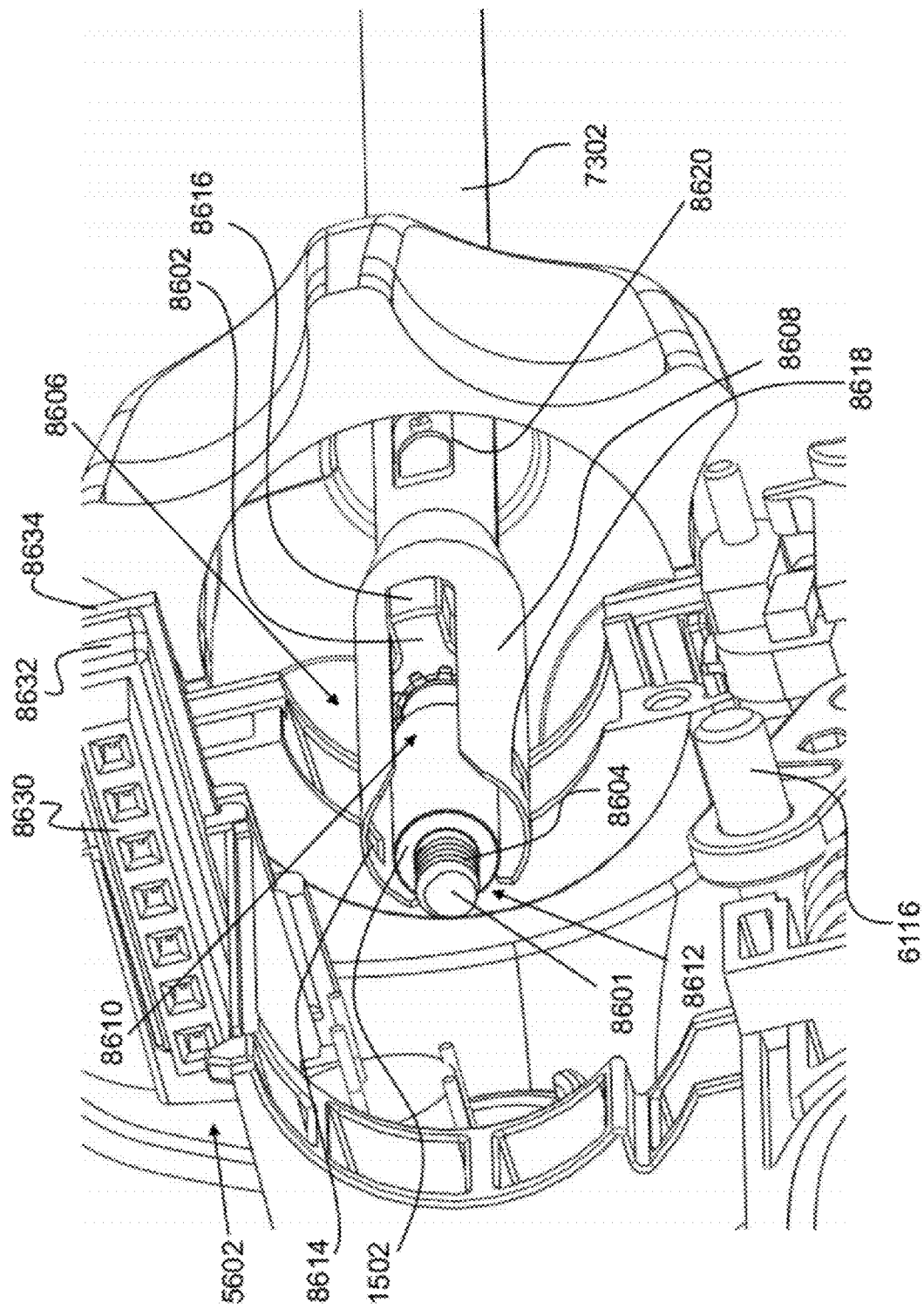
FIG. 86 is a fragmentary, enlarged, perspective view of a TAG attachment dock and a waveguide attachment dock of the handle assembly of FIG. 46 with a right half of the handle body, a rotation-prevention wheel, and a spring and bobbin of the jaw force-limiting assembly removed.

The electrical connector 5602 of the handle 302 is best shown in FIGS. 86 and 108. The electrical connection occurs as the TAG assembly 303 is being mechanically joined to the handle 302. The electrical connector 5010 of the TAG assembly 303 can be seen in FIGS. 50 and 54 and includes a chamfered rectangular blind hole having conductive pins 5470 extend out from the bottom of the hole centered along the longitudinal extent of the hole. The electrical connector 5602 of the handle 302 can be seen in FIGS. 86 and 108 as including a conductor rail 8630, a soft gasket 8632, and a stiff backing 8634, which also is a stiffening part of the flex circuit harness 3516 electrically connecting the electrical connector 5602 of the handle 302 to the flex circuit board 3514 at the multi-lead handle terminal assembly 3502.

Contact occurs first between the electrical connector 5010 of the TAG assembly 303 and a soft gasket 8632. Further coupling compresses the gasket 8632, which compression against the stiffer portion 8634 of the flex harness 3516 creates a fluid-tight seal between the connector 5010 and the flex harness 3516. This connection fully surrounds the connector rail 8630 and prevents fluid from being able to enter any gap between the connector 5010 and the stiffener 8634. The pins 5470 of the connector 5010 that insert into the conductor rail 8630 are, themselves, potted to prevent fluid contact with the interior of the generator 904. This same configuration is used to create the seal between the handle 302 and the housing of the battery 301.

In accordance with other exemplary embodiments of the present invention, the ultrasonic surgical device 300 is able to accept and drive a plurality of waveguide types, e.g., having varying dimensions. Where the handheld ultrasonic surgical cautery assembly 300 is able to accept and drive waveguides 1502 of varying types/dimensions, the handheld ultrasonic surgical cautery assembly 300 is provided with a waveguide detector coupled to the generator 904 and operable to detect the type (i.e., the dimensions or characteristics) of the waveguide 1502 attached to the transducer 902 and to cause the generator 904 to vary the driving-wave frequency and/or the driving-wave power based upon the detected waveguide type. The waveguide detector can be any device, set of components, software, electrical connections, or other that is/are able to identify at least one property of a waveguide 1502 connected to the handheld ultrasonic surgical cautery assembly 300.

XIV. Waveguide Assembly

FIGS. 73 to 87 provide detailed illustrations of exemplary embodiments of the waveguide assembly 304. The waveguide assembly 304 receives ultrasonic movement directly from the transducer 902 when the waveguide 1502 is physically coupled to the TAG assembly 303. The blade portion 7304 of the waveguide 1502 transfers this ultrasonic energy to tissue being treated. The ultrasonically-moving blade portion 7304 facilitates efficient cutting of organic tissue and accelerates blood vessel clotting in the area of the cut, i.e., accelerated coagulation through cauterization.

Figure 73:
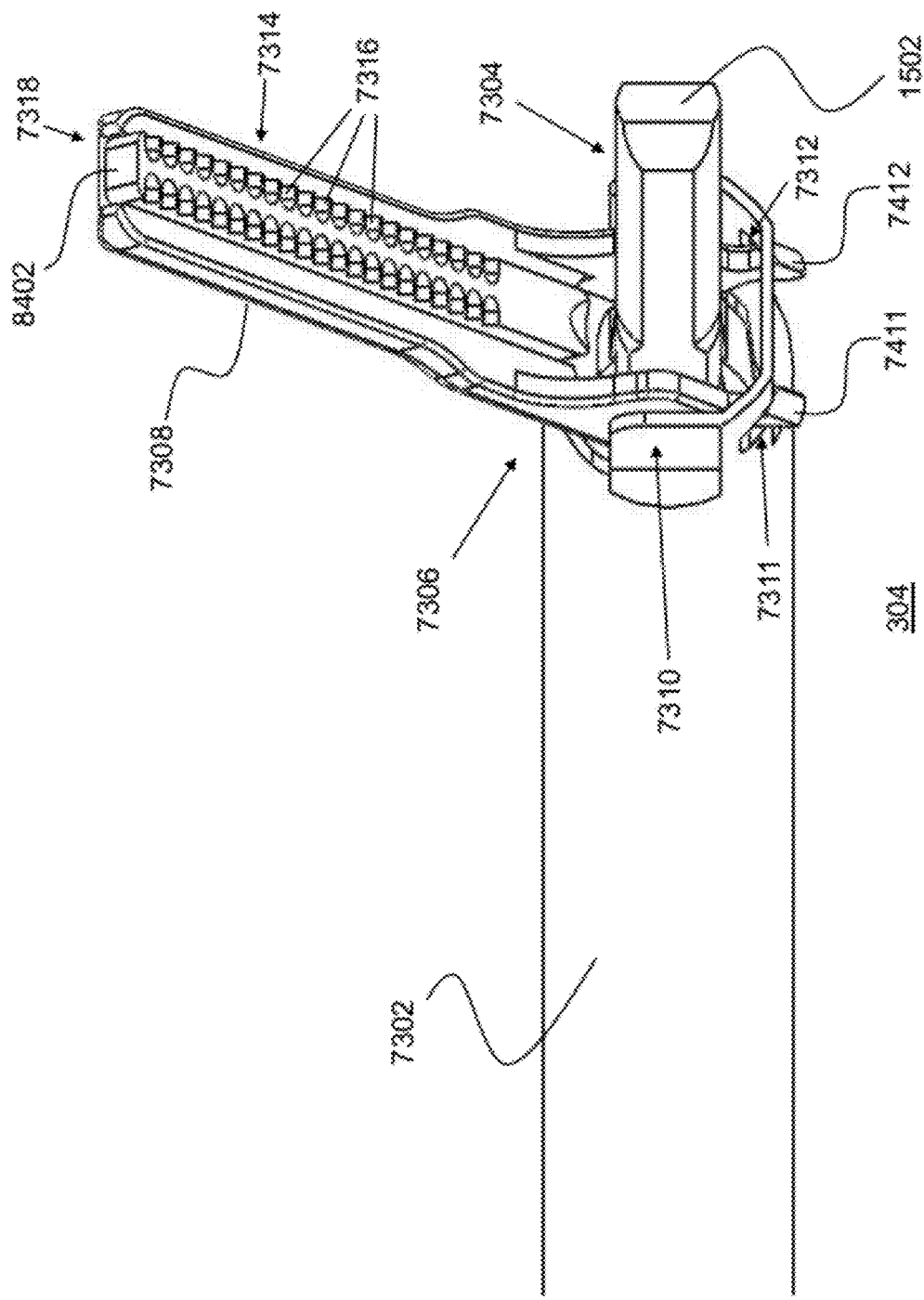
FIG. 73 is a fragmentary, enlarged perspective view of an exemplary embodiment of an end effector according to the invention from a distal end with a jaw in an open position.

Referring to FIG. 73, a perspective partial view of the distal end 7306 of the waveguide assembly 304 is shown. The waveguide assembly 304 includes an outer tube 7302 surrounding a portion of the waveguide 1502. A blade portion 7304 of the waveguide 1502 protrudes from the distal end 7306 of the outer tube 7302. It is this blade portion 7304 that contacts the tissue during a medical procedure and transfers its ultrasonic energy to the tissue. The waveguide assembly 304 also includes a jaw member 7308 that is coupled to both the outer tube 7302 and an inner tube (not visible in this view).

The jaw member 7308, together with the inner and outer tubes 7302, 7402 and the blade portion 7304 of the waveguide 1052, can be referred to as an end effector. As will be explained below, the outer tube 7302 and the non-illustrated inner tube slide longitudinally with respect to each other. As the relative movement between the outer tube 7302 and the non-illustrated inner tube occurs, the jaw 7308 pivots upon a pivot point 7310, thereby causing the jaw 7308 to open and close. When closed, the jaw 7308 imparts a pinching force on tissue located between the jaw 7308 and the blade portion 7304, insuring positive and efficient blade-to-tissue contact.

Figure 74:
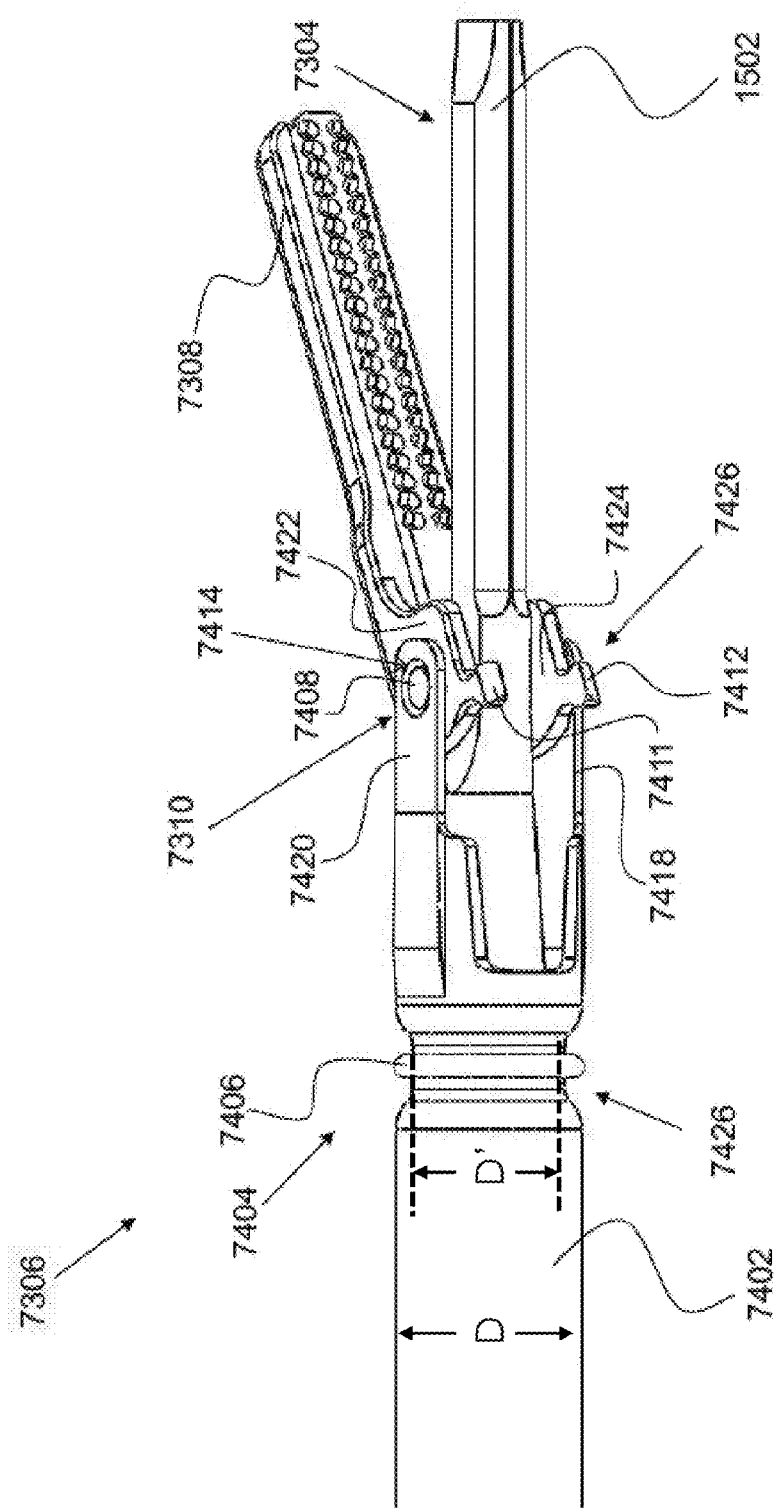
FIG. 74 is a fragmentary, enlarged perspective view of the end effector of FIG. 73 from below with an outer tube removed.

FIG. 74 provides a perspective underside view of the distal end 7306 of the waveguide assembly 304 shown in FIG. 73 with the outer tube 7302 removed. In this view, a distal end 7306 of the inner tube 7402 can be seen coupled to the jaw 7308. This coupling is provided by, in the exemplary embodiment illustrated in FIG. 74, a union of a pair of bosses 7408 on the jaw 7308 with boss-engaging openings 7414 in each of a pair of clevis arms 7418, 7420 that capture the bosses 7408 when the jaw 7308 is inserted therebetween. This relationship is better shown in the cross-sectional perspective underside view of FIG. 75. From this view, it can be seen that the boss-engaging openings 7414 of the clevis arms 7418, 7420 of the inner tube 7402 are coined 7502. The coined clevis arms 7418, 7420 provide a solid connection between the inner tube 7402 and the jaw 7308. By coining the openings 7414, the inner tube 7402 is able to engage the bosses 7408 on the jaw 7308 without having to rely on the outer tube 7302 for structural pressure/support.

Figure 75:
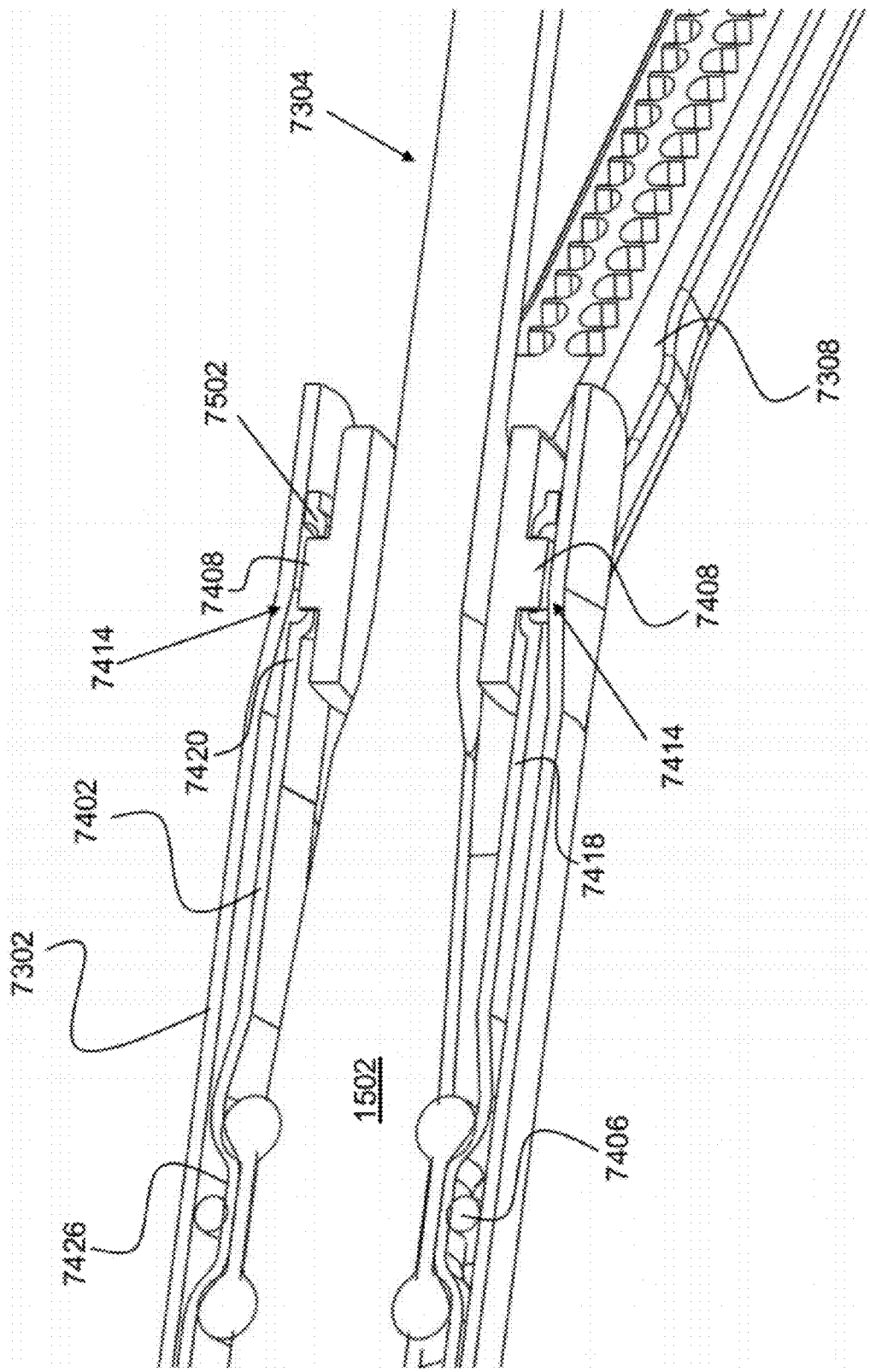
FIG. 75 is a fragmentary, enlarged cross-sectional and perspective view of the end effector of FIG. 73 from below with the section taken transverse to the jaw-operating plane through the waveguide.

FIG. 75 also shows that the waveguide 1502 is separate from, i.e., not attached to, the jaw 7308 or inner tube 7402. In other words, the waveguide 1502, when energized with ultrasonic energy, will move relative to the inner tube 7402 and jaw 7308 but will not contact the inner tube 7402 and will only contact the jaw 7308 if the latter is pivoted against the blade portion 7304 without the presence of tissue therebetween. Features of the present invention that facilitate this independent movement of the waveguide 1502 will be described below.

Returning to FIG. 74, the jaw 7308 is provided with a pair of flanges 7422, 7424 at a proximal end 7426 thereof. The flanges 7422, 7424 extend and surround the waveguide 1502 on opposing sides thereof. Each one of the flanges 7422, 7424 has, at its end, a pivot control tab 7411, 7412, respectively, extending below the waveguide 1502 when the bosses 7408 of the jaw 7308 are secured within the boss-engaging openings 7414 in the clevis arms 7418, 7420. It is not a requirement for the pivot control tabs 7411, 7412 to extend below the waveguide 1502 as shown in FIG. 74; this configuration exists in the exemplary embodiment shown.

The jaw 7308 may be lubricated to reduce friction between the pivot control tabs 7411, 7412 and the outer tube 7302, as well as the bosses 7408 and the inner tube 7402. Such lubrication permits smoother actuation and reduces wear between the mating faces. Lubrication also allows the proximal side of the pivot control tabs 7411, 7412 to have a tighter fit and a more precise profiling with the outer tube 7302, which reduces backlash on the jaw 7308. To avoid rapid displacing of topically applied lubricants, one exemplary embodiment of the lubricant is a baked-on PTFE lubricant. This exposed lubricant on the top surface of the jaw further aids in the insertion of the device through a trocar. In the exemplary embodiment depicted, the pivot control tabs 7411, 7412 are shown as two arms that straddle the waveguide 1502. However, the same function can be achieved with a single arm that wraps around the waveguide 1502 and interacts with the outer tube 7302 on a bottom centerline. In both cases, the bottom of the control tab(s) 7411(, 7412) are rounded to match a maximum shaft diameter and allow for insertion into trocar, as well as reducing the presence of sharp edges.

Returning briefly back to FIG. 73, the elevational end view of the waveguide assembly 304 shows that the pivot control tabs 7411, 7412 of the flanges 7422, 7424 of the jaw 7308 engage a pair of openings 7311, 7312 in a distal portion 7306 of the outer tube 7302. These features are better illustrated in the fragmentary, cross-sectional side view of FIG. 77.

Figure 77:
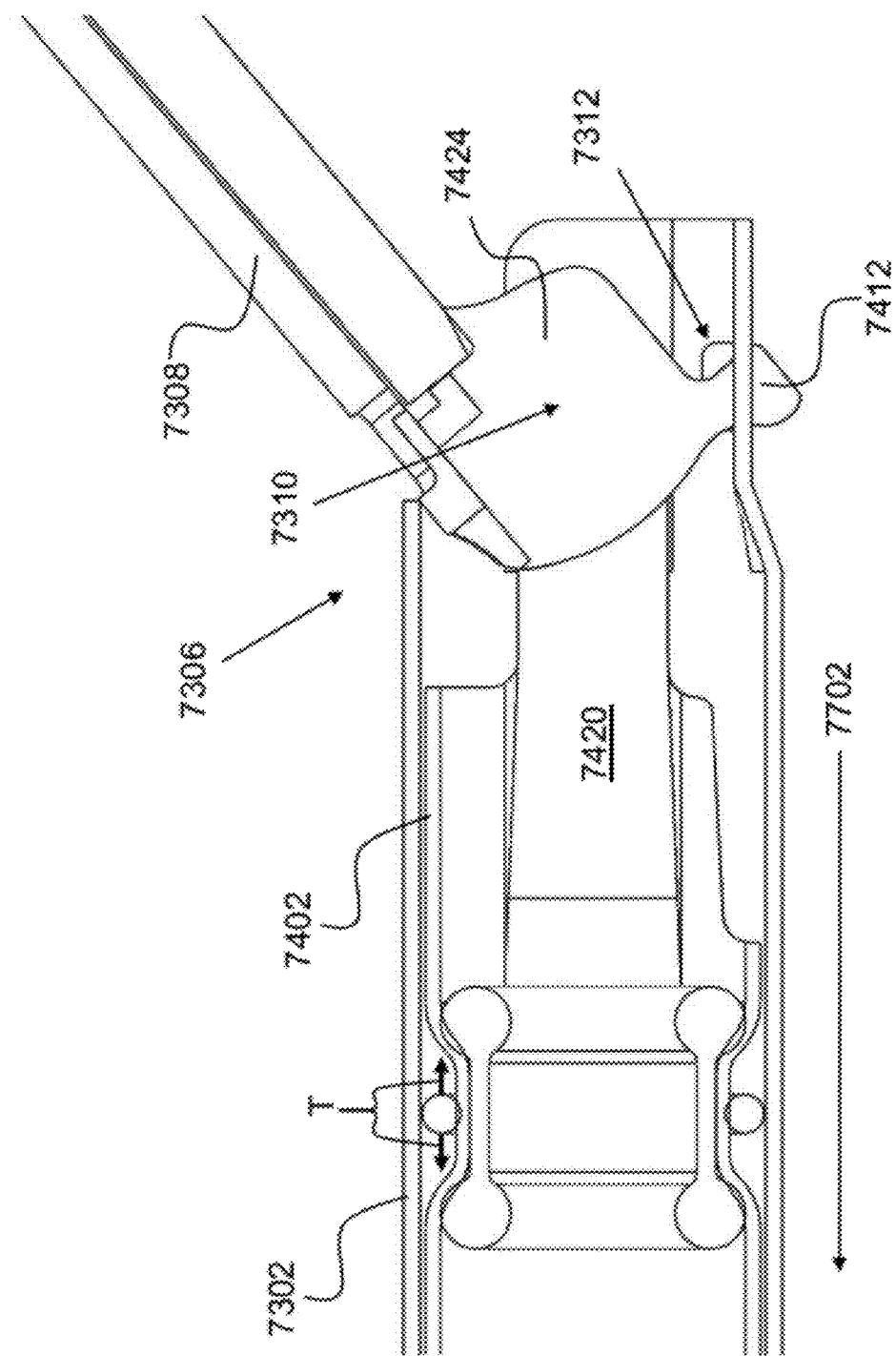
FIG. 77 is a fragmentary, enlarged cross-sectional side view of the end effector of FIG. 73 with the section taken parallel to the jaw-operating plane with the waveguide removed.

Because the view of FIG. 77 is a cross-sectional view, only one 7424 of the two flanges 7422, 7424 is shown and the surface shown is an inside surface of the flange 7424. Correspondingly, only one of the pivot control tabs 7412 is shown, as well as a single one of the pair of openings 7312 in the distal portion 7306 of the outer tube 7302. This view makes clear that the opening 7312 surrounds and captures the pivot control tab 7412. Therefore, if the outer tube 7302 is moved toward the jaw 7308, the opening 7312 will also move relative to the jaw 7308. Conversely, if the outer tube 7302 is moved away from the jaw 7308, the opening 7312 will also move relative to the jaw 7308 in the opposite direction. The captured pivot control tab 7412 nested within the opening 7312 causes a corresponding rotational movement of the jaw 7308 around the pivot point 7310.

Figure 78:
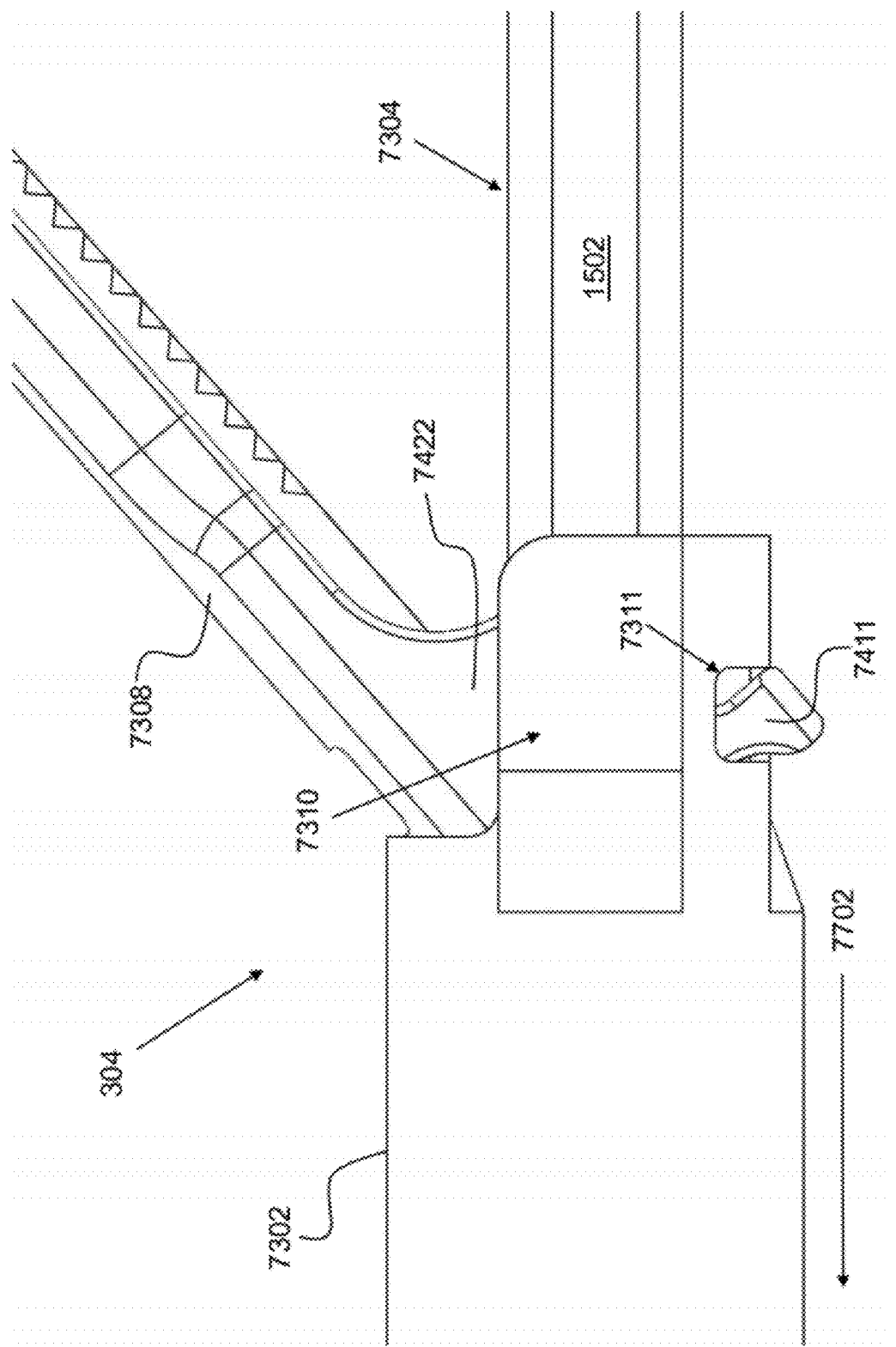
FIG. 78 is a fragmentary, enlarged, side elevational view of the end effector of FIG. 73.
Figure 79:
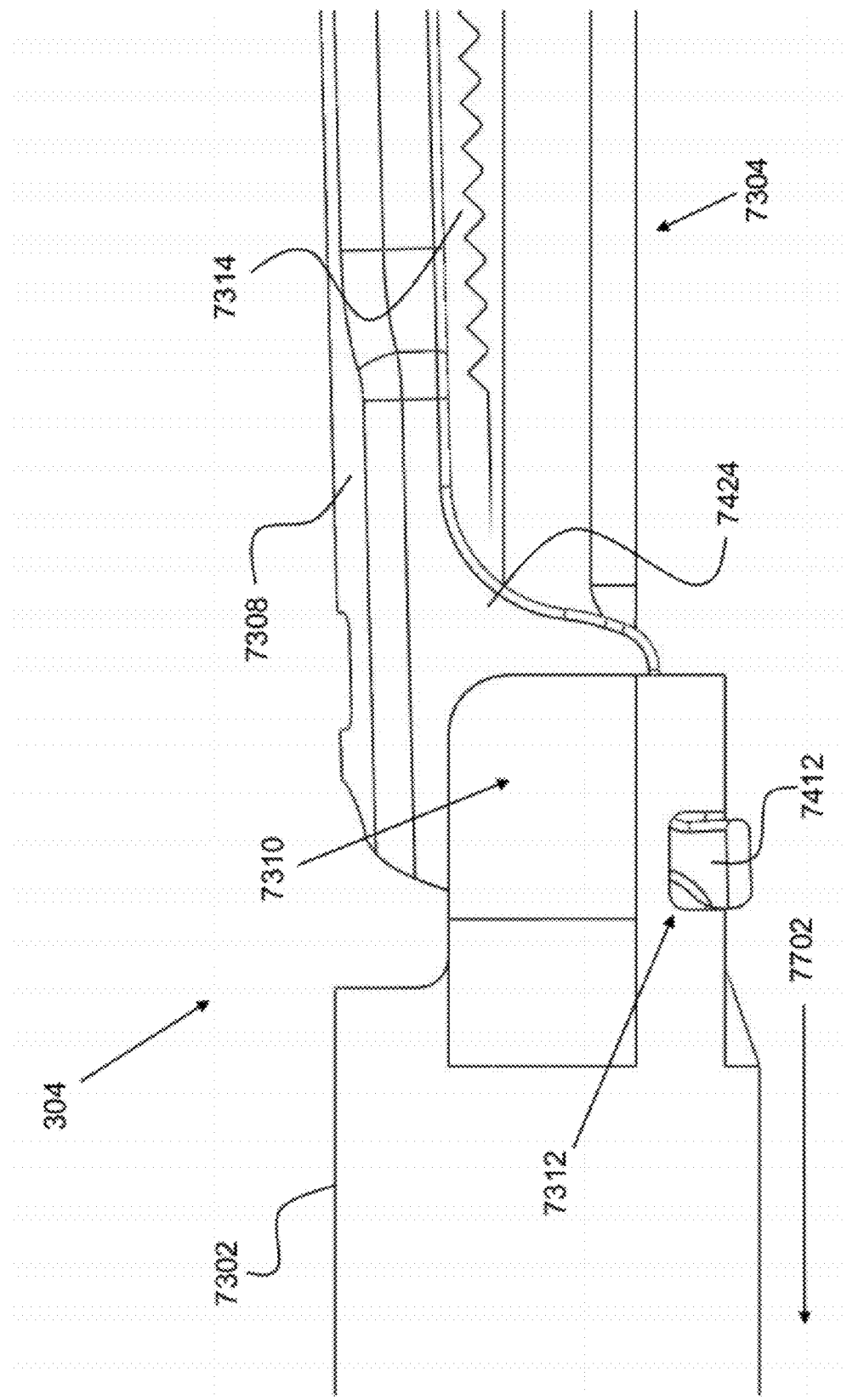
FIG. 79 is a fragmentary, enlarged, side elevational view of the end effector of FIG. 78 with the jaw in a substantially closed position.

FIG. 78 provides an elevational partial side view of the end effector of the waveguide assembly 304. This view shows the outer tube 7302 substantially covering the flange 7422 of the jaw 7308, leaving only the pivot control tab 7411 extending from the opening 7311. It should now be apparent that, when the outer tube 7302 is slid in a proximal direction 7702, i.e., in a direction away from the jaw 7308, the outer tube 7302 will pull the pivot control tabs 7411, 7412 in the proximal direction 7702. This action causes the jaw 7308 to pivot around the pivot point 7310 clockwise in FIG. 78 to close, i.e., clamp, toward the blade portion 7304 of the waveguide 1502. This closed position of the jaw 7308 is shown in FIG. 79. The configuration of the exemplary embodiment of the waveguide assembly 304 is advantageous because assembly can occur without riveting or welding; the parts are all mechanically captured—e.g., the pivot control tab 7411, 7412 falls into the opening 7311 to allow the waveguide to be locked in mechanically without riveting or welding. This assembly procedure is discussed in further detail below.

Figure 80:
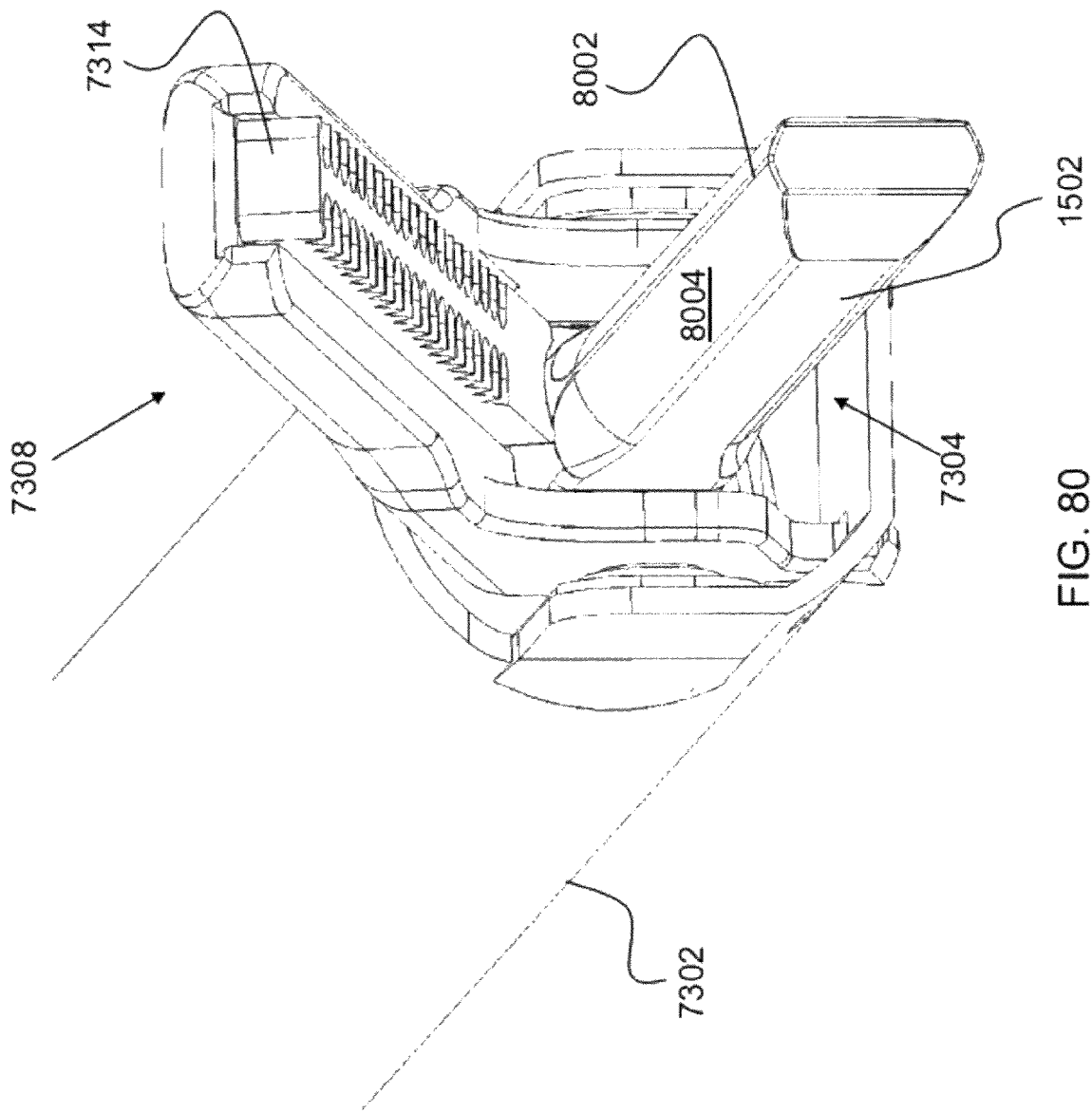
FIG. 80 is a fragmentary, enlarged, perspective view of the end effector of FIG. 73 with the jaw in a partially closed position.

FIG. 80 provides another view of the distal end of the jaw 7308 in a slightly closed position where the jaw 7308 is about to be placed in contact with the blade portion 7304 of the waveguide 1502. The end effector traps tissue between an interior of the jaw member 7308 and an opposing surface of the blade portion 7304. Trapping tissue in this way advantageously places the tissue in solid physical contact with the waveguide 1502. Accordingly, when the waveguide 1502 moves ultrasonically, the movement of the waveguide is directly transferred to the tissue, causing a cut, a cauterization, or both. It has been discovered to be beneficial to create an interference that will account for a deflection of the blade portion 7304 of the waveguide 1502 under the clamping forces imparted at the end effector. Deflection of the waveguide 1502 is a combination of bending and compression of a distal seal (i.e., a coupling spool 8104). Even though the configuration of the distal seal of the invention minimizes a thickness of elastomeric support, deflection of the waveguide 1502 can be substantial. If the initial contact between the blade portion 7304 and a liner 7314 of the end effector jaw 7308 was parallel, a gap would open at the root of the jaw 7308 as the waveguide 1502 deflected. Therefore, the invention configures initial contact to apply force at the root of the jaw 7308 and come into parallel with the blade portion 7304 when the full clamping force is applied. FIG. 80 shows an exemplary embodiment of the cutting profile of the cutting blade 7304. To achieve desired tissue or vessel cutting and cauterizing/sealing (excluding clamp force, displacement, and frequency), the cutting blade 7304 contains a composite of high and low stress concentrations between the profile of the blade portion 7304 and the liner 7314 of the jaw 7308. For desired vessel sealing, the vessel needs to have a seam where the top and the bottom of the vessel are bonded to each other. The seam needs to be centrally cut and a relief volume is desired to allow tissue to flow when sealing and to not char or burn. The profile shown in FIG. 80 provides both desirable characteristics. First, the blade profile features a narrow, relatively flat spine section 8002 that concentrates pressure from the clamping force to a localized seam at a level that allows tissue to momentarily dwell to allow coagulation and eventual cutting. During this dwell time (i.e., the sealing process) adjacent tissue is displaced by providing a curved side profile 8004 away from the cut. The high stress seam on the top and bottom of the blade portion 7304 is used to aid dissection (i.e., back scoring). During the cutting/sealing of tissue or a vessel, it can be beneficial to track tissue/vessel integrity. The invention utilizes the metallic waveguide 1502 as one pole of a two-pole electrical circuit to measure properties such as impedance and/or capacitance of the tissue at the blade portion 7304 of the waveguide 1502. The electrically conductive material of the waveguide 1502 is already electrically connected to the TAG. This connection forms the first of the two-pole measurement circuit. The opposing pole is part of the liner 7314 in the jaw 7308. In an exemplary embodiment, a separate electrically conductive lead or other electrically conductive components in the handle 302 can connect the liner 7314 to the TAG.

To facilitate outer tube 7302 translation, and with reference back to FIG. 74, one or more corsets 7404 are provided on the inner tube 7402. The corset 7404 is an area of the inner tube 7402 having a smaller diameter D' than the average outer diameter D of the inner tube 7402. See FIG. 74. In accordance with an exemplary embodiment of the present invention, the corset 7404 is/are provided at a node(s) of the ultrasonic waveguide 1502. In other words, the corsets 7404 are located at points along the waveguide 1502 where the waveguide 1502 does not exhibit ultrasonic motion at resonant frequency. Therefore, the decreased diameter of the inner tube 7402 and its physical coupling to an interior surface of the outer tube 7302 does not adversely affect the waveguide's ability to resonate at an ultrasonic frequency. As also illustrated in FIGS. 74 and 75, for example, a seal 7406 resides within the corset 7404. The seal 7406, according to one exemplary embodiment, is an elastomeric O-ring type seal. Of course, many other materials may be selected as well. The seal 7406 has an outer diameter sufficiently larger than the outer diameter D of the 7402 so that the sealing effect is maintained but not too much to prevent the outer tube 7302 and the inner tube 7402 from translating with respect to one another without substantial friction when the jaw 7308 is actuated.

As is also shown in FIGS. 74 and 75, a thickness of the seal 7406 is smaller than a longitudinal length of the corset 7404 in which the seal 7406 resides. This difference in dimension allows the seal 7406 to travel along the longitudinal extent of saddle 7426 when shaped, as shown, as an annulus having a substantially circular cross-section. In particular, this traveling feature of the seal 7406 takes place when the outer tube 7302 is translated with respect to the inner tube 7402. Even more specifically, the seal 7406 is dimensioned, i.e., has an annular height, to bridge a gap between an inner surface of the outer tube 7302 and the saddle 7426 of the inner tube 7402 as shown in FIGS. 75 and 77. By filling this gap completely, the seal 7406 at the distal end 7306 of the waveguide assembly 304 prevents intrusion of moisture or other contaminants within the region between the outer tube 7302 and the inner tube 7402. Nonetheless, as the outer tube 7302 is translated, the tight fit between the outer tube 7302, the inner tube 7402, and the seal 7406 causes the seal 7406 to translate (e.g., roll or slide) within the saddle 7426 while, at all times maintaining a water-tight seal between the outer tube 7302 and the inner tube 7402. This translation T is illustrated, for example, with the thick arrows in FIG. 77.

Figure 81:
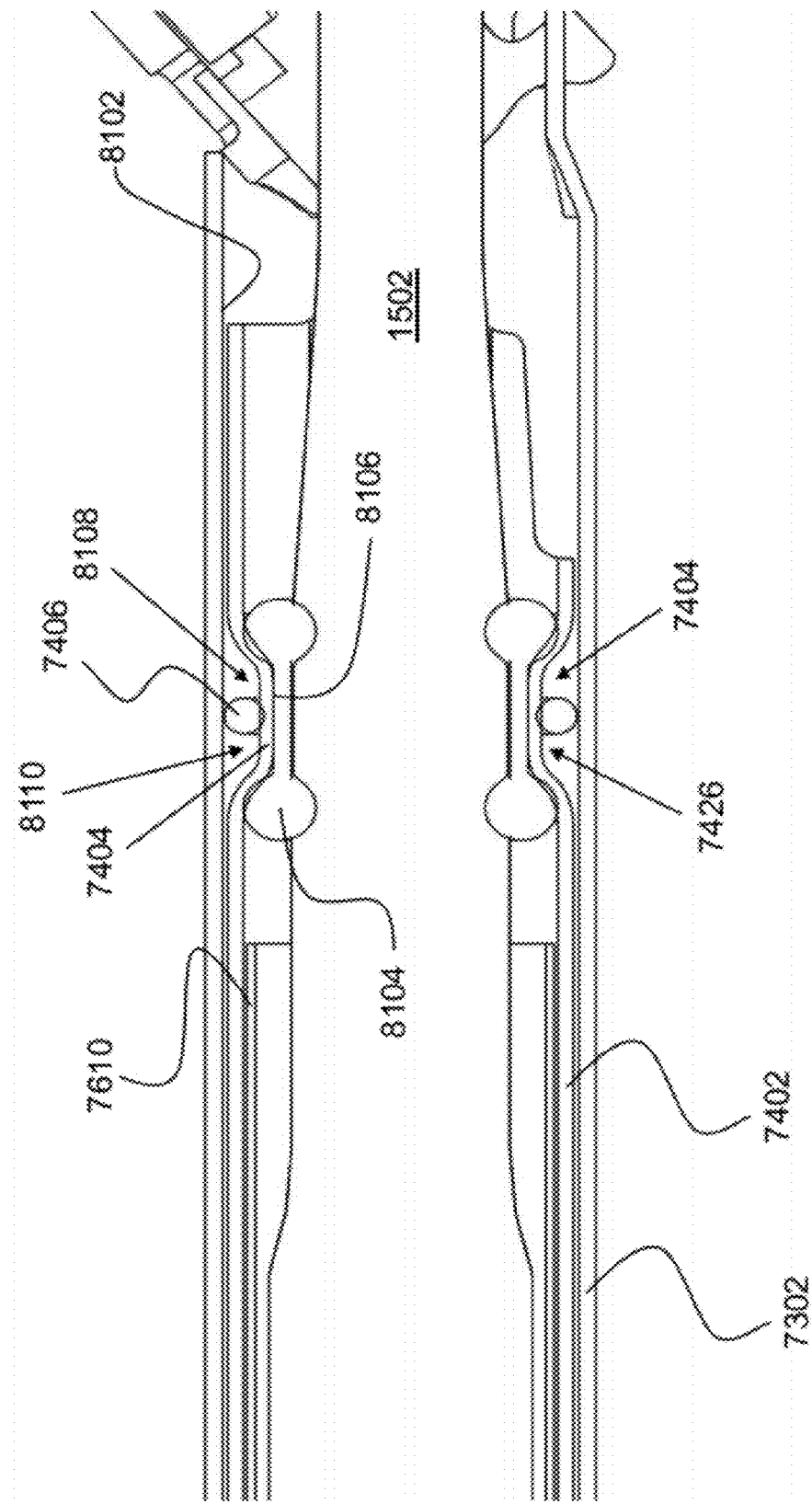
FIG. 81 is a fragmentary, enlarged cross-sectional side view of the end effector of FIG. 73 with the section taken in the jaw-operating plane.

Referring now to FIG. 81, the distal end of the waveguide assembly 304 at the saddle 7426 is shown in cross-section. This view shows the outer tube 7302 surrounding the inner tube 7402 and the seal 7406 disposed therebetween in the saddle 7426 of the corset 7404. As explained, the deformable seal 7406 is a water-tight connection between the inner wall 8102 of the outer tube 7302 and the outer surface of the saddle 7426 to prevent moisture or other contaminants from passing from a distal side 8108 of the seal 7406 to a proximal side 8110 of the seal 7406. FIG. 81 also shows a cross-section a coupling or sealing spool 8104. The coupling spool 8104 encircles a distal portion of the waveguide 1502 and is disposed at substantially the same longitudinal location as the corset 7404. As stated above, the corset 7404 is located at or substantially near an ultrasonic-movement node of the waveguide 1502. Therefore, the coupling spool 8104 is also located at or substantially near that node of the waveguide 1502 and, likewise, does not couple with the waveguide 1502 to receive ultrasonic movement. The coupling spool 8104 provides a support structure that physically links the waveguide 1502 to an inside surface 8106 of the corset 7404. In the cross-sectional view of FIG. 81, the coupling spool 8104 has a barbell-shaped longitudinal cross-section. This reduced cross-section of elastomeric material reduces the amount of deflection of the waveguide 1502 when the jaw 7308 is clamping tissue against the waveguide 1502. The relatively thick cross-section of the barbell ends of the seal 8104 maintains a water tight seal when the middle section of the waveguide 1502 deflects during clamping. A non-metallic material such as, but not limited to, Ultem, PTFE, Rulon, and Graphite filled materials may be used as the rigid coupling spool 8104. The coupling spool 8104 being rigid limits the amount of waveguide 1502 deflection with respect to the jaw 7308 while still providing a non-metallic waveguide support and seal. It is important to design an interference to account for the deflection of the waveguide 1502 under such clamping forces. Deflection of the waveguide 1502 is a combination of bending and compression of the distal seal (7404, 7406). Even though the distal seal configuration minimizes a thickness of elastomeric support, deflection of the waveguide 1502 still can be substantial. If an initial contact between the waveguide 1502 and the jaw liner 7314 was parallel, the waveguide 1502 would deflect and a gap would open at the root of the jaw 7308. Therefore, the clamping assembly configures the initial contact to apply force at the root of the jaw 7308 and to later be parallel with the waveguide 1502 when the full clamping force is applied. With the aforementioned rigid material in the coupling spool 8104, the deflection and variation in parallelism is minimized. Also present in FIG. 81 is an inner sleeve 7610, which encircles the waveguide 1502. As set forth below in detail, the sleeve 7610 assists in preventing metal-to-metal contact between the waveguide 1502 and the inner tube 7402.

Figure 82:
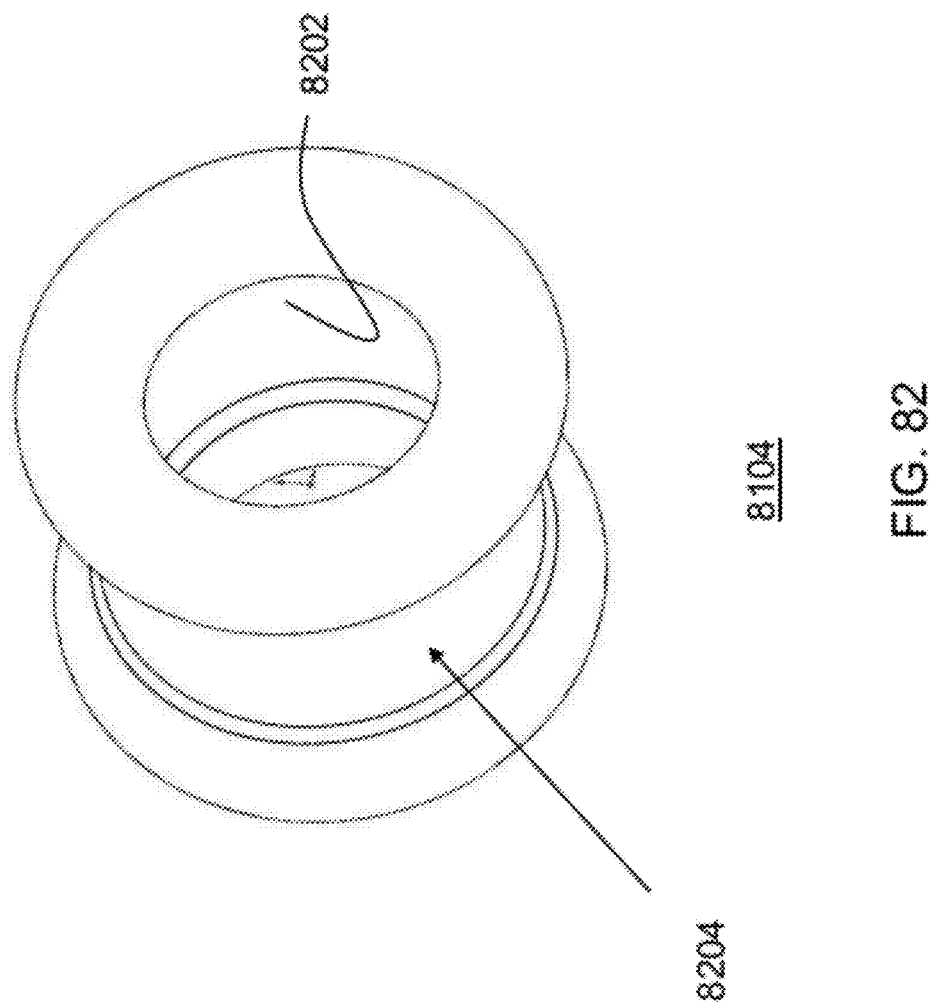
FIG. 82 is an enlarged perspective view of a coupling spool of the end effector of FIG. 73.
Figure 83:
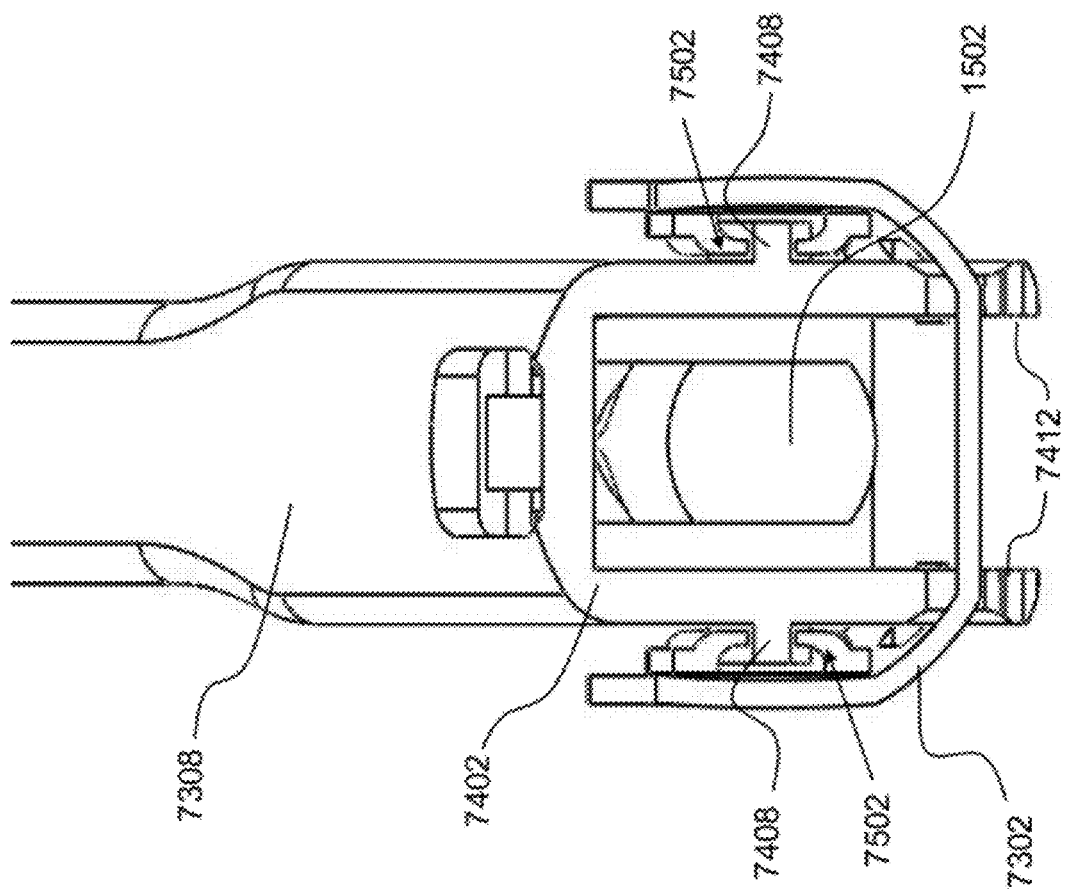
FIG. 83 is a fragmentary, enlarged, cross-sectional view of the end effector of FIG. 73 with the section taken orthogonal to the longitudinal axis of the waveguide at a jaw pivot.

FIG. 82 provides a perspective view of an embodiment of the coupling spool 8104. In this view, an interior surface 8202 of the coupling spool 8104 can be seen. This interior surface 8202 is in direct physical contact with the waveguide 1502 when the waveguide assembly 304 is assembled, as shown in FIG. 81, for example. The perspective view of FIG. 82 also reveals an exterior saddle shape 8204 of the coupling spool 8104 that substantially corresponds to the interior shape of the saddle 7426, which is illustrated in FIG. 81 too.

Figure 100:
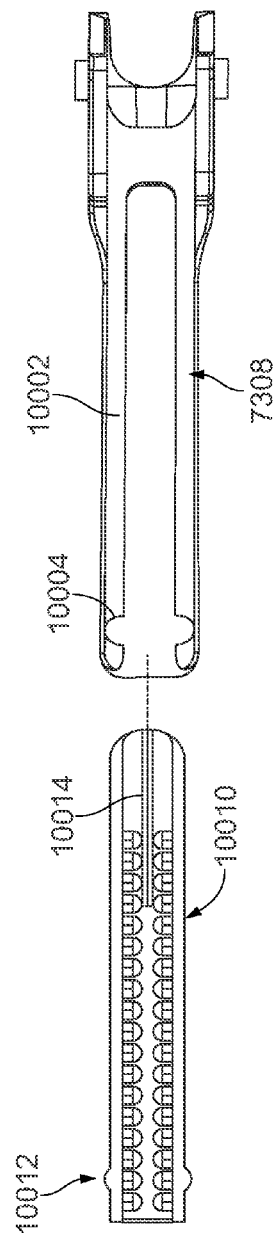
FIG. 100 is an exploded, bottom perspective view of an alternative exemplary embodiment of a jaw and liner according to the invention.

To help capture and retain tissue between the jaw member 7308 and the waveguide 1502, the jaw member 7308 includes a liner 7314 having a plurality of teeth 7316. This liner 7314 provides the jaw member 7308 with an increased ability to grip the tissue. This liner can be made of multiple non-metallic, high-temperature, lubricious materials such as, but not limited to, VESPEL®, RULON®, Modified PTFE, and glass filled and graphite filled versions of these. An exemplary embodiment of the liner 7314 is shown in the perspective views of FIG. 84 (from a distal-most end of the liner 7314) and FIG. 85 (from a proximal-most end of the liner 7314). In addition to the plurality of teeth 7316, the liner 7314 includes a distal-most surface 8402, a central smooth channel 8404 located between first 7316*a* and second 7316*b* longitudinal rows of the plurality of teeth 7316 on a lower surface 8403, a flat proximal clamping surface 8405, and an upper flange 8406 for securing the liner 7314 to the jaw member 7308. This central smooth channel 8404 may also contain a groove 10014 that originates from the proximal end and runs distally as shown, for example, in FIG. 100. This groove acts as an alignment feature between the liner 7314 and the waveguide 1502, which aids in evening the effect upon tissue while using the device. The distal-most surface 8402 is, as can be seen in FIG. 73, an exposed blunt front surface of the distal end of the waveguide assembly 304. FIG. 73 illustrates a channel 7318 of the jaw member 7308 in which the liner 7314 is disposed when assembled. The inner surfaces of the channel 7318 substantially correspond to the outer surfaces of the upper flange 8406 so that the liner 7314 may be retained in the jaw member 7308 in a substantially movement-free manner. In the exemplary embodiment of the channel 7318 illustrated, the distal end of the channel 7318 is narrower than the intermediate portion so that the liner 7314 may slide from a proximal end of the jaw member 7308 up to but not past the distal end of the channel 7318. Also shown in the exemplary embodiment of FIG. 85 is a retaining tab 8502 that, when the liner 7314 is placed in the jaw 7308 all the way distally, can be bent downward (towards the liner 7314) and below the top plane of the liner 7314. In such a bent configuration, the distal end of the retaining tab 8502 will oppose, and possibly rest against, the rear surface 8504 of the liner 7314 and/or flange 8406. With such an opposition, the liner 7314 is prevented from exiting the jaw 7308. This single retaining tab could be replaced with two smaller tabs on either side of the channel 7318 that are bent downwards below the top plane of liner 7314. Alternatively, the jaw liner 7314 can be made to be loaded from a distal end of the jaw 7308 with features that capture and retain the liner 7314 through a single surgical procedure. An exemplary embodiment of such a configuration is shown in FIG. 100. More specifically, the jaw 7308 is formed with a distal-entry passage or channel 10002 in which the distal-loading liner 10010 is loaded. To secure the liner 10010 in the channel 10002, the channel can define orifices 10004 that are shaped to catch and removably hold therein detents 10012 of the liner 10010. These opposing features can be reversed or changed in any equivalent way that removably secures the liner 10010 in the jaw 7308. Easy replacement of the liner 10010 allows for potential reprocessing of the handle and/or waveguide assembly with an easy change of this high-wear part for potential reprocessing of the device.

Figure 84:
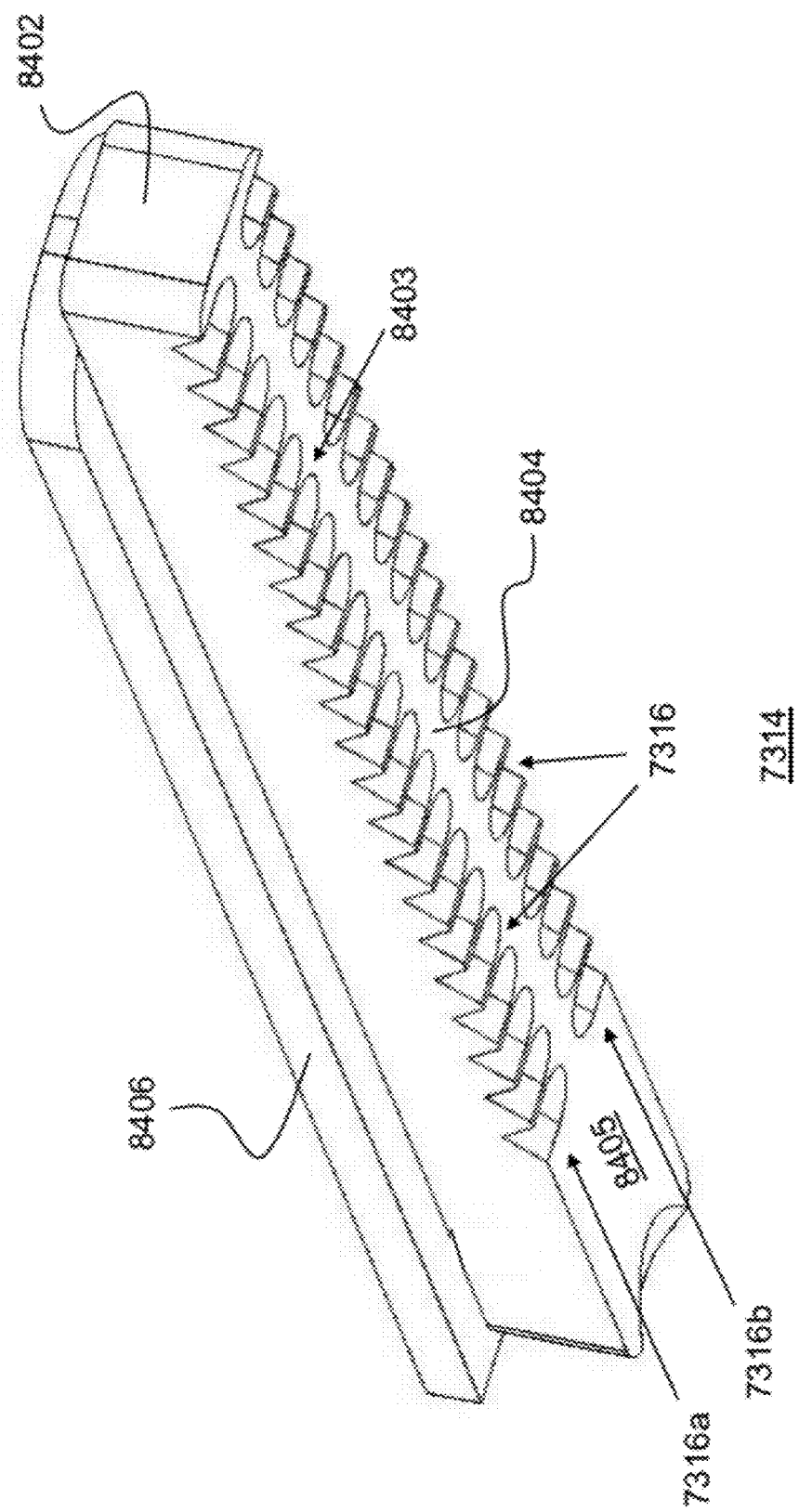
FIG. 84 is an enlarged, perspective view of a jaw liner of the end effector of FIG. 73 viewed from below a distal end.
Figure 85:
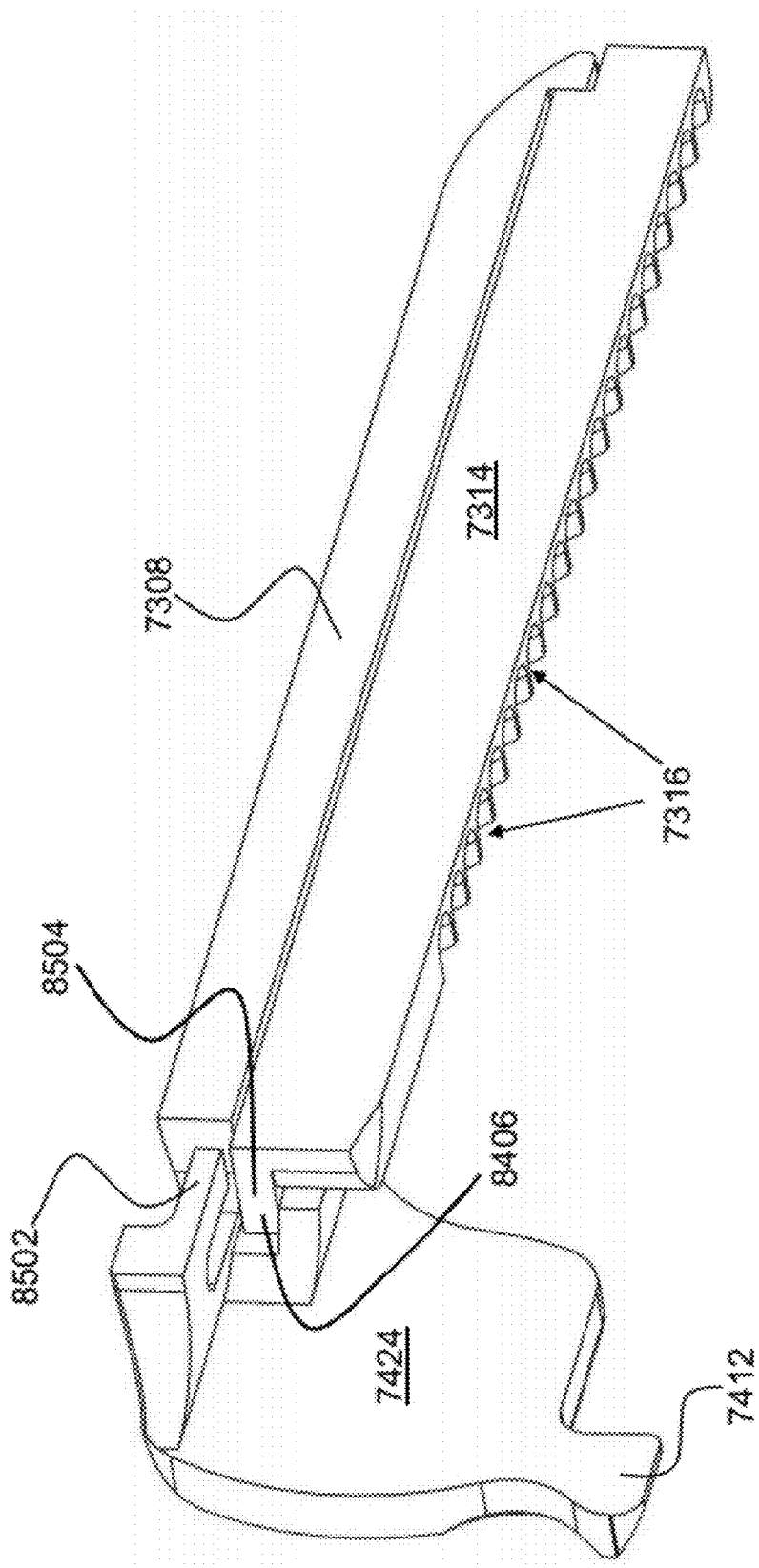
FIG. 85 is an enlarged, cross-sectional and perspective view of a left portion of the jaw liner of FIG. 84 seated within a left portion of the jaw of FIG. 73 viewed from below a proximal end.

The offset between the proximal-most surface 8402 and the flange 8406, shown in FIG. 84, facilitates the placement of proximal-most surface 8402 at the distal most portion of the jaw member 7308. That is, the liner 7314 slides within the jaw member 7308 until it is fully seated within the jaw member 7308. It is, however, the flange 8406 that is physically secured by the jaw member 7308. More specifically, as is shown in FIGS. 84 and 85, the flange 8406 extends beyond the plurality of teeth 7316 on both sides thereof. However, the flange 8406 does not extend all the way to the proximal-most surface 8402. When the liner 7314 is slid inside the jaw member 7308, the extending side portions of the flange 8402 travel within the channel 7318 formed in the jaw member 7308. Because the flange 8406 does not extend all the way to the proximal-most surface 8402, when the flange 8406 reaches the end of the channel 7318, the proximal-most surface 8402 of the liner 7314 will extend beyond the channel 7318 up to the position shown in FIG. 73.

Focusing now on the exemplary embodiment of the teeth 7316, it can be seen in FIGS. 84 and 85 that the teeth 7316 do not extend completely across the lower surface 8408 of the liner 7314. Instead, in the embodiment of FIGS. 84 and 85, a first row of teeth 7316a and a second row of teeth 7316b, which oppose the first row of teeth 7316a, are separated by a central smooth channel 8404. The central smooth channel 8404 provides a solid smooth surface that lines up directly over the waveguide 1502. It is this smooth surface 8404 that comes into contact with the ultrasonically-moving waveguide 1502 during a procedure and helps seal the tissue by facilitating continued, non-impeded, ultrasonic movement of the waveguide 1502 with even pressure along its length. Due to the fact that the liner 7314 runs the full length of the jaw 7308 (from the root to the tip), contact over the entire length of the treatment portion (i.e., the blade portion 7304) of the waveguide 1502 is made with even pressure.

Moving now to FIG. 86, a fragmentary perspective view of an interior of the handle portion 302 is illustrated. This view shows a proximal-most end 8601 of the waveguide 1502, which features a set of threads 8604 used to couple the waveguide 1502 to the TAG assembly 303. As described above, the illustrated location of the proximal-most end 8601 of the waveguide 1502 within the handle portion 302 is substantially the location where the waveguide assembly 304 remains when it is coupled to the TAG assembly 303. When the TAG assembly 303 is inserted into the handle portion 302, see, for example FIG. 45, the transducer horn 5002 aligns with and thereby allows a secure longitudinal coupling of the threads 8604 and the ultrasonic waveguide couple 5004.

The waveguide 1502 is surrounded by the inner tube 7402 and, then, the outer tube 7302. This view of the proximal-most end 8606 of the outer tube 7302 shows that the outer tube 7302 terminates at its proximal-most end 8606 with a flared section 8608. The flared section 8608 features a pair of channels 8610 and 8612 (8612 not fully shown in this view) forming a keyway. These channels are shown as opposing but need not be in this configuration. Residing within the channels 8610, 8612 is a torque adapter 8602 that is fixedly coupled to the waveguide 1502. The coupling of the torque adapter 8602 and the waveguide 1502 will be shown in more detail in the following figure, FIG. 87. Continuing with FIG. 86, it can be seen that the torque adapter 8602 is provided with a boss 8616 that extends out through the channel 8610. Although not shown in this view, the torque adapter 8602 is also provided with a second boss that extends likewise within the second opposing channel 8612. Engagement between the bosses 8616 of the torque adapter 8602 and the channels 8610, 8612 of the flared section 8608 provides a rotational-locking relationship between the waveguide 1502, the inner 7402, and the outer tube 7302. That is, because the bosses engage the channels 8610, 8612, any rotation of the waveguide 1502 is shared by both the inner tube 7402 and the outer tube 7302. The proximal end of the inner tube 7402 does not extend past the torque adapter 8602. The rotational connection between the torque adapter 8602 and the inner tube 7402 occurs through an internal feature of the waveguide rotation spindle 3704.

Focusing now on FIG. 87, a perspective view of an interior of the handle portion 302 is once again illustrated. In this view, however, the outer tube 7302 has been removed (along with a right half of the waveguide rotation spindle 3704). The removed outer tube 7302 exposes a majority of the torque adapter 8602. Although not viewable in either FIG. 86 or FIG. 87, the torque adapter 8602 is, in one exemplary embodiment of the present invention, symmetrical with a second boss extending in a direction substantially directly opposite the first boss 8616. The reason why the torque adapter 8602 is so-named is because it provides the structures for resisting rotational movement when the torque wrench 8800 is used to connect the waveguide coupler 5004 of the transducer horn 5002 to the waveguide 1502. As described above, rotation of the waveguide 1502 needs to be prevented as the torque wrench 8800 is used to rotate the spindle 3704 of the transducer 902.

To get an adequate holding force, the waveguide 1502 needs to be rotationally keyed. But, any rotationally keyed waveguide feature suffers from same drawbacks as other supports along the waveguide 1502 in that vibration is transmitted if the keyed feature is not located on a node of the waveguide 1502. As shown in FIGS. 86 and 87, for example, the keyed feature for torque transmission is located at the most proximal node, i.e., the node furthest from the blade and closest to the threads. The torque transmission feature of an exemplary embodiment of the invention is a plurality of splines or teeth 8702 in a radial pattern symmetrically disposed about the waveguide 1502. Each spline 8702 extends away radially from a central longitudinal axis 8706 of the waveguide 1502.

The torque adapter 8602 is provided with a plurality of interior keyways 8704, each keyway 8704 aligning with one of the extensions of the spline 8702 and having a shape substantially corresponding to a respective one of the splines 8702 so that, when connected as shown, the torque adapter 8602 securely rests at its shown longitudinal position on the waveguide 1502. This longitudinal position on the waveguide 1502, too, is located at an ultrasonic vibration node where movement is minimal/non-existent. This aligning and securing engagement between the keyways 8704 and the splines 8702 places the keyways 8704 and the splines 8702 in a fixed rotational relationship. In other words, as the waveguide 1502 rotates, so too must the torque adapter 8602.

The splines 8702 each protrude beyond average diameter of the waveguide 1502. The splines 8702 can be rectangular columns but they are not limited thereto; they can have angled faces. One exemplary embodiment of the splines 8702 has an overall shape of a frusto-rectangular pyramid but with the two side edges of the top plane being sloped and the distal and proximal edges of the top plane being square. The maximum spline outer diameter can be kept within the largest diameter of the waveguide material to allow for use of stock material having the lowest cost. The torque transmission splines 8702 on the waveguide 1502 are mated to the torque adapter 8602 with correspondingly shaped female keyways 8704. Assembly of the torque adapter 8602 occurs by pressing it onto the waveguide and finally to be constrained concentrically by the torque transmission faces of the splines 8702 and longitudinally by providing the keyways 8704 as blind holes, here on the non-illustrated end of the torque adapter of FIG. 87. To rotationally align the torque adapter 8602 with respect to the waveguide 1502 and always place the bosses 8616 inside a pocket 9504 of the spindle 3704 (see, e.g., FIG. 95), in an exemplary embodiment, some of the splines 8702 are removed selectively to permit only one correct component orientation (that can be symmetric but keyed to only be at 0 or 180 degrees). As such, when connecting the transducer 902 to the waveguide 1502, the spindle 3704 is grounded (e.g., by the user's hand) torque is generated on the spinner 3704 by the torque wrench 8800. The bosses 8616 are loaded and transmit the torque to the threads 8604 of the waveguide 1502. Overall geometry and mass of the torque adapter 8602 are tuned to reduce acoustic coupling from the waveguide 1502 through the torque adapter 8602 to the spindle 3704. The materials of the spindle 3704 and the torque adapter 8602 are selected to be different to further isolate any acoustic energy coupling. For example, a high-temperature, glass-filled polymer Radel (20% glass filled polyphenylsulfone PPSU) can be used for best acoustic energy impedance while still providing strength for torque transmission. A polymer filled with low friction materials such as Nylon or PTFE (Polytetrafluoroethylene) is also advantageous when minimizing acoustic transmission. In addition, an elastomeric material can also be insert molded into the spindle 3704 at the torque transmission face to further isolate acoustic energy.

Referring back now to FIG. 66, it can now be seen that the channels 8610, 8612 of the flared section 8608 of the outer tube 7302 are the features that also engage the rotation-prevention wheel 6502. Due to this engagement, any rotation imparted on the waveguide rotation spindle 3704 by the user will result in a direct and corresponding rotation of the rotation-prevention wheel 6502, the outer tube 7302, the inner tube 7402, the torque adapter 8602, and the waveguide 1502. The following is a result of this connection configuration: when the rotational lockout number 6508 is engaged with the rotation-prevention wheel 6502, not only is the rotation-prevention wheel 6502 prevented from rotating, so too is the entire waveguide assembly 304, 3704, 7302, 7402, 8602, 1502. In the same sense, when the rotation-prevention wheel 6502 is not engaged with the rotational lockout number 6508, a user can freely rotate the spindle 3704, which is physically coupled to the rotation-prevention wheel 6502, and cause a rotation of the waveguide assembly 304 along a longitudinal axis 8706.

Figure 95:
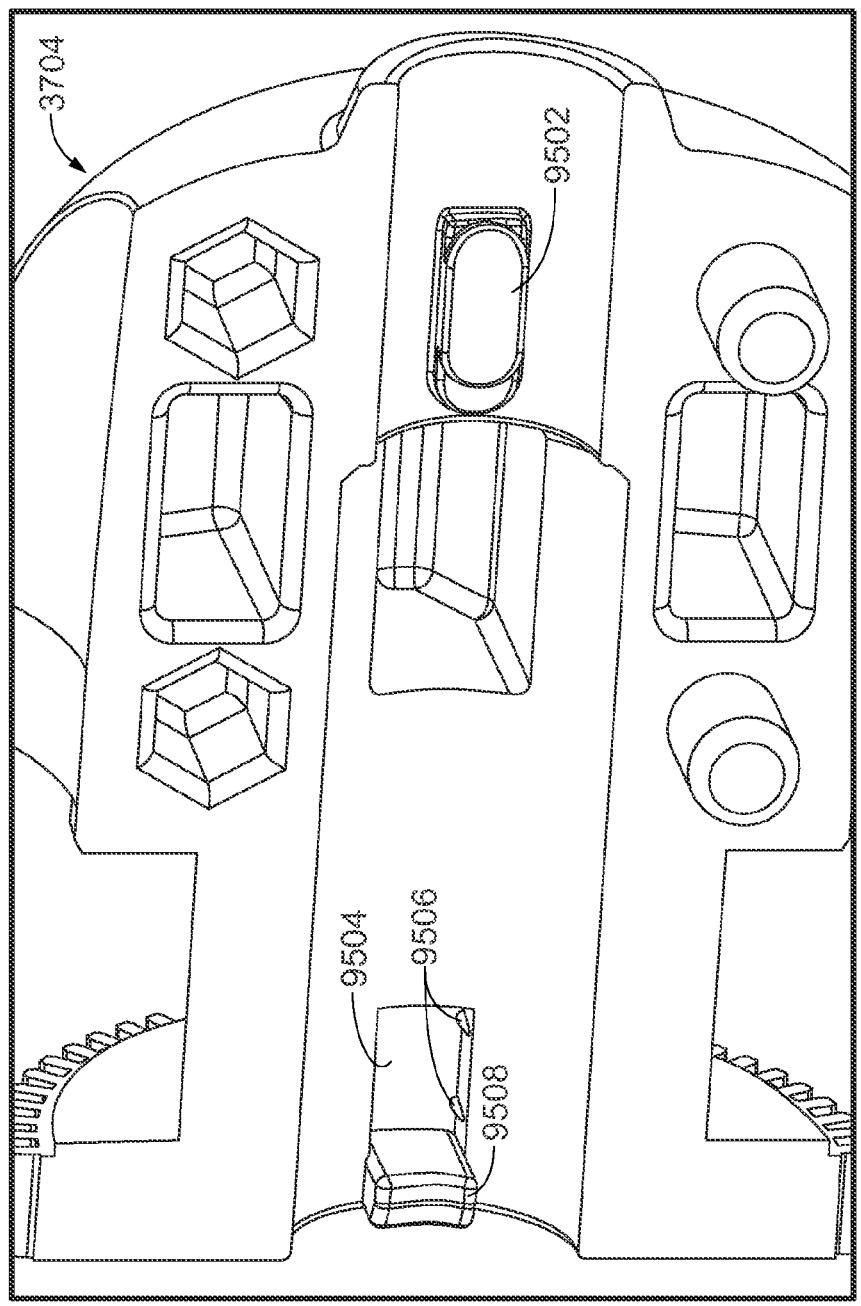
FIG. 95 is a perspective side view of half of a spindle assembly according to an exemplary embodiment of the invention.
Figure 99:
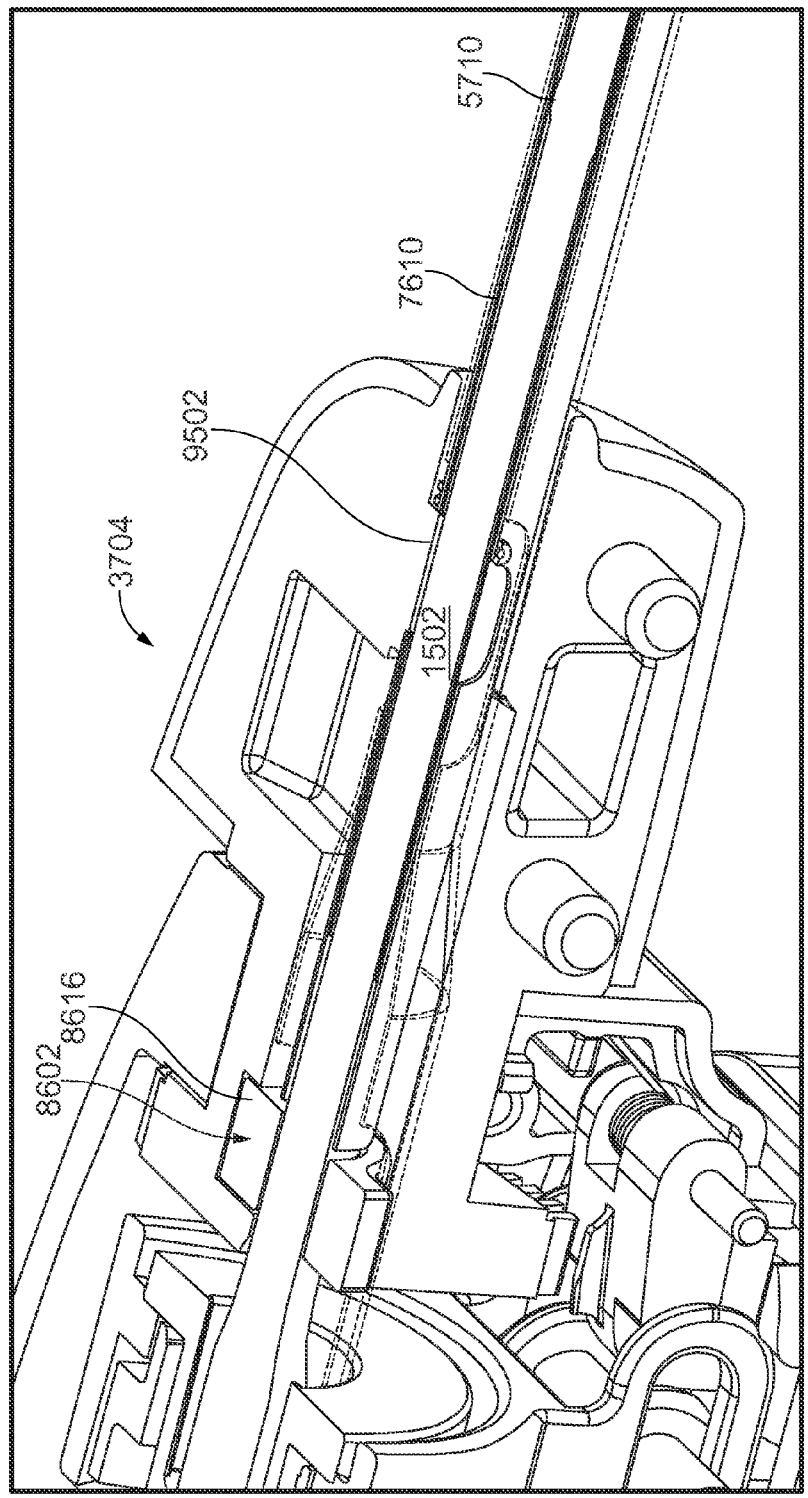
FIG. 99 is a fragmentary, horizontal cross-sectional view of a proximal portion of the waveguide assembly and a distal portion of the handle according to an exemplary embodiment of the invention.
Figure 101:
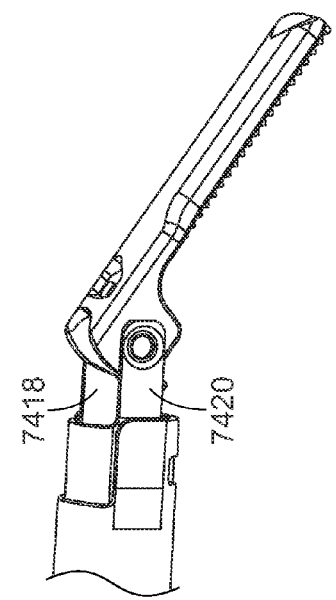
FIG. 101 is a fragmentary, exploded perspective view of the jaw assembly according to the invention in a first installation step.
Figure 102:
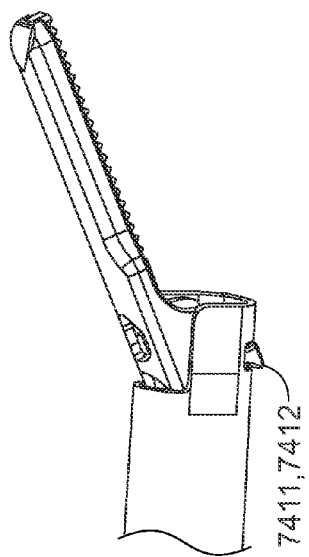
FIG. 102 is a fragmentary, exploded perspective view of the jaw assembly according to the invention in a second installation step.

As shown in FIG. 95, the spindle 3704 has oval bosses 9502 on its interior. These bosses 9502 engage both the inner 7402 and outer 7302 tubes, which locks the tubes 7302, 7402 together rotationally while allowing only the inner tube 7402 to have longitudinal displacement. The area in which the bosses 9502 lock the tubes 7302, 7402 is shown well in FIG. 93. Looking at both of FIGS. 93 and 95 together, it can be seen that the protrusion of the boss 9502 is configured to enter the opening of the inner tube 7402 but not pass therethrough (to possibly contact the inner sleeve 7610 or to press the sleeve 7610 into the waveguide 1502). At the same time, the bosses 9502 are shaped to have a longitudinal length sufficient to prevent longitudinal displacement of the inner tube 7402 but to permit longitudinal translation (proximal-distal) of the outer tube 7302 for moving the jaw 7308. This complex locking feature, in conjunction with a pocket 9504 on a proximal end of the spindle 3704 that engages the torque adapter 8602, locks the tubes 7302, 7402 and the waveguide 1502 with respect to one another. In the exemplary embodiment, the torque adapter pocket 9504 has crush-features 9506 that force the torque adapter 8602 to center during assembly. Also in the pocket 9504 is a boss 9508 that traps the waveguide 1502 and prevents it from pulling out proximally. Assembly of the spindle 3704, therefore, occurs by pressing two hermaphroditic spindle halves together. Once pressed together, it is desirable to have minimum friction between the mating rotational faces: the exterior of the intermediate annular groove 4610 of the waveguide rotation spindle 3704 and the annular boss 4605 of the handle halves 4503, 4603. As shown in FIGS. 95 and 99, the mating rotational faces have a minimized contact area by chamfering the outer edges of the groove 4610 to set back the castellations on the proximal size and the finger grooves on the distal side of the spindle 3704 and by raising those contacting surfaces in the center of the groove 4610. Likewise, the outer faces of the boss 4605 are raised at the center portions thereof.

Figure 89:
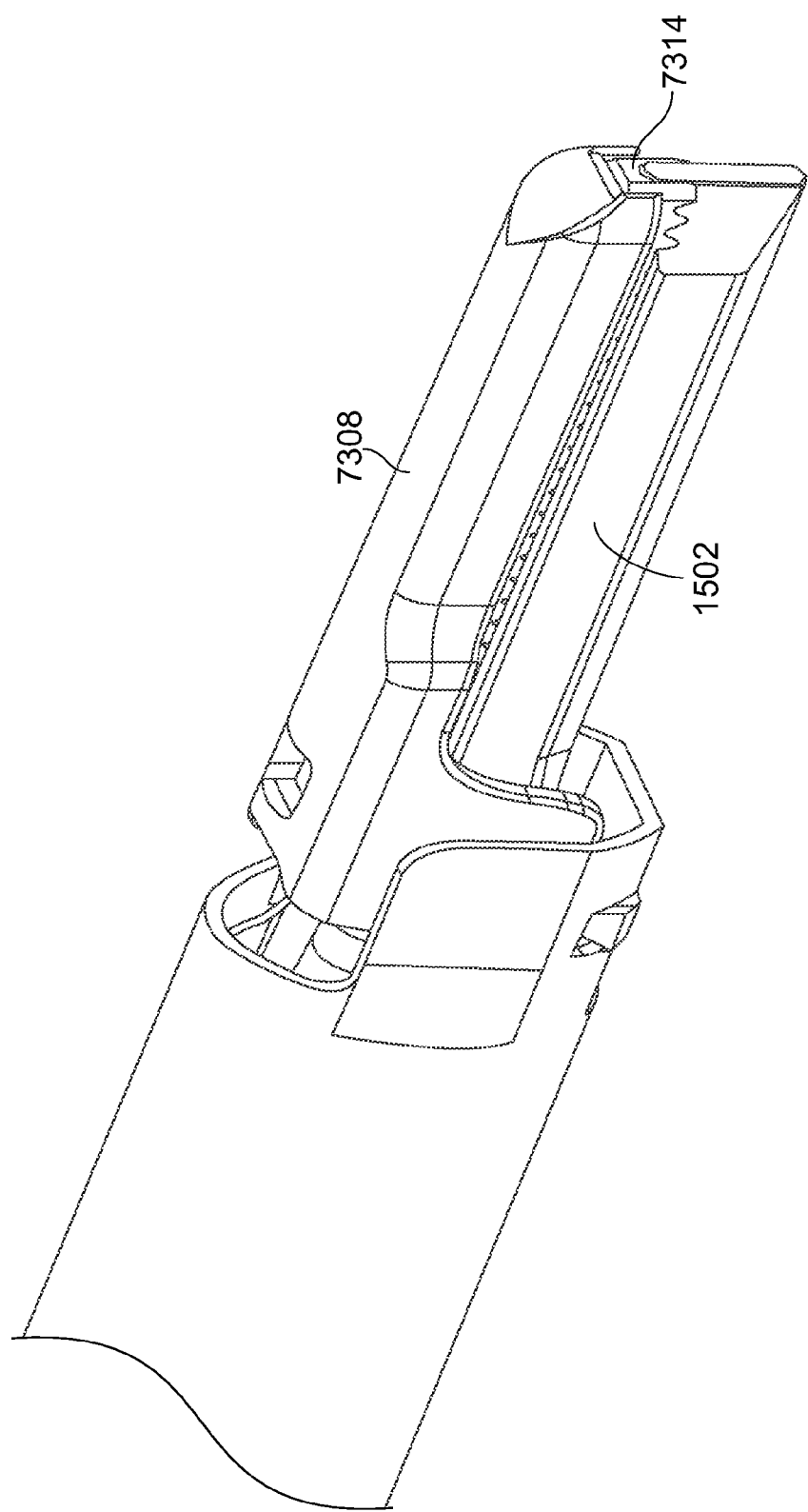
FIG. 89 is a fragmentary, enlarged, perspective view of the end effector of FIG. 73 with the jaw in a closed position with liner wear.

As can be seen from FIGS. 73, 74, and 78, and especially FIG. 84, the lower surface 8403, including the proximal clamping surface 8405, is flat and parallel to the upper surface of the blade portion 7304 of the waveguide 1502. This means that, when the jaw 7308 is clamped shut without any interposing material, the clamping surface 8405 will contact the blade portion 7304 at its proximal end first, as shown in FIGS. 79 and 80. As such, when the waveguide 1502 is ultrasonically actuated, it is possible for the blade portion 7304 to cut into the liner 7314 at least to a point the two parts are parallel as shown in FIG. 89. In the exemplary configuration of the jaw control device, however, it is possible for the jaw 7308 to pivot past parallel with respect to the waveguide 1502. Therefore, it is possible for the blade portion 7304 to cut entirely through the liner 7314. In such a case, the metallic blade portion 7304 would be vibrating against the metallic jaw 7308—a condition that is to be avoided as either or both parts will break within a short period of time.

Figure 96:
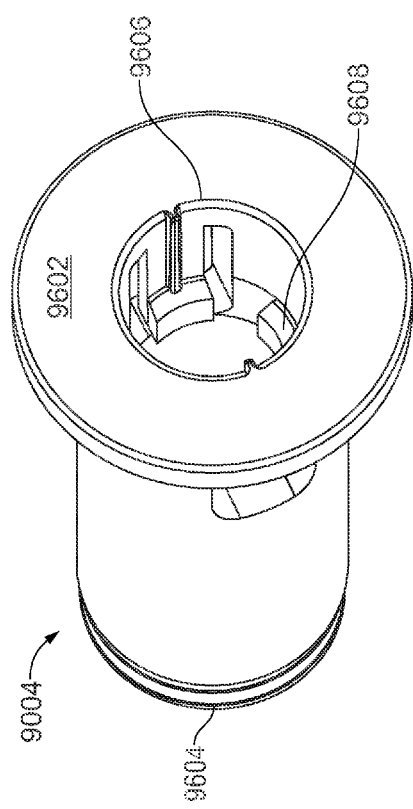
FIG. 96 is a perspective view of a bobbin portion of a waveguide assembly according to an exemplary embodiment of the invention.
Figure 97:
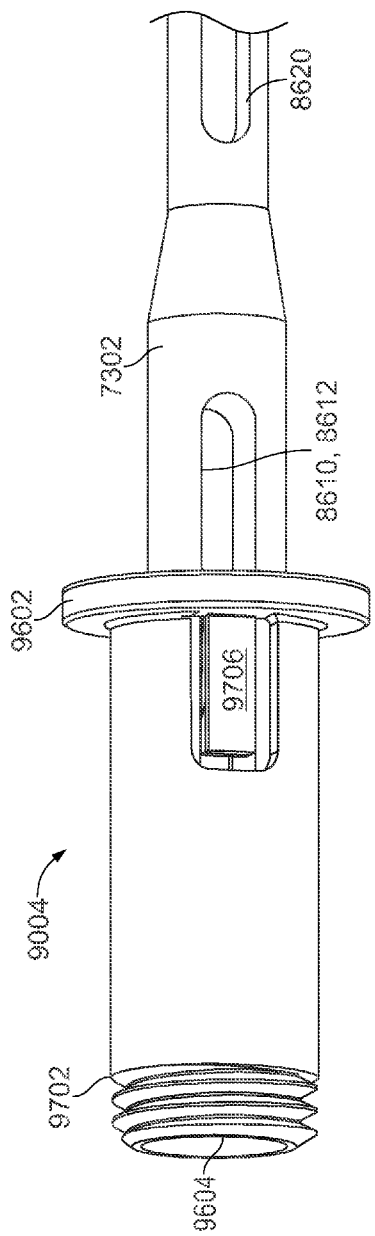
FIG. 97 is a fragmentary, perspective view of the bobbin of FIG. 96 connected to the waveguide.
Figure 98:
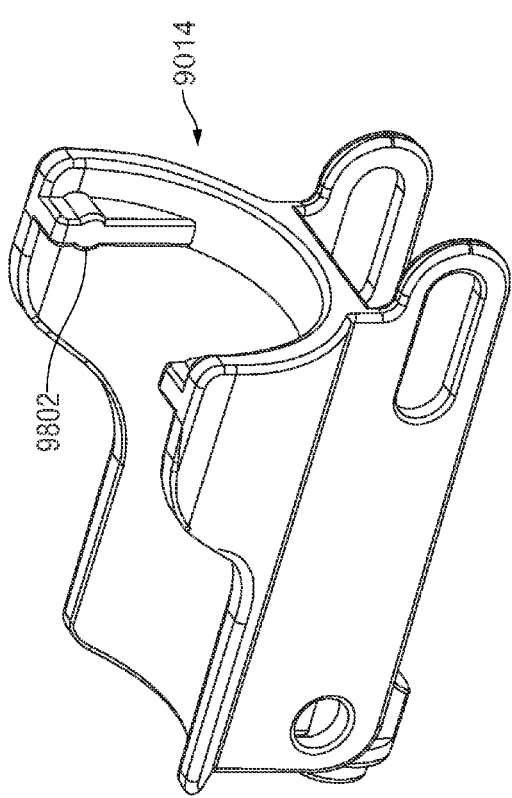
FIG. 98 is a perspective side view of a yoke of a jaw control assembly according to an exemplary embodiment of the invention.

An exemplary embodiment of the inventive system solves this problem by including an overstroke prevention device 9002 and outer tube stop 9012. The overstroke prevention device is comprised of a bobbin 9004, a nut 9006, an overstroke spring 9008, and a distal slider 9010. The bobbin 9004 is longitudinally fixed to the outer tube 7302 and translates along with the outer tube 7302 as the outer tube 7302 is moved with respect to the inner tube 7402 and waveguide 1502, the latter two of which are longitudinally fixed in position with respect to the handle assembly 302 as set forth above. An exemplary embodiment of the attachment mechanism for the bobbin 9004 is shown, for example, in FIG. 86, where two opposing windows 8614, 8618 exist in the proximal end of the outer tube 8608. The bobbin 9004 has a mushroom-shaped head 9602 on its distal end and a threaded portion 9604 on its proximal end for receiving the nut 9006 thereon and is illustrated, for example, in FIGS. 96 and 97. The nut 9006 and the bobbin 9004 are configured to have the nut tightened to a hard stop 9702 that, in conjunction with a consistent spring 9008 yields consistent clamp forces from device to device. The spring 9008 has a low rate so that variations in tissue thickness will still yield similar clamp forces. The low rate has a flatter force profile so, regardless of where the spring is on the profile, the user is as close to the desired force as possible. As illustrated in FIG. 97, the mushroom-shaped head 9602 connects longitudinally to the outer tube 7302, in this example, through two opposing windows. The slider 9010 is able to longitudinally slide upon the outer surface of the main body of the bobbin 9004 between the nut 9006 and the distal head of the bobbin 9004. As such, with the overstroke spring 9008 disposed between the movable slider 9010 and the stationary nut 9006, any movement of the slider 9010 will cause a compression of the spring 9008. As an aside, during assembly of the waveguide 1502 and tubes 7302, 7402, the proximal section of the outer tube 7302 can compress, due to the elongated channel 8610, 8612 that runs out to the proximal end of the outer tube 7302. The compressed proximal end of the outer tube 7302 is able to fit into the distal opening 9606 of the bobbin 9004 and, in so doing, forces apart lockout fingers 9706 (radially outward). Once fully inserted, the outer tube 7302 returns to its normal full diameter. At this point, the fixed bosses 9502 in the bobbin 9004 engage distal windows 8620 in the outer tube 7302. At the same time, two rigid bosses 9608 extending from the interior surface of the bobbin 9004 engage the two opposing windows 8614, 8618 at the proximal end of the outer tube 7302 as the lockout fingers 9706 spring inwards to enter the opposing channels 8610, 8612 at the proximal end of the outer tube 7302. The inward movement of the lockout fingers 9706 prevents further compression of the outer tube 7302, thereby locking the bobbin 9004 onto the outer tube 7302.

Figure 90:
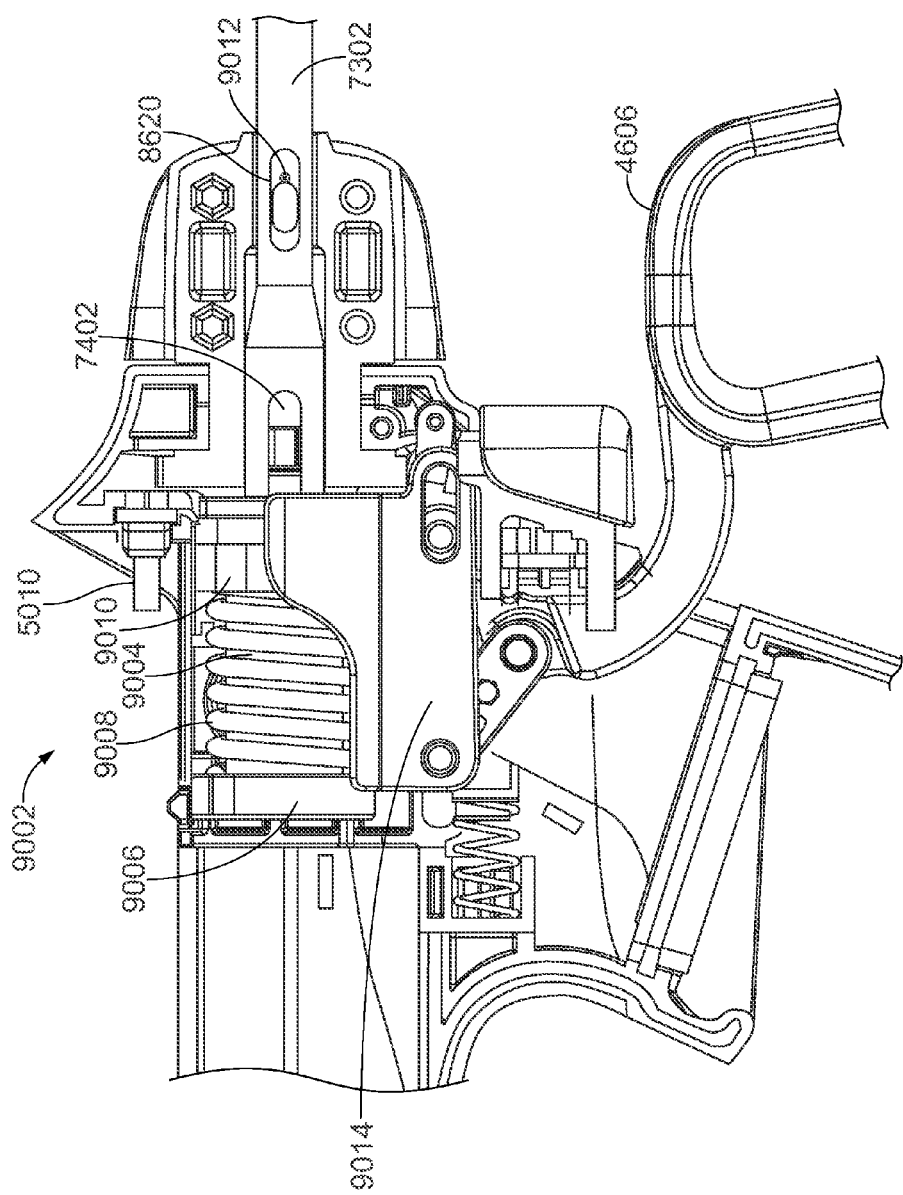
FIG. 90 is an elevational right-hand view of the handle assembly of FIG. 3 with the right shell half removed showing controls in accordance with an exemplary embodiment of the present invention with the trigger in an unactuated state.
Figure 91:
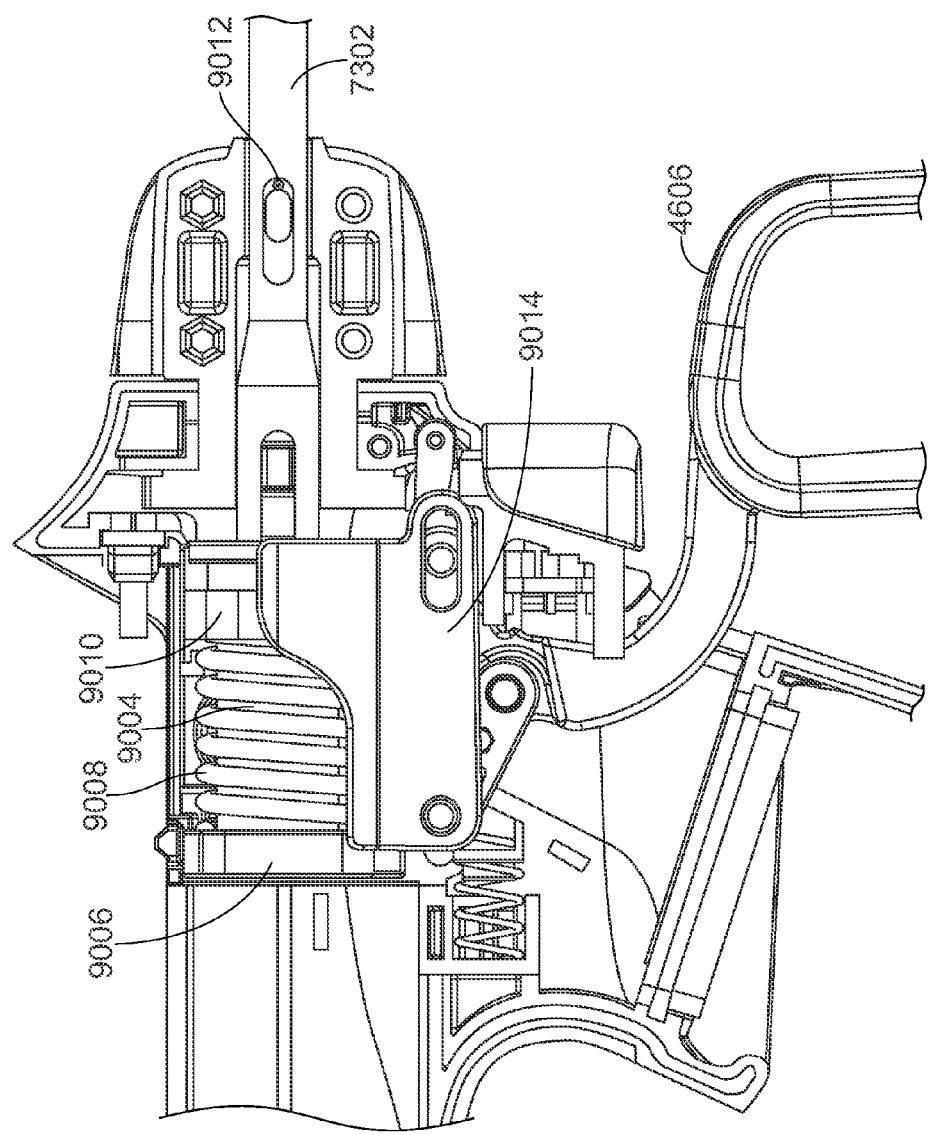
FIG. 91 is an elevational right-hand view of the handle assembly of FIG. 90 with the trigger in a partially actuated state.
Figure 92:
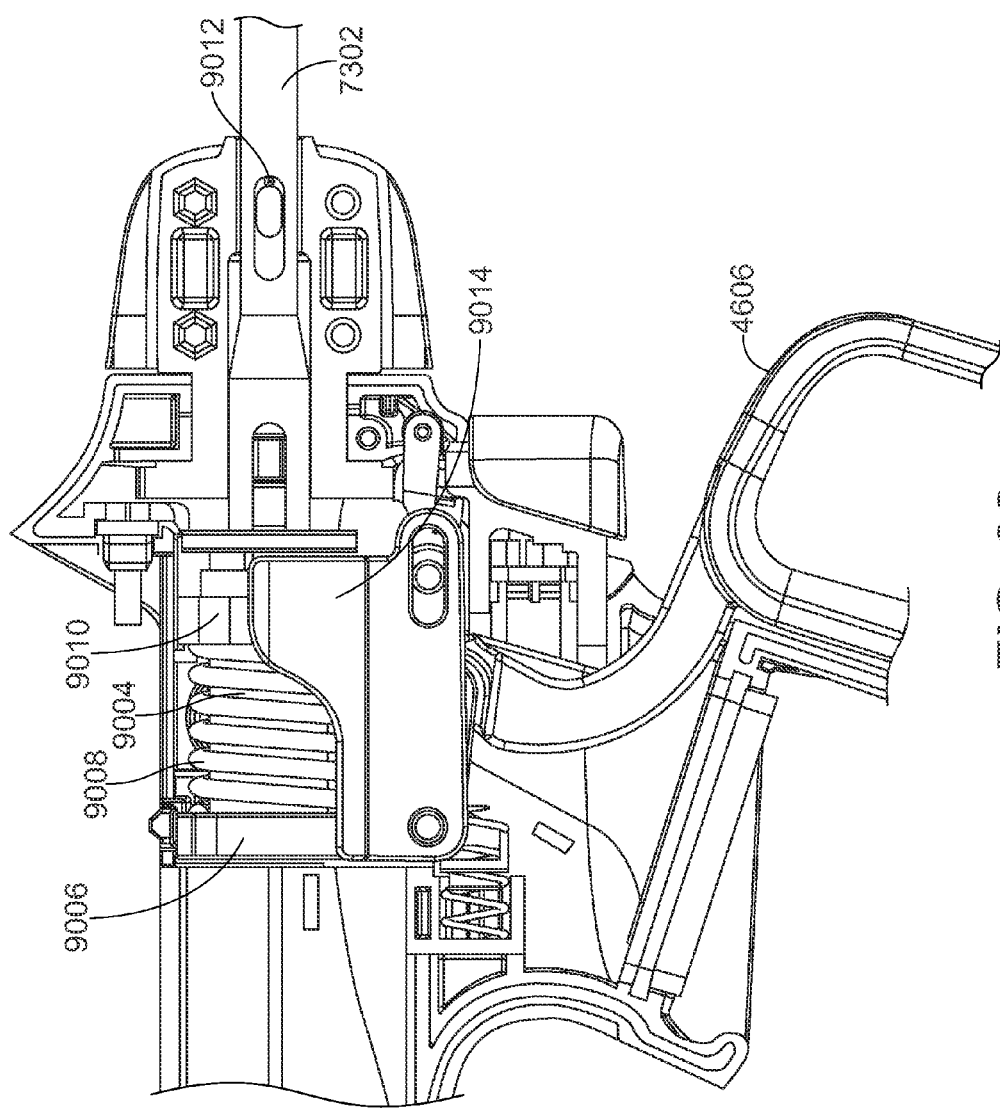
FIG. 92 is an elevational right-hand view of the handle assembly of FIG. 90 with the trigger in a fully actuated state.

A yoke 9014 connects the slider 9010 to the trigger 4606 as shown in FIGS. 90 to 92. The progression of FIGS. 90 to 92 shows how the yoke 9014, the slider 9010, the spring 9008, the bobbin 9004, and the outer tube 7302 move as the trigger 4606 is depressed to close the jaw 7308. The location where the yoke 9014 interfaces with the bobbin 9004 is a rotational interface and, therefore, it is desired to only have minimal friction forces that do not impede rotation of the spindle 3704. Minimizing such friction is achieved by including bumps 9802 on the yoke 9014. These bumps 9802 create a point-contact having a greatly reduced surface area for the bobbin/slider interface. In the trigger state shown in FIG. 90, the trigger 4606 is unactuated and the jaw 7308 is in the open, steady-state position (see, e.g., FIG. 73). In the trigger state shown in FIG. 91, the trigger 4606 is partially actuated and the jaw 7308 is in the closed position shown, e.g., in FIG. 79. In this position, the yoke 9014 has moved the slider 9010 proximally to compress the spring 9008 partially, thereby applying a proximally directed force to the nut 9006. As the nut is fixed longitudinally to the bobbin 9004 and the bobbin 9004 is fixed longitudinally to the outer tube 7302, trigger movement causes closure of the jaw 7308.

Figure 93:
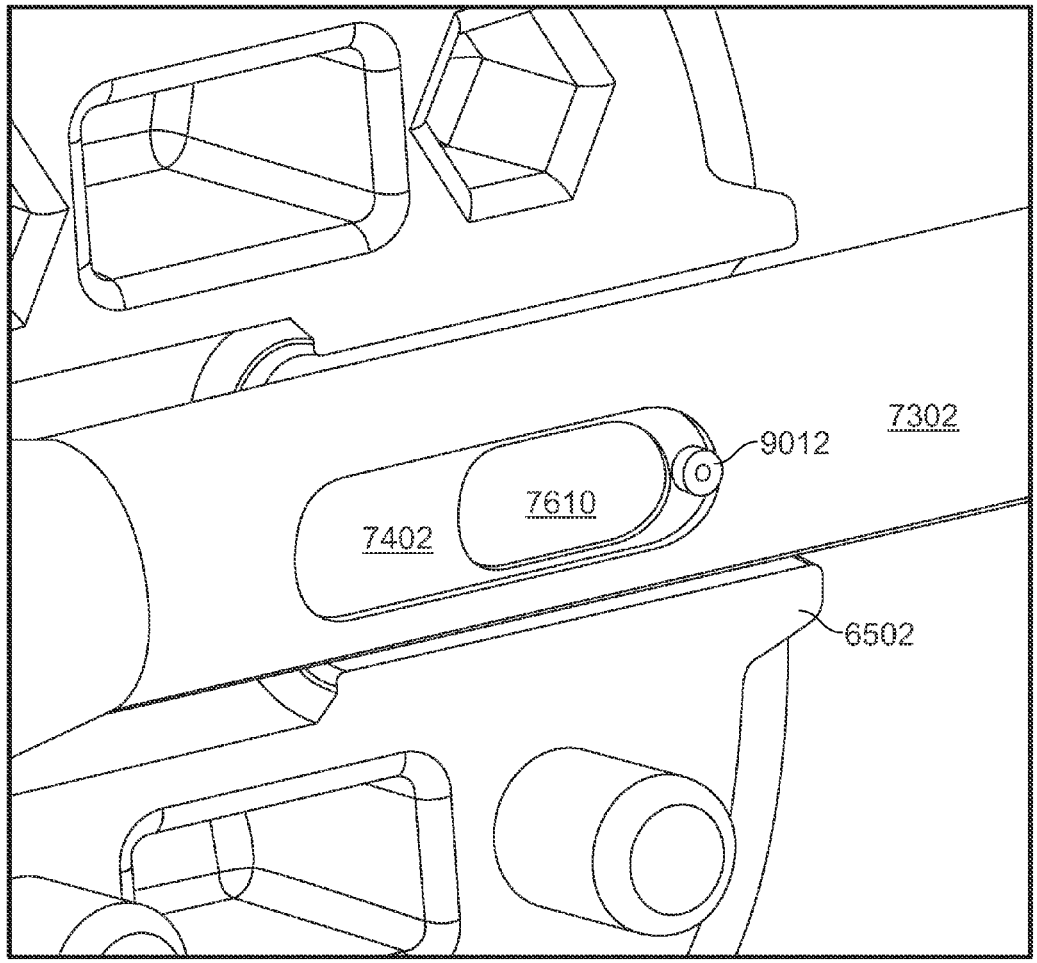
FIG. 93 is a fragmentary, enlarged, perspective view of a tube stop assembly in accordance with an exemplary embodiment of the present invention.

It is at this point that further closing of the jaw 7308 (rotation towards the waveguide) is not desired. To prevent the force from further movement of the outer tube 7302, an outer tube stop 9012 is located on an exterior surface of the inner tube 7402 as best shown in FIG. 93. In such a configuration, any attempt to move the outer tube 7302 further in a proximal direction will require a corresponding movement of the inner tube 7402.

But, the jaw 7308 and the blade portion 7304 are used to cut tissue disposed therebetween. This means that when the jaw 7308 is clamped shut, any load that is transferred into the blade portion 7304 from either tissue clamped by the jaw 7308, or by the liner 7314 itself, will deflect the blade portion 7304 both as a function of compressing the sealing spool 8104 and of bending the cantilevered beam of the blade portion 7304. As the blade portion 7304 is bent, its ultrasonic movement characteristics alter. It is, therefore, desirable to prevent bending of the blade portion 7304 as much as possible.

Figure 94:
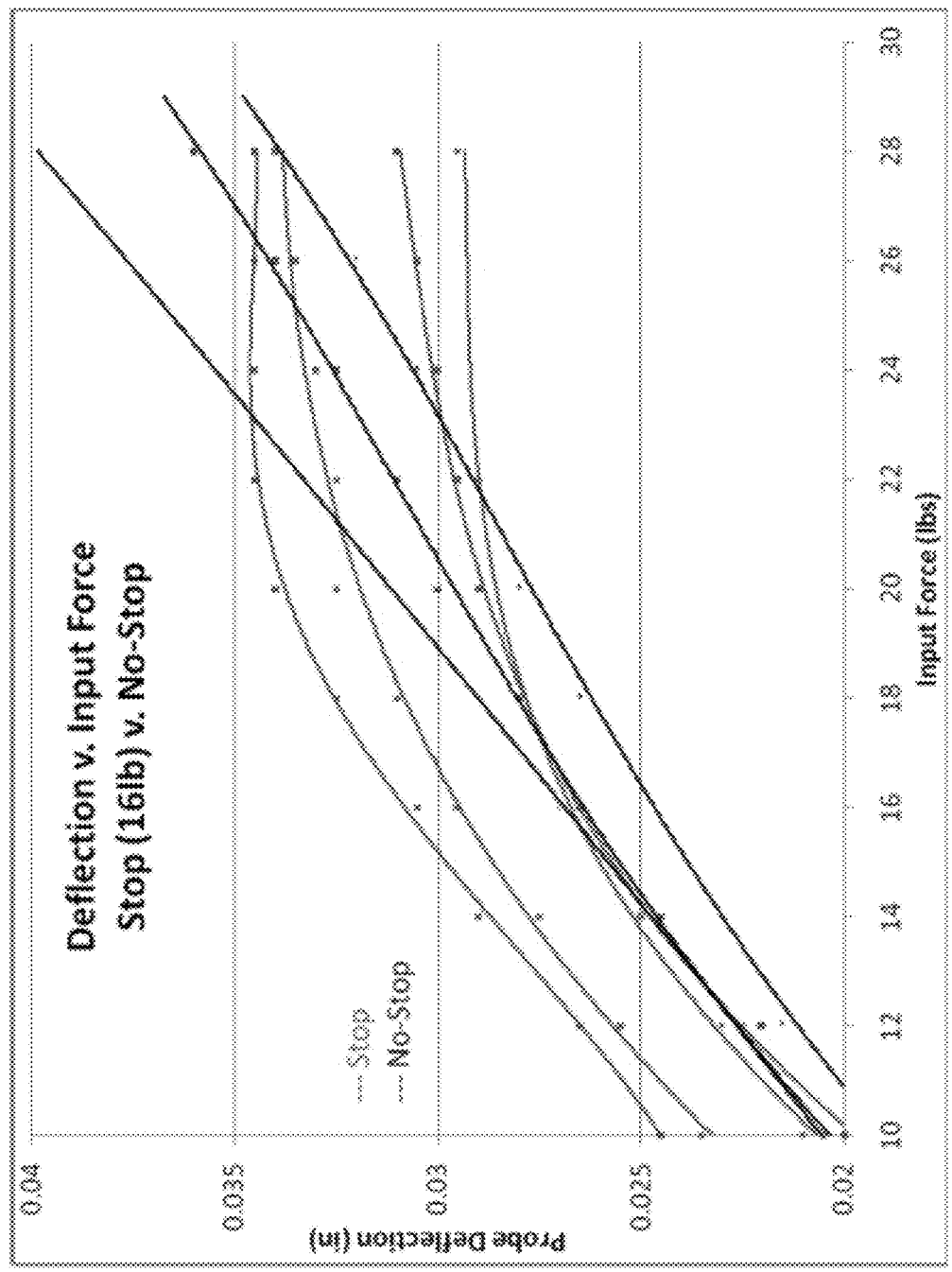
FIG. 94 is a graph illustrating blade deflection characteristics associated with the tube stop assembly of FIG. 93.

When the trigger 4606 is closed, the spring 9008 is compressed. An exemplary nominal force spring load when clamped on nothing between the jaw 7308 and the blade portion 7304 is approximately 24 pounds. This load increases with the rate of the spring as the thickness of tissue in the jaw increases to a maximum, which, in this exemplary embodiment is approximately 28 pounds when the jaw 7308 is pinned fully open by the tissue. When clamped, any load that is transferred into the blade portion 7304 from the liner 7314 deflects the waveguide both as a function of compressing the distal sealing spool 8104 and of bending the cantilevered beam of the probe. The distal sealing spool 8104 compression creates a non-linearity in a force v. deflection curve at the beginning of compression, but once the load is over 10 pounds, the curve straightens out. FIG. 94 is a curve illustrating deflection of the waveguide blade portion 7304 as a function of input force. With the jaw 7308 fully clamped with no tissue, the load input through the spring is applied both into the clamping of the liner 7314 against the blade portion 7304 and into the outer tube stop 9012. The stop 9012 is attached (e.g., welded) with a strength able to withstand the maximum load. The placing of the stop is done in an already assembled system. The stop is tuned by placing the stop while a measured force is applied to the system to take up all of the tolerances and deflect the probe appropriately. As can be seen from the graph, the blade deflects at 10 pounds of force and continues deflecting until approximately 16 pounds of load. At this point, the outer tube 7302 contacts the stop 9012. As the load increases at the spring 9008, the stop 9012 begins to resist further motion of the outer tube 7302. Any further increased load starts to be entirely borne by the stop 9012, with no additional load being imparted into deflecting the blade portion 7304. Once the force on the spring 9008 reaches approximately 22 pounds, any further increase in load does not translate into additional deflection of the blade portion 7304. On the other hand, however, as shown by the straight lines in the graph of FIG. 94, the load transfer to the blade portion 7304 continues linearly without the stop 9012, as does the deflection of the probe. This outer tube stop could be achieved in multiple configurations. In the exemplary embodiment shown, it is a fixed stop 9012 placed on the proximal end of the shaft assembly. This same affect could be achieved at the distal end. For example, a non-illustrated tab on the end of the outer tube 7302 or the inner tube 7402 can be bent into place and act as a stop against further jaw 7308 movement. Similarly, a non-illustrated tab on the jaw 7308 could oppose either or both of the tubes 7302, 7402 that is bent to interfere with this tube set, the tab could allow for assembly where jaw is moved past horizontal but prevents jaw movement past horizontal after assembly. Also, as opposed to a bend tab, a weld or a punch can be used to create a feature that acts as the stop. Furthermore, similar stopping features could be incorporated into the plastic of the handle.

As the invention is used in a procedure, the liner 7314 can wear. Meaning that the jaw 7308 will be free to pivot towards the blade portion 7304. This wear, therefore, allows the outer tube 7302 to translate proximally. With the stop 9012 in place, however, such motion is prevented and the position of the jaw 7308 relative to the outer tube 7302 quickly becomes limited (i.e., it cannot continue to pivot closer to the blade portion 7304). However, since the blade portion 7304 has already deflected away from the jaw 7308, the blade portion 7304 is made free to move less away from the jaw as the liner 7314 wears away. As this happens, the amount of blade deflection and force required to maintain that deflection declines. This reduction in force creates less friction and heating in the liner 7314 and prolongs the life of the liner 7314. With the invention, the maximum amount of deflection of the blade portion 7304 is between 0.030" and 0.035". The available thickness of the liner 7314 is made to be similar. Therefore, in an abusive condition with extended use without tissue (i.e., empty jaws), the worn liner 7314 might allow the metal jaw to touch the blade portion 7304, but after such wear the force between them will be minimal or non-existent.

As already describe herein, the waveguide 1502 is mechanically fixed in the handle portion 302 at the torque adapter 8602—in a proximal area of the waveguide 1502, it is fixed concentrically within the handle portion 302 and the waveguide assembly 304 both rotationally and longitudinally; it is also fixed concentrically at a distal area of the waveguide 1502 by a coupling spool 8104 that acts as a distal seal. When the blade of the waveguide 1502 is placed under load during cutting and/or sealing, this relatively long waveguide beam (even though it is made of titanium in the exemplary embodiment) bends and can potentially contact the inner tube 7402 and, in such a case, it is probable that the touching will occur at acoustically active points along the waveguide 1052. When the waveguide 1502 is bent as such and is active, metal to metal contact occurs. Such contact causes audible high frequency sound (e.g., squeeling) and significant power loss by generating heat at the contact point. This contact is to be avoided. Accordingly, the invention provides a contact support in the form of a waveguide bump 5710 at the waveguide 1502, more particularly, at various locations along the waveguide 1502.

An ideal location for any contact/support along length of an active waveguide 1502 is at node locations. Node locations are points of high stress and no displacement along a standing acoustic wave generated by the transducer 902 in the waveguide 1502. Node lengths are infinitely short sections and displace about nominal (i.e., natural) locations due to drift of resonance frequency of standing wave. The bumps 5710 are larger diameter sections of the waveguide 1502 that extend virtually all the way to the innermost tube in the waveguide assembly 304. Because the nodes displace longitudinally about a note point due to the drift of resonance frequency of the standing wave, each bump 5710 is centered about the nominal/natural node locations and have longitudinal lengths that encompass any displacement of the node location. The larger diameter of the bumps 5710 relative to an outer diameter of the waveguide 1502 provides another advantageous feature. As is understood with regard to ultrasonic vibration in waveguides, an increase in diameter results in a reduction of waveguide displacement, referred to as an step of anti-gain and making node location less active. As such, if the bump 5710 possibly transmitted any vibration to what it was touching, the amplitude of the vibration would be reduced with respect to the remaining, narrower sections of the waveguide 1502. The number of the bumps 5710 are chosen selectively and do not equal the number of node locations along the waveguide 1502 in the exemplary embodiment of the invention, which is illustrated, for example, in FIG. 57 where four bumps 5710 are present. A minimum quantity of the bumps 5710 is chosen for ease of manufacturing and to prevent the above disadvantageous contact.

Even though the node locations are less active at the bumps 5710, the above-mentioned metal to metal contact still can be an issue. Accordingly, to further prevent such contact, the invention provides an inner sleeve 7610 that encompasses the section of the waveguide 1502 within the inner tube 7402. The sleeve 7610 is made out of a low-coefficient of friction, high-temperature material (e.g., Teflon, PTFE, HDPE, Polyethylene). As can be seen in FIGS. 81 and 99, respectively, the sleeve 7610 is naturally fixed concentrically about the waveguide 1052 and is mechanically fixed against longitudinal translation by the torque adapter 8602 at a proximal end of the sleeve 7610 and by the sealing spool 8104 at the distal end of the sleeve 7610. The sleeve 7610 has an inner diameter selected to only contact the waveguide 1502 at the bumps 5710. The outer diameter of the sleeve 7710 is allowed to contact the inner surface of the inner tube 7402 but can be slightly smaller. An alternate configuration of the sleeve 7610 has the sealing spool 8104 and the sleeve 7610 as a single piece. These components can share material, providing the concurrent benefits of lower part count and simpler assembly. In this exemplary embodiment the integral distal spool 8104 and sleeve 7610 are constrained by the corset on the inner tube 7402.

When assembled the cross-sectional diameters of the waveguide 1502, the sleeve 7610, the inner tube 7402, and the outer tube 7302 are configured to allow an air gap for ETO sterilization, for example. Airgaps along the bumps 5710 also reduce the amount of acoustic energy that can be coupled to the sleeve 7610 from the waveguide 1502. Further, due to the low coefficient of friction of the material that makes up the sleeve (e.g., Teflon, PTFE), the acoustic energy that ever is imparted to the inner or outer tubes 7302, 7402 is virtually non-existent. As an alternative embodiment to the singular, smooth, tubular sleeve 7610, a more complex sleeve can be included that entirely eliminates the need to place the bumps 5710 on the waveguide 1502. For example, the sleeve 7610 can have longitudinally extending parts, e.g., two, clam-shell-like halves that surround the waveguide 1502 between the torque adapter 8602 and the sealing spool 8104. Each half can have inwardly protruding bosses and outwardly protruding bosses. The outwardly projecting bosses do not entirely surround the two outer surfaces of the halves to create gaps at each outer support point. These gaps permit penetration of ETO sterilization gasses all the way from the distal end to the proximal of the sleeve on the outer surface next to the inner tube 7402. The outwardly projecting bosses can be staggered. The inwardly projecting bosses, on the other hand, are configured to contact the waveguide 1502 only at the nodes. As the longitudinal lengths of the bumps 5710 are sufficiently large, the inwardly projecting bosses can have smaller longitudinal lengths and the overall longitudinal length of the halves can extend all the way from the torque adapter 8602 to the sealing spool 8104 and, if desire, one can be integral with the sealing spool 8104. In this way, the sleeve remains longitudinally stable with the inwardly projecting bosses located on the waveguide nodes. Another configuration can have the sleeve be a blow-molded part with both the inwardly and outwardly projecting bosses and, yet another configuration has the sealing spool 8104 blow molded integrally with this sleeve.

All prior art node supports are greater than one in number and are fixed to the outer diameter of the respective waveguide with 100% contact (pressed, bonded, molded). As such, acoustic energy is always coupled to such supports, which results in a higher natural power draw and in high assembly complexity and manufacturing cost. In contrast, the bumps 5710 and sleeve 7610 waveguide support of the invention are simple and cost-effective. The sleeve's constraint and one-piece configuration lends itself to a far simpler and cost effective assembly. Also, the bump features are not far different than the average diameter of the waveguide 1502 and are less than the maximum diameter of the waveguide 1052 to make extra fabrication a non-issue.

Figure 103:
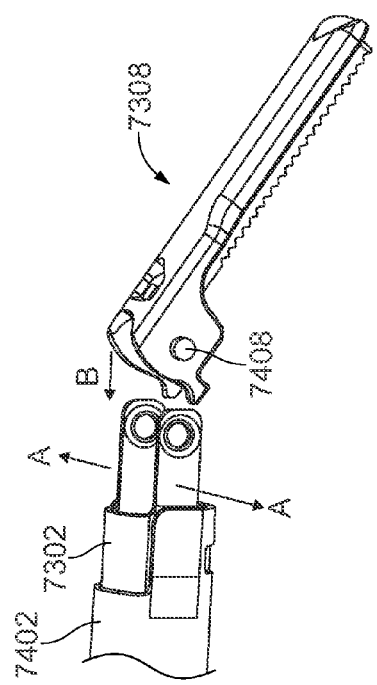
FIG. 103 is a fragmentary, exploded perspective view of the jaw assembly according to the invention in a third installation step.
Figure 104:
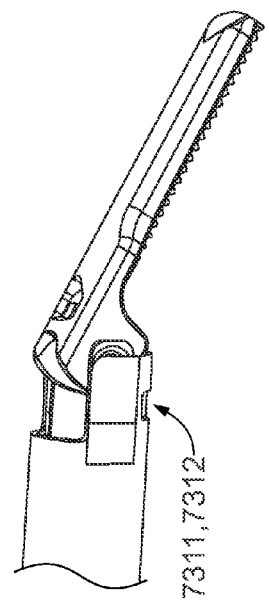
FIG. 104 is a fragmentary, exploded perspective view of the jaw assembly according to the invention in a fourth installation step.

Construction of the waveguide assembly 304 is described with reference to FIGS. 100 to 105. Initially, the liner jaw 7308, 10010 in inserted and secured in the jaw 7308. See, for example, FIGS. 100 and 101. The inner tube 7402 is shaped to be extended beyond the distal end of the outer tube 7302 sufficiently far to allow a flexing open (as shown by arrows A) of the clevis arms 7418, 7420 for receipt therein (arrow B) of the opposing bosses 7408 of the jaw in the progression of FIGS. 101 to 102. With the jaw 7308 assembled in the inner tube 7402, the jaw 7308 is pivoted below the centerline of the tubes 7302, 7402 and the inner tube 7402 is slid into the outer tube 7402 as shown in FIG. 103. This presents the pivot control tabs 7411, 7412 of the jaw 7308 into a position to enter the outer tube 7302. The jaw is, as shown in FIG. 104, pivoted open above the centerline of the tubes 7302, 7402 while the pivot control tabs 7411, 7412 are inserted into the openings 7311, 7312 of the outer tube 7302.

The waveguide 1502 is, then, inserted through the set of tubes 7302, 7402 to, thereby, trap the jaw 7308 therein—because the jaw 7380 can no longer travel towards longitudinal centerline of the tubes 7302, 7402 due to the presence of the waveguide 1502. This final assembly position is illustrated in many figures of the drawings, for example, in FIGS. 73 and 76. Use of isopropyl alcohol, for example, allows the waveguide 1502 to be slid through distal dumbbell seal 8104 with ease. Thereafter, the alcohol evaporates so that no residue remains at the dumbbell seal 8104. As is apparent, this assembly process is unique because it does not require any operations other than mechanically positional joining. No welding, crimping, or deforming occurs nor are there needed any other parts for full assembly.

This assembly process has a significant benefit with regard to manufacture. Lubrication of the inner and outer tubes 7302, 7402 can occur at the tube manufacturer and not on the clean room assembly line, which prevents any contamination arising from such joining. Before coaxially fitting the inner and outer tubes 7302, 7402 together, the translating o-ring 7406 is placed in the corset 7404 of the inner tube 7402 and, then, the outer tube 7302 is slid onto the inner tube 7402 up to the o-ring 7406. Lubrication is placed on the o-ring 7406 and the outer tube 7302 is moved with respect to the inner tube 7402 (or vice versa) to have the o-ring 7406 roll and translate within the corset 7404. Moisture in the lubrication is allowed to dry, which leaves only lubricant between the tubes 7302, 7402 and around the o-ring 7406.

A common issue in developing displacement-dependant ultrasonic systems is the complexity and inaccuracies of measuring waveguide displacement. The most accurate measurement systems are laser vibrometers that cannot be calibrated by equivalent high-frequency dynamic standards and are expensive. One crude and simple calibration method is to observe displacement of reflected "spots" on the surface of a dynamic high-frequency system under magnification. Peak-to-peak displacement is observed and can be correlated to known length standards. The principal issue with magnification observation method is the randomness or inconsistencies of such "spots". In an exemplary embodiment of measuring waveguide displacement, the invention uses a controlled visual feature such as an intentionally applied spot, mark, artwork, machined hole, groove or the like to the blade portion 7304 of the waveguide 1502. Placing such a feature on the blade 7304 increases precision of magnified displacement observation and measurement.

XV. Additional Safety Features

In an exemplary safety embodiment for any of the configurations of the invention, the system can have a safety mechanism grounding the surgeon using the device to the handheld ultrasonic surgical cautery assembly 300. In the event the waveguide 1502 accidentally makes contact with the surgeon, the handheld ultrasonic surgical cautery assembly 300 senses this grounding and immediately ceases movement of the waveguide 1502, thereby instantly preventing the surgeon from cutting him/herself. It is possible to provide a safety circuit that can sense contact with the surgeon and interrupt ultrasonic power delivery because the hand-held instrument 300 is not connected to earth ground. For example, a capacitive contact patch located on the handle assembly 302 is connected to a capacitive-touch sensing circuit (such as is used for capacitive switching and known to those in the art) and disposed to detect contact of the working tip with the surgeon. When such contact is detected, the drive circuit 904 of the instrument will be shut down to avoid applying cutting energy to the surgeon. Such a sensing circuit would be impractical in systems of the prior art, where the handpiece is connected to a large piece of earth-grounded electrical equipment.

Another exemplary embodiment allows the transducer to work in a receiving mode where vibrations in the waveguide are turned into a signal that the electronics of the device could monitor. For example, vibrations associated with blood flowing through a vessel could be detected and used to provide feedback to the user about the type of tissue that has been clamped. For instance, during clamping of the jaw, this detection is able to determine that significant blood flow existed just before clamping. A signal could alert the user that the device is clamped on heavy vasculature and, for example, that low power for sealing should be used. Alternatively, if heavy vasculature is detected, high energy activation could be prohibited as a safety mechanism.

In accordance with another exemplary embodiment of the present invention, after the battery assembly 301 is physically and electrically coupled to the handle assembly 302, the handheld ultrasonic surgical cautery assembly 300 will not operate until the button 4608 is changed from a depressed state to a released state, i.e., actively placed into a non-depressed position. This feature prevents the handheld ultrasonic surgical cautery assembly 300 from operating immediately upon connection of the battery assembly 301 to the handle assembly 302, which otherwise could occur if the operator was unintentionally depressing the button 4608 when connecting the battery assembly 301 to the handle assembly 302.

Because the present invention is comprised of three interconnected but separable components (i.e., the battery assembly 301, the handle assembly 302, and the TAG assembly 303), each having its own accessible (as well as selectively exposed) electrical connections, there is a danger of electrostatic discharge (ESD) occurring between or among the three separable components. Accordingly, an another exemplary embodiment, the invention employs an ESD protection strategy to prevent damage to the device and the possibility of latent failures. A wide range of solutions for implementing this type of protection is contemplated as being within the scope and spirit of the present invention. Examples include, but are not limited to, using discrete ESD protection components and spark gaps as well.

In yet another exemplary embodiment for protecting against injury or damage from the electrical components of the device, the battery cells may be positioned in such a way (e.g., inverted) that their connector tabs point away from the electrical boards. This configuration reduces a likelihood of creating accidental shorts, as well as allowing the use of a cell interconnect board, which facilitates the connection of the battery cell tabs to the circuitry.

As has been described, the present invention provides a small and efficient hand-held ultrasonic cutting device that is self-powered and, therefore, cordless, which eliminates entirely the expensive set-top box required by the prior art devices. Advantageously, the device of the invention allows a user to operate completely free of cords or other tethering devices. In addition to the advantages of reduced cost, reduced size, elimination of a tethering cord for supplying power and carrying signals, and providing a constant motional voltage, the instant invention provides unique advantages for maintaining the sterile condition in a surgical environment. As has been explained, the inventive device is comprised entirely of sterilizable components that are maintained wholly in a sterile field. In addition, all electronic controls of the inventive system exist within the sterile field. Therefore, any and all troubleshooting can take place inside the sterile field. That is, because the inventive device is not tethered to a desktop box, as required in the prior art, a user need never exit the sterile field to perform any function with the inventive handheld ultrasonic surgical cautery assembly 300 (e.g., troubleshooting, replacing batteries, replacing waveguide assemblies, etc.). Furthermore, the inventive two-stage button allows an operator complete control of any surgical task without requiring the operator to focus their visual attention on the instrument itself. In other words, the operator does not have to look to ensure (s) he is preparing to push the proper button, as only one button is used.

The invention also provides low-voltage or battery-voltage switching or wave-forming stages prior to the transformer voltage step-up stage. By "marrying" all of the frequency sensitive components within one place (i.e., the handle), the present invention eliminates any inductive losses that occur between prior art set-top boxes and hand pieces—a disadvantage suffered by all prior-art ultrasonic cautery/cutting devices. Because of the close coupling between the drive circuitry and the matching network 1012, the overall power modification circuit is tolerant of higher Q factors and larger frequency ranges.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A battery assembly, comprising:
    a housing:
        having an exterior shape formed to removably connect with a battery terminal of a surgical device;
        containing a modular battery operable to supply power to the surgical device at the battery terminal;
        having a control circuit comprising at least one microprocessor, a memory, and a real-time clock, the control circuit being communicatively coupled to the modular battery and:
        detecting an identity of the surgical device;
        determining information pertaining to an operational parameter of the surgical device based upon the detected identity;
        recording the information at least in the memory; and
        selectively allowing or preventing the modular battery from supplying power to the surgical device dependent upon the information, the information including an actual use count of at least one portion of the surgical device, wherein an actual use is a completed use of the at least one portion of the surgical device and is determined by the control circuit detecting a length of time that has elapsed since the last actual use of the at least one portion of the surgical device.

2. The battery assembly according to claim 1, wherein the surgical device comprises:
    an ultrasonic waveguide;
    a cordless ultrasonic-movement-generation assembly having:
        an output couple imparting ultrasonic movement to the ultrasonic waveguide when the waveguide is connected thereto; and
        a securing connector; and
    a surgical handle having:
        the battery terminal;
        a waveguide attachment dock rotatably coupling the ultrasonic waveguide thereto; and
        an ultrasonic-movement-generation assembly dock electrically connecting the battery assembly to the ultrasonic-movement-generation assembly and physically connecting the ultrasonic waveguide to the output couple of the ultrasonic-movement-generation assembly when the securing connector of the ultrasonic-movement-generation assembly is removably secured at the surgical handle.

3. The battery assembly according to claim 2, wherein the ultrasonic-movement-generation assembly comprises:
    a driving-wave generation circuit having a generator output; and
    a transducer communicatively coupled to the generator output.

4. The battery assembly according to claim 1, wherein the control circuit records a total number of actual uses of the at least one portion of the surgical device.

5. The battery assembly according to claim 4, wherein the control circuit prevents the modular battery from supplying power to the surgical device when the recorded total number of actual uses is at least a pre-defined maximum number of actual uses.

6. The battery assembly according to claim 4, wherein:
    the information includes a momentary lapse in use of at least a portion of the surgical device; and
    the control circuit determines the momentary lapse in use by:
        detecting a length of time that has elapsed since the last actual use of the at least one portion; and
        if the detected length of time is less than a pre-defined threshold, determining that a momentary lapse in use of the at least one portion has occurred.

7. The battery assembly according to claim 1, wherein the control circuit determines the actual use count by:
    determining a length of time that has elapsed since the last of the actual uses of the at least one portion with the real-time clock; and
    if the determined length of time exceeds a pre-defined threshold, incrementing the recorded total number of actual uses of the at least one portion contained in the memory.

8. The battery assembly according to claim 1, wherein the control circuit determines if either of an actual use and a momentary lapse in use of the surgical device has occurred by:
    detecting a length of time that has elapsed since a last use of the surgical device;
    if the detected length of time meets or exceeds a pre-defined threshold, determining that an actual use has occurred; and
    if the detected length of time is less than the pre-defined threshold, determining that a momentary lapse in use has occurred.

9. The battery assembly according to claim 8, wherein the control circuit records a total number of actual uses of the surgical device.

10. The battery assembly according to claim 9, wherein the control circuit prevents the modular battery from supplying power to the surgical device when the recorded total number of actual uses meets or exceeds a pre-defined maximum number of actual uses.

11. The battery assembly according to claim 1 in combination with a surgical device, the surgical device comprising:
an ultrasonic waveguide having a proximal end for receiving ultrasonic movement thereat;
a cordless ultrasonic-movement-generation assembly having:
a driving-wave generation circuit having a generator output; and
a transducer communicatively coupled to the generator output and having an ultrasonic-movement-producing end removably connected to the proximal end of the ultrasonic waveguide; and
a surgical handle having:
the battery terminal;
a waveguide attachment dock rotatably coupling the ultrasonic waveguide thereto; and
an ultrasonic-movement-generation assembly dock
electrically connecting the battery assembly to the ultrasonic-movement-generation assembly and
physically connecting the ultrasonic waveguide to the ultrasonic-movement-producing end of the ultrasonic-movement-generation assembly when the ultrasonic-movement-generation assembly is removably secured at the surgical handle.

12. The battery assembly according to claim 11, wherein the control circuit records a total number of actual uses of the at least one portion of the surgical device.

13. The battery assembly according to claim 12, wherein the control circuit prevents the modular battery from supplying power to the surgical device when the recorded total number of actual uses is at least a pre-defined maximum number of actual uses.

14. The battery assembly according to claim 12, wherein the control circuit determines the actual use count by:
determining a length of time that has elapsed since the last of the actual uses of the at least one portion with the real-time clock; and
if the determined length of time exceeds a pre-defined threshold, incrementing the recorded total number of actual uses of the at least one portion contained in the memory.

15. The battery assembly according to claim 11, wherein:
the information includes a momentary lapse in use of at least one portion of the surgical device; and
the control circuit determines a momentary lapse in use by:
detecting a length of time that has elapsed since the last actual use of the at least one portion; and
if the detected length of time is less than a pre-defined threshold, determining that a momentary lapse in use of the at least one portion has occurred.

16. The battery assembly according to claim 11, wherein the control circuit determines if either of an actual use and a momentary lapse in use of the surgical device has occurred by:
detecting a length of time that has elapsed since a last use of the surgical device;
if the detected length of time meets or exceeds a pre-defined threshold, determining that an actual use has occurred; and
if the detected length of time is less than the pre-defined threshold, determining that a momentary lapse in use has occurred.

17. The battery assembly according to claim 16, wherein the control circuit records a total number of actual uses of the surgical device.

18. The battery assembly according to claim 17, wherein the control circuit prevents the modular battery from supplying power to the surgical device when the recorded total number of actual uses meets or exceeds a pre-defined maximum number of actual uses.

19. A battery assembly, comprising:
a housing:
having an exterior shape formed to removably connect with a battery terminal of a surgical device;
containing a modular battery supplying power to the surgical device at the battery terminal;
having a control circuit comprising at least one microprocessor, a memory, and a real-time clock, the control circuit being communicatively coupled to the modular battery and:
detecting an identity of the surgical device;
determining information pertaining to an operational parameter of the surgical device based upon the detected identity;
recording the information at least in the memory; and
selectively allowing or preventing the modular battery from supplying power to the surgical device dependent upon the information, the information including an actual use count and a momentary lapse in use of at least one portion of the surgical device, wherein an actual use is a completed use of the at least one portion of the surgical device.

\* \* \* \* \*